(12) United States Patent
Hunter et al.

(10) Patent No.: US 11,793,945 B2
(45) Date of Patent: Oct. 24, 2023

(54) DROPLET DELIVERY DEVICE WITH PUSH EJECTION

(71) Applicant: PNEUMA RESPIRATORY, INC., Boone, NC (US)

(72) Inventors: Charles Eric Hunter, Boone, NC (US); Michael Scoggin, Boone, NC (US); Jeffrey Miller, Boone, NC (US); Jose Salazar, Boone, NC (US); Brian Beach, Boone, NC (US); Caley Modlin, Boone, NC (US); Matthew Culpepper, Boone, NC (US); Jianqiang Li, Shenzhen (CN); Chengjie Li, Shenzhen (CN); Shi Bo Wang, Shenzhen (CN); Chao-Ping Lee, Kaohsiung (TW); Gregory Rapp, Boone, NC (US); Judson Sidney Clements, Boone, NC (US)

(73) Assignee: Pneuma Respiratory, Inc., Boone, NC (US)

( * ) Notice: Subject to any disclaimer, the term of this patent is extended or adjusted under 35 U.S.C. 154(b) by 0 days.

(21) Appl. No.: 17/846,902

(22) Filed: Jun. 22, 2022

(65) Prior Publication Data
US 2022/0401661 A1 Dec. 22, 2022

Related U.S. Application Data

(60) Provisional application No. 63/280,643, filed on Nov. 18, 2021, provisional application No. 63/256,546, (Continued)

(51) Int. Cl.
*A61M 11/00* (2006.01)
*A61M 15/00* (2006.01)

(52) U.S. Cl.
CPC ......... *A61M 11/003* (2014.02); *A61M 11/005* (2013.01); *A61M 15/0001* (2014.02);
(Continued)

(58) Field of Classification Search
CPC .............. A61M 11/003; A61M 11/005; A61M 15/0001; A61M 15/001; A61M 15/0033;
(Continued)

(56) References Cited

U.S. PATENT DOCUMENTS

| 3,934,585 A | 1/1976 | Maurice |
| 3,970,250 A | 7/1976 | Drews |

(Continued)

FOREIGN PATENT DOCUMENTS

| AU | 2012258488 | 1/2013 |
| CA | 2364248 | 8/2006 |

(Continued)

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.

(Continued)

*Primary Examiner* — Joseph D. Boecker
*Assistant Examiner* — Brian T Khong
(74) *Attorney, Agent, or Firm* — Polsinelli PC

(57) ABSTRACT

A droplet delivery device includes a housing with a mouthpiece port or outlet from a nasal device for releasing fluid droplets, a fluid reservoir, and an ejector bracket having a membrane positioned between a mesh with a plurality of openings and a vibrating member that is coupled to an electronic transducer, such as an ultrasonic transducer. The (Continued)

transducer vibrates the vibrating member which causes the membrane to push fluid supplied by the reservoir through the mesh to generate droplets in an ejected stream released through the outlet.

7 Claims, 125 Drawing Sheets

Related U.S. Application Data filed on Oct. 16, 2021, provisional application No. 63/256,245, filed on Oct. 15, 2021, provisional application No. 63/213,634, filed on Jun. 22, 2021.

(52) U.S. Cl.
CPC ...... *A61M 15/002* (2014.02); *A61M 15/0085* (2013.01); *A61M 2206/11* (2013.01)

(58) Field of Classification Search
CPC .......... A61M 15/0035; A61M 15/0036; A61M 15/004; A61M 15/0041; A61M 15/002; A61M 15/0085; A24F 40/42
See application file for complete search history.

(56) References Cited

U.S. PATENT DOCUMENTS

| | | | |
|---|---|---|---|
| 5,021,701 A | 6/1991 | Takahashi et al. |
| 5,164,740 A | 11/1992 | Ivri |
| 5,239,993 A | 8/1993 | Evans |
| 5,363,842 A | 11/1994 | Mishelevich et al. |
| 5,487,378 A | 1/1996 | Robertson et al. |
| 5,497,763 A | 3/1996 | Lloyd et al. |
| 5,586,550 A | 12/1996 | Ivri et al. |
| 5,607,410 A | 3/1997 | Branch |
| 5,630,793 A | 5/1997 | Rowe |
| 5,724,959 A | 3/1998 | McAughey et al. |
| 5,758,637 A | 6/1998 | Ivri et al. |
| 5,826,570 A | 10/1998 | Goodman et al. |
| 5,828,394 A | 10/1998 | Khuri-Yakub et al. |
| 5,881,716 A | 3/1999 | Wirch et al. |
| 5,884,620 A | 3/1999 | Gonda et al. |
| 5,894,841 A | 4/1999 | Voges |
| 5,906,202 A | 5/1999 | Schuster et al. |
| 5,938,117 A | 8/1999 | Ivri |
| 5,979,247 A | 11/1999 | Kizawa |
| 6,011,062 A | 1/2000 | Schneider et al. |
| 6,026,809 A | 2/2000 | Abrams et al. |
| 6,062,212 A | 5/2000 | Davison et al. |
| 6,071,498 A | 6/2000 | Narodylo et al. |
| 6,085,740 A | 7/2000 | Ivri et al. |
| 6,158,431 A | 12/2000 | Poole |
| 6,196,219 B1 | 3/2001 | Hess et al. |
| 6,235,177 B1 | 5/2001 | Borland et al. |
| 6,358,058 B1 | 3/2002 | Strupat et al. |
| 6,443,146 B1 | 9/2002 | Voges |
| 6,511,718 B1 | 1/2003 | Paz de Araujo et al. |
| 6,523,762 B1 | 2/2003 | Luginbuhl et al. |
| 6,615,826 B1 | 9/2003 | Gabrio et al. |
| 6,629,524 B1 | 10/2003 | Goodall et al. |
| 6,637,430 B1 | 10/2003 | Voges et al. |
| 6,896,910 B2 | 5/2005 | Kim et al. |
| 6,978,941 B2 | 12/2005 | Litherland et al. |
| 6,981,499 B2 | 1/2006 | Anderson et al. |
| 7,131,599 B2 | 11/2006 | Katase |
| 7,191,777 B2 | 3/2007 | Brand et al. |
| 7,198,044 B2 | 4/2007 | Trueba |
| 7,219,664 B2 | 5/2007 | Ruckdeschel et al. |
| 7,628,339 B2 | 12/2009 | Ivri et al. |
| 7,648,957 B2 | 1/2010 | Heyden et al. |
| 7,708,011 B2 | 5/2010 | Hochrainer et al. |
| 7,883,031 B2 | 2/2011 | Collins, Jr. et al. |
| 7,900,625 B2 | 3/2011 | Kleinstreuer et al. |
| 7,954,486 B2 | 6/2011 | Papania et al. |
| 7,976,140 B2 | 7/2011 | Umeda |
| 8,012,136 B2 | 9/2011 | Collins, Jr. et al. |
| 8,367,734 B1 | 2/2013 | Gao et al. |
| 8,474,452 B2 | 7/2013 | Gumaste et al. |
| 8,545,463 B2 | 10/2013 | Collins, Jr. et al. |
| 8,555,874 B2 | 10/2013 | Fink et al. |
| 8,616,195 B2 | 12/2013 | Power et al. |
| 8,684,980 B2 | 4/2014 | Hunter et al. |
| 8,733,935 B2 | 5/2014 | Ballou, Jr. et al. |
| 8,753,308 B2 | 6/2014 | Palmer et al. |
| 8,936,021 B2 | 1/2015 | Collins, Jr. |
| 8,985,100 B2 | 3/2015 | Minocchieri et al. |
| 9,022,027 B2 | 5/2015 | Addington et al. |
| 9,087,145 B2 | 7/2015 | Ballou, Jr. et al. |
| 9,227,029 B2 | 1/2016 | Addington et al. |
| 9,242,054 B2 | 1/2016 | Fink et al. |
| 9,352,108 B1 | 5/2016 | Reed et al. |
| 9,452,274 B2 | 9/2016 | Addington et al. |
| 9,463,486 B2 | 10/2016 | Wilkerson et al. |
| 9,539,604 B2 | 1/2017 | Wilkerson et al. |
| 9,956,360 B2 | 5/2018 | Germinario et al. |
| 9,962,507 B2 | 5/2018 | Germinario et al. |
| 10,449,314 B2 | 10/2019 | Germinario et al. |
| 10,525,220 B2 | 1/2020 | Hunter et al. |
| 10,568,543 B2 | 2/2020 | Yan |
| 10,857,310 B2 | 12/2020 | Muellinger et al. |
| 10,898,666 B2 | 1/2021 | Germinario et al. |
| 2002/0002975 A1 | 1/2002 | Power |
| 2002/0032387 A1 | 3/2002 | Geva et al. |
| 2002/0046750 A1 | 4/2002 | Gonda et al. |
| 2002/0071871 A1 | 6/2002 | Snyder et al. |
| 2002/0077369 A1 | 6/2002 | Noolandi et al. |
| 2002/0121274 A1 | 9/2002 | Borland et al. |
| 2003/0062042 A1 | 4/2003 | Wensley et al. |
| 2003/0072717 A1 | 4/2003 | Reinhold et al. |
| 2003/0098022 A1 | 5/2003 | Nakao et al. |
| 2003/0101991 A1 | 6/2003 | Trueba |
| 2003/0127538 A1 | 7/2003 | Patel et al. |
| 2003/0140921 A1 | 7/2003 | Smith et al. |
| 2003/0150445 A1 | 8/2003 | Power et al. |
| 2003/0196654 A1 | 10/2003 | Stein |
| 2003/0205229 A1 | 11/2003 | Crockford et al. |
| 2004/0009231 A1 | 1/2004 | Jackson et al. |
| 2004/0045547 A1 | 3/2004 | Yamamoto et al. |
| 2004/0084044 A1 | 5/2004 | Childers et al. |
| 2004/0139963 A1 | 7/2004 | Ivri et al. |
| 2004/0195403 A1 | 10/2004 | Atterybury et al. |
| 2004/0215157 A1 | 10/2004 | Peclat et al. |
| 2004/0256487 A1 | 12/2004 | Collins, Jr. et al. |
| 2005/0011514 A1 | 1/2005 | Power et al. |
| 2005/0077315 A1 | 4/2005 | Pavlu et al. |
| 2005/0121025 A1 | 6/2005 | Gamard et al. |
| 2005/0150489 A1 | 7/2005 | Dunfield et al. |
| 2005/0172476 A1 | 8/2005 | Stone et al. |
| 2005/0172958 A1 | 8/2005 | Singer et al. |
| 2005/0217666 A1 | 10/2005 | Fink et al. |
| 2005/0224075 A1 | 10/2005 | Childers et al. |
| 2005/0236501 A1 | 10/2005 | Zimlich, Jr. et al. |
| 2007/0023036 A1 | 2/2007 | Grychowski et al. |
| 2007/0044793 A1 | 3/2007 | Kleinstreuer et al. |
| 2007/0083677 A1 | 4/2007 | Cecka et al. |
| 2007/0119968 A1 | 5/2007 | Collins et al. |
| 2007/0119969 A1 | 5/2007 | Collins, Jr. et al. |
| 2007/0125370 A1 | 6/2007 | Denyer et al. |
| 2007/0157931 A1 | 7/2007 | Parker et al. |
| 2007/0240714 A1 | 10/2007 | Dunne et al. |
| 2007/0248645 A1 | 10/2007 | Bague et al. |
| 2007/0267010 A1 | 11/2007 | Fink et al. |
| 2008/0000470 A1 | 1/2008 | Minocchieri et al. |
| 2008/0059228 A1 | 3/2008 | Bossi et al. |
| 2008/0142010 A1 | 6/2008 | Weaver et al. |
| 2008/0243050 A1 | 10/2008 | Power et al. |
| 2008/0271732 A1 | 11/2008 | Weaver et al. |
| 2008/0283049 A1 | 11/2008 | Mahoney et al. |
| 2008/0283057 A1 | 11/2008 | Rohrschneider et al. |
| 2008/0295827 A1 | 12/2008 | Kobayashi |
| 2008/0308096 A1 | 12/2008 | Borgschulte et al. |
| 2009/0038610 A1 | 2/2009 | Bogh et al. |

(56) References Cited

U.S. PATENT DOCUMENTS

| | | |
|---|---|---|
| 2009/0093772 A1 | 4/2009 | Genosar et al. |
| 2009/0101144 A1 | 4/2009 | Gamard et al. |
| 2009/0107492 A1 | 4/2009 | Ooida |
| 2009/0114218 A1 | 5/2009 | Veatch |
| 2009/0114742 A1 | 5/2009 | Collins, Jr. |
| 2009/0118243 A1 | 5/2009 | Gjorstrup |
| 2009/0134235 A1 | 5/2009 | Ivri |
| 2009/0167812 A1 | 7/2009 | Asai et al. |
| 2009/0192443 A1 | 7/2009 | Collins, Jr. |
| 2009/0212133 A1 | 8/2009 | Collins, Jr. |
| 2009/0235925 A1 | 9/2009 | Power et al. |
| 2009/0270752 A1 | 10/2009 | Coifman |
| 2009/0272818 A1 | 11/2009 | Valpey, III et al. |
| 2009/0314292 A1 | 12/2009 | Overfield et al. |
| 2009/0317496 A1 | 12/2009 | Park et al. |
| 2010/0037894 A1 | 2/2010 | Rouse et al. |
| 2010/0078013 A1 | 4/2010 | Power et al. |
| 2010/0089395 A1 | 4/2010 | Power et al. |
| 2010/0156995 A1 | 6/2010 | Kanda et al. |
| 2010/0181387 A1 | 7/2010 | Zaffaroni et al. |
| 2010/0222752 A1 | 9/2010 | Collins, Jr. et al. |
| 2010/0273895 A1 | 10/2010 | Stinchcomb et al. |
| 2010/0282247 A1 | 11/2010 | Kadrichu et al. |
| 2011/0094523 A1 | 4/2011 | Thorens et al. |
| 2011/0108025 A1 | 5/2011 | Fink et al. |
| 2011/0114090 A1 | 5/2011 | Piper |
| 2011/0230820 A1 | 9/2011 | Lillis et al. |
| 2011/0253139 A1 | 10/2011 | Guthrie et al. |
| 2011/0253140 A1 | 10/2011 | Smyth et al. |
| 2011/0253805 A1 | 10/2011 | Lee |
| 2012/0037154 A1 | 2/2012 | Gallem et al. |
| 2012/0048265 A1 | 3/2012 | Smaldone |
| 2012/0092416 A1 | 4/2012 | Platt et al. |
| 2012/0266878 A1 | 10/2012 | Watanabe et al. |
| 2012/0291781 A1 | 11/2012 | Kaufmann et al. |
| 2013/0064777 A1 | 3/2013 | Tamarkin et al. |
| 2013/0079732 A1 | 3/2013 | Burt et al. |
| 2013/0150812 A1* | 6/2013 | Hunter .................. A61F 9/0026 604/295 |
| 2013/0172830 A1 | 7/2013 | Hunter et al. |
| 2013/0239956 A1 | 9/2013 | Schulz et al. |
| 2013/0267864 A1 | 10/2013 | Addington et al. |
| 2013/0284165 A1 | 10/2013 | Krimsky |
| 2013/0299607 A1 | 11/2013 | Wilkerson et al. |
| 2013/0319404 A1 | 12/2013 | Feriani et al. |
| 2013/0327323 A1 | 12/2013 | Rubin |
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 | 5/2014 | Mullinger et al. |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0230817 A1* | 8/2014 | Richardson ........ A61M 15/0091 128/203.15 |
| 2014/0231538 A1* | 8/2014 | Tabata ................ B05B 17/0638 239/102.1 |
| 2014/0283859 A1 | 9/2014 | Minskoff et al. |
| 2014/0336618 A1 | 11/2014 | Wilkerson et al. |
| 2015/0018694 A1 | 1/2015 | Gomo |
| 2015/0101596 A1 | 4/2015 | Hogan |
| 2015/0136129 A1 | 5/2015 | Mahadevan et al. |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0196060 A1 | 7/2015 | Wensley et al. |
| 2015/0273165 A1 | 10/2015 | Hadash |
| 2015/0283339 A1 | 10/2015 | Mahadevan et al. |
| 2015/0328151 A1 | 11/2015 | Ballou, Jr. et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0082208 A1 | 3/2016 | Ballam et al. |
| 2016/0106341 A1 | 4/2016 | Adam et al. |
| 2016/0129182 A1 | 5/2016 | Schuster et al. |
| 2016/0166768 A1 | 6/2016 | Edwards et al. |
| 2016/0213864 A1 | 7/2016 | Eilat et al. |
| 2016/0213866 A1 | 7/2016 | Tan |
| 2016/0245830 A1 | 8/2016 | Mace et al. |
| 2016/0310982 A1 | 10/2016 | Von Hollen |
| 2016/0325055 A1 | 11/2016 | Cameron |
| 2016/0354557 A1 | 12/2016 | McPherson Allnutt et al. |
| 2017/0007449 A1 | 1/2017 | Nielsen |
| 2017/0035924 A1 | 2/2017 | Yang et al. |
| 2017/0039344 A1 | 2/2017 | Bitran et al. |
| 2017/0106153 A1 | 4/2017 | Davidson et al. |
| 2017/0106155 A1 | 4/2017 | Reed et al. |
| 2017/0128677 A1 | 5/2017 | Eilat et al. |
| 2017/0158776 A1 | 6/2017 | Feltquate et al. |
| 2017/0203058 A1 | 7/2017 | Davidson et al. |
| 2017/0203323 A1 | 7/2017 | Gschwind et al. |
| 2017/0224706 A1 | 8/2017 | Surber |
| 2017/0270260 A1 | 9/2017 | Shetty et al. |
| 2017/0274163 A1 | 9/2017 | Oliveras et al. |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 | 11/2017 | Germinario et al. |
| 2017/0333646 A1 | 11/2017 | Hemy et al. |
| 2018/0021528 A1* | 1/2018 | Hsieh ..................... B05B 15/18 128/200.16 |
| 2018/0021530 A1 | 1/2018 | Fink et al. |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0224426 A1 | 7/2019 | Farina et al. |
| 2019/0343793 A1 | 11/2019 | Gunther et al. |
| 2019/0358420 A1 | 11/2019 | Hunter et al. |
| 2020/0060346 A1 | 2/2020 | Danek |
| 2020/0147325 A1 | 5/2020 | Wilson et al. |
| 2020/0230329 A1 | 7/2020 | Danek |
| 2020/0246556 A1* | 8/2020 | Osoegawa ........ A61M 15/0026 |
| 2020/0276398 A1 | 9/2020 | Hebrank et al. |
| 2020/0289770 A1 | 9/2020 | Hebrank et al. |
| 2020/0315842 A1 | 10/2020 | Palanker et al. |
| 2020/0345588 A1 | 11/2020 | Merrell et al. |
| 2020/0353186 A1 | 11/2020 | Hebrank et al. |
| 2021/0106772 A1 | 4/2021 | Hebrank et al. |
| 2021/0236745 A1 | 8/2021 | Germinario et al. |
| 2021/0275760 A1 | 9/2021 | Hunter et al. |
| 2022/0001122 A1 | 1/2022 | Hunter et al. |
| 2022/0296823 A1 | 9/2022 | Hebrank et al. |

FOREIGN PATENT DOCUMENTS

| | | |
|---|---|---|
| CH | 715947 | 11/2020 |
| CN | 1788806 | 6/2006 |
| CN | 104511072 | 4/2015 |
| CN | 204995458 | 1/2016 |
| CN | 205019058 | 2/2016 |
| EP | 0923957 | 10/2001 |
| EP | 2724741 | 4/2014 |
| EP | 3127616 | 2/2017 |
| JP | H11-042219 | 2/1999 |
| JP | 2003-265994 | 9/2003 |
| JP | 2006-68508 | 3/2006 |
| KR | 10-2019-122453 | 10/2019 |
| WO | WO 93/12823 | 7/1993 |
| WO | WO 96/09846 | 4/1996 |
| WO | WO 96/14163 | 5/1996 |
| WO | WO 98/48873 | 11/1998 |
| WO | WO 00/10634 | 3/2000 |
| WO | WO 00/47335 | 8/2000 |
| WO | WO 00/50112 | 8/2000 |
| WO | WO 01/85244 | 11/2001 |

(56) References Cited

FOREIGN PATENT DOCUMENTS

| WO | WO 01/87378 | 11/2001 |
|----|----|----|
| WO | WO 02/068128 | 9/2002 |
| WO | WO 03/020349 | 3/2003 |
| WO | WO 03/059413 | 7/2003 |
| WO | WO 2004/078025 | 9/2004 |
| WO | WO 2006/013952 | 2/2006 |
| WO | WO 2006/083014 | 8/2006 |
| WO | WO 2006/102345 | 9/2006 |
| WO | WO 2006/108558 | 10/2006 |
| WO | WO 2007/107160 | 9/2007 |
| WO | WO 2008/056986 | 5/2008 |
| WO | WO 2008/058941 | 5/2008 |
| WO | WO 2008/116165 | 9/2008 |
| WO | WO 2009/012371 | 1/2009 |
| WO | WO 2009/111612 | 9/2009 |
| WO | WO 2010/065452 | 6/2010 |
| WO | WO 2011/042212 | 4/2011 |
| WO | WO 2011/083377 | 7/2011 |
| WO | WO 2011/091268 | 7/2011 |
| WO | WO 2011/163272 | 12/2011 |
| WO | WO 2012/026963 | 3/2012 |
| WO | WO 2013/098334 | 7/2013 |
| WO | WO 2013/158352 | 10/2013 |
| WO | WO 2013/158967 | 10/2013 |
| WO | WO 2013/173321 | 11/2013 |
| WO | WO 2014/147550 | 9/2014 |
| WO | WO 2015/004554 | 1/2015 |
| WO | WO 2015/106150 | 7/2015 |
| WO | WO 2015/136529 | 9/2015 |
| WO | WO 2015/176033 | 11/2015 |
| WO | WO 2015/191478 | 12/2015 |
| WO | WO 2015/191481 | 12/2015 |
| WO | WO 2016/001923 | 1/2016 |
| WO | WO 2016/001924 | 1/2016 |
| WO | WO 2016/003738 | 1/2016 |
| WO | WO 2017/015303 | 1/2017 |
| WO | WO 2017/056103 | 4/2017 |
| WO | WO 2018/213834 | 11/2018 |
| WO | WO 2019/071008 | 4/2019 |
| WO | WO 2019/079461 | 4/2019 |
| WO | WO 2019/136437 | 7/2019 |
| WO | WO 2019/219865 | 11/2019 |
| WO | WO 2019/219873 | 11/2019 |
| WO | WO 2020/072478 | 4/2020 |
| WO | WO 2020/141424 | 7/2020 |
| WO | WO 2020/154497 | 7/2020 |
| WO | WO 2020/227717 | 11/2020 |
| WO | WO-2020227717 A1 * | 11/2020 ......... A61M 11/005 |
| WO | WO 2020/264501 | 12/2020 |
| WO | WO-2020264501 A1 * | 12/2020 ......... A61M 11/002 |
| WO | WO 2021/090135 | 5/2021 |
| WO | WO 2021/203038 | 10/2021 |
| WO | WO 2022/051496 | 3/2022 |
| WO | WO 2022/226407 | 10/2022 |
| WO | WO 2023/278551 | 1/2023 |
| WO | WO 2023/064477 | 4/2023 |
| WO | WO 2023/091637 | 5/2023 |

OTHER PUBLICATIONS

Kharitonov, "Exhaled markers of inflammatory lung diseases: ready for routine monitoring?" *Swiss Med Wkly*, 2004; 134: 175-192.

Broeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnea in patients with COPD," *Respiratory Medicine*, 2011, 105, 316-312.

Steller, "Microcontroller Based Diagnostic Smart Inhaler," University of Cincinnati, Dec. 7, 2014, 63 pages.

Carvalho et al., "The function and performance of aqueous aerosol devices for inhalation therapy," Journal of Pharmacy and Pharmacology, vol. 68, No. 5, Apr. 8, 2016, pp. 556-578.

Pneuma Respiratory, Digitally breath-actuated inhaler device with precision droplet ejector technology and digital dose confidence. Available on Mar. 18, 2017 [retrieved on Jun. 30, 2017]. Retrieved from the Internet: URL: https://pneumarespiratory.com/. 3 pp.

Azzopardi, "Sauter Mean Diameter" Sep. 30, 2012, 4 pages, https://web.archive.org/web/20120930225842/http://www.termopedia.com/content/1108, retrieved May 26, 2014.

Ultrasonic Vibrating member catalog—Emerson. Catalog—Ultrasonic Vibrating member (2014). Available at: https://www.emerson.com/documents/automation/catalog-ultrasonic-vibratingmember-branson-en-us-160126.pdf. (Accessed: Aug. 9, 2023).

Lin, J. & Lin, S. "Study on a large-scale three-dimensional ultrasonic plastic welding vibration system based on a quasi-periodic phononic crystal structure," Crystals 2020, 10, 21, MDPI, 18 pages.

Industrial resonators Available at: http://www.krell-engineering.com/fea/industr/industrial_resonators.htm, accessed Aug. 9, 2023, 7 pages.

* cited by examiner

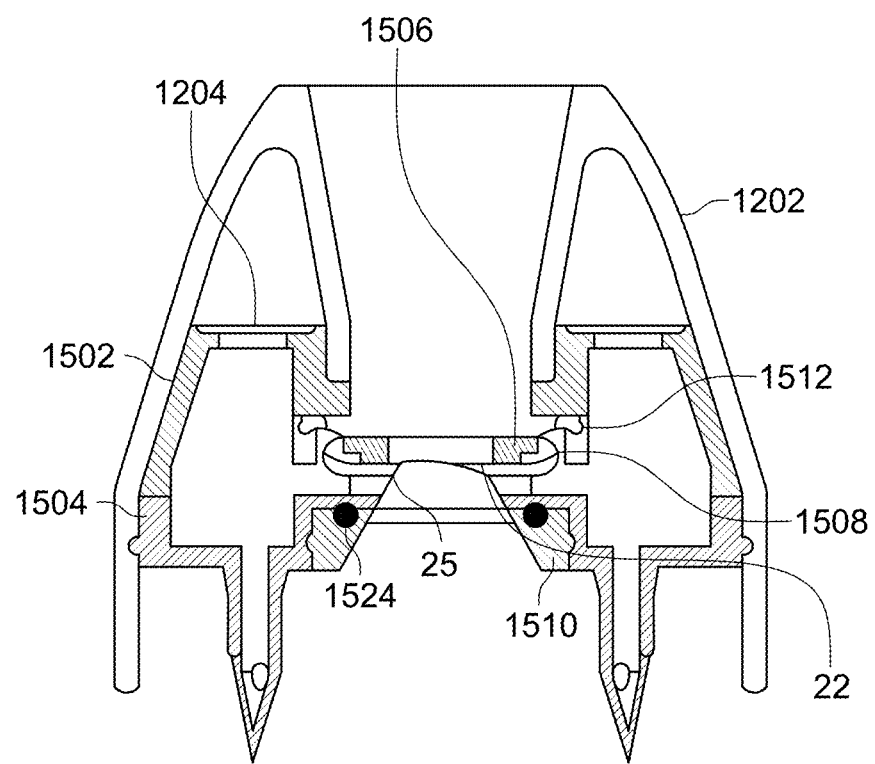
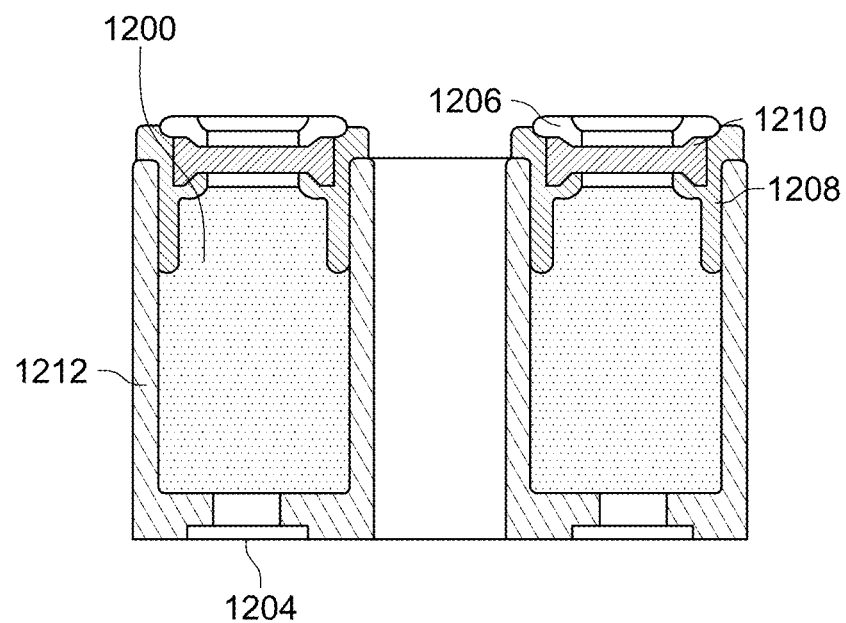
FIG. 24

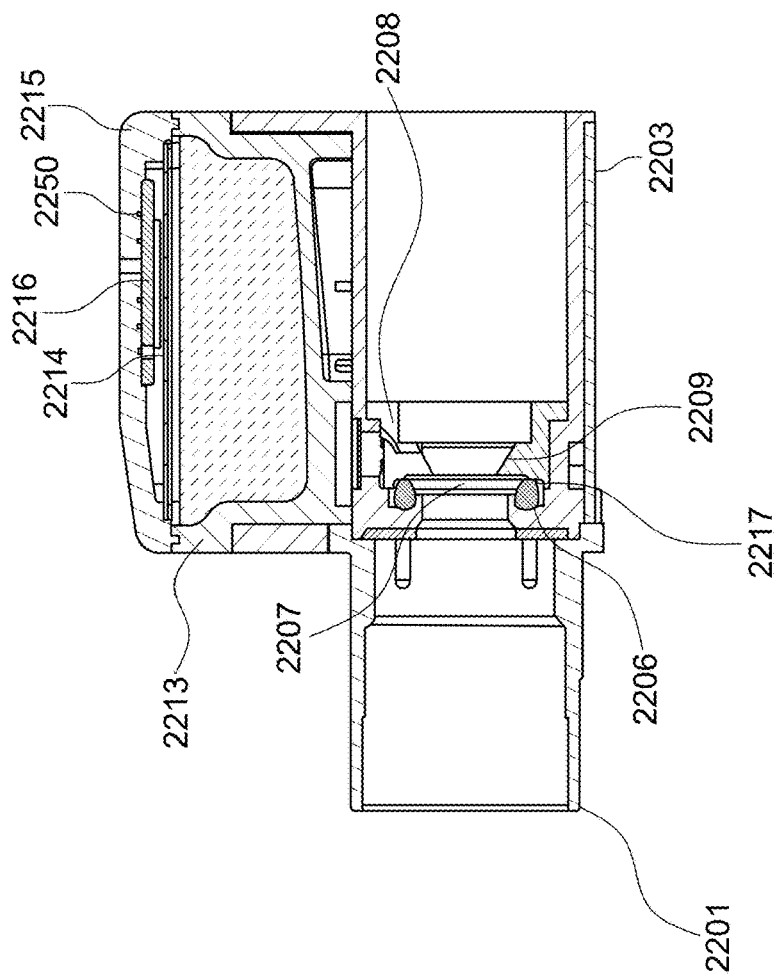
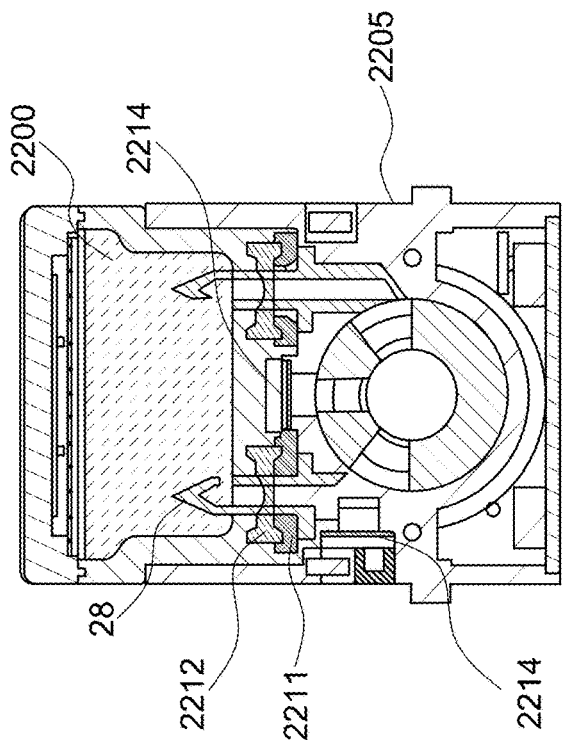
FIG. 30B
FIG. 30A (a) Structure diagram of the vibrating member tip (b) Dimensional drawing of vibrating member tip on the XZ surface (c) Dimensional drawing of vibrating member tip on the YZ surface

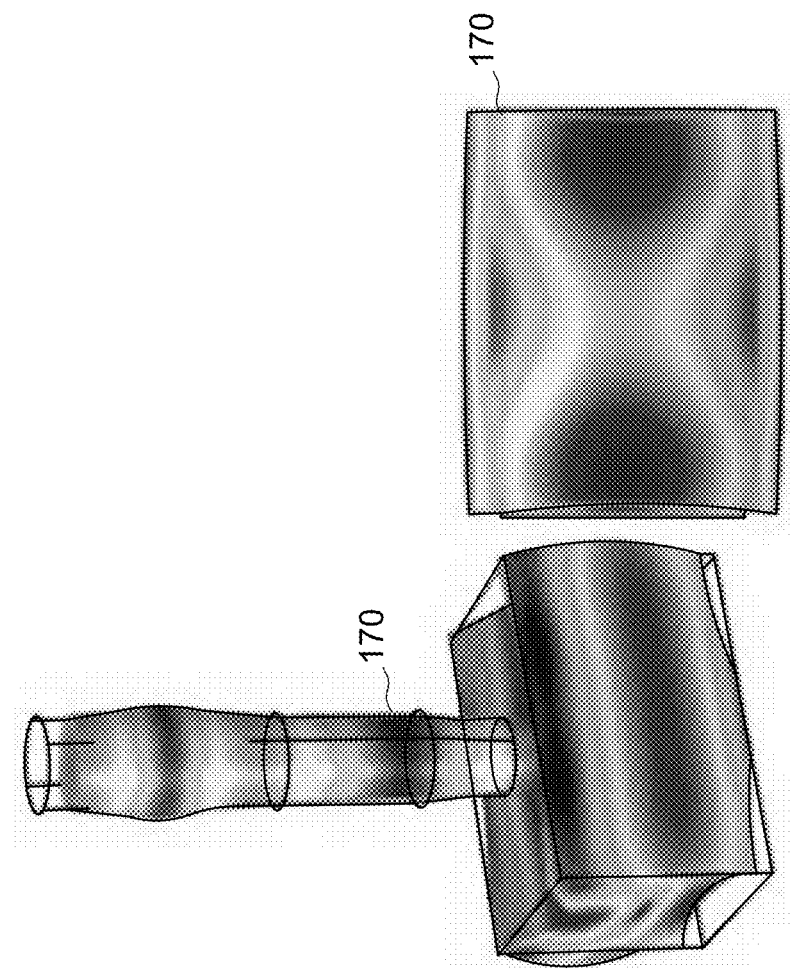
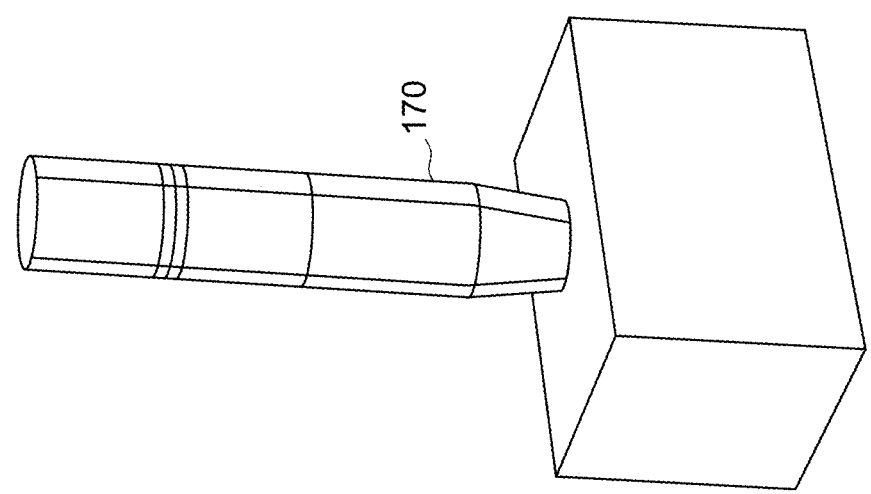
FIG. 48C   FIG. 48B   FIG. 48A

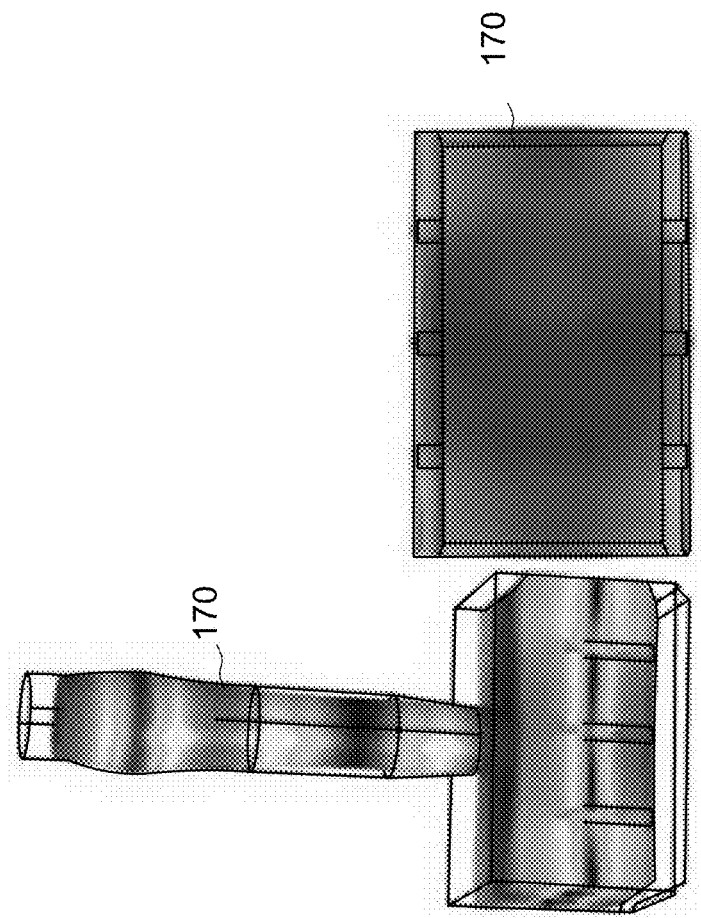
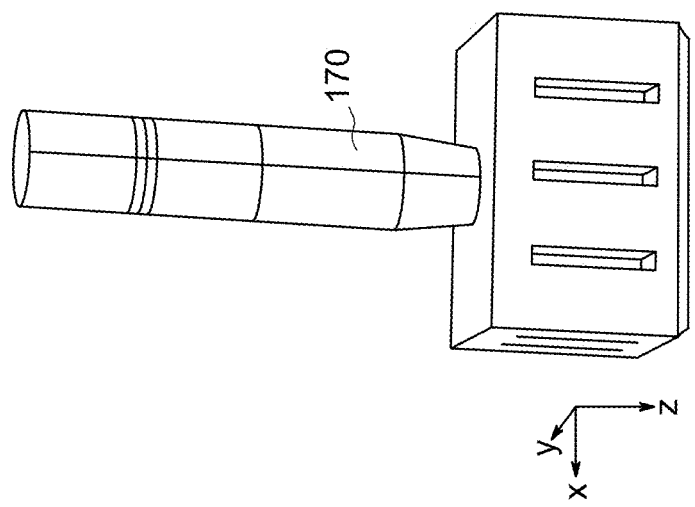
FIG. 49A  FIG. 49B  FIG. 49C

SECTION A_A

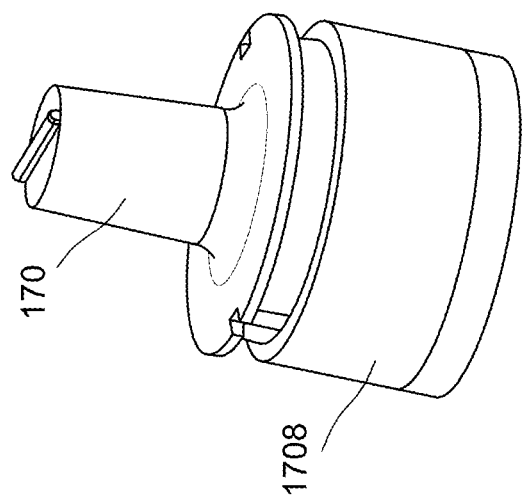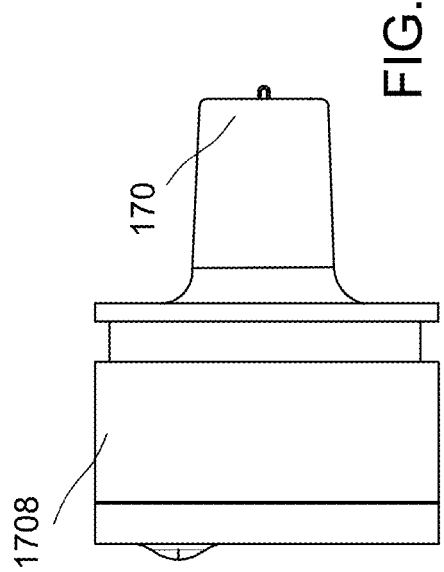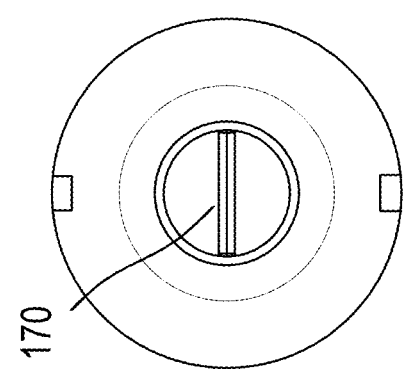

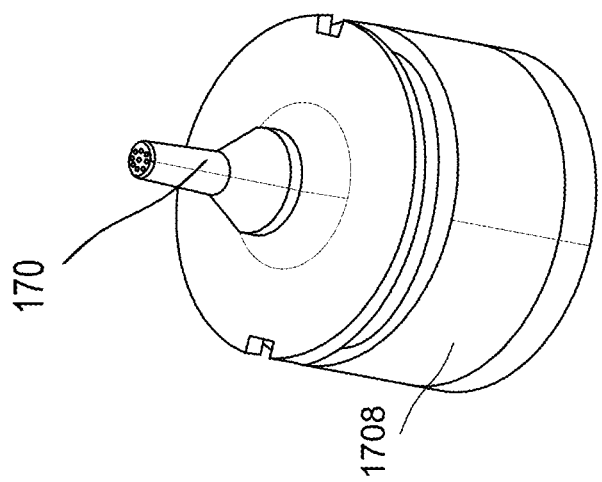
FIG. 72A
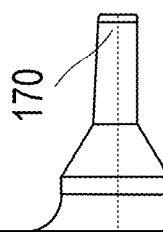
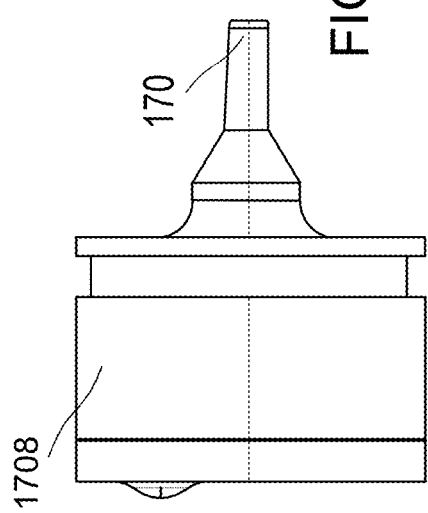
FIG. 72C
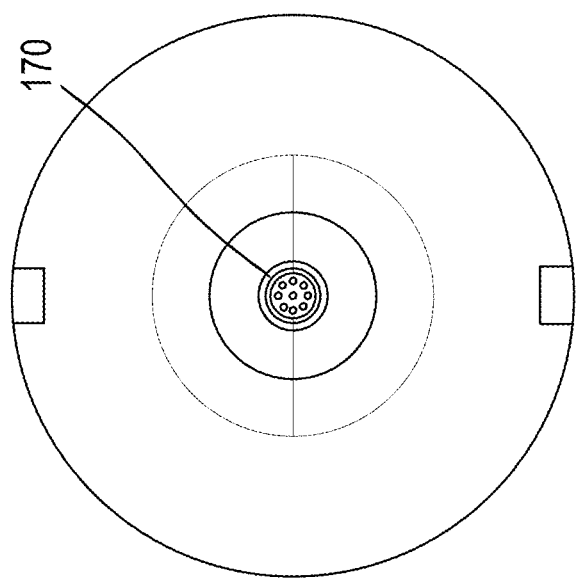
FIG. 72B

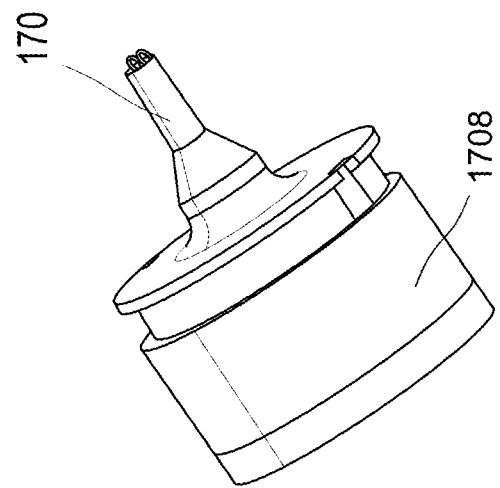
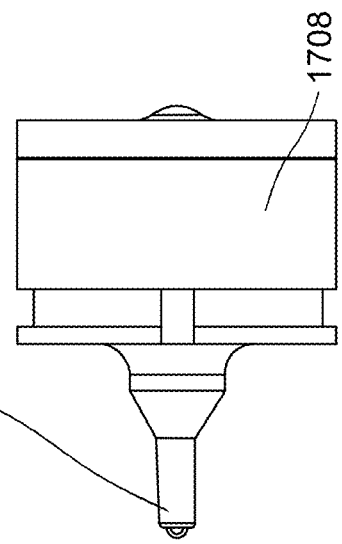
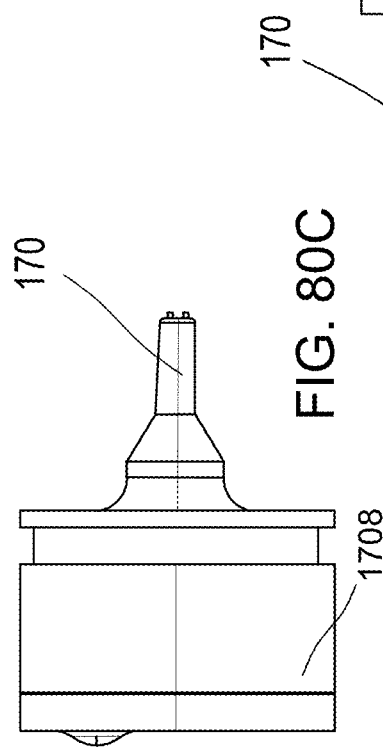
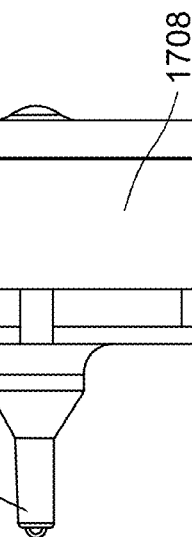
FIG. 80A
FIG. 80D
FIG. 80C
FIG. 80B

SECTION A-A
SCALE 4 : 1

SECTION B-B
SCALE 4 : 1

SECTION A-A
SCALE 4 : 1

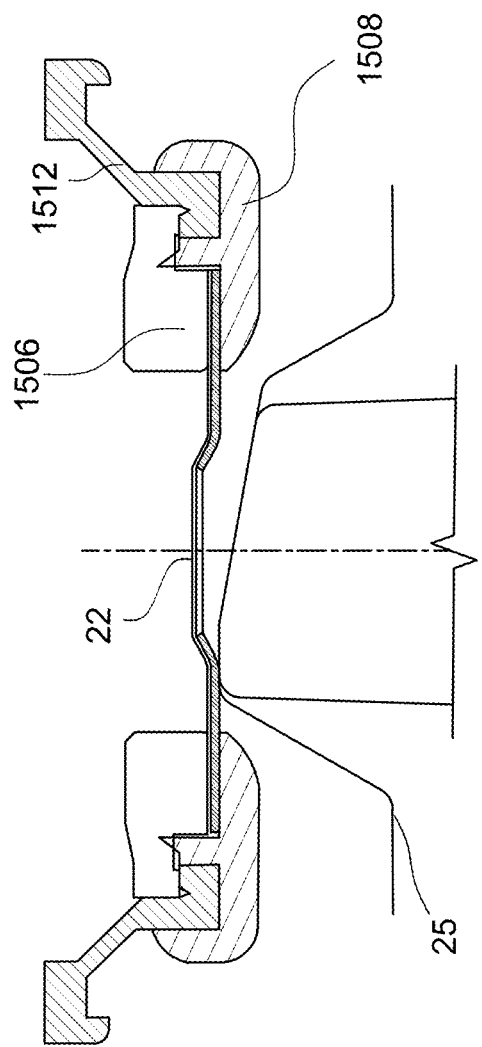
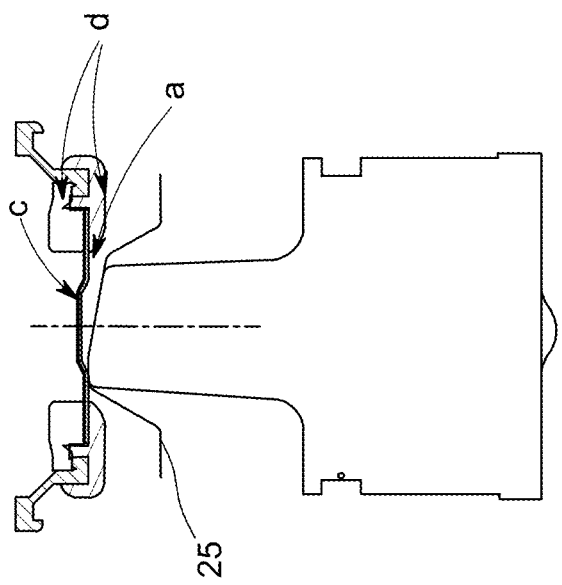
FIG. 97B
FIG. 97A
a:SUS316 L
b:SUS316 L
c:Polymer mesh
d:Plastic

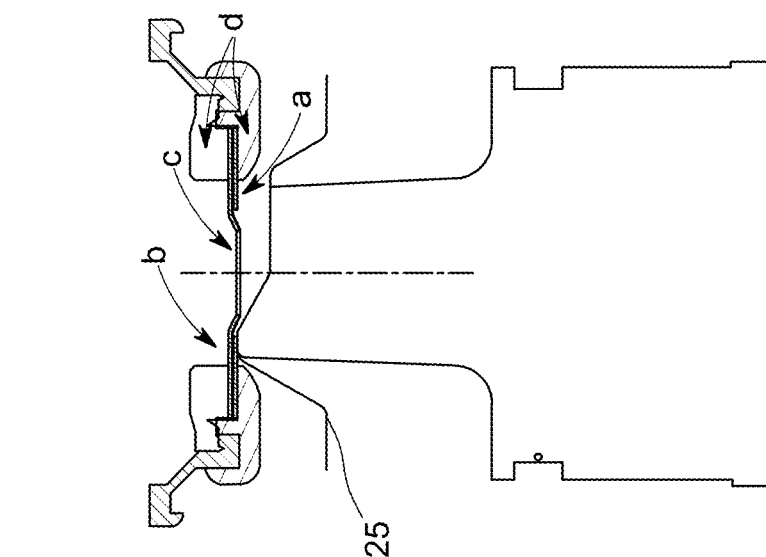
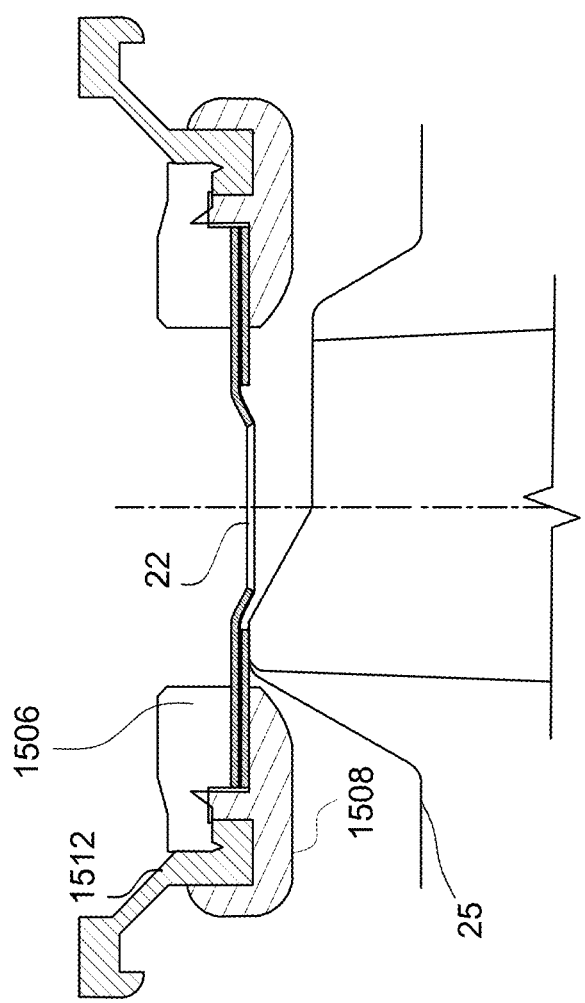
FIG. 100A
FIG. 100B c:Polymer mesh
d:Plastic

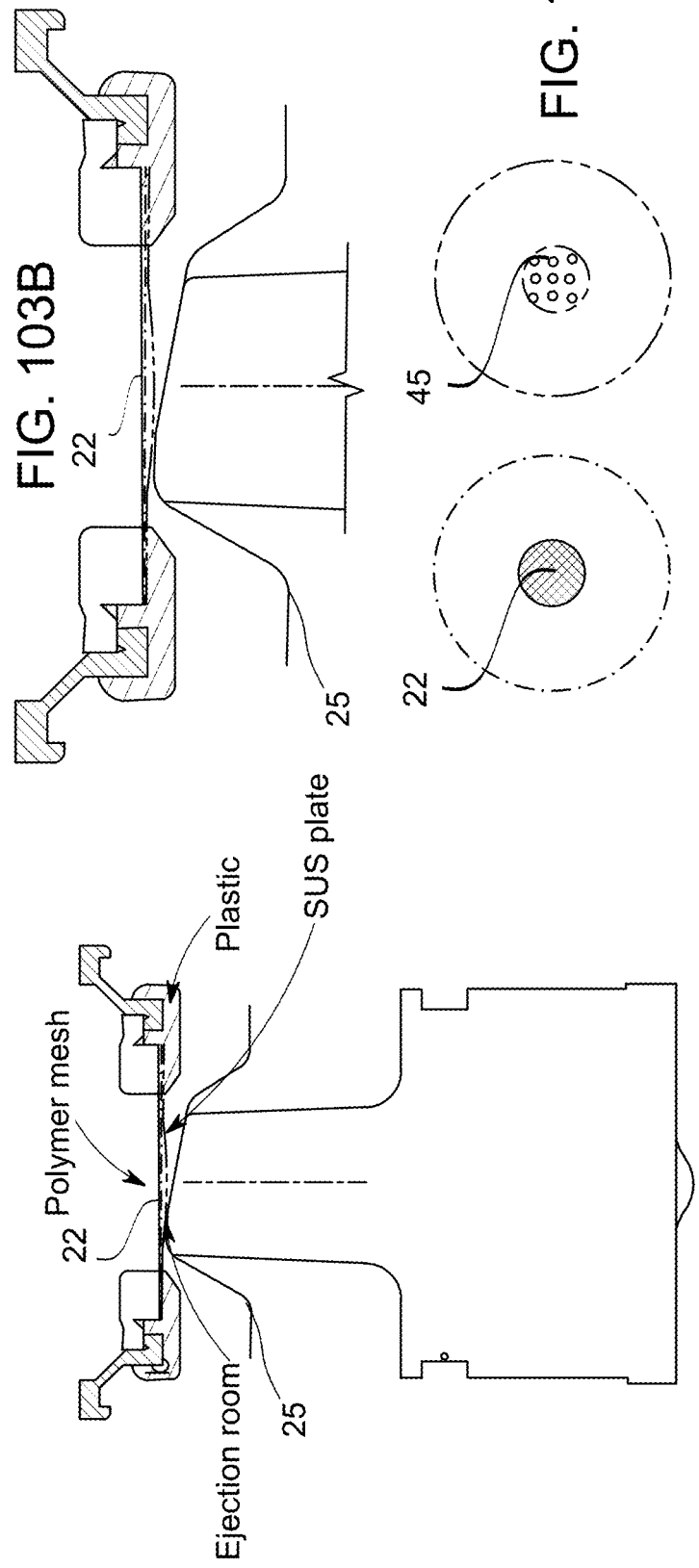

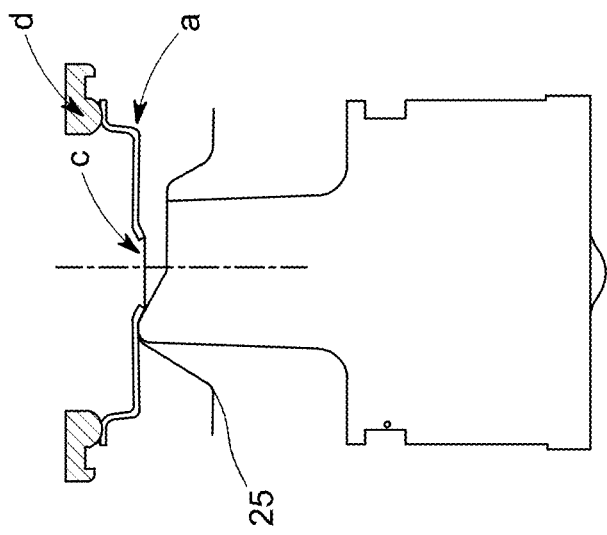
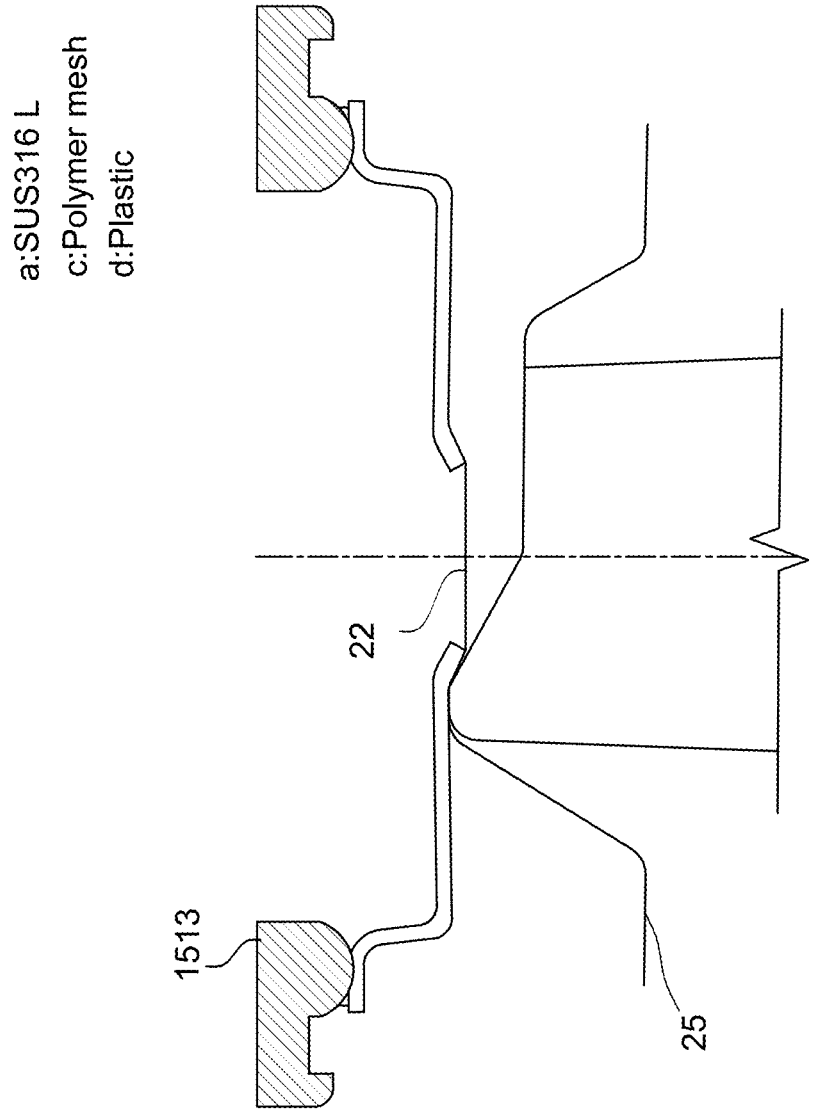

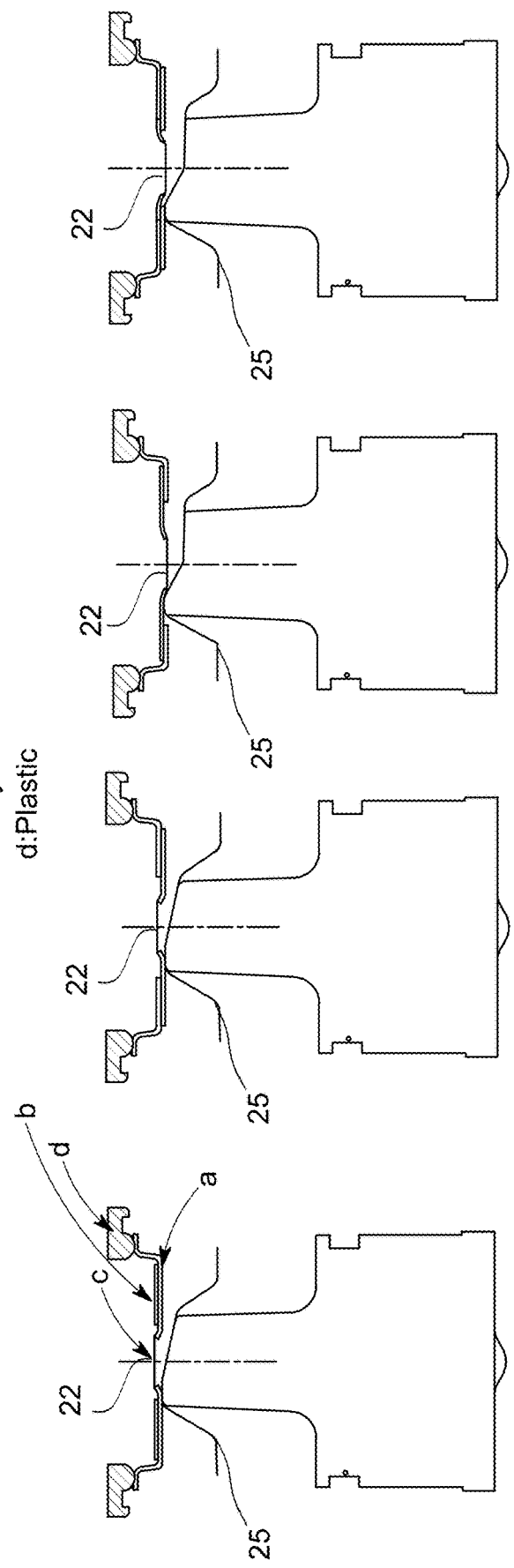

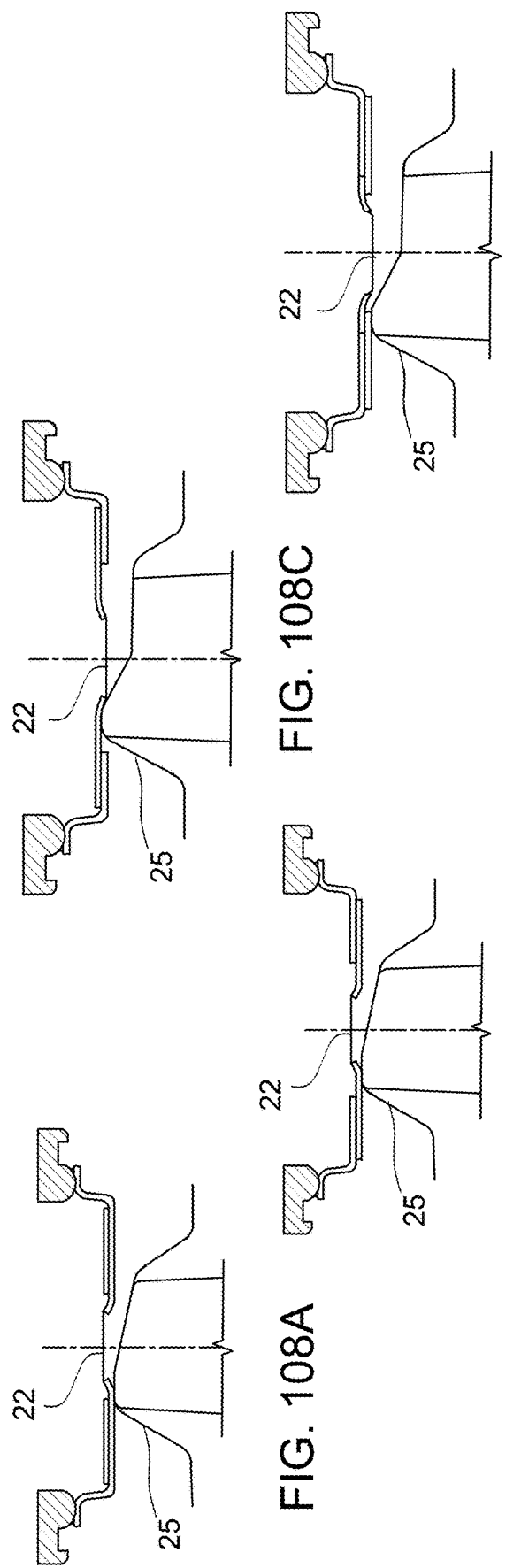

Section C-C

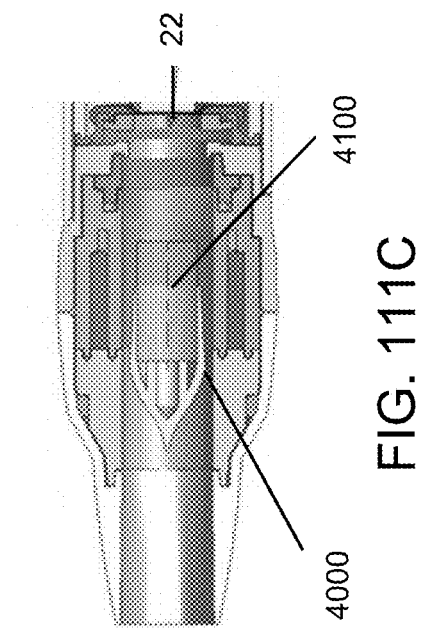
FIG. 111C
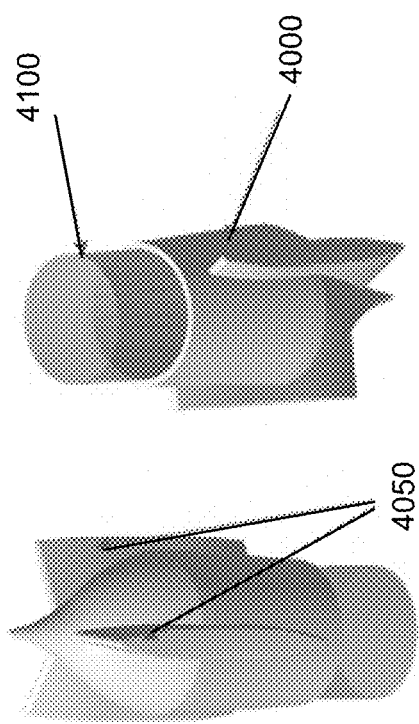
FIG. 111B
FIG. 111A

DROPLET DELIVERY DEVICE WITH PUSH EJECTION

CROSS-REFERENCE TO RELATED APPLICATIONS

The present application claims the benefit of priority of U.S. Provisional Patent Application No. 63/280,643 filed Nov. 18, 2021, U.S. Provisional Patent Application No. 63/256,546 filed Oct. 16, 2021, Provisional Patent Application No. 63/256,245 filed Oct. 15, 2021, and Provisional Patent Application No. 63/213,634 filed Jun. 22, 2021, all of which are incorporated herein by reference in their entirety.

FIELD OF THE PUSH MODE INVENTION

This disclosure relates to droplet delivery devices with ejector mechanisms and more specifically to droplet delivery devices for the delivery of fluids that are inhaled into mouth, throat nose, and/or lungs.

BACKGROUND OF THE PUSH MODE INVENTION

The use of droplet generating devices for the delivery of substances to the respiratory system is an area of large interest. A major challenge is providing a device that delivers an accurate, consistent, and verifiable amount of substance, with a droplet size that is suitable for successful delivery of substance to the targeted area of the respiratory system.

Currently most inhaler type systems, such as metered dose inhalers (MDI), pressurized metered dose inhalers (p-MDI), or pneumatic and ultrasonic-driven devices, generally produce droplets with high velocities and a wide range of droplet sizes including large droplets that have high momentum and kinetic energy. Droplet plumes with large size distributions and high momentum do not reach a targeted area in the respiratory system, but rather are deposited throughout the pulmonary passageways, mouth, and throat. Such non-targeted deposition may be undesirable for many reasons, including improper dosing and unwanted side effects.

Droplet plumes generated from current droplet delivery systems, as a result of their high ejection velocities and the rapid expansion of the substance carrying propellant, may also lead to localized cooling and subsequent condensation, deposition and crystallization of substance onto device surfaces. Blockage of device surfaces by deposited substance residue is also problematic.

Further, conventional droplet delivery devices for delivery of nicotine, including vape pens and the like, typically require fluids that are inhaled to be heated to temperatures that negatively affect the liquid being aerosolized. Specifically, such levels of heating can produce undesirable and toxic byproducts as has been documented in the news and literature.

Accordingly, there is a need for an improved droplet delivery device that delivers droplets of a suitable size range, avoids surface fluid deposition and blockage of apertures, avoids producing undesired chemical byproducts through heating, and in an amount that is consistent and reproducible.

SUMMARY OF THE PUSH MODE INVENTION

In one embodiment of the push mode invention, a "push mode" droplet delivery device does not include a heating requirement that could result in undesirable byproducts and comprises: a container assembly with an mouthpiece port; a reservoir disposed within or in fluid communication with the container assembly to supply a volume of fluid, an ejector bracket in fluid communication with the reservoir, the ejector bracket including a mesh with a membrane operably coupled to an electronic transducer with the membrane between the transducer and the mesh, wherein the mesh includes a plurality of openings formed through the mesh's thickness, and wherein the transducer is coupled to a power source and is operable to oscillate the membrane and generate an ejected stream of droplets through the mesh, and an ejection channel within the container assembly configured to direct the ejected stream of droplets from the mesh to the outlet. The vibrating membrane "pushing" liquid through the mesh is referred to herein as "push mode" ejection and devices in embodiments of the push mode invention may be referred to as push mode devices.

In another embodiment of the push mode invention, a droplet delivery device having a membrane that cooperates with a mesh further includes an ultrasonic transducer as an electronic transducer, and preferably an ultrasonic transducer that includes piezoelectric material.

In another embodiment of the push mode invention, a droplet delivery device having a membrane that cooperates with a mesh further includes the container assembly having a fluid reservoir.

In another embodiment of the push mode invention, a droplet delivery device having a membrane that cooperates with a mesh further includes an ejector bracket configured for releasably coupling to the container assembly and the ejector bracket further configured for releasable coupling to an enclosure system including an electronic transducer and a power source.

In another embodiment of the push mode invention, a droplet delivery device having a membrane that cooperates with a mesh further includes magnets configured to releasably couple the ejector bracket and enclosure system.

In another embodiment of the push mode invention, a droplet delivery device having a membrane that cooperates with a mesh further includes a snap mechanism and/or magnets configured to releasably couple the ejector bracket and the container assembly.

In another embodiment of the push mode invention, a droplet delivery device having a membrane that cooperates with a mesh further includes a fluid reservoir with a self-sealing mating mechanism configured to couple to a fluid release mating mechanism of the ejector bracket.

In another embodiment of the push mode invention, a droplet delivery device having a membrane that cooperates with a mesh further includes a fluid release mating mechanism that has a fluid conduit configured for insertion into the self-sealing mating mechanism. In a preferred embodiment, a fluid release mating mechanism includes a spike-shaped structure with a hollow interior configured to provide fluid communication between the reservoir and the membrane.

In another embodiment of the push mode invention, a droplet delivery device having a membrane that cooperates with a mesh is configured so that the membrane does not contact the mesh and pushes fluid to be ejected as droplets from the droplet delivery device through openings in the mesh.

In another embodiment of the push mode invention, a droplet delivery device having a membrane that cooperates with a mesh further includes the membrane having a slanted upper surface configured to contact fluid supplied from the reservoir.

In another embodiment of the push mode invention, a droplet delivery device having a membrane that cooperates with a mesh further includes a vibrating member having a slanted tip contacting an opposite underlying surface of a slanted upper surface of the membrane.

In further embodiments of the push mode invention, an electronic transducer includes piezoelectric material that is coupled to a vibrating member with a ring-shaped beveled tip, rod-shaped beveled tip, rod-shaped tip, or a ring-shaped non-beveled tip.

In another embodiment of the push mode invention, a droplet delivery device having a membrane that cooperates with a mesh further includes a mesh with a bottom surface in a parallel configuration with an upper surface of the membrane.

In another embodiment of the push mode invention, a droplet delivery device having membrane that cooperates with a mesh further includes the mesh including a bottom surface in a non-parallel, i.e., slanted at an angle, configuration with an upper surface of the membrane.

In another embodiment of the push mode invention, a droplet delivery device having a membrane that cooperates with a mesh further includes a central axis of the droplet delivery device passing through the ejection channel and the membrane, and wherein the transducer is coupled to a vibrating member that is coupled to the membrane at a position offset from the central axis.

In another embodiment of the push mode invention, a droplet delivery device having a membrane that cooperates with a mesh further includes a fluid in the reservoir including at least one of a non-therapeutic substance, nicotine, or cannabinoid.

In another embodiment of the push mode invention, a droplet delivery device having a membrane that cooperates with a mesh further includes a fluid in the reservoir including a therapeutic substance that treats or prevents a disease or injury condition.

In another embodiment of the push mode invention, a droplet delivery device having a membrane that cooperates with a mesh further includes a laminar flow element positioned in an ejection channel of a container assembly before a mouthpiece port of the delivery device. In preferable embodiments, the laminar flow element includes a plurality of cellular apertures. In some embodiments, a laminar flow element includes blade-shaped walls defining the plurality of cellular apertures. In further embodiments, one or more of the plurality of cellular apertures include a triangular prismatic shape, quadrangular prismatic shape, pentagonal prismatic shape, hexagonal prismatic shape, heptagonal prismatic shape, or octagonal prismatic shape.

In another embodiment of the push mode invention, a droplet delivery device having a membrane that cooperates with a mesh further includes a breath-actuated sensor, such as a pressure sensor, operatively coupled to the power source, wherein the breath-actuated senor is configured to activate the electronic transducer upon sensing a predetermined pressure change within the ejection channel or within a passageway of the droplet delivery device in fluid communication with the ejection channel.

In another embodiment of the push mode invention, a droplet delivery device having a membrane that cooperates with a mesh further includes the mesh made of a material of at least one of palladium nickel, polytetrafluoroethylene, and polyimide.

In another embodiment of the push mode invention, a droplet delivery device having a membrane that cooperates with a mesh further includes the mesh made of a material of at least one of poly ether ketone, polyetherimide, polyvinylidine fluoride, ultra-high molecular weight polyethylene, Ni, NiCo, Pd, Pt, NiPd, and metal alloys.

In other embodiments a mesh may be made of single crystalline or poly crystalline materials such as silicon, silicon carbide, aluminum nitride or germanium with hole structures formed using semiconductor processes such as photo lithography and isotropic and anisotropic etching. With photolithography and isotropic and/or anisotropic etches different hole shapes can be formed in a single crystalline wafer with very high precision. Using sputtering, films can be deposited on the surface with different contact angles. Thin layers formed or deposited on the surface will have, in certain embodiments, much better adherence than film deposited on metal mesh formed by galvanic deposition or polymer mesh formed by laser ablation. This better adherence is because the surfaces on the single crystalline wafers "slices" are atomically smooth and can be etched to produce exact surface roughness to facilitate mechanical bonding with glue or other materials. Silicon carbide would be a preferable material because of its high strength and toughness. An important advantage of using semiconductor processes to fabricate hole structures from a single crystalline wafer "slice" in a mesh of embodiment of the push mode invention is that the holes and surface contact angles will be exact without the variation we see in conventional ejector plates using mesh made from galvanic deposition or laser ablation.

In another embodiment of the push mode invention, a droplet delivery device having a membrane that cooperates with a mesh further includes the membrane made a of material of at least one of polyethylene naphthalate, polyethylenimine and poly ether ketone.

In another embodiment of the push mode invention, a droplet delivery device having a membrane that cooperates with a mesh further includes the membrane made a of material of at least one of metal membranes, metalized polymers, threaded polymers, threaded nylon, threaded polymers that are coated with polymers or metal, threaded nylon coated with polymers or metal. threaded metals, threaded SiC, threaded graphite composites, metalized graphite composites, graphite composites coated with polymers, polymer sheets filled with carbon fibers, poly ether ketone filled with carbon fibers, polymer sheets filled with SiC fibers, polymer sheets filled with ceramic or metal fibers, ULPA filter media, NITTO DENKO™ Temic Grade filter media, NITTO DENKO™ polymer sheets, threaded polymers bonded to a polymer sheet, nylon weave bonded to poly ether ketone or polyimide, graphite composites bonded to polymer sheets, polymer fiber weave with metalized coating, and nylon with sputtered on Al or vapor deposited Al.

In another embodiment of the push mode invention, a droplet delivery device having a membrane that cooperates with a mesh further includes a PZT-based ultrasonic transducer coupled to a vibrating member having a tip portion made of at least one of Grade 5 titanium alloy, Grade 23 titanium alloy, and about 99% or higher purity titanium. In certain embodiments, the vibrating member's tip includes a sputtered on outer layer of and about 99% or higher purity titanium providing a smooth tip surface configured to contact an underlying bottom surface of the membrane that is opposite an exterior top surface of the membrane positioned nearest the mesh so as to help reduce wear of the membrane and increase the longevity and operation consistency of the membrane (and also possibly vibrating member's tip portion).

In another embodiment of the push mode invention, a droplet delivery device having a membrane that cooperates with a mesh further includes an exterior surface of the membrane, opposite an underlying surface of the membrane contacting the vibrating member, having a hydrophobic coating.

In another embodiment of the push mode invention, a droplet delivery device having a membrane that cooperates with a mesh further includes an exterior surface of the membrane, opposite an underlying surface of the membrane contacting the vibrating member, having a hydrophilic coating.

In another embodiment of the push mode invention, a droplet delivery device having a membrane that cooperates with a mesh further includes a hydrophilic coating on one or more surfaces of the mesh.

In another embodiment of the push mode invention, a droplet delivery device having a membrane that cooperates with a mesh further includes a mesh including a hydrophobic coating on one or more surfaces of the mesh.

In another embodiment of the push mode invention, a droplet delivery device having a membrane that cooperates with a mesh further includes a hydrophobic coating on a first surface of the mesh and a hydrophilic coating on a second surface of the mesh.

In another embodiment of the push mode invention, a droplet delivery device having a membrane that cooperates with a mesh further includes the membrane having an operable lifespan of over 55,000 aerosol-creating activations by the transducer.

In another embodiment of the push mode invention, a droplet delivery device having a membrane that cooperates with a mesh further includes at least one superhydrophobic vent in fluid communication with the reservoir that is covered with a removable aluminized polymer tab during storage.

In another embodiment of the push mode invention, a droplet delivery device having a membrane that cooperates with a mesh further includes a removable aluminized polymer tab coupled to an exterior surface of the membrane adjacent the mesh during storage.

In another embodiment of the push mode invention, a droplet delivery device having a membrane that cooperates with a mesh includes a pre-assembly step of removing a sealed packaging including aluminum and/or aluminum coating that contains the reservoir with a fluid, preferably wherein the reservoir is included in the container assembly that is also packaged for storage in the sealed packaging. In some embodiments, sealed packaging may include dry nitrogen, argon or other gas that does not contain oxygen.

In various embodiments of the push mode invention, a droplet delivery device having a membrane that cooperates with a mesh may be used for mouth inhalation or nasal inhalation. The mouthpiece port may be sized, shaped and include materials that are better suited for that particular mouth or nasal inhalation use and purpose.

BRIEF DESCRIPTION OF THE DRAWINGS

The push mode invention will be more clearly understood from the following description given by way of example, in which:

FIG. 24 illustrates a cross-sectional and separated view of a two-part cartridge design in a droplet delivery device in accordance with one embodiment of the disclosure.

FIGS. 30A and 30B illustrate respective front and side cross-sectional views of a fluid cartridge of a droplet delivery device adapted for pharmaceutical use (but may be other uses in other embodiments) and utilizing membrane-driven aerosolization (i.e. "push mode functionality") in accordance with one embodiment of the disclosure.

FIGS. 48A-48C illustrate a perspective view (FIG. 48A), a perspective vibration amplitude map view (FIG. 48B) and a top vibration amplitude plan view (FIG. 48C) of an eigenmode vibrating member tip without slots or tuning and the resulting vibration amplitude maps in a droplet delivery device utilizing membrane-driven aerosolization (i.e. "push mode functionality") in accordance with one embodiment of the disclosure.

FIGS. 49A-49C illustrate a perspective view (FIG. 49A), a perspective vibration amplitude map view (FIG. 49B) and a top vibration amplitude plan view (FIG. 49C) of an eigenmode vibrating member tip with slots and the resulting vibration amplitude maps in a droplet delivery device utilizing membrane-driven aerosolization (i.e. "push mode functionality") in accordance with one embodiment of the disclosure.

FIGS. 71A-71C illustrate a perspective view (FIG. 71A), top plan view (FIG. 71B) and front plan view (FIG. 71C) of an alternative vibrating member that couples to a transducer of droplet delivery devices in accordance with an embodiment of the disclosure.

FIGS. 72A-72C illustrate a perspective view (FIG. 72A), top plan view (FIG. 72B) and front plan view (FIG. 72C) of an alternative vibrating member that couples to a transducer of droplet delivery devices in accordance with an embodiment of the disclosure.

FIGS. 80A-80D illustrate a perspective view (FIG. 80A), top plan view (FIG. 80B), front plan view (FIG. 80C) and side plan view (FIG. 80D) of an alternative vibrating member that couples to a transducer of droplet delivery devices in accordance with an embodiment of the disclosure.

FIGS. 97A and 97B illustrate a cross-sectional view (FIG. 97A) and a zoomed view (FIG. 97B) of a polymer mesh supported in a raised position by a stainless-steel annulus with respect to a membrane and transducer coupled to a vibrating member having a tip portion in a droplet delivery device in accordance with an embodiment of the disclosure.

FIGS. 100A and 100B illustrate a cross-sectional view (FIG. 100A) and a zoomed view (FIG. 100B) of a polymer mesh supported in a lowered position by a first stainless-steel annulus and having a second stainless steel annulus as a reinforcement coupled, such as by bonding with glue or adhesive, below the first annulus with respect to a membrane and transducer coupled to a vibrating member having a tip portion in a droplet delivery device in accordance with an embodiment of the disclosure.

FIGS. 103A and 103B illustrate a cross-sectional view (FIG. 103A) and a zoomed view (FIG. 103B) of a polymer mesh and stainless-steel capillary plate having openings in the plate and the plate underlying the polymer mesh between a membrane covering a vibrating member tip portion and the mesh in a droplet delivery device in accordance with an embodiment of the disclosure.

FIG. 103C is a schematic top plan view of a polymer mesh illustrated in FIGS. 103A and 103B.

FIG. 103D is a schematic top plan view of a stainless-steel capillary plate illustrated in FIGS. 103A and 103B.

FIGS. 106A and 106B illustrates a cross-sectional view (FIG. 106A) and zoomed view (FIG. 106B) of a polymer mesh with a plastic or silicone ring-shaped type bracket center portion of the annulus that couples to a polymer mesh with respect to a membrane and transducer coupled to a vibrating member having a tip portion in a droplet delivery device in accordance with an embodiment of the disclosure.

FIGS. 107A-107B illustrate cross-sectional views of a polymer mesh with a plastic or silicone ring-shaped type bracket coupled to double-reinforced stainless-steel annuluses (similar to FIGS. 99 and 100) wherein the polymer mesh is raised with further extending top reinforcement (FIG. 107A), the polymer mesh is raised with extending top reinforcement (FIG. 107B), the polymer mesh is lowered with extending underlying reinforcement (FIG. 107C), the polymer mesh is lowered with further extending underlying reinforcement (FIG. 107D) with respect to membrane and transducer coupled to a vibrating member having a tip portion in droplet delivery devices in accordance with embodiments of the disclosure.

FIGS. 108A-108D illustrates zoomed views of FIG. 107A (FIG. 108A), FIG. 107B (FIG. 108B), FIG. 107C (FIG. 108C) and FIG. 107D (FIG. 108D).

FIGS. 111A-111C illustrate a perspective view of a first end of absorber and baffle with fins (FIG. 111A), a perspective view of a second opposite end of a baffle with fins (FIG. 111B) and a cross-sectional, partial schematic view a droplet delivery device airway and ejector plate with mesh including a baffle with fins in accordance with an embodiment of the disclosure.

DETAILED DESCRIPTION

Push Mode Overview

Figure 1A:
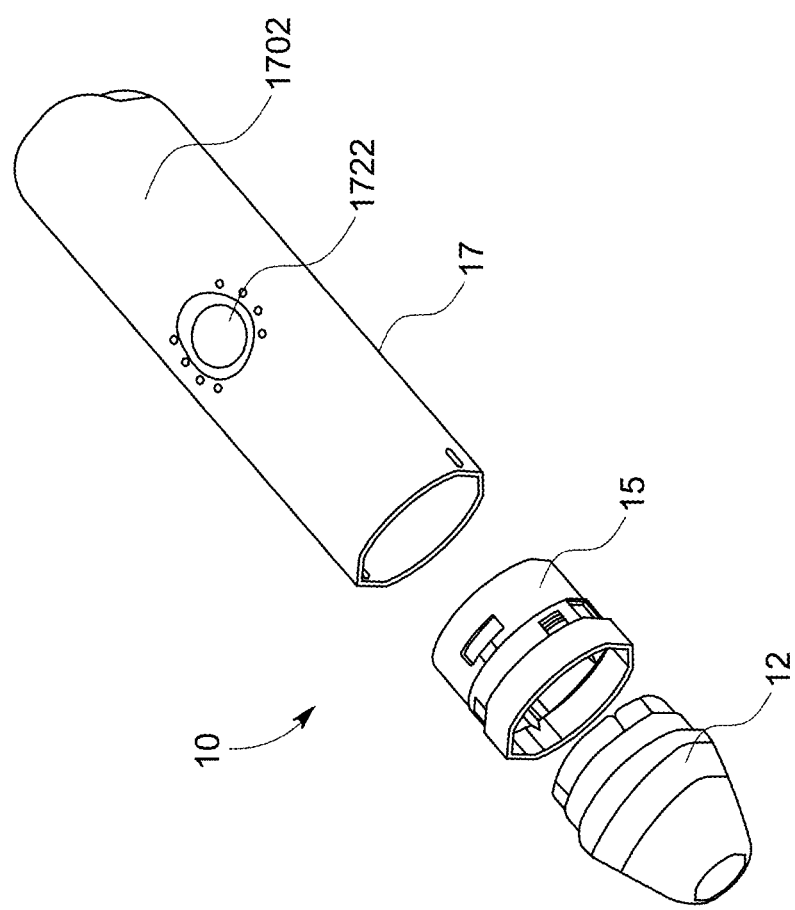
FIG. 1A is an exploded view of major components of a droplet delivery device in accordance with an embodiment of the disclosure.

Push mode has been developed as a reduced-risk product to deliver (i) nicotine, cannabinoids, and other non-therapeutic substances (devices described herein as "BlueSky" are preferable for use with such substances), as well as (ii) therapeutic and prescriptive drug products (devices described herein as "Norway" are preferable for use with such products). The push mode device is designed to deliver the user a safe and controlled dose. The push mode droplet delivery device 10 is capable of delivering aqueous and nonaqueous solutions and suspensions at room temperature. Large molecule formulations, whether water soluble or not, can also be delivered with this technology. Harmful chemical by-products commonly found with heated nicotine, and other substances, are eliminated in the push mode device making it a safer option for aerosol delivery.

Push mode utilizes a vibrating member 1708 and transducer 26 that work in conjunction with a membrane 25 and mesh 2 to aerosolize fluid 901, which is held in a reservoir 1200 and supplied to the mesh 22 using various methods (e.g., wick material, hydrophilic coatings, capillary action, etc.). Preferably the vibrating member is coupled to the transducer, such as by bonding (e.g. adhesives and the like), welding, gluing, physical connections (e.g. brackets and other mechanical connectors), and the like. The transducer and vibrating member interact with the membrane to push fluid through the mesh. As illustrated and described in various embodiments, the membrane may in some cases contact the mesh while also "pushing" fluid through holes in the mesh, and may in other cases be separated without contacting the mesh to push liquid through holes in the mesh. The transducer may comprise one or more of a variety of materials (e.g., PZT, etc.). In certain embodiments the transducer is made of lead-free piezoelectric materials to avoid creation of unwanted or toxic materials in a droplet delivery device intended for human inhalation. The vibrating member may be made of one or more of a variety of different materials (e.g., titanium, etc.). The mesh may be one or more of a variety of materials (e.g., palladium nickel, polyimide, etc.). After the fluid is pushed through the mesh, a droplet spray is formed and ejected through a mouthpiece port, carried by entrained air.

The device is tunable and precise. The device can be optimized for individual user preferences or needs. The aerosol mass ejection and mass median aerodynamic diameter (MMAD) can be tuned to desired parameters via the mesh hole size, mesh treatment, membrane design, vibrating member design, airflow, manipulation of power to the transducer, etc. The design produces an aerosol comprised of droplets with a high respirable fraction, such that the lungs can absorb the aerosol most efficiently.

The vibrating member and transducer are both separate from the cartridge, isolated by the membrane. Not only does this create a safer product, but it eases manufacturability. The vibrating member and transducer are both typically expensive components. Keeping these components in the enclosure system rather than the cartridge reduces the cost of goods sold (COGS).

Element Number Tables

Substance, feature, and part numbers are provided for convenient reference with respect to the descriptions and figures provided herein in Table 1:

TABLE 1

| Element Numbers | | | |
|---|---|---|---|
| Substance Number | | Substance Name | |
| 100 | | Airflow | |
| 800 | | Air | |
| 900 | | Fluid flow | |
| 901 | | Fluid | |
| Feature Number | | Feature Name | |
| 10 | | Droplet delivery device | |
| 12 | | Container assembly | |
| 15 | | Ejector bracket | |
| 17 | | Enclosure system | |
| 20 | | Airflow outlet | |
| 24 | | Airflow inlet | |
| 26 | | Heat exchange area | |
| 28 | | Spike | |
| 30 | | Air exchange outlet | |
| 40 | | Mouthpiece Port | |
| 41 | | Nasal Inhalation Port | |
| 42 | | Ejection Port | |
| 43 | | Nasal Inhalation Cap | |
| 45 | | Mesh plate with holes | |
| 47 | | Mesh and mesh plate spacer | |
| 170 | | Vibrating member tip | |
| 220 | | Central Axis | |
| 230 | | Vibrating member central axis | |
| 1200 | | Fluid reservoir | |
| 2200 | | Fluid reservoir | |
| 2250 | | Spiral | |
| Part Number | Part Name | Material | Embodiment Push Mode I and/or II |
| 22 | Mesh | Palladium nickel | I and II |
| 25 | Membrane | Various Material | I and II |
| 26 | Transducer | PZT, lead-free material | I and II |
| 1200's | BlueSky Container | | |
| 1202 | Mouthpiece | COC | I and II |
| 1204 | Vent material | Sintered PTFE - PMA20 | I and II |

TABLE 1-continued

Element Numbers

| | | | |
|---|---|---|---|
| 1206 | Upper container | COC | I and II |
| 1208 | Middle container | COC | I and II |
| 1210 | Septum | Butyl rubber | I and II |
| 1212 | Lower container | COC | I |
| 1213 | Extended lower container | COC | II |
| 1214 | Container ring | COC | I and II |
| 1500's | BlueSky Ejector Bracket | | |
| 1502 | Upper ejector bracket | COC | I and II |
| 1504 | Lower ejector bracket | COC | I and II |
| 1506 | Upper mesh carrier | COC | I |
| 1508 | Lower mesh carrier | COC | I |
| 1510 | Membrane holder | COC | I and II |
| 1512 | Suspension gasket | Silicone | I |
| 1513 | Carrier gasket | Silicone | II |
| 1518 | Stainless steel mesh carrier | SUS316L | II |
| 1519 | Wick | | I and II |
| 1520 | Magnet | N54 Ni coating | I and II |
| 1522 | Carrier O-Ring | Silicone | II |
| 1524 | Small O-Ring | Silicone | Simplified cartridge |
| 1526 | Large O-Ring | Silicone | Simplified cartridge |
| 1528 | Parallel plate capacitor | | |
| 1600 | Laminar flow element | COC | I and II |
| 1700's | BlueSky Enclosure System | | |
| 1702 | Enclosure | Aluminum 6063 alloy | I and II |
| 1704 | Vibrating member front cover | PC/ABS | I and II |
| 1706 | Vibrating member rear cover | PC/ABS | I and II |
| 1708 | Vibrating member | Titanium alloy | I and II |
| 1710 | Transducer contact pin | Brass 3604 alloy, gold-plated | I and II |
| 1712 | Fingerprint/button/sealing bracket | PC/ABS | I and II |
| 1714 | Fingerprint/button cover | PC/ABS | I and II |
| 1716 | Enclosure rear cover | PC/ABS | I and II |
| 1718 | Enclosure sealing ring | Silicone | I and II |
| 1720 | Sensor director | Silicone | I and II |
| 1722 | Fingerprint/button | PC/ABS | I and II |
| 1725 | PCB | Many materials | All |
| 1726 | Spring electrode | SUS304 | All |
| 1728 | USB-C port | PC/ABS | All |
| 1730 | Battery/Power supply | Li-Ion | Heater-Beluga |
| 1732 | Airflow Sleeve | PC/ABS | Air resistance |
| 1734 | Speaker | | Speaker-Beluga |
| 1760 | Nodal-mounted sensing device | | |
| 1762 | Sensor control unit | | |
| 1900's | Heating Components | | |
| 1902 | Heating element | Nichrome 80 | Heater |
| 1904 | Heat insulation | | Heater |
| 1906 | Airflow accelerator | | |
| 1908 | Electrode | | All |
| 1910 | Temperature Sensor | | Heater |
| 2200's | Norway Ejector Bracket and Container | | |
| 2201 | Mouthpiece | COC | Norway D |
| 2202 | Faceplate | SUS316L | Norway D |
| 2203 | Ejector Bracket Bottom Cover | COC | Norway D |
| 2204 | Ejector Bracket ID Chip | Many Materials | Norway D |
| 2205 | Ejector Bracket | COC | Norway D |
| 2206 | O-Ring | Silicon | All |
| 2207 | Mesh | | Norway D |
| 2208 | Membrane Carrier | COC | Norway D |
| 2209 | Membrane | | Norway D |
| 2210 | Cartridge Spacer | COC | Norway D |
| 2211 | Septum Cap | COC | Norway D |
| 2212 | Septum | Butyl Rubber | Norway D |
| 2213 | Lower Container | COC | Norway D |
| 2214 | Vent Material | | Norway D |
| 2215 | Upper Container | COC | Norway D |
| 2216 | Vent Spacer | | Norway D |
| 2217 | Mesh Carrier | | |
| 2218 | Suspension gasket | | |
| 2219 | Carrier gasket | | |
| 2220 | Upper mesh carrier | COC | |
| 2221 | Lower mesh carrier | COC | |
| 2222 | Stainless steel mesh carrier | SUS316L | |
| 2400's | Norway Face Seal | | |
| 2401 | Screw | | Norway D |
| 2402 | Cartridge Sealer Top Piece | | Norway D |
| 2403 | O-Ring | Silicon | Norway D |
| 2404 | Cartridge Sealer Middle Piece | | Norway D |
| 2405 | Screw | | Norway D |
| 2406 | Cartridge Sealer Bottom Piece | | Norway D |
| 2407 | Cap Spring | Steel Alloy | Norway D |
| 2408 | Screw | | Norway D |
| 2409 | Device Cap | COC | Norway D |
| 2410 | Screw | | Norway D |
| 2411 | Pin Screw | COC | Norway D |
| 2412 | Magnet | | All |
| 2600's | Norway Vibrating Member Components | | |
| 2601 | Vibrating Member Enclosure | Aluminum Alloy | Norway D |
| 2602 | Vibrating Member Front Cover | COC | Norway D |
| 2603 | Vibrating Member and Transducer Assembly | Titanium Alloy and PZT4 | Norway D |
| 2604 | Vibrating Member Rear Cover | COC | Norway D |
| 2605 | Vibrating Member Cover Front Holder | Silicon | Norway D |
| 2606 | Vibrating member assembly Spring | Steel Alloy | Norway D |
| 2607 | Vibrating Member Device Bracket | COC | Norway D |
| 2608 | Vibrating Member Cover Rear Holder | | |
| 2609 | Screw | | |
| 2800's | Norway Enclosure System | | |
| 2801 | Device Cap Release Axel | | Norway D |
| 2802 | Cartridge Release Button Cover | | Norway D |
| 2803 | Cartridge Release Button Actuator | | Norway D |
| 2804 | Spacer | | Norway D |
| 2805 | Cartridge Release Spring | | Norway D |
| 2806 | 7-Seg Display | | Norway D |
| 2807 | Device Battery Cover Release | | Norway D |
| 2808 | Device Battery Cover Release Spring | | Norway D |
| 2809 | Device Battery Cover Axel | | Norway D |
| 2810 | Device Enclosure Gasket | | Norway D |
| 2811 | Device Bottom Enclosure | | Norway D |
| 2812 | AAA Batteries | | Norway D |
| 2813 | Device Battery Cover Gasket | | Norway D |
| 2814 | Device Battery Cover | | Norway D |
| 2815 | LED Display Cover | | Norway D |
| 2816 | Device Front Cover Buttons | | Norway D |
| 2817 | 7-Seg Display Cover | | Norway D |
| 2818 | Device Top Enclosure | | Norway D |
| 2819 | Device Cap Release | | Norway D |
| 3300 | Aluminized polymer tab | | |
| 4000 | Baffle | | |
| 4050 | Baffle fin | | |
| 4100 | Absorbent Plug | | |

"BlueSky" Embodiments

Figure 1B:
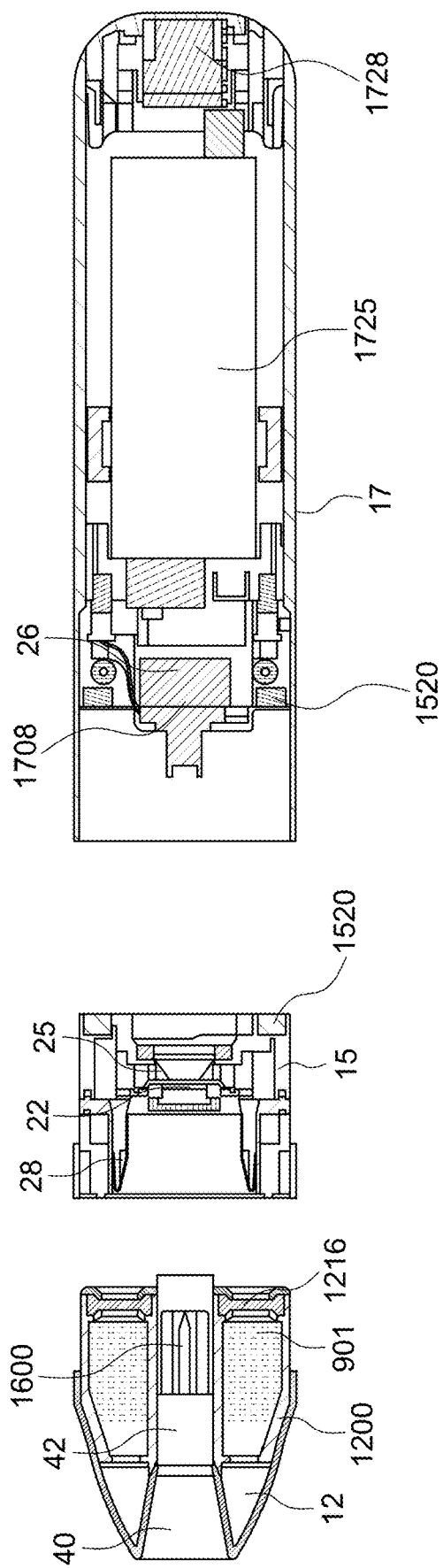
FIG. 1B is a cross-sectional view of major components of a droplet delivery device in accordance with an embodiment of the disclosure.
Figure 3:
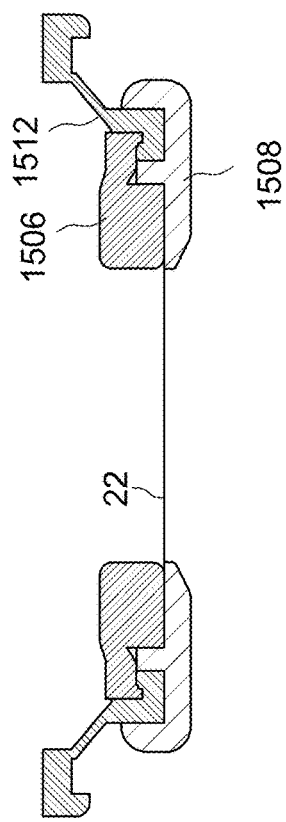
FIG. 3 is a schematic view of a mesh supported by inner and outer tablet rings and an elastic sealing ring of a droplet delivery device in an accordance with an embodiment of the disclosure referred to as push mode I.
Figure 2:
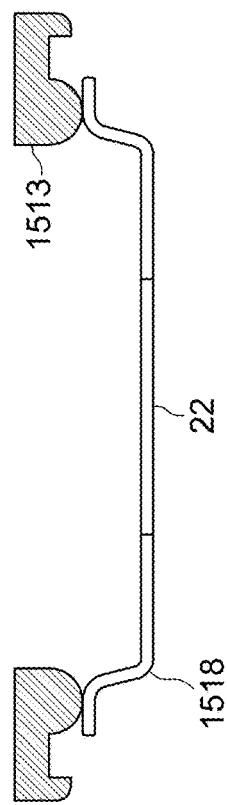
FIG. 2 is a schematic view of a mesh bonded to a stainless-steel ring that supports an elastic sealing ring of a droplet delivery device in an accordance with an embodiment of the disclosure referred to as push mode II.

Referring to FIGS. 1A and 1B, a BlueSky push mode device 10 includes main components of container assembly 12, ejector bracket 15 and enclosure system 17. Currently, two embodiments of BlueSky push mode, I and II, have been prototyped and tested. Referring to FIG. 2, inclusion of a mesh supported by a stainless-steel ring and elastic sealing ring in a droplet delivery device 10 is referred to as "push mode II" herein. Referring to FIG. 3 inclusion of a mesh supported by upper and lower mesh carrier and an elastic sealing ring in a droplet delivery device 10 is referred to as "push mode I" herein.

The push mode I and II embodiments have a transducer consisting of a lead zirconate titanate (PZT) disc bonded to the bottom of a vibrating member made of titanium alloy. The vibrating member and transducer are encased by a plastic cover in an enclosure system 17. A membrane made of polyethylene naphthalate (PEN) in the ejector bracket 15 isolates the transducer and vibrating member from the fluid that is supplied from a reservoir in the container assembly 12. The membrane can be thermoformed to the shape of the vibrating member tip. The embedded system on the device consists of the transducer, pressure sensor, and lithium-ion battery all connected on a single board microcontroller. The aluminum enclosure that houses the embedded system contains a button that can double as a fingerprint sensor for use with controlled substances. The device is charged through a USB-C charging port. Magnets are used to hold the cartridge in the enclosure.

Embodiments use a two-component cartridge system to keep the fluid from contacting the mesh in storage. This design involves two spikes, one of which contains wicking material, on one part of the cartridge, the ejector bracket. The other part of the cartridge, the container, houses a fluid reservoir and two septa. The user pushes the ejector bracket and container together, and the spikes puncture the septa, creating a path for fluid to flow to the mesh. The wicking material in one spike aids in the supply of fluid to the mesh. The other spike, which does not include wicking material, allows air to enter the container for pressure equalization. Vents covered with vent material are located at the top of each side of the fluid reservoir and are connected to the open atmosphere via airflow outlets, allowing for equalization of pressure.

Figure 4:
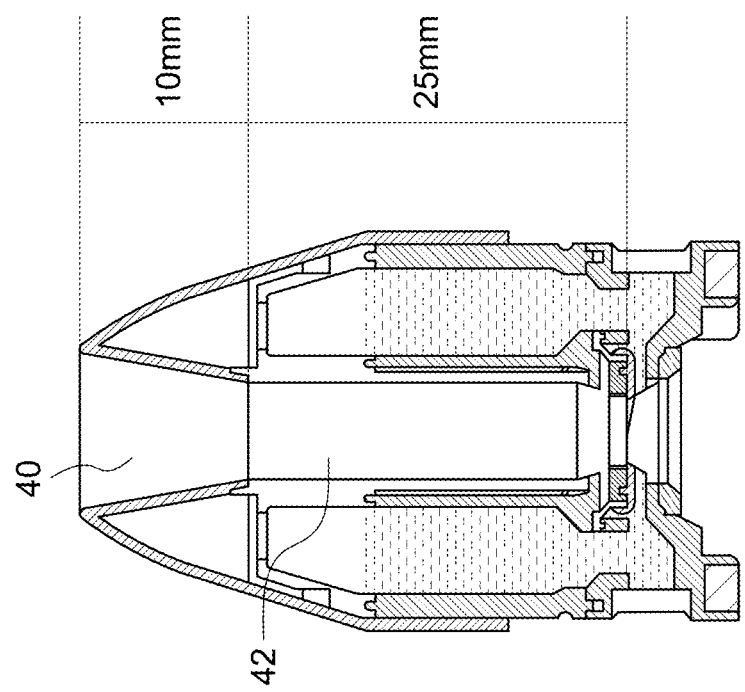
FIG. 4 illustrates a cross-sectional view of certain dimensions of ejection and mouthpiece ports of a droplet delivery device in accordance with one embodiment of the disclosure.
Figure 5:
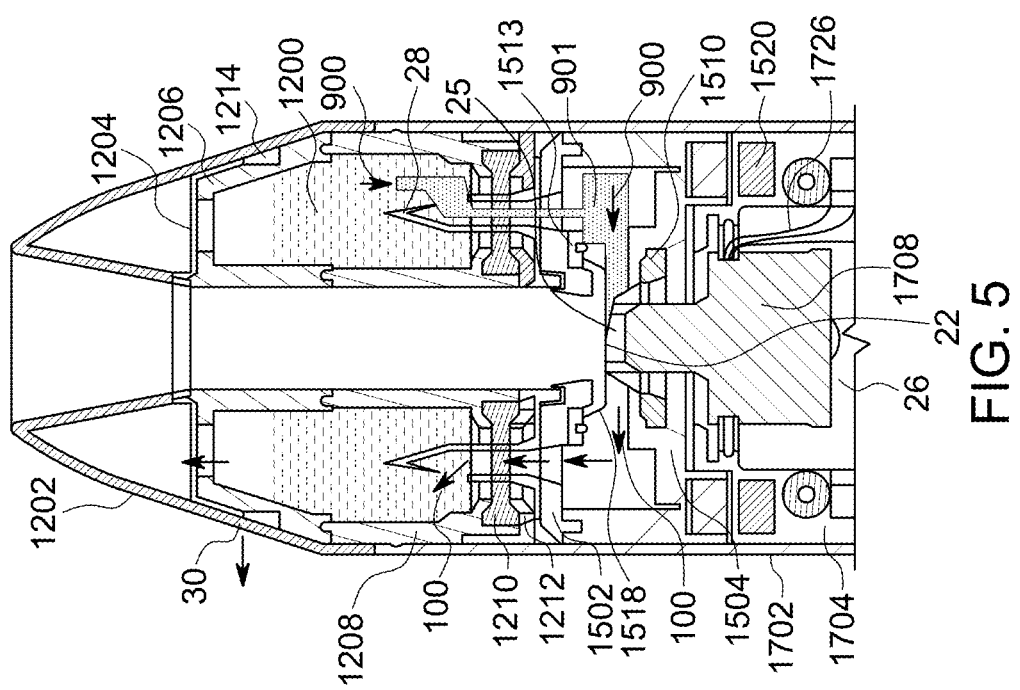
FIG. 5 illustrates a cross-sectional view of fluid flow path of a droplet delivery device with a two-part cartridge in accordance with one embodiment of the disclosure.
Figure 6B:
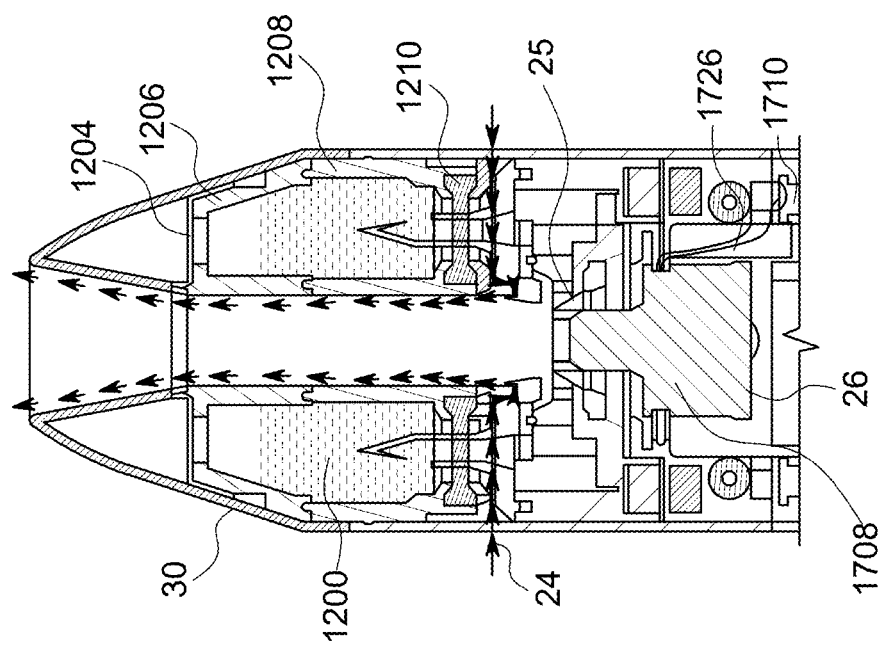
FIGS. 6A and 6B illustrate airflow of a droplet delivery device with a two-part cartridge in accordance with an embodiment of the disclosure.
Figure 6A:
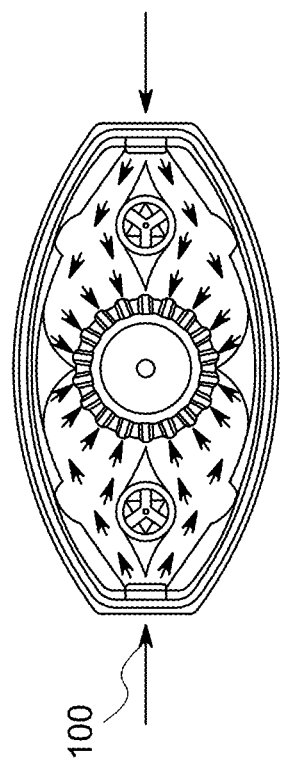

Referring to FIG. 4, there is an ejection port 42 with a length of 25 mm and a mouthpiece port with a length of 10 mm. The preferred length of the ejection port is 0 mm-50 mm. The preferred mouthpiece port length is 0 mm-50 mm. FIG. 5 shows the fluid 900 and ventilation 100 flow paths through the spikes 28 in prototyped embodiments. FIGS. 6A and 6B show the entrained air path of prototyped embodiments.

BlueSky I Push Mode

Figure 7A:
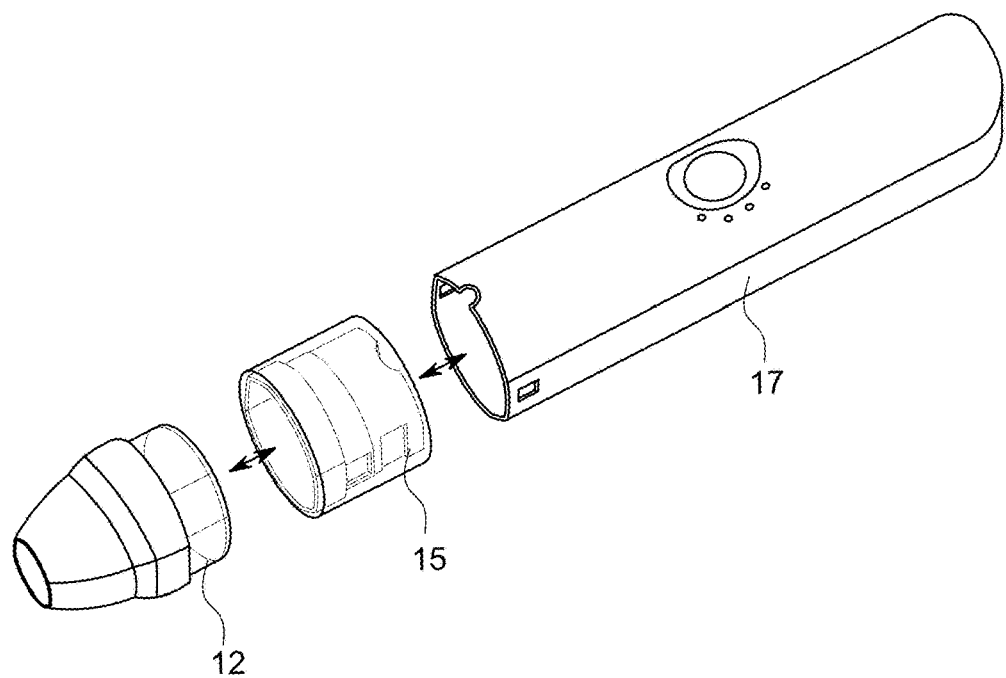
FIGS. 7A and 7B illustrate perspective views of the disassembly of major components of a push mode I droplet delivery device (utilizing mesh support shown in FIG. 3) in an embodiment of the disclosure.
Figure 7B:
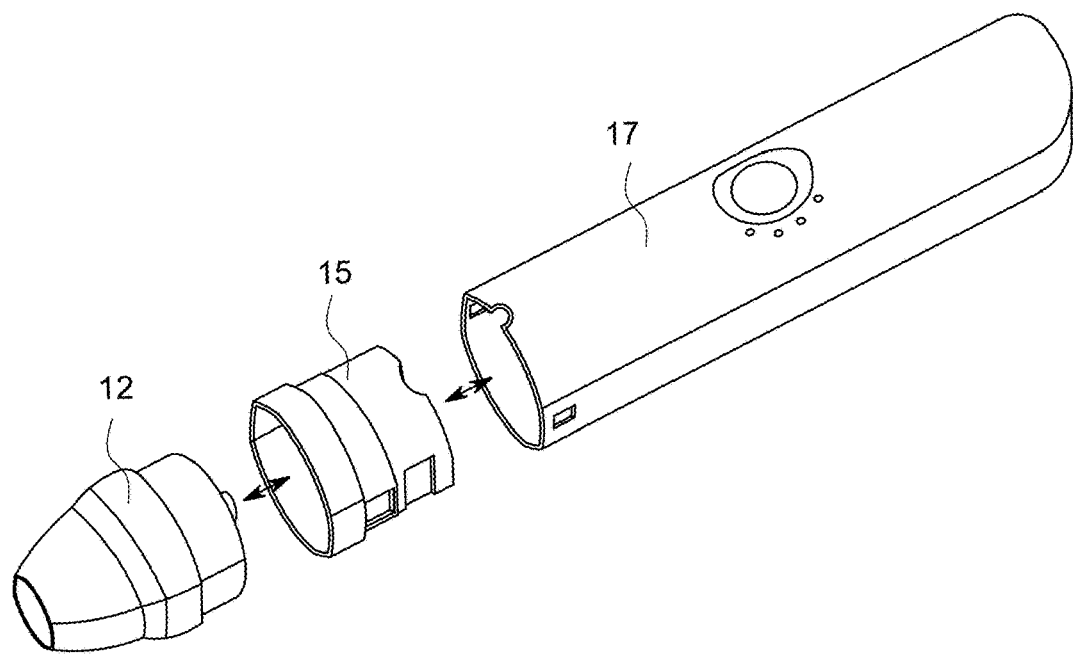

FIGS. 7A and 7B show a rendering and a CAD overview, respectively, of the push mode I embodiment. The overviews in FIGS. 7A and 7B show the container assembly 12, ejector bracket 15, and the enclosure system 17, from left to right.

Figure 8:
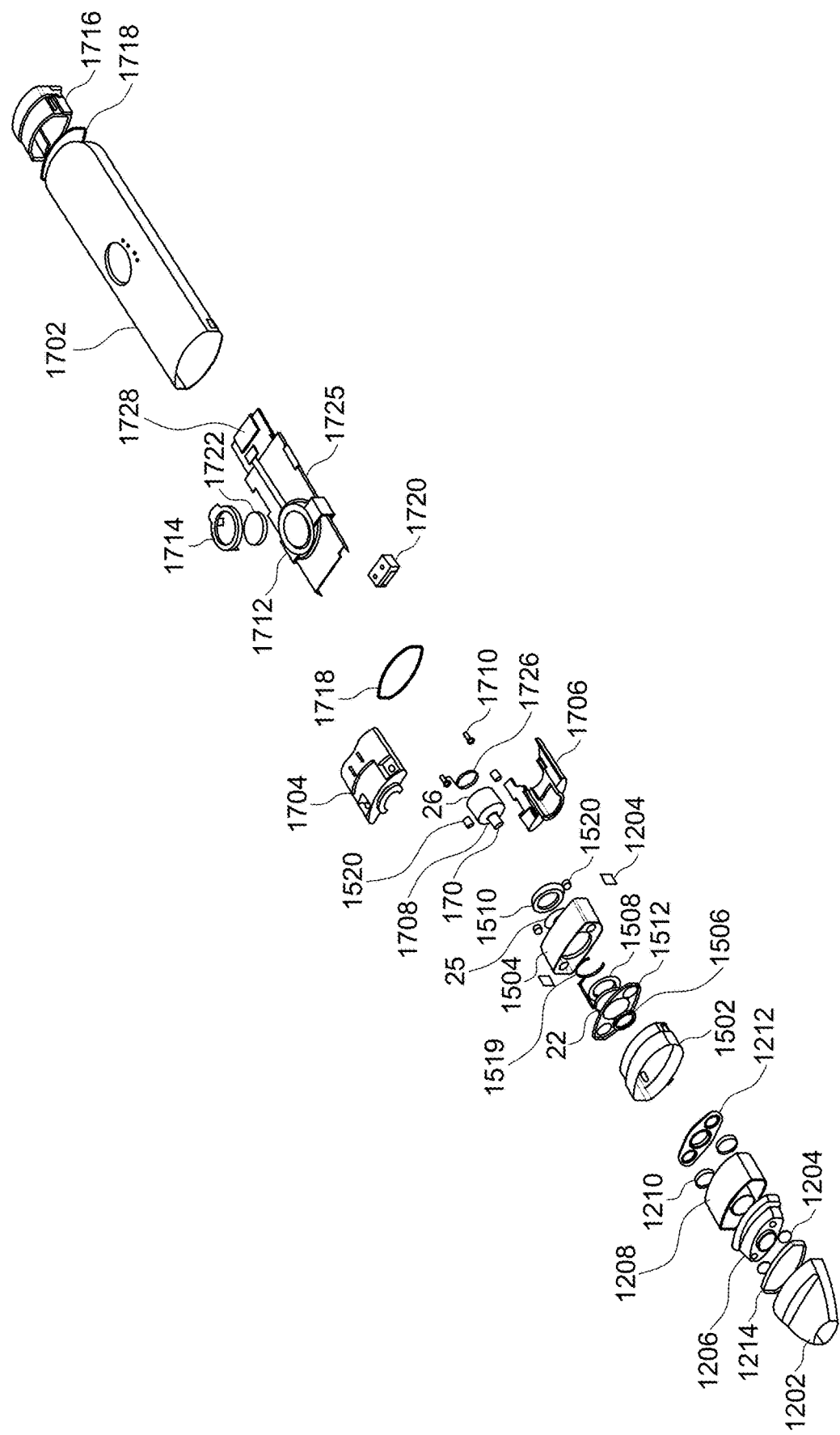
FIG. 8 illustrates an exploded view of a push mode I droplet delivery device (utilizing mesh support shown in FIG. 3) in an embodiment of the disclosure.
Figure 9A:
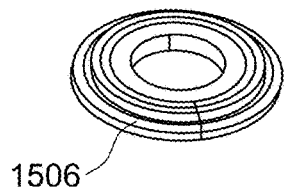
FIGS. 9A-9E illustrate isolated perspective views of COC (cyclic olefin copolymer) rings, including mesh (22), of a push mode I droplet delivery device (utilizing mesh support shown in FIG. 3) in an embodiment of the disclosure.
Figure 9B:
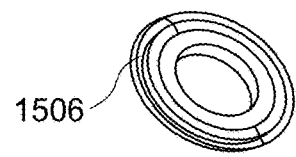
Figure 9F:
Figure 9C:
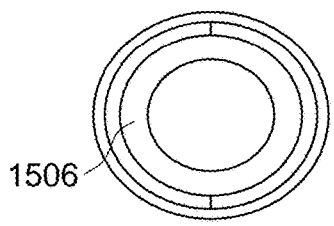
Figure 9D:
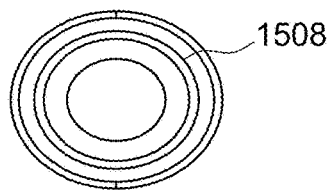
Figure 9E:
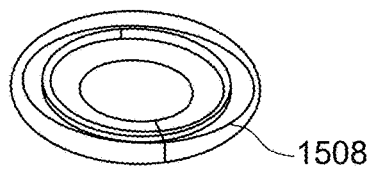

FIG. 8 provides an exploded view of the components from the push mode I embodiment.

Figure 10:
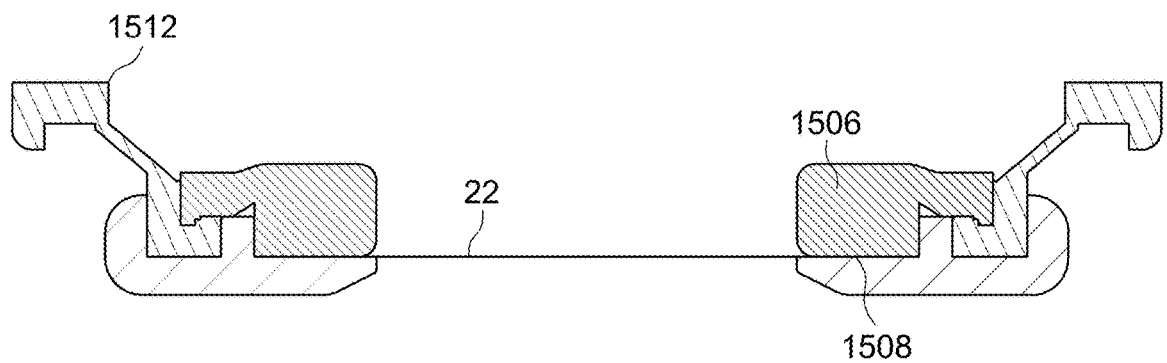
FIG. 10 illustrates a schematic view of a push mode I droplet delivery device mesh suspension system (redundant to FIG. 3) in an embodiment of the disclosure.

Referring to FIG. 9, the push mode I embodiment includes a mesh carrier that includes two COC rings 1506, 1508 that are ultrasonically welded holding the mesh 22 and suspension gasket 1512. The COC rings sandwich the mesh and suspension gasket as shown in FIG. 10. The gasket is placed between the upper and lower ejector brackets.

Figure 11:
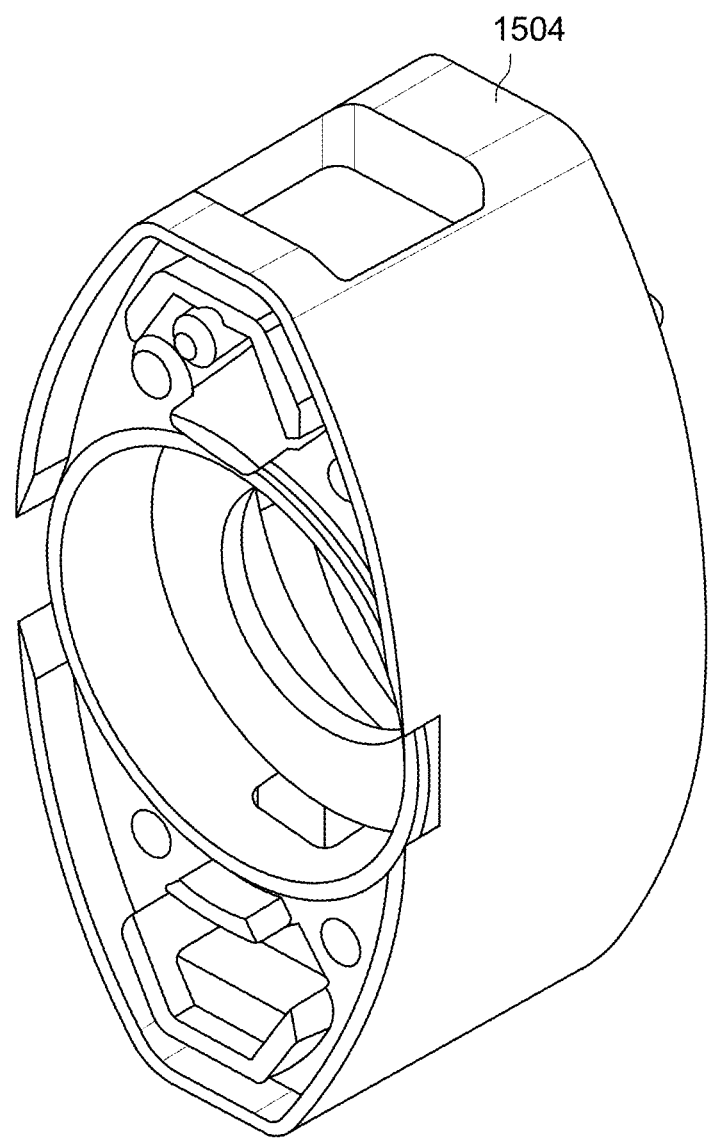
FIG. 11 illustrates a perspective view of lower ejector bracket including vents located on each narrow side of the bracket of a push mode I droplet delivery device (utilizing mesh support shown in FIG. 3) in an embodiment of the disclosure.

Referring to FIG. 11, two vents are located on the narrow sides of the lower ejector bracket 1504 in the push mode I embodiment. The spikes are located on the upper ejector bracket 1502. The container, which houses the fluid reservoir 1200, includes three COC pieces. The two septa 1210 are held between the middle and lower container pieces. A container ring is bonded onto the upper 1206 and middle 1208 container pieces and the mouthpiece 1202 snaps onto the upper container piece 1206.

BlueSky II Push Mode

Figure 12A:
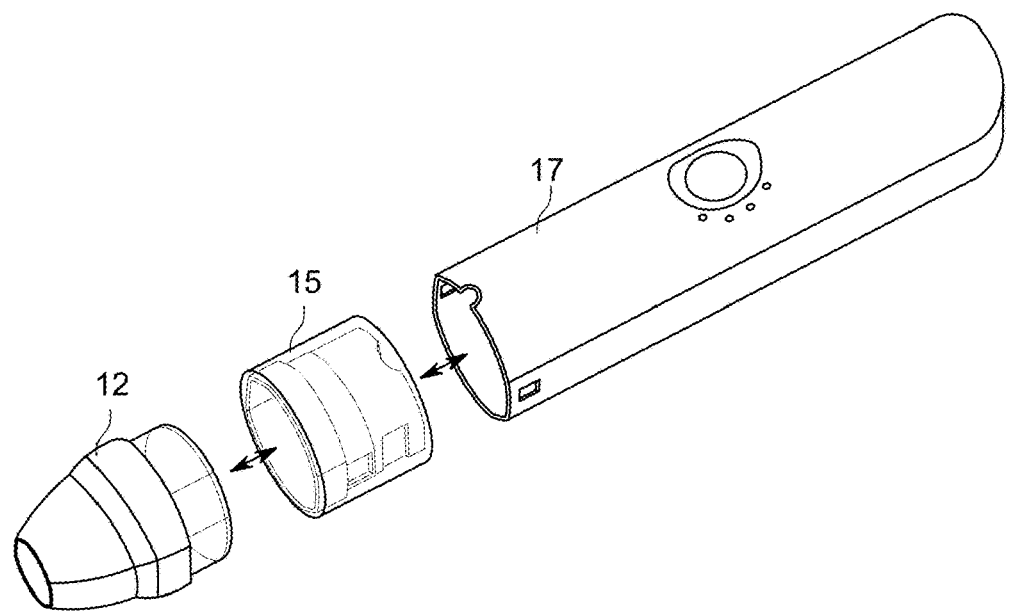
FIGS. 12A and 12B illustrate perspective views of the disassembly of major components of a push mode II droplet delivery device (utilizing mesh support shown in FIG. 2) in an embodiment of the disclosure.
Figure 12B:
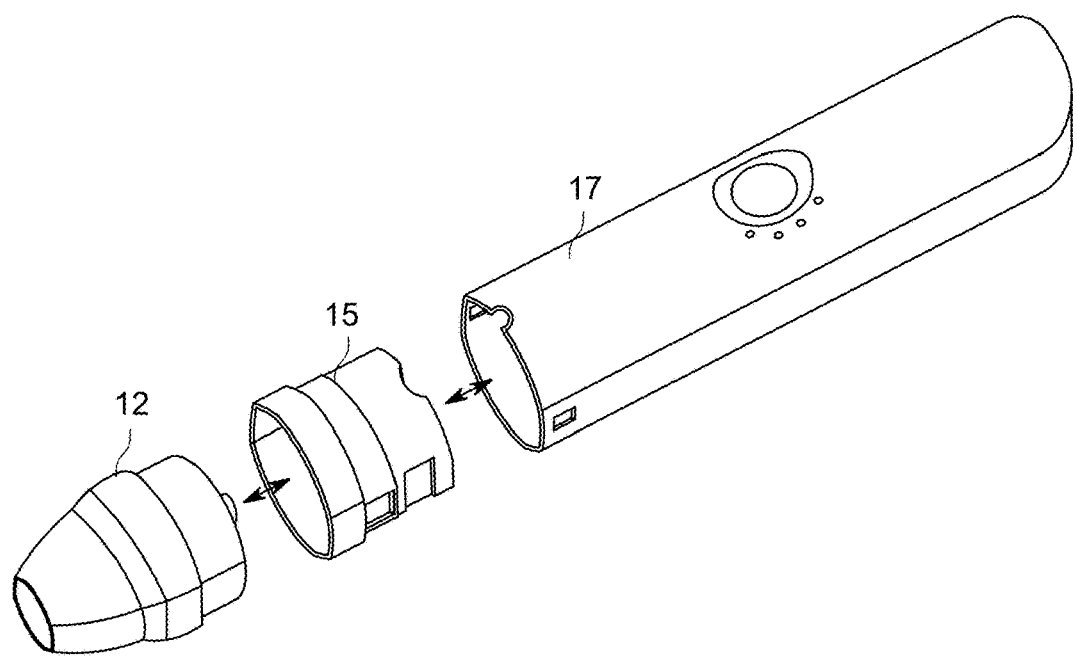

FIGS. 12A and 12B show a rendering and a diagrammatic overview of the push mode II embodiment, respectively. The overviews in FIGS. 12A and 12B show the container assembly 12, ejector bracket 15, and the enclosure assembly 17, from left to right.

Figure 13:
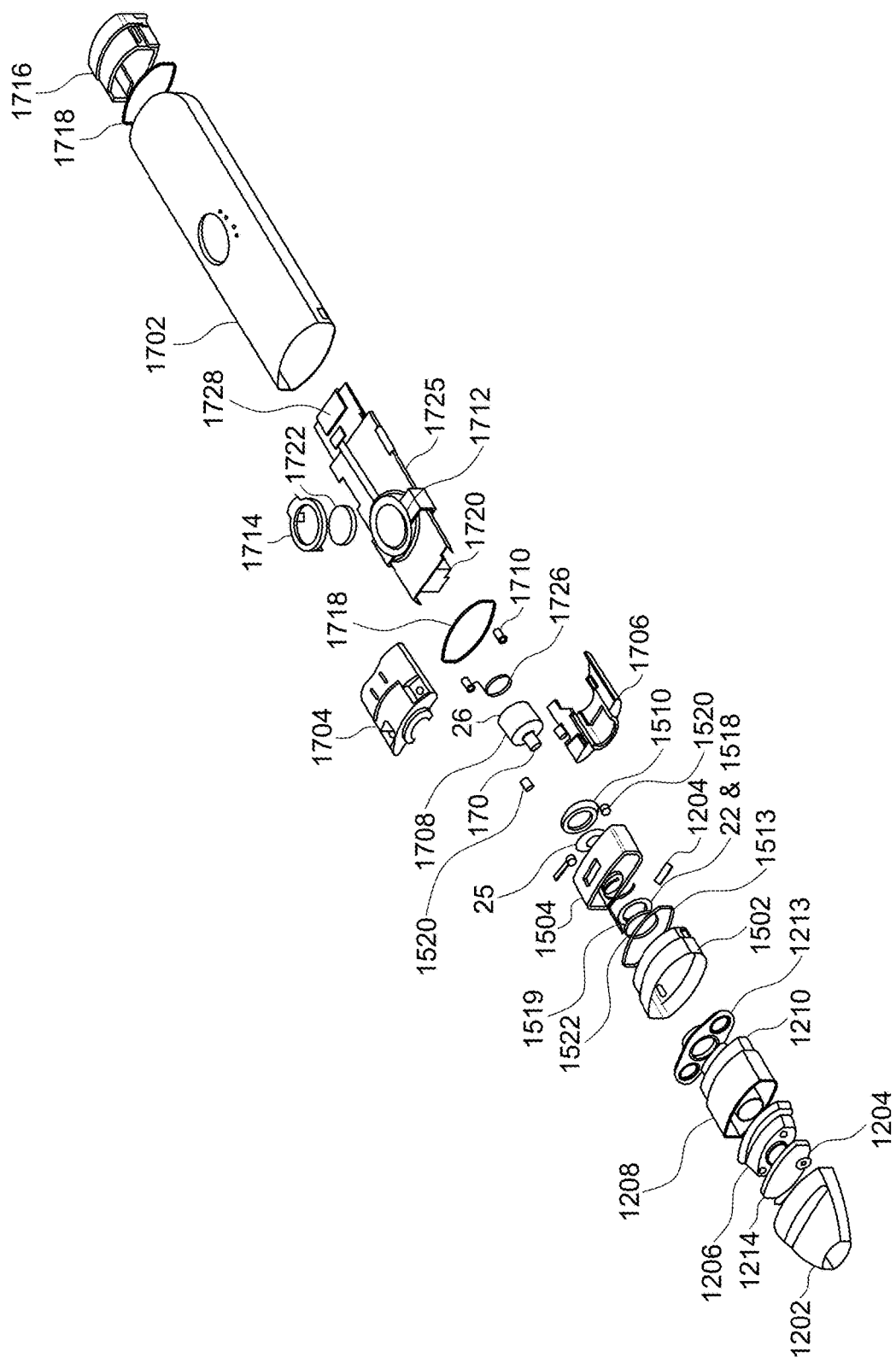
FIG. 13 illustrates an exploded view of a push mode II droplet delivery device (utilizing mesh support shown in FIG. 2) in an embodiment of the disclosure.

FIG. 13 illustrates an exploded view of the components of the push mode II embodiment.

Figure 14:
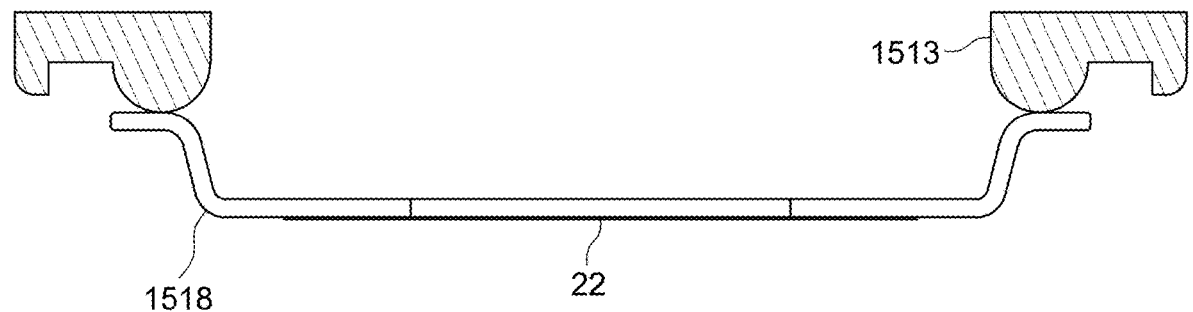
FIG. 14 illustrates a schematic view of a push mode II droplet delivery device mesh suspension system (as also shown in FIG. 2) in an embodiment of the disclosure.

In the push mode II embodiment, a stainless-steel annulus carrier 1518 is bonded to the mesh 22. A gasket 1513 is placed above the mesh and mesh carrier between the upper 1502 and lower 1504 ejector brackets. FIG. 14 illustrates the push mode II embodiment mesh carrier 1518 and gasket 1513.

Figure 15:
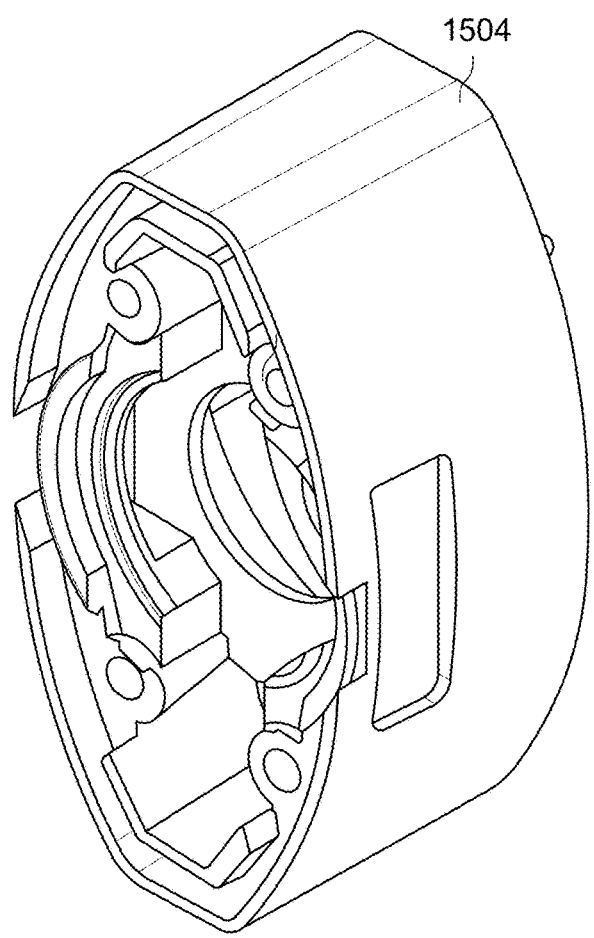
FIG. 15 illustrates a perspective view of lower ejector bracket including vents located on each wide side of the bracket of a push mode II droplet delivery device (utilizing mesh support shown in FIG. 2) in an embodiment of the disclosure.

Two vents are located on the wide sides of the lower ejector bracket 1504 as shown in FIG. 15. The spikes are located on the upper ejector bracket 1502.

As in push mode I, the container, which houses the fluid reservoir, includes three COC pieces. The lower container for the push mode II embodiment extends further than in push mode I, with the tubular portion extending into the upper ejector bracket.

Figure 16:
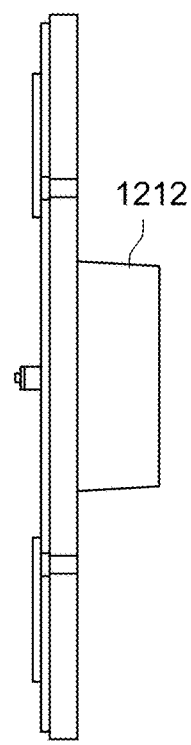
FIG. 16 illustrates a lower container of a push mode II droplet delivery device (utilizing mesh support shown in FIG. 2) in an embodiment of the disclosure.
Figure 17:
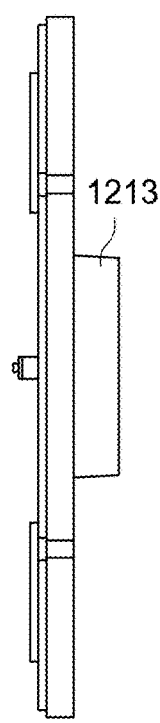
FIG. 17 illustrates a lower container of a push mode I droplet delivery device (utilizing mesh support shown in FIG. 3) in an embodiment of the disclosure.

FIG. 16 (push mode II) and FIG. 17 (push mode I) illustrate a comparison of the lower containers of each embodiment. The extension is necessary because the mesh sits lower, compared to I, due to the stainless-steel mesh carrier being thinner than the COC carrier of I. The two septa are held between the middle and lower containers. A container ring is bonded onto the upper and middle container pieces and the mouthpiece snaps onto the upper container piece.

BlueSky Vibrating Member and Membranes

Figure 18:
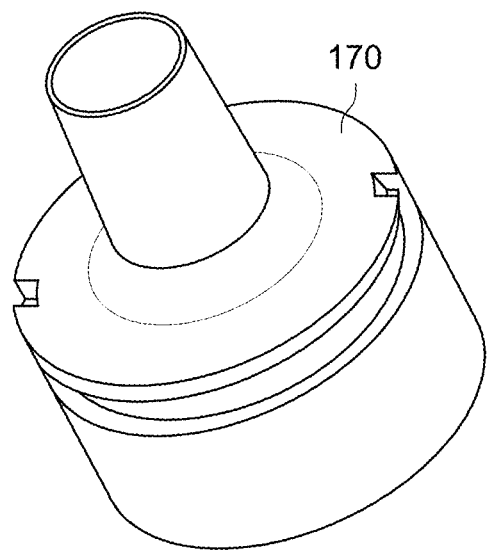
FIG. 18 illustrates a perspective view of a rod tip design for a vibrating member of a droplet delivery device in accordance with one embodiment of the disclosure.
Figure 19:
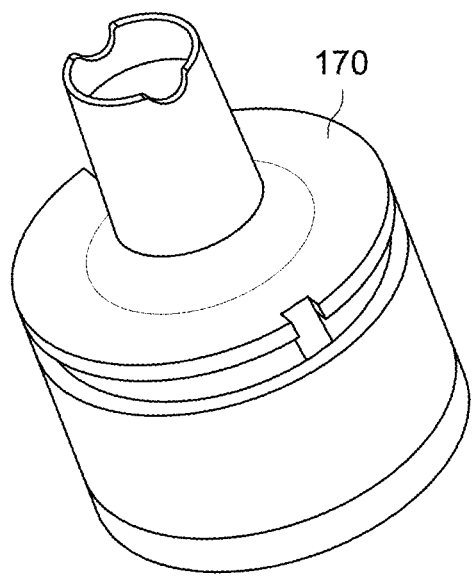
FIG. 19 illustrates a perspective view of a ring tip design for a vibrating member of a droplet delivery device in accordance with one embodiment of the disclosure.
Figure 20:
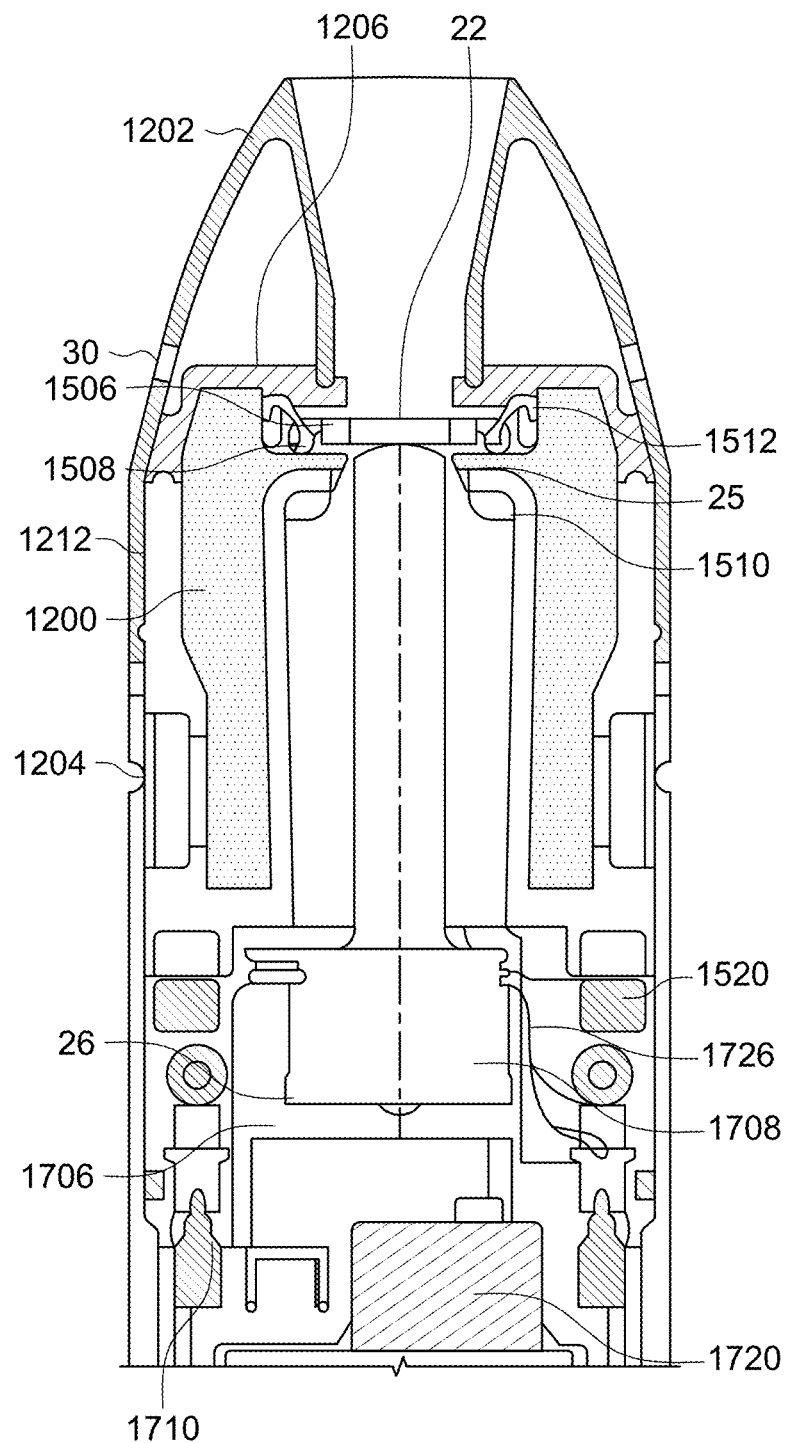
FIG. 20 illustrates a cross-sectional view of single part cartridge design with a long vibrating member in a droplet delivery device in accordance with one embodiment of the disclosure.
Figure 21A:
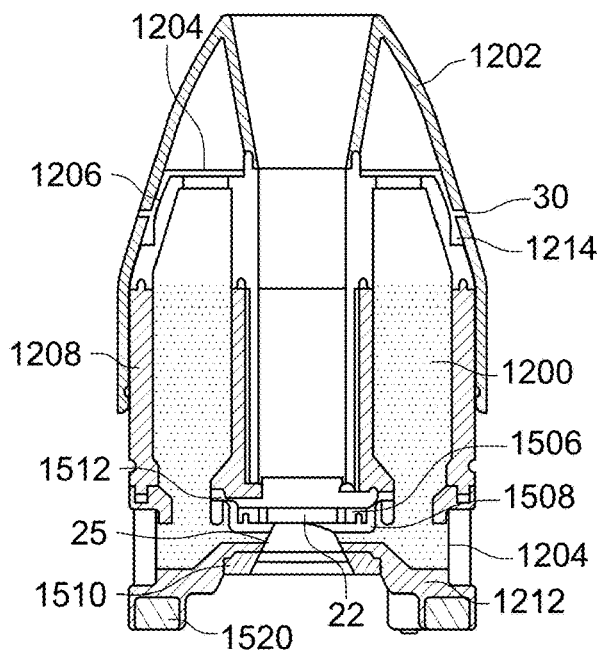
FIGS. 21A and 21B illustrate cross-sectional views of single part cartridge design with a short vibrating member in a droplet delivery device in accordance with one embodiment of the disclosure.
Figure 21B:
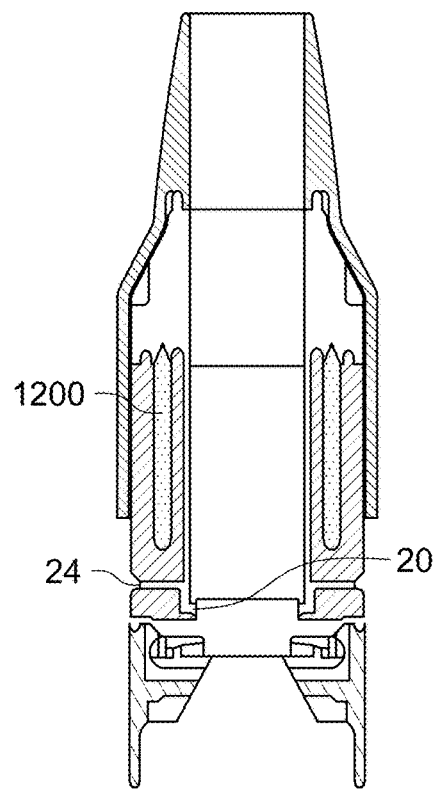
Figure 22A:
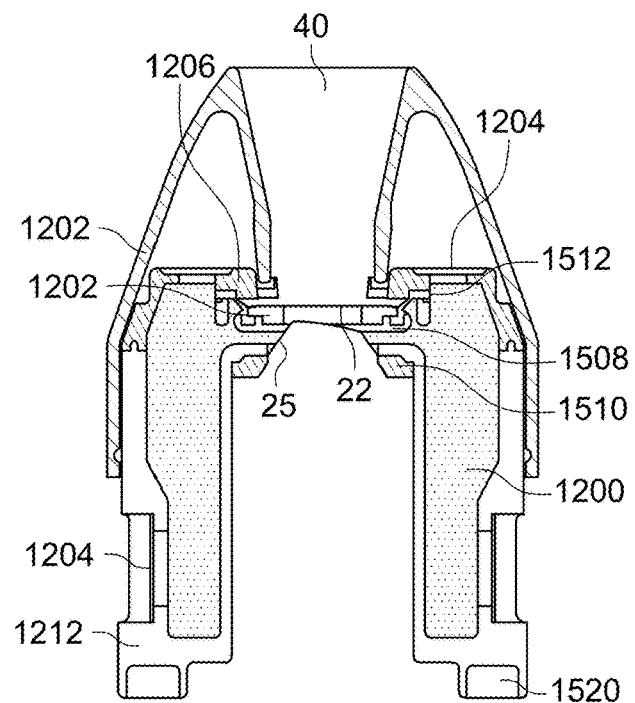
FIGS. 22A and 22B illustrate cross-sectional views of single part cartridge alternative designs with a long vibrating member in a droplet delivery device in accordance with one embodiment of the disclosure.
Figure 22B:
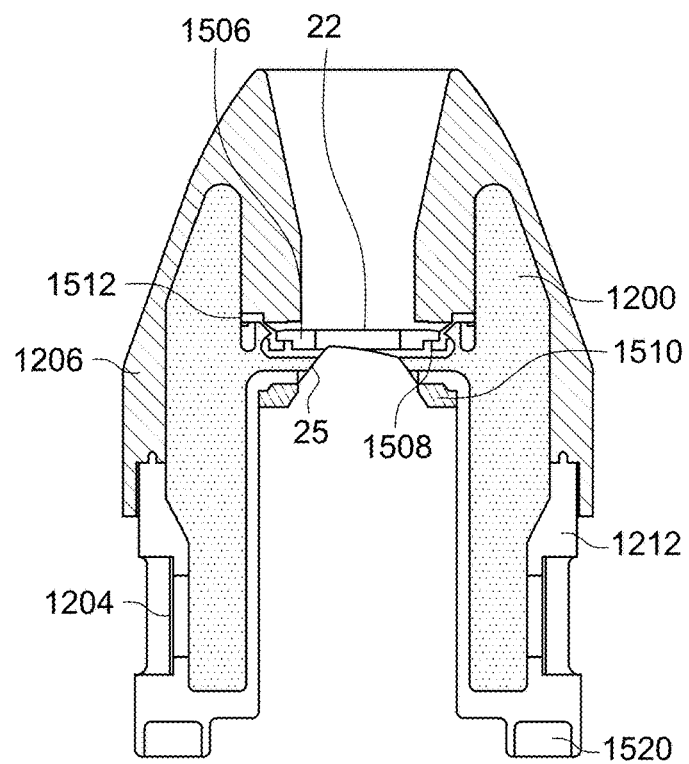
Figure 23A:
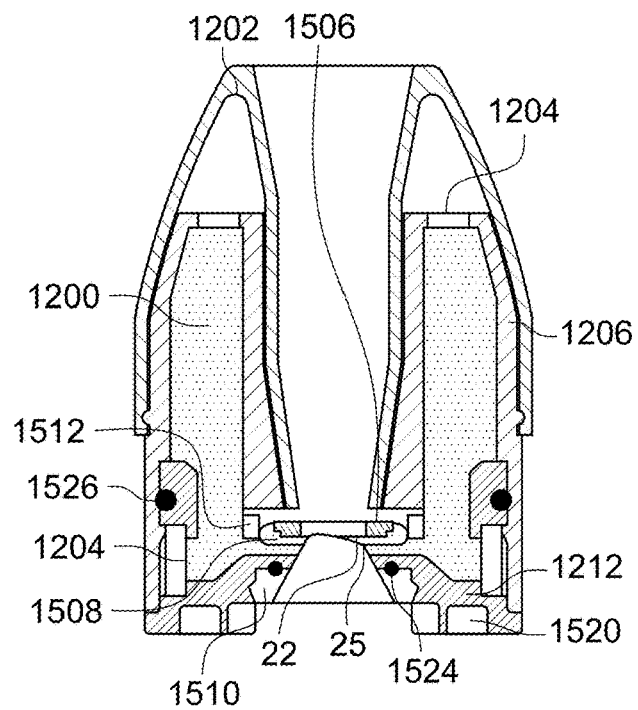
FIGS. 23A and 23B illustrate cross-sectional views of single part cartridge alternative designs with a short vibrating member in a droplet delivery device in accordance with one embodiment of the disclosure.
Figure 23B:
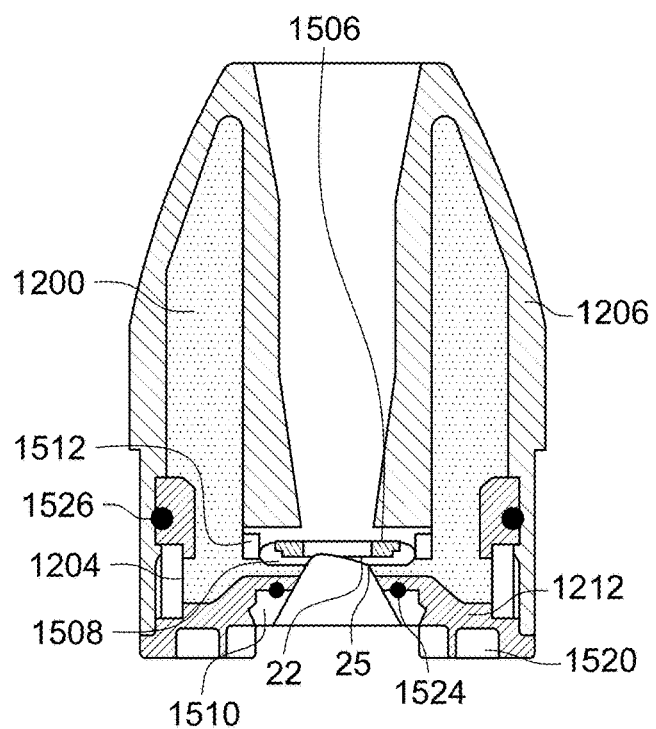

Push mode has multiple vibrating member and membrane designs. Table 2 and Table 3 contain descriptions of the vibrating member and membrane designs, respectively, that have been prototyped and tested. Referring to FIGS. 18 and 19, there are currently two different tips for the vibrating member rod tip and ring tip, respectively.

TABLE 2

Description of vibrating members

| Vibrating Member | Description |
| --- | --- |
| H1 | 1.0 mm diameter rod tip |
| H2 | 1.5 mm diameter rod tip |
| H3 | 2.0 mm diameter rod tip |
| H4 | 3.5 mm diameter rod tip |
| H5 | 3.5 mm diameter ring tip with a 2-degree tilt |
| H6 | 3.5 mm diameter ring tip with a 5-degree tilt |
| H7 | 3.5 mm diameter ring tip with an 8-degree tilt |
| H8 | 3.5 mm diameter ring tip with no tilt |
| H9 | 3.5 mm diameter rod tip with 3-degree tilt |

TABLE 3

Description of membranes

| Membrane Style | Description |
| --- | --- |
| M1 | Thermoformed to a 1.0 mm diameter circle with a round plateau, used with H1 |
| M2 | Thermoformed to a 1.0 mm diameter circle with a 2-degree tilt, used with H1 |
| M3 | Thermoformed to a 1.0 mm diameter circle with a 5-degree tilt, used with H1 |
| M4 | Thermoformed to a 1.0 mm diameter circle with an 8-degree tilt, used with H1 |
| M5 | Thermoformed to a 1.5 mm diameter circle with a 2-degree tilt, used with H2 |
| M6 | Thermoformed to a 1.5 mm diameter circle with a 5-degree tilt, used with H2 |
| M7 | Thermoformed to a 1.5 mm diameter circle with an 8-degree tilt, used with H2 |
| M8 | Thermoformed to a 2.0 mm diameter circle with a 2-degree tilt, used with H3 |
| M9 | Thermoformed to a 2.0 mm diameter circle with a 5-degree tilt, used with H3 |
| M10 | Thermoformed to a 2.0 mm diameter circle with an 8-degree tilt, used with H3 |
| M11 | Thermoformed to a 3.5 mm diameter circle with a round plateau, used with H4 |
| M12 | Thermoformed to a 3.5 mm diameter circle with a 2-degree tilt, used with H5 |
| M13 | Thermoformed to a 3.5 mm diameter circle with a 5-degree tilt, used with H6 |
| M14 | Thermoformed to a 3.5 mm diameter circle with an 8-degree tilt, used with H7 |
| M15 | Thermoformed to a 3.5 mm diameter circle with no tilt, used with H4 or H8 |

The transducer requires a large amount of power during the actuation of the device. As the power usage increases, the heat generated by the printed circuit board assembly (PCBA) increases. The effect from the heat is mitigated through several design features in the PCBA. A four-layer PCBA increases anti-interference and heat dissipation capabilities. The PCBA also contains a large amount of copper foil, making it conducive to heat dissipation. The MOSFET driving the transducer adopts a high-current package to avoid damage caused by heating in long-term continuous operation. The automatic transformer, to increase the voltage output, it is suspended to insulate it from the rest of PCBA. These features allow the device to operate for days without concern of overheating or being subjected to electrical noise.

BlueSky Life Testing

The prototype BlueSky push mode embodiments, I and II, have gone through life testing. The life test consisted of repeated three-second dosing with one-second resting intervals over the course of several days. Mass ejection was done before and after the life test. Mass ejection is defined as the mass the device aerosolizes over one three-second dose. Mass ejection data before the life test is listed in Table 3 and the data for after life testing is listed in Table 4. The mass ejection of one embodiment remained consistent before and after 55,000 doses and can likely go beyond. This embodiment, II push mode with H4 and M11, has a stainless-steel mesh carrier. There is a second embodiment, I push mode, which has a COC plastic mesh carrier. Due to heat from the extreme dosing cycling, the plastic mesh carrier warped during testing. This led to a decrease in mass ejection after the life test. However, the stainless-steel carrier in II push mode did not warp from the heat, which allowed it to remain consistent after testing. In both I and II, thermal management is improved through a four-layer PCBA, a larger than standard amount of copper foil, and a high current MOSFET driver. The conditions of the testing are not representative of normal consumer use. During normal daily use, where extreme heating does not occur, both embodiments, I and II, show consistent mass ejection. Tables 2 and 3 provide details of the referenced Vibrating Member and Membrane, respectively.

TABLE 4

| Mass ejection data for push mode devices before life testing | | | | | |
|---|---|---|---|---|---|
| Type | Vibrating Member | Membrane | Ejector | Average Scale Ejection (mg) | Average Nicotine (μg) |
| II | H4 | M11 | R52 | 2.45 | 73.5 |
| I | H5 | M12 | W11 | 3.30 | 99 |
| I | H8 | M15 | W11 | 3.60 | 108 |

TABLE 5

| Mass ejection data for push mode devices after life testing | | | | | |
|---|---|---|---|---|---|
| Type | Vibrating Member | Membrane | Ejector | Average Scale Ejection (mg) | Average Nicotine (μg) |
| II | H4 | M11 | R52 | 3.26 | 97.8 |
| I | H5 | M12 | W11 | 1.16 | 34.8 |
| I | H8 | M15 | W11 | 1.54 | 46.2 |

Comparison of Push Mode and Prior Art Ring Mode

As set forth in Example 1 described subsequently, prototypes of BlueSky I and II push mode were tested and compared to prior technology, referred to as BlueSky ring mode (such as described and shown with respective test data for that technology in WO 2020/264501), is provided as follows:

Example 1

Ejectors with a hole size of 2.0 μm were tested in each device. Half of the ejectors tested had a hydrophilic entrance and hydrophobic exit (R). The other half had a hydrophobic entrance and exit (W). The testing was performed with a TSI Mini-MOUDI Model 135 and a THERMO FISHER™ Vanquish UHPLC. Eight different design combinations (vibrating members, membranes, ejector treatments) were tested with BlueSky I and II. Based on the results of the testing, push mode I appears to be the preferred embodiment for push mode. The push mode I design resulted in more consistent mass ejection and MMAD values versus II. Seven of the eight design combinations resulted in comparable mass ejections and MMADs. One outlier, H5 with M12 and R-treated ejector, had a significantly higher mass ejection than the others. Upon comparison of I push mode to BlueSky ring mode, I delivered higher and more consistent mass ejection and lower MMADs. Table 6, Table 7 and Table 8 provide the data obtained from ring mode, I push mode, and II push mode, respectively. The data in the tables include micrograms of nicotine ejected, MMAD, geometric standard deviation (GSD), and the percentage of ejected solution in stage 1 and stage 2 of the mini-MOUDI. All the vibrating member and membrane combinations tested with I push mode, found in Table 7, performed well with both ejector treatments. As seen in Table 8, the best performing combinations with II push mode were H4 with M11 and H5 with M12, both using W-treated ejectors.

TABLE 6

Ring Mode Mini-MOUDI results:

| Treatment | Nicotine (μg) | MMAD (μm) | GSD | Stage 1 (%) | Stage 2 (%) | Stage 1 and 2 (%) |
|---|---|---|---|---|---|---|
| R | 47.040 | 1.38 | 1.76 | 0.299 | 1.322 | 1.62 |
| R | 59.367 | 1.61 | 1.68 | 0.406 | 4.340 | 4.75 |
| R | 23.830 | 1.12 | 1.76 | 0.340 | 1.073 | 1.41 |
| W | 38.057 | 1.50 | 1.77 | 0.288 | 4.159 | 4.45 |
| W | 69.387 | 1.77 | 1.69 | 1.057 | 10.316 | 11.37 |
| W | 39.653 | 1.22 | 1.86 | 0.207 | 1.443 | 1.65 |

The results obtained from Push Mode I device are shown in Table 7. Tables 2 and 3 provide details of the referenced Vibrating Member and Membrane, respectively.

TABLE 7

Push Mode I Mini-MOUDI results:

| Treatment | Vibrating member Style | Membrane Stye | Nicotine (μg) | MMAD (μm) | GSD | Stage 1 (%) | Stage 2 (%) | Stage 1 and 2 (%) |
|---|---|---|---|---|---|---|---|---|
| R | H4 | M11 | 85.880 | 1.40 | 1.95 | 6.20 | 3.07 | 9.27 |
| R | H4 | M15 | 76.250 | 1.14 | 1.56 | 1.06 | 0.45 | 1.51 |
| R | H5 | M12 | 141.957 | 1.30 | 1.81 | 2.00 | 1.66 | 3.66 |
| R | H8 | M15 | 90.124 | 1.26 | 1.81 | 1.61 | 1.27 | 2.88 |
| W | H4 | M11 | 99.705 | 1.40 | 1.78 | 0.72 | 2.78 | 3.50 |
| W | H4 | M15 | 108.750 | 1.27 | 1.82 | 1.07 | 1.71 | 2.78 |
| W | H5 | M12 | 102.493 | 1.37 | 1.79 | 0.87 | 2.41 | 3.28 |
| W | H8 | M15 | 102.177 | 1.22 | 1.69 | 0.55 | 1.14 | 1.69 |

The results obtained from Push Mode II device are shown in Table 8. Tables 2 and 3 provide details of the referenced Vibrating Member and Membrane, respectively.

TABLE 8

Push Mode II Mini-MOUDI results:

| Treatment | Vibrating member Style | Membrane Stye | Nicotine (μg) | MMAD (μm) | GSD | Stage 1 (%) | Stage 2 (%) | Stage 1 and 2 (%) |
|---|---|---|---|---|---|---|---|---|
| R | H3 | M10 | 32.64 | 1.02 | 1.59 | 0.51 | 0.53 | 1.04 |
| R | H4 | M11 | 96.29 | 1.85 | 1.59 | 0.84 | 9.37 | 10.21 |
| R | H5 | M12 | 50.58 | 1.21 | 1.84 | 1.69 | 2.57 | 4.26 |
| R | H7 | M14 | 45.22 | 1.17 | 1.66 | 0.69 | 1.32 | 2.01 |
| W | H3 | M10 | 13.75 | 0.96 | 1.63 | 1.35 | 0.27 | 1.62 |
| W | H4 | M11 | 75.77 | 1.4 | 1.73 | 0.64 | 1.47 | 2.11 |
| W | H5 | M12 | 88.26 | 1.28 | 1.87 | 4.45 | 1.24 | 5.69 |
| W | H7 | M14 | 229.53 | 1.45 | 4.37 | 20.5 | 7.84 | 28.34 |

Based on the results of the testing, I push mode is the preferred embodiment when compared to II.

BlueSky Single Piece Cartridge and Low Cost of Goods Sold Designs

Another embodiment of push mode incorporates the two-part cartridge system into a singular component. Having the cartridge in one piece simplifies setup for the user and increases manufacturability while reducing cost. FIGS. 20, 21A and 21B show two single piece cartridge embodiments. The embodiment shown in FIG. 20 includes a long vibrating member with the fluid reservoir residing under the mesh. In this design, the container is two pieces that are assembled during manufacturing.

In another embodiment, there is a short vibrating member with the fluid reservoir above the mesh (see FIGS. 21A and 21B). In this design, the container is comprised of three pieces that are assembled during manufacturing. After the fluid reservoir is filled, the mouthpiece snaps onto the container with the container ring between.

The vibrating member and transducer work in conjunction with a membrane and mesh, as previously described embodiments of BlueSky push mode. The membrane also serves to isolate the vibrating member and transducer from the fluid. A mesh carrier is used in both designs. Magnets on the bottom of the containers hold the cartridge in the enclosure.

Further embodiments, shown in FIGS. 22A and 22B, of a single piece cartridge include a simpler design, reducing the COGS in manufacturing by decreasing the number of injection molded parts and bonds. FIG. 22A illustrates a simplified version of the design in FIG. 21A but with a long vibrating member. The design in FIG. 22A reduces the number of ultrasonic welds and injection molded parts. FIG. 22B further simplifies the design from FIG. 21A with fewer ultrasonic welds and injection molded parts.

The low COGS designs shown in FIGS. 23A and 23B are a simplification of the design shown in FIG. 21B. This design is a single part cartridge that can be inserted into the enclosure. Air exchanges between the seal of the mouthpiece and the upper container. The cartridges shown in FIGS. 22A-22B and FIG. 24 have removed the ejection port leaving the 10 mm mouthpiece port. The preferable ejection port and mouthpiece port lengths are the same as previously set forth, 0 mm-50 mm.

BlueSky Two-Piece Cartridge

FIG. 24 illustrates a two-piece cartridge design for a long vibrating member. The container and ejector bracket are swapped where the ejector bracket is connected to the mouthpiece and the container is below. The spikes on the ejector bracket face downward onto the septa on the container.

Pharmaceutical/Therapeutic (Norway) Embodiments

Figure 25:
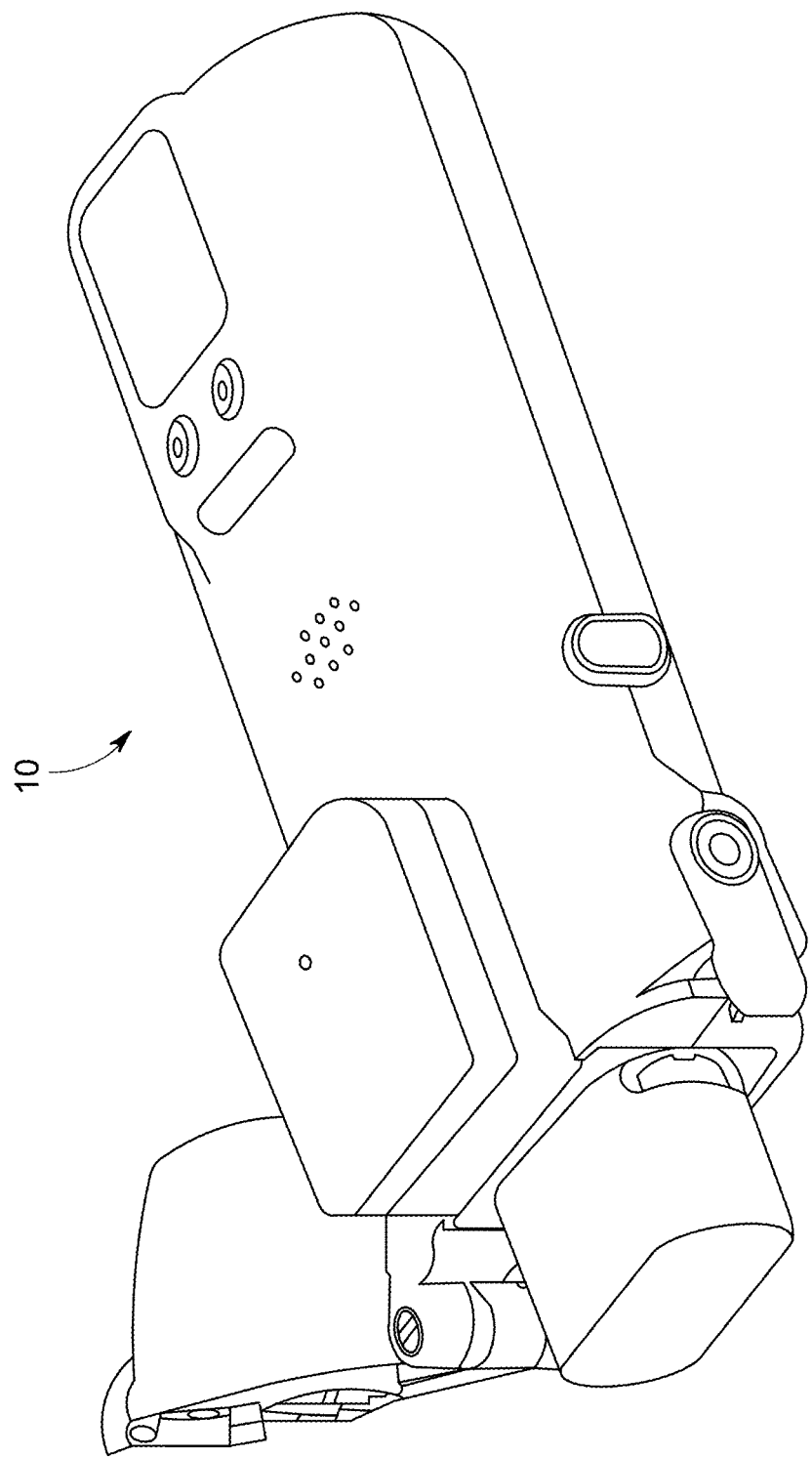
FIG. 25 illustrates a perspective view of a droplet delivery device adapted for pharmaceutical use (but may be other uses in other embodiments) and utilizing membrane-driven aerosolization (i.e. "push mode functionality") in accordance with one embodiment of the disclosure.

Another embodiment of push mode, Norway, is similar to its BlueSky counterpart in most aspects, except that is tailored for prescriptive and medical use. Much like BlueSky, Norway features a releasable cartridge which contains a fluid reservoir and ejector bracket. The device can also be used to assess lung health using spirometry. FIG. 25 shows one embodiment of Norway push mode.

Patients diagnosed with lung diseases can use the Norway device to track their medication dosages and take lung function tests so their treatment progression can be assessed. The patient can perform lung function tests and view dosage history via a phone app which pairs to the Norway device with Bluetooth. The device saves pressure sensor measurements from each dosage of medication. Inspiratory flow measurements can be derived from the pressure sensor measurements to ensure the user is inhaling their medication at a flow rate which delivers the solution most efficiently. The device can also perform lung function tests to measure a patient's forced expiratory volume over 1 second, forced vital capacity, peak expiratory flow, and other spirometry measurements. The data from dosage tracking and lung function tests are uploaded to the cloud so that the patient and doctor may view the patient's progression.

The ejector bracket has been designed to accept many different sizes of containers, where the fluid reservoir volume changes. This makes the device capable of being used with biologics, or one time use ejections. Possible fluid reservoir volumes range from 14 to 20 mL.

The mouthpiece for the Norway embodiment has a preferred length of 15 mm. There are two slits on the sides of the mouthpiece with a dimension of 9 mm by 3 mm for an area of 27 mm². The length of the mouthpiece could be anywhere from 5 mm to 30 mm. The area for the mouthpiece could be from 1 mm² to 100 mm². The mouthpiece opening has dimensions of 14 mm×24 mm for an area of 336 mm². The area of the mouthpiece opening could be anywhere from 10 mm² to 500 mm².

Figure 26:
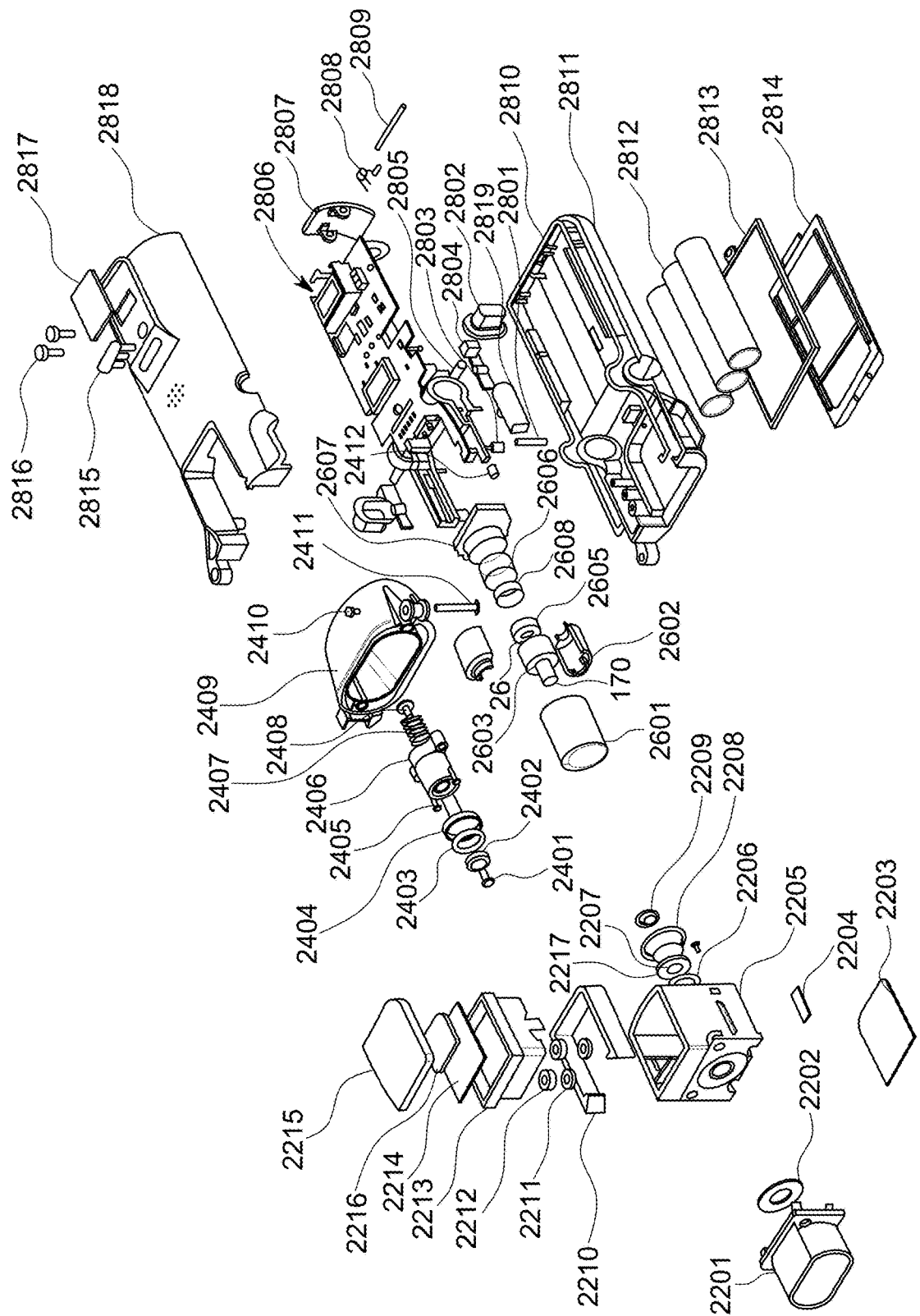
FIG. 26 illustrates an exploded view of a droplet delivery device adapted for pharmaceutical use (but may be other uses in other embodiments) and utilizing membrane-driven aerosolization (i.e. "push mode functionality") in accordance with one embodiment of the disclosure.

The cartridge can be inserted into the main body of the device. The front of the cartridge can be sealed by an O-Ring attached to the cap that presses around the mesh on a stainless-steel annulus when closed to prevent any evaporation through the mesh, this is the face seal. The device features voice coaching and LED lights to guide the user through the ejection inhalation. There is an LCD screen to display dose count, and other necessary information. FIG. 26 shows an exploded view of one embodiment of Norway push mode.

Figure 27B:
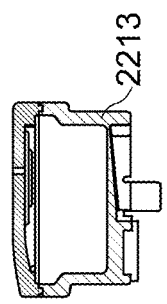
FIGS. 27A-27D illustrate views of major components of a droplet delivery device adapted for pharmaceutical use (but may be other uses in other embodiments) and utilizing membrane-driven aerosolization (i.e. "push mode functionality") in accordance with one embodiment of the disclosure.
Figure 27C:
Figure 27D:
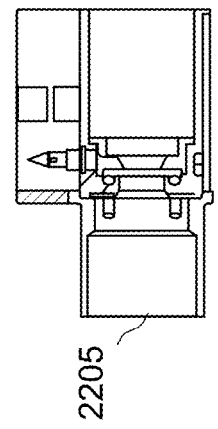
Figure 27A:
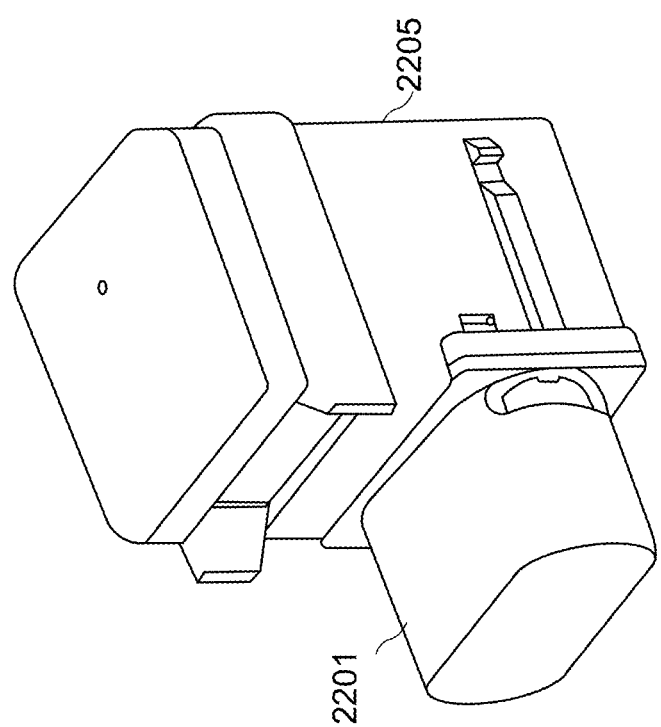

Referring to FIGS. 27A-D, the cartridge assembly (FIG. 27A) is composed of three parts: the container (FIG. 27B), cartridge spacer (FIG. 27C), and the ejector bracket (FIG. 27D). The cartridge spacer keeps the ejector bracket separated from the container to prevent the fluid from contacting the mesh during storage prior to the push mode Initial use.

Figure 28:
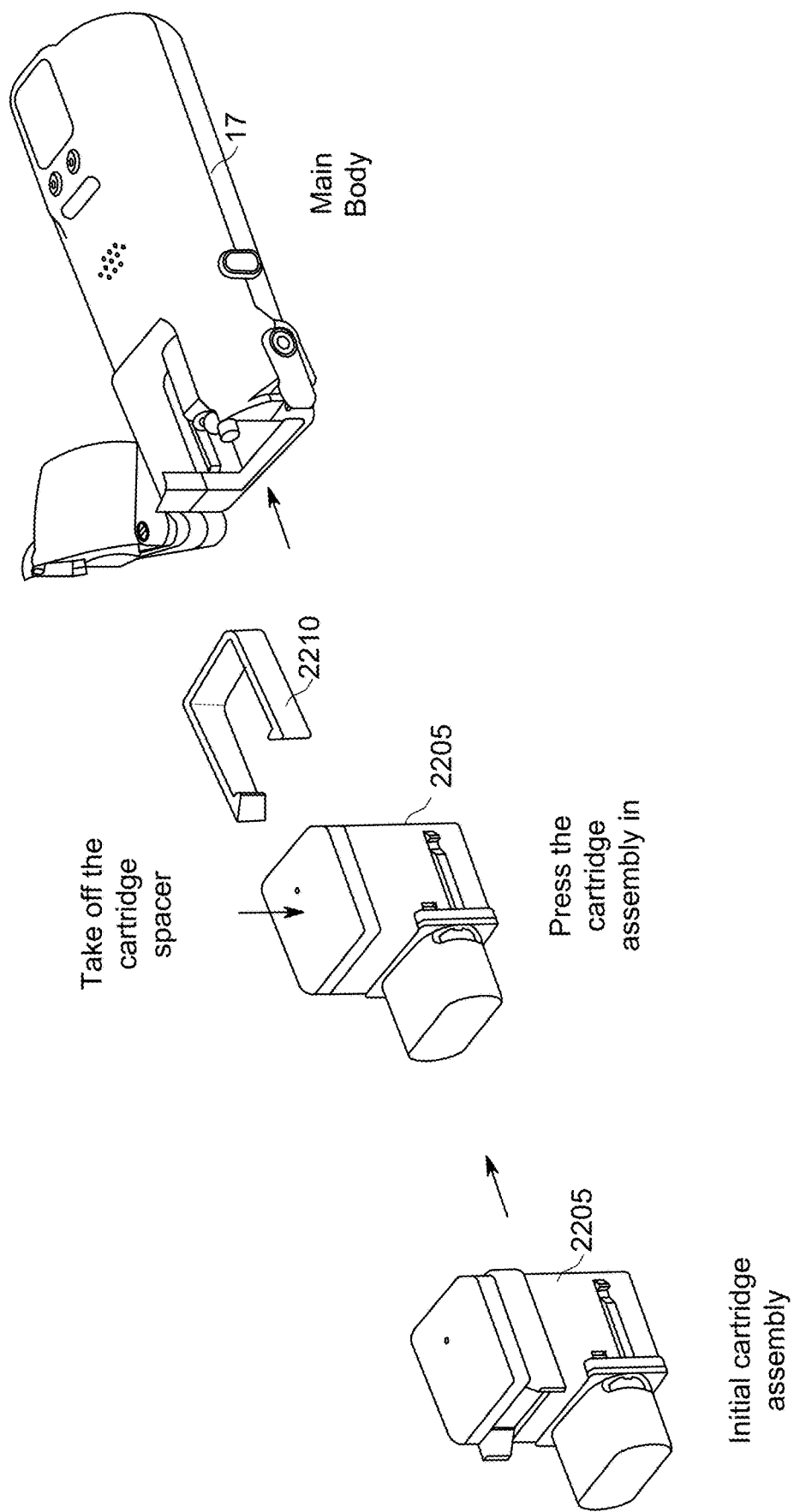
FIG. 28 illustrates an assembly view of major components of a droplet delivery device adapted for pharmaceutical use (but may be other uses in other embodiments) and utilizing membrane-driven aerosolization (i.e. "push mode functionality") in accordance with one embodiment of the disclosure.

The cartridge spacer can be removed so the container can be pushed down onto the ejector bracket such that the spikes pierce the septa making the cartridge one piece. Then, the cartridge can be pushed into the main body of the device to complete the device. This process is illustrated in FIG. 28.

Figure 29:
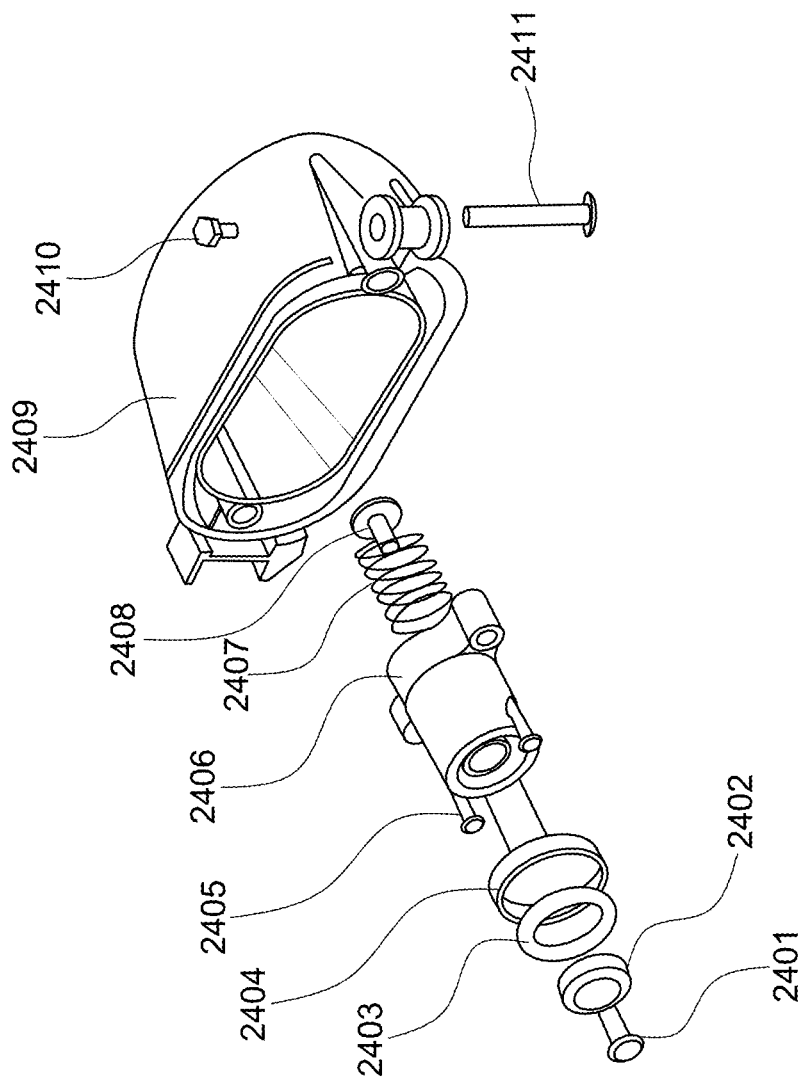
FIG. 29 illustrates an exploded view of a cap of a droplet delivery device adapted for pharmaceutical use (but may be other uses in other embodiments) and utilizing membrane-driven aerosolization (i.e. "push mode functionality") in accordance with one embodiment of the disclosure.

The cap of the Norway embodiment is designed to create a firm seal around the cartridge after each use. An O-Ring seated on a spring-loaded plastic piece which lightly compresses onto the cartridge assembly when the cap is closed, generating a seal between the cartridge and open atmosphere. The components of the cap are shown isolated in as illustrated in FIG. 29.

The critical components to generate precise aerosol of the ejector bracket include the mesh, gasket, membrane, vent material, and mouthpiece. The membrane is positioned such that the membrane face is held parallel to the mesh face, or at a small precise angle. The ejector bracket also has two spikes protruding out of the top that pierce the container. One is for fluid supply, and the other provides a ventilation path for air generated by ejection. On the side of the ejector bracket with the air ventilation spike there is an opening covered by vent material to help relieve pressure and build-up of air. The mouthpiece is positioned following the face of the mesh.

The critical components of the container to maintain consistent aerosol are vent material, a spiral, septa, and septa caps. The vent material is positioned between the fluid and the spiral. The spiral is created by the upper container and vent spacer which minimizes evaporation of the fluid through the vent material. The vent spacer is bonded onto the top of the upper container to create the sealed spiral with an opening to the push mode Inside of the container assembly and another opening to atmosphere. The septa are at the bottom of the container. The septa are placed into a cavity in the lower container and held in place with septa caps that are bonded onto the lower container. The critical components of both the ejector bracket and container can be seen in FIGS. 30A and 30B.

Figure 31:
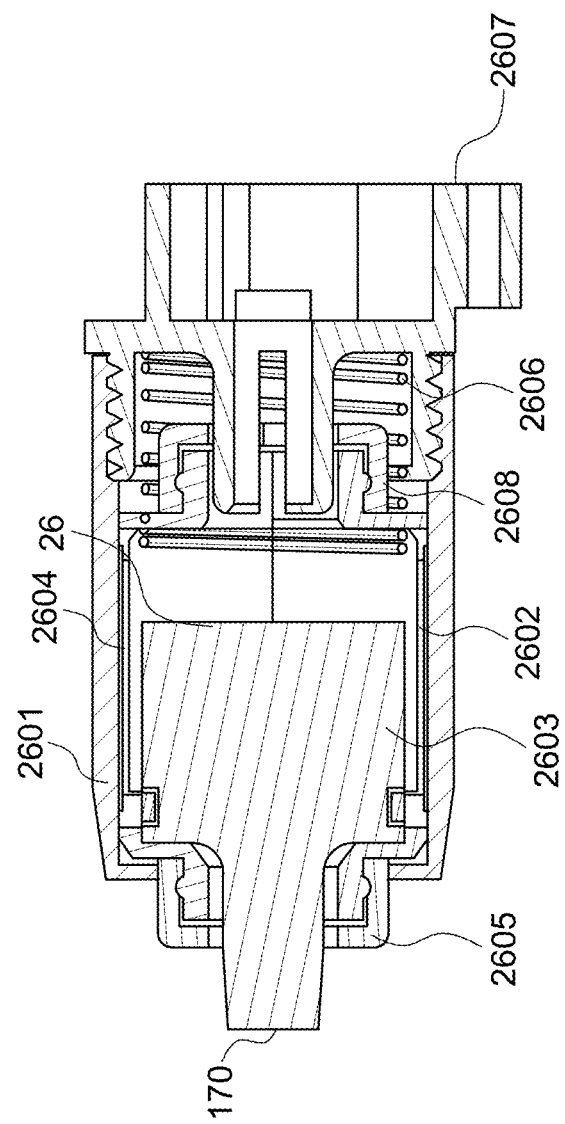
FIG. 31 illustrates a cross-sectional view of a vibrating member enclosure of a droplet delivery device adapted for pharmaceutical use (but may be other uses in other embodiments) and utilizing membrane-driven aerosolization (i.e. "push mode functionality") in accordance with one embodiment of the disclosure.

The main body of the Norway contains the vibrating member and transducer assembly. In one embodiment, as shown in FIG. 31, the vibrating member and transducer assembly is encased by a vibrating member front cover and vibrating member rear cover. The covers are held together by circular caps called the front and rear vibrating member cover holders. The encased vibrating member is then put into the vibrating member enclosure, followed by the vibrating member assembly spring, and finally seated into the vibrating member device bracket. The vibrating member enclosure allows the spring to press the vibrating member and transducer assembly to the membrane.

Figure 33:
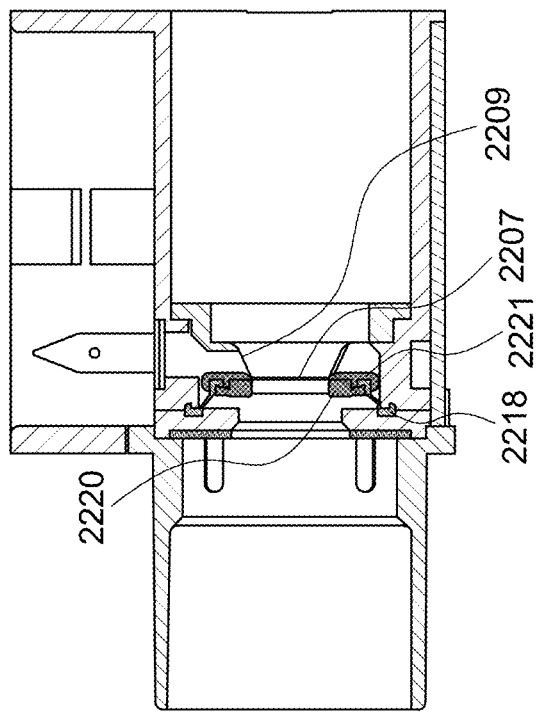
FIG. 33 illustrates a cross-sectional view of an ejector bracket adapted for phar
Figure 32:
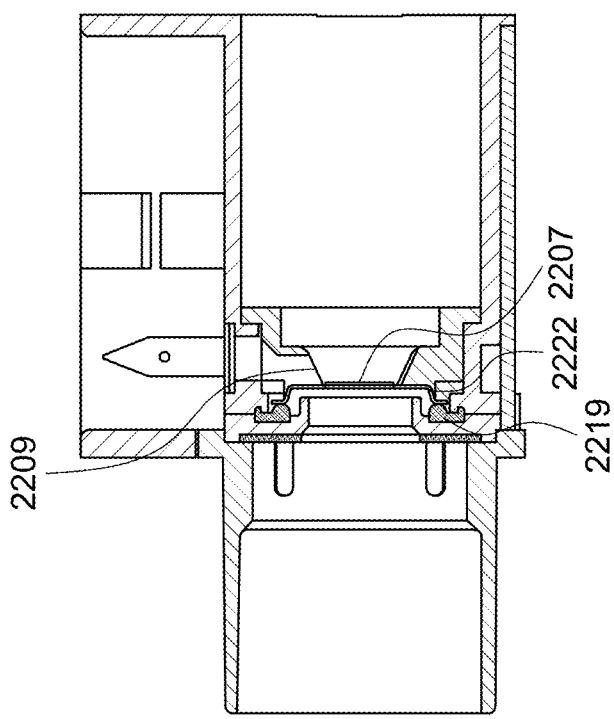
FIG. 32 illustrates a cross-sectional view of an ejector bracket adapted for pharmaceutical use (but may be other uses in other embodiments) and utilizing a mesh suspension system that follows structure and function of the mesh support shown in FIG. 14 in accordance with one embodiment of the disclosure.

Additional embodiments of Norway push mode include different suspension systems to hold the mesh in the cartridge, similar to those in BlueSky push mode. With the suspension systems seen in FIGS. 32 and 33, the vibrating member and transducer assembly no longer has a spring; therefore, it no longer needs to be in the vibrating member enclosure, nor does it need the vibrating member device bracket.

Figure 34B:
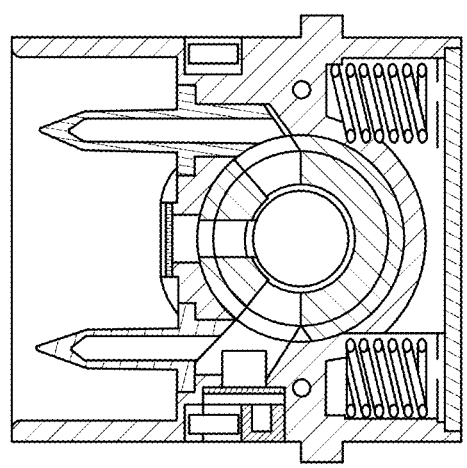
Figure 34A:
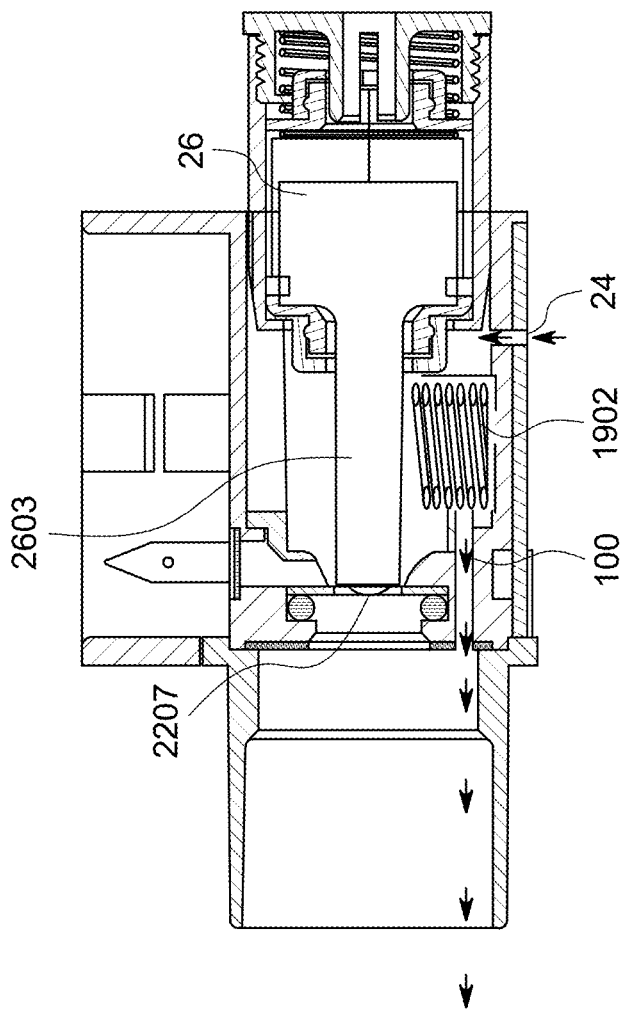
Figure 35A:
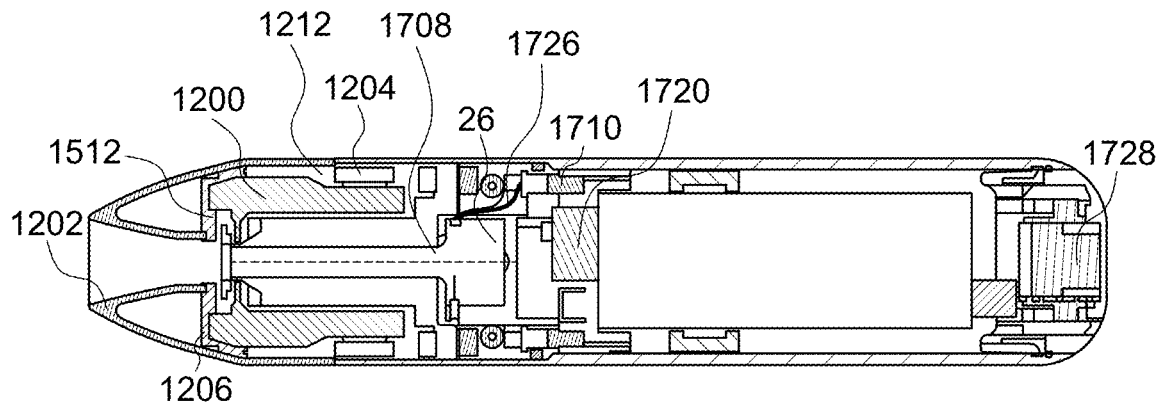
Figure 35B:
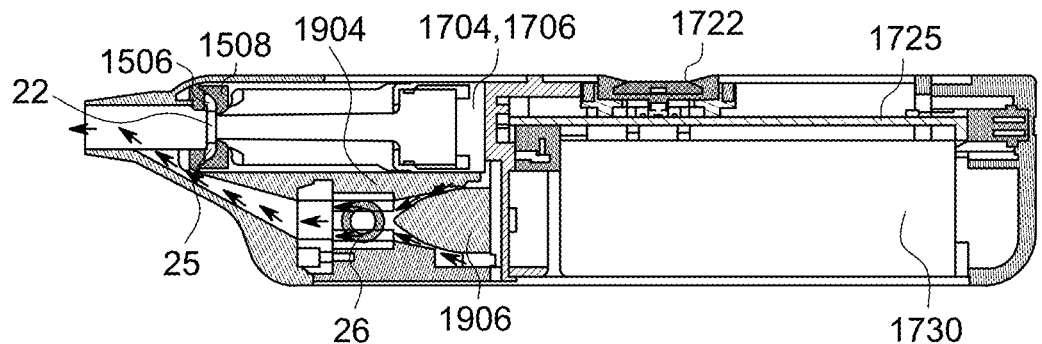
Figure 35C:
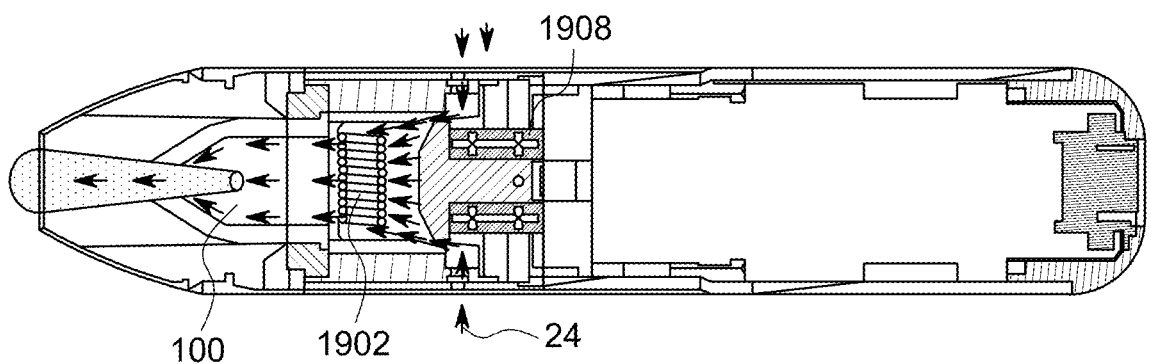
Figure 36:
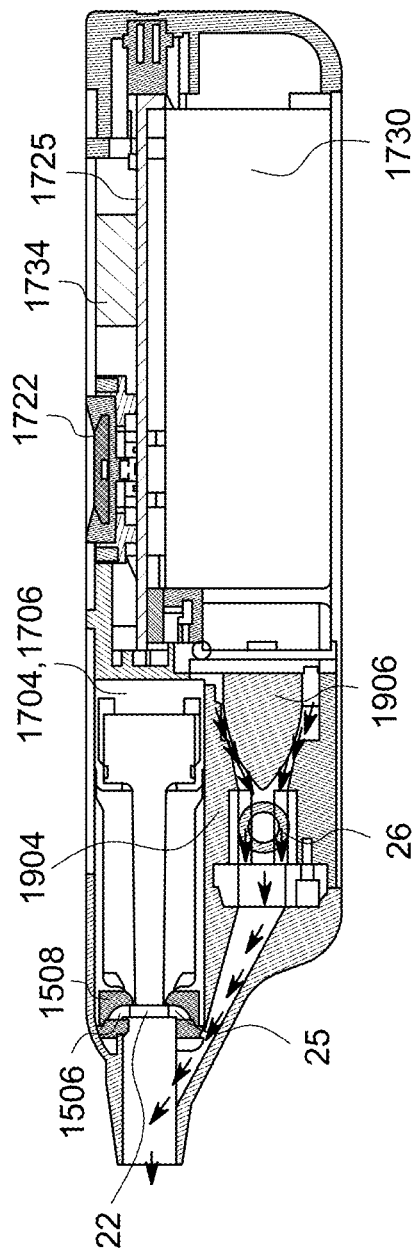
Figure 37:
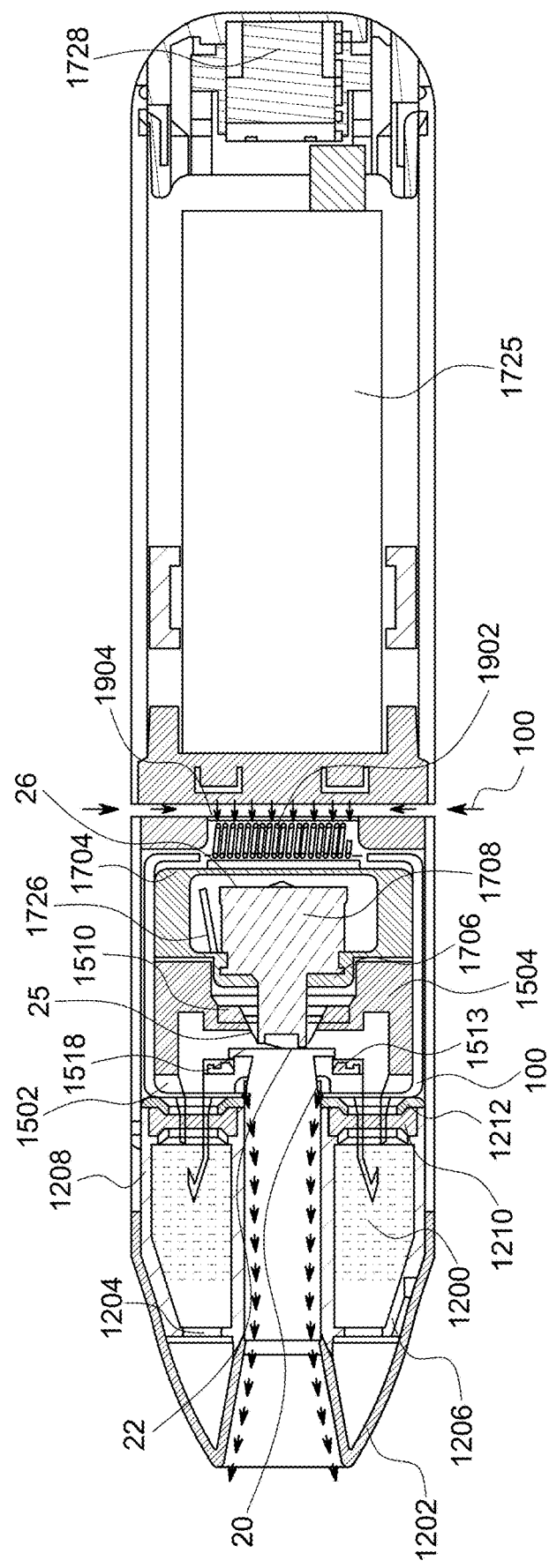
Figure 38:
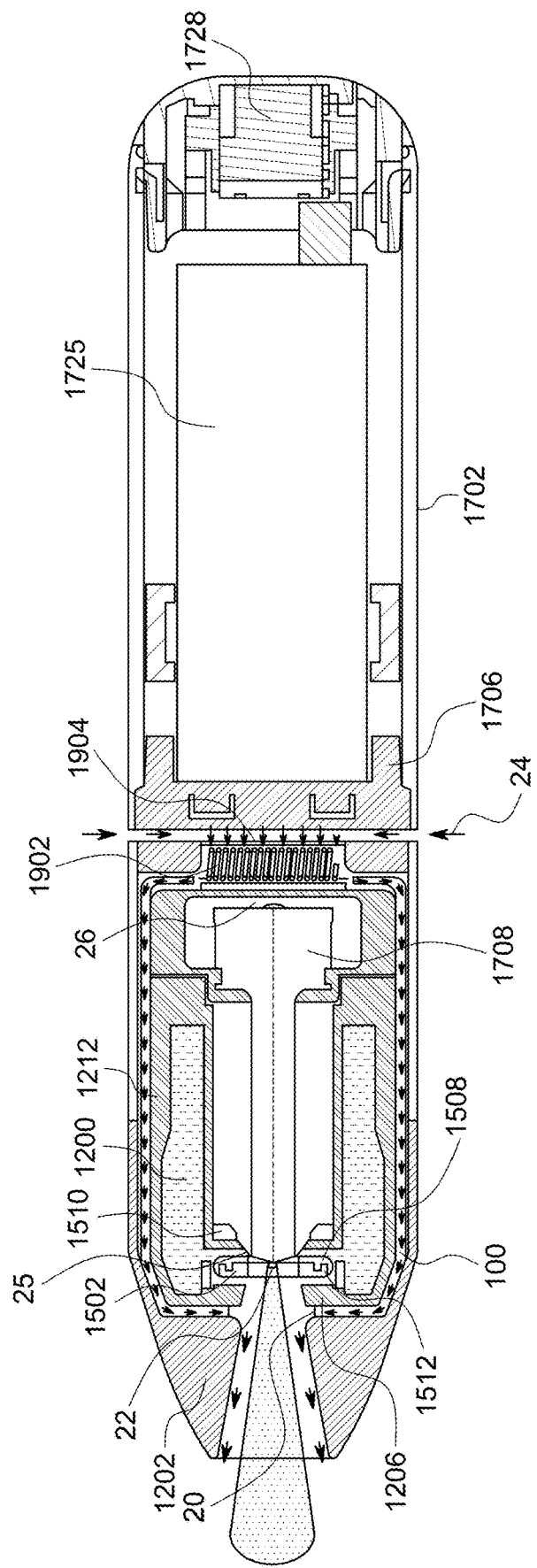
Figure 39:
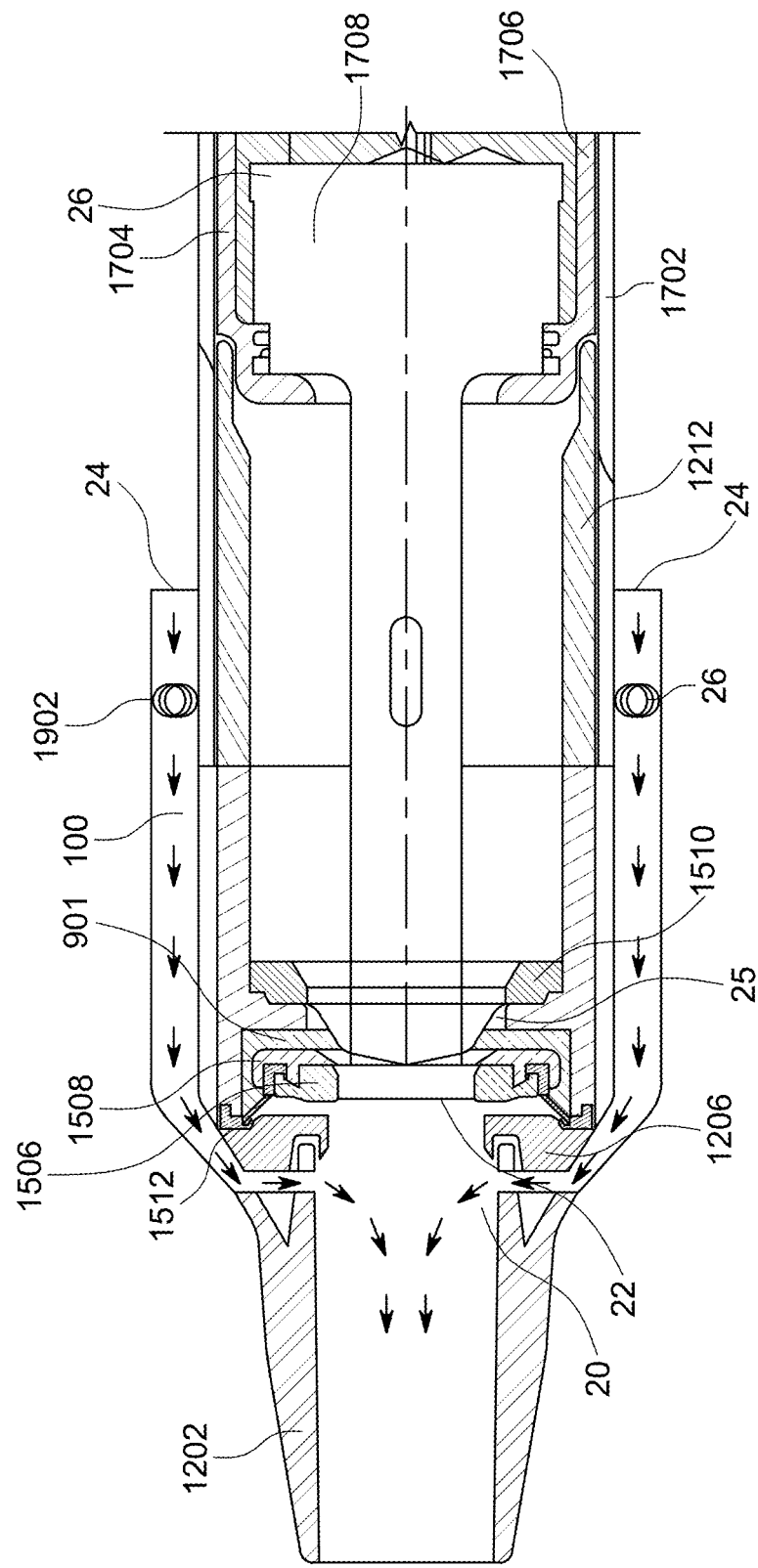
Figure 40:
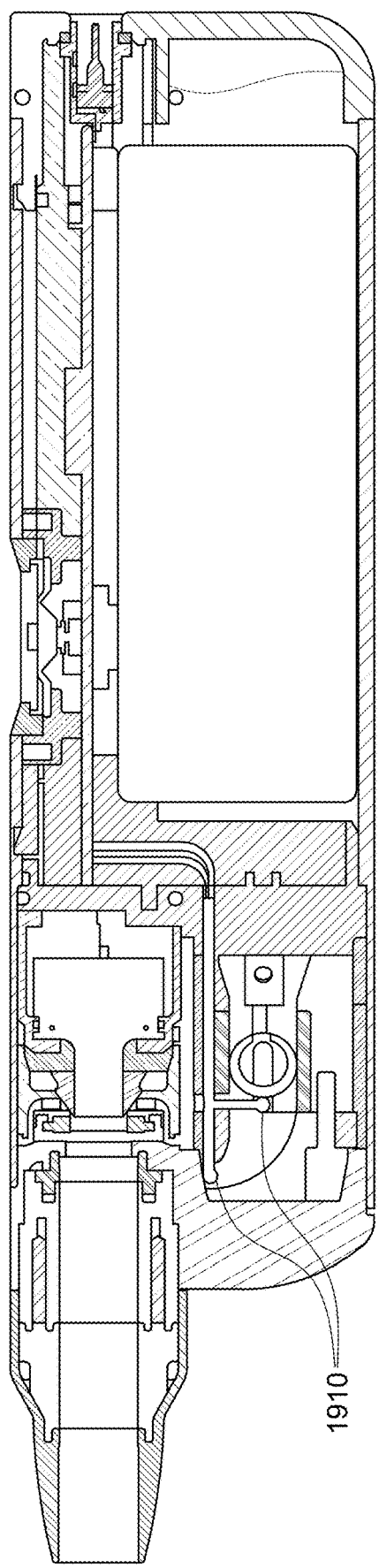
Figure 41A:
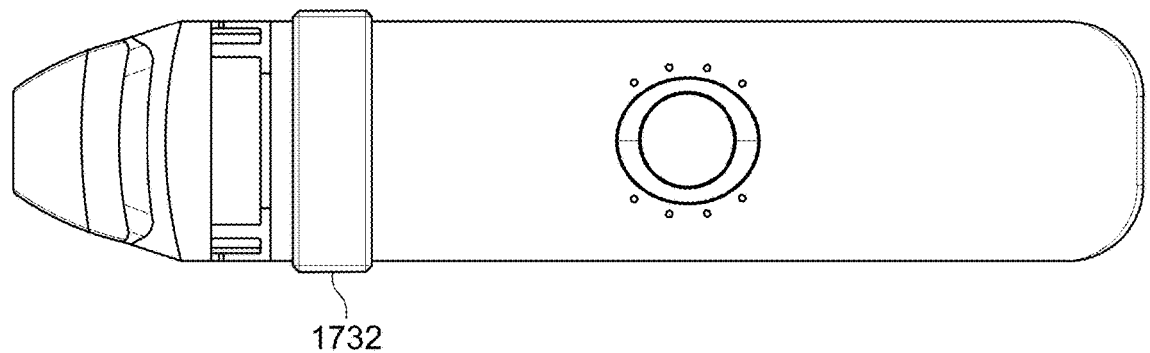
Figure 41B:
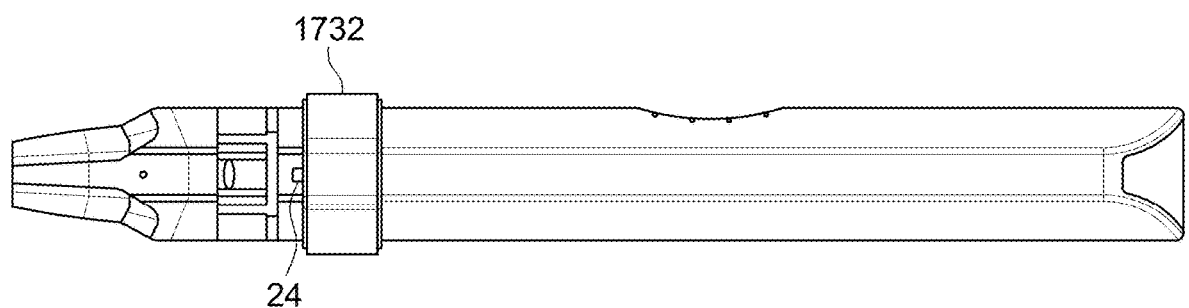
Figure 42:
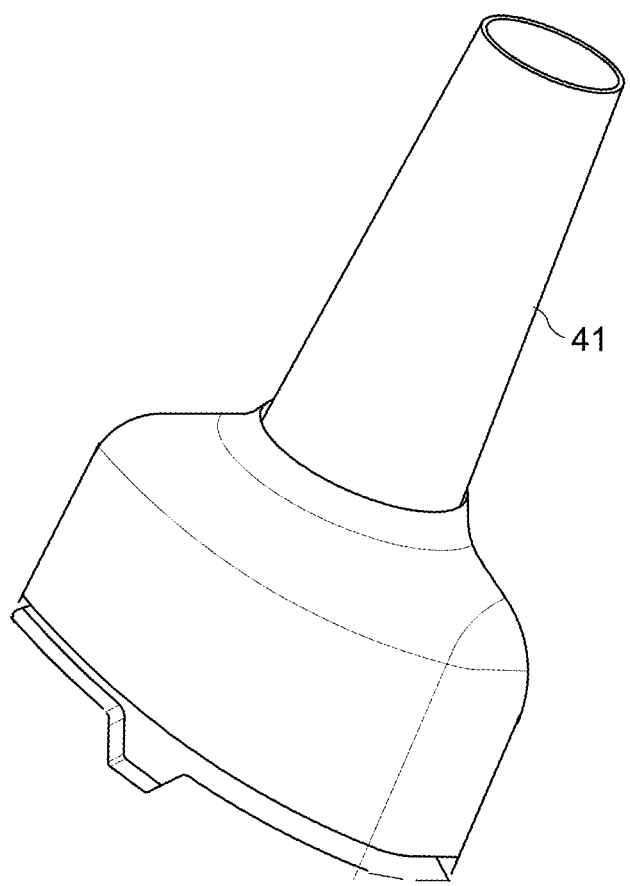
Figure 43:
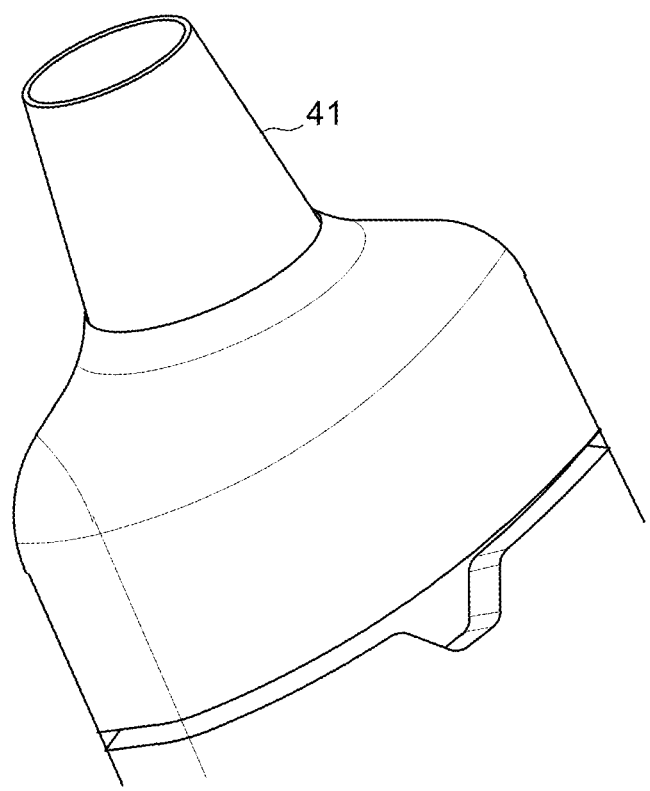

An additional embodiment of the Norway push mode device includes a heating element that increases the push mode Inhaled air temperature to roughly 50° C. to make the dose more comfortable. As with the BlueSky designs that include heating elements, the heated air temperature is kept below thermal degradation levels, so the push mode Integrity of the formulation is maintained, and no harmful by-products are produced. This can be accomplished because, as with BlueSky, the device does not depend on heat to aerosolize. FIGS. 34A and 34B illustrate one design that includes two heating elements positioned beneath the vibrating member on either side of the ejector bracket. As seen in FIGS. 34A and 34B, air enters through openings in the bottom of the ejector bracket, passes through the heating elements, and exits into the mouthpiece. Additionally, the warmer air will cause minimal evaporation of the aerosolized fluid resulting in a decrease in MMAD.

Biocompatibility

Figure 44A:
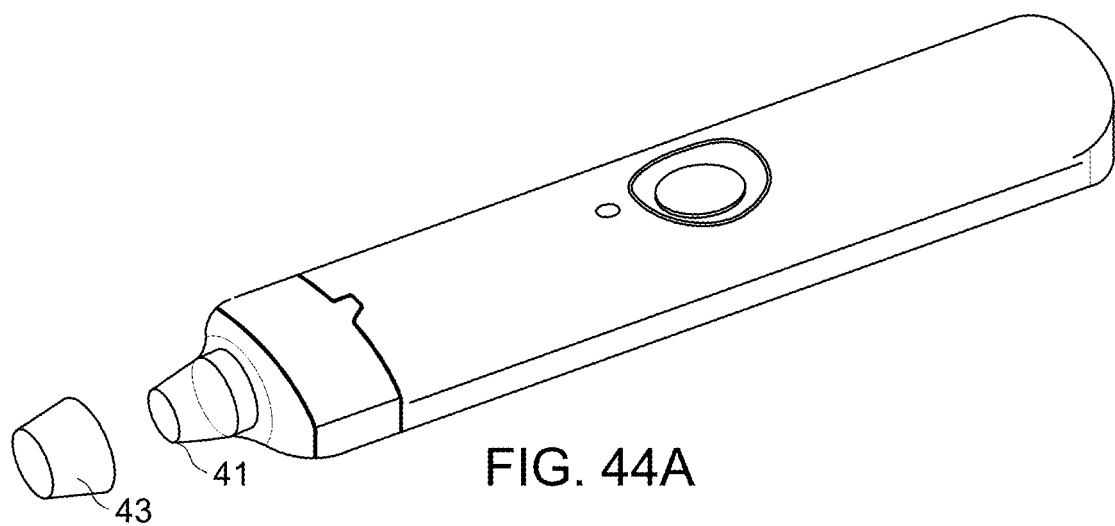
Figure 44B:
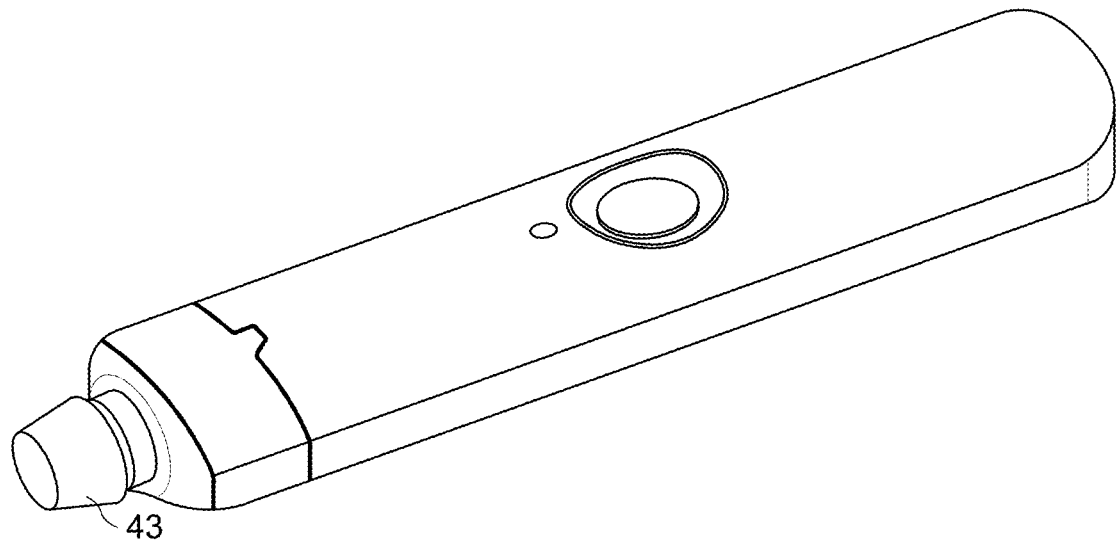
Figure 45:
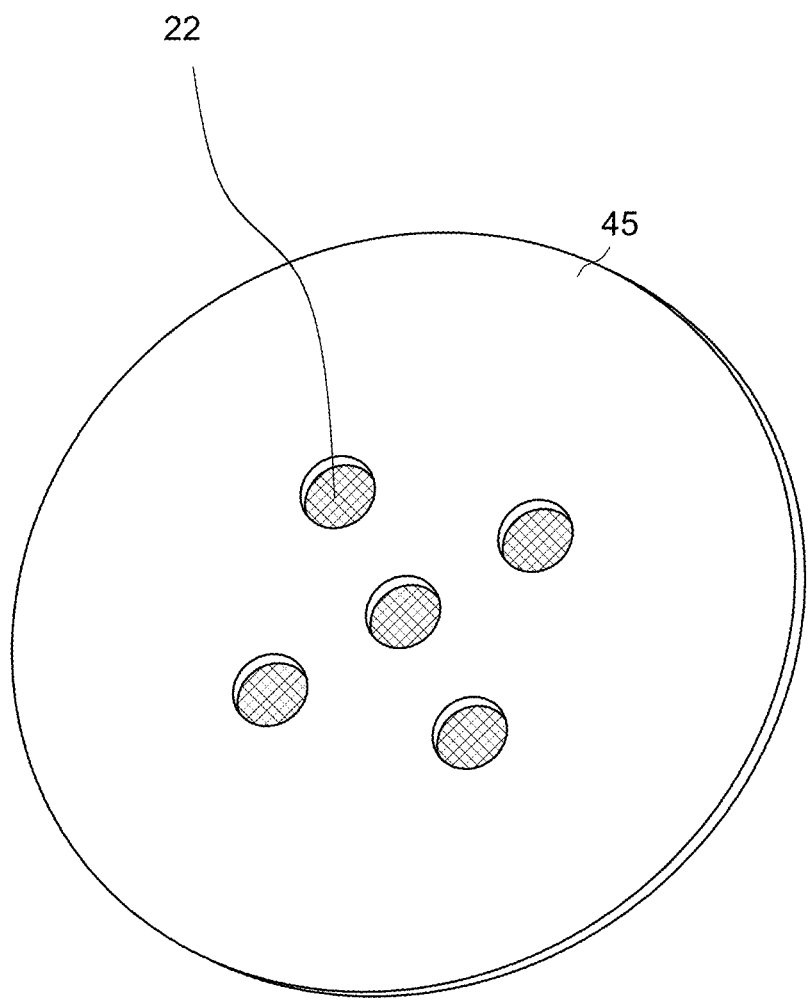
Figure 46:
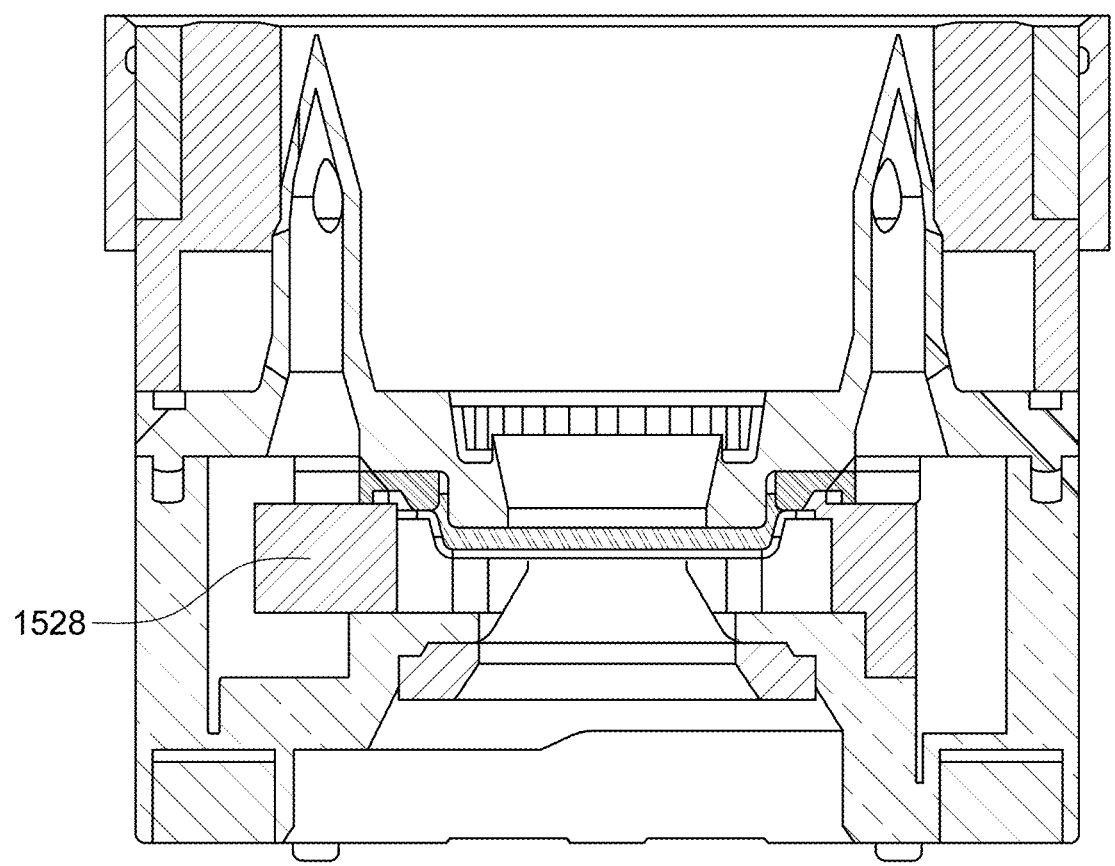
Figure 47A:
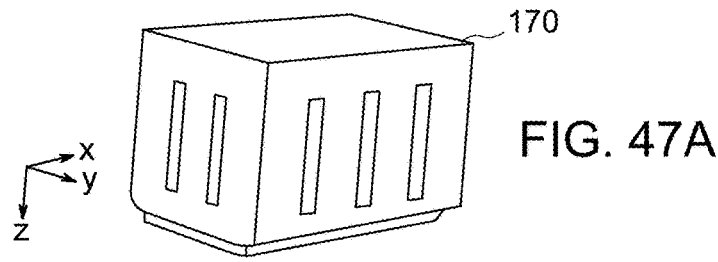
FIGS. 47A-47C illustrate a perspective view (FIG. 47A), front plan view (FIG. 47B) and side plan view (FIG. 47C) of a rectangular vibrating member tip in a droplet delivery device utilizing membrane-driven aerosolization (i.e. "push mode functionality") in accordance with one embodiment of the disclosure.
Figure 47B:
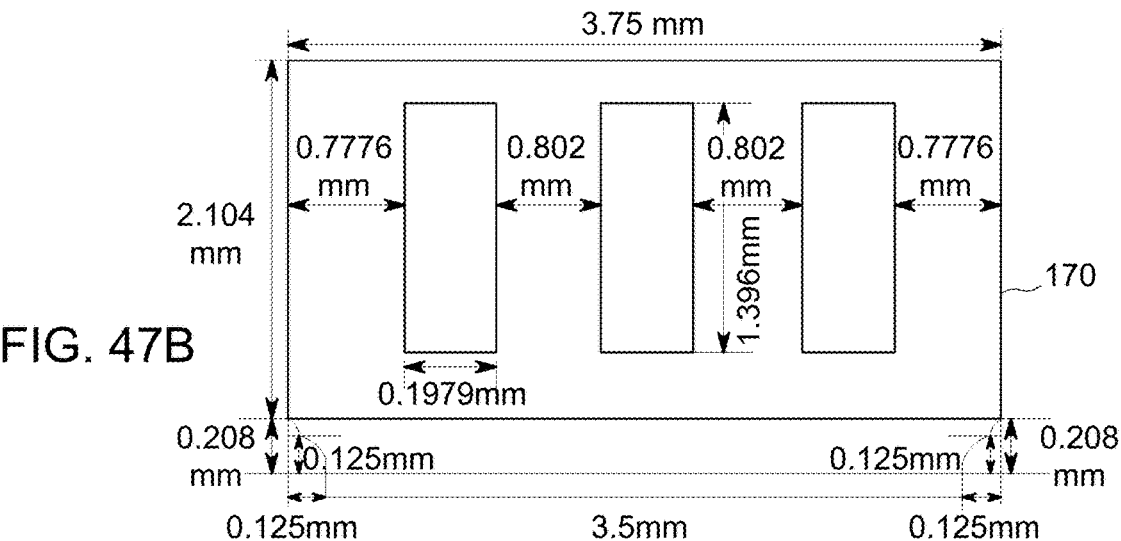
Figure 47C:
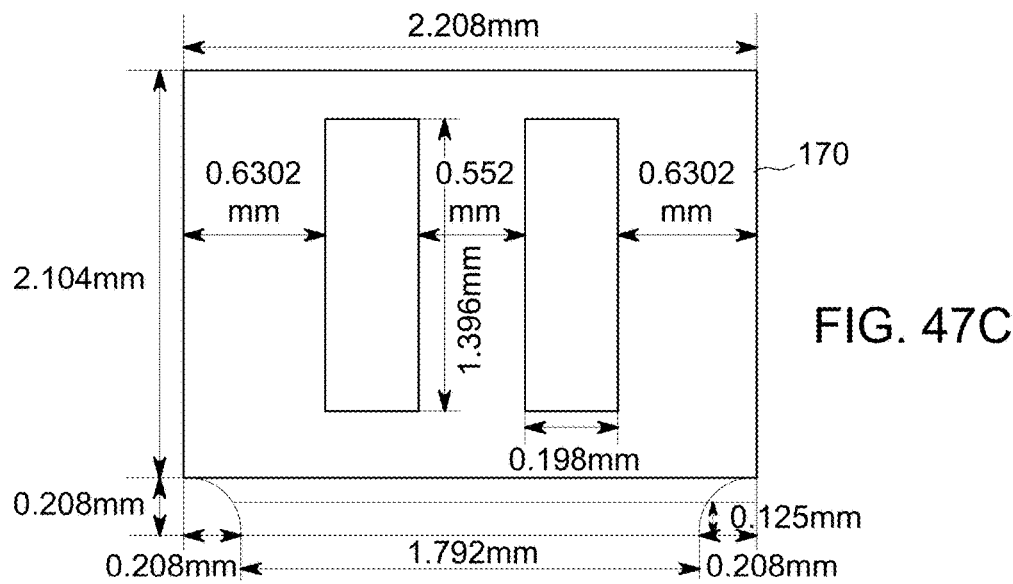

In the push mode design, the vibrating member and transducer are completely isolated from the push mode Inhaled solution by a membrane. The transducer, which typically contains heavy metals, is located behind a vibrating member, such that it is completely removed from the ejection area and fluid reservoir. The membrane separates the fluid reservoir from the vibrating member, presenting a chemically inert barrier that permits little or no diffusion, and subsequent evaporation. In one embodiment, a palladium nickel alloy mesh is used to atomize the fluid. A polyimide mesh has also been tested and was shown to be a viable option. Using a polymer mesh would significantly reduce manufacturing cost and potentially improve the extractable/leachable profile of the device. The non-metallic components in prototyped embodiments are primarily comprised of cyclic olefin copolymer (COC) and silicone, both widely accepted materials used in the medical device industry.

Heated Air Design

FIGS. 35A-35C through FIG. 38 show embodiments which include a heating element to increase the push mode I inhaled air temperature to roughly 50° C., making the dose more comfortable. Air passes perpendicularly through the heating element to be most efficiently heated. Since the heated air temperature is kept below thermal degradation levels, the push mode Integrity of the formulation is maintained, and no harmful by-products are produced. Also, the specific heat of the fluid is much greater than air; therefore, the temperature of the aerosolized fluid will heat minimally. This can be accomplished because the device does not depend on heat to aerosolize. Here, the heat is only used to optimize the user experience. Additionally, the warmer air will cause minimal evaporation of the aerosolized fluid resulting in a decrease in MMAD. Finally, the heating element will be surrounded by insulation material to keep all the components of the device insulated from heat.

The heating element is breath actuated such that the element only heats air as the user inhales. This allows the battery to have a much longer life. It also creates a much safer device in that the heating element is not always on. This can be accomplished due to the push mode Incorporation of small gauge wire. This wire heats up very quickly, so the heating element responds as soon as the user inhales.

In the embodiment shown in FIGS. 35A-35C, after air enters the device, the air pathway is narrowed by the airflow accelerator to increase velocity. Then, the air is passed through the heating element, which is positioned in the heat exchange area. Finally, the heated air flows into the mouthpiece. FIGS. 35A-35C features three views of this embodiment. This design allows for a larger battery to be installed in the device which supplements the heating element.

Referring to FIG. 36, a speaker can also be incorporated into any of the heated air BlueSky embodiments. This will allow for an additional sensory experience for the user (i.e., crackling/heating sound upon inhalation).

In the embodiments shown in FIG. 37 and FIG. 38, the heating element is positioned below the vibrating member in a separate chamber inside the enclosure. The air enters through the airflow inlet, is passed through the heating element, and exits above the ejector. This design can be used in the two-part cartridge design (FIG. 37) or the single piece cartridge design (FIG. 98). These embodiments offer the advantage of a more compact device, compared to the embodiment shown in FIGS. 35A-35C, at the cost of battery life.

Another embodiment features external heating elements seated on the outside of the enclosure (FIG. 39). Air passes through the heating elements, enters the mouthpiece above the mesh, and exits through the end of the mouthpiece. This design may in some embodiments provide a removable heating element.

In another embodiment of a heated air push mode device, closed loop control is used to regulate the power delivered to the heating element. The power is adjusted to keep the airstream temperature constant and at safe levels. Referring to FIG. 40, the airstream temperature is measured by a temperature sensor such as an RTD. The power delivered to the heating element changes as a result of the temperature sensor readings.

In another embodiment of the heated air push mode device, open loop control is used to regulate the power delivered to the heating element. The power is adjusted to keep the airstream temperature constant. The pressure drop from inhalation is sensed. The amount of power needed to supply the heating element to keep the air stream temperature constant due to changes in pressure drop is known. A look-up table is created to determine the amount of power needed to supply the heating element to keep the air stream temperature constant based upon the pressure sensor value.

In another embodiment of the heated air push mode device, one or more of the push mode Internal device components that are in contact with heated air is preferably made of metal (i.e., aluminum, Inconel, etc.). This will insulate the heating element and enhance biocompatibility of the device.

In another embodiment of the heated air push mode device, any component that could be compromised by the heated air is preferably made of metal (i.e., titanium, aluminum, Inconel, etc.). These components include, but are not limited to the mouthpiece, the heating chamber, and like components that heated air could negatively affect.

In one embodiment of the heated air push mode device, the metal components that are in contact with the heated air are preferably made of a material with a low thermal conductivity, such as Inconel.

In one embodiment of the heated air push mode device, ceramic is used to insulate the heating element.

Adjustable Air Resistance Design

Another embodiment of push mode incorporates a mechanism to adjust the size of the airflow inlets. The airflow inlets can be opened and closed using a sleeve or an adjustable aperture. In this way, the resistance experienced by the user can be adjusted to individual preferences. FIGS. 41A and 41B show a BlueSky device with a sliding sleeve 1732 around the enclosure. The sleeve can be adjusted to partially or completely cover the airflow inlets, increasing the resistance felt by the user. Additionally, the airflow in the mouthpiece will change as the position of the sleeve is changed. This will also change the MMAD of the dose due to changes in the airflow current.

Nasal Device Embodiments

BlueSky push mode has also been adapted for nasal inhalation. FIGS. 42-44 show several embodiments of a nasal BlueSky push mode device. As seen in FIGS. 42-44, there are multiple variations of the push mode Inhalation port. However, preferable embodiments of the nasal device have longer and narrower inhalation ports (see FIG. 42) than in other designs with shorter inhalation ports (see FIG. 43)

for optimal nostril use. As seen in FIG. 44, a cap may be added to protect the push mode Inhalation port and keep it clean. The preferred droplet sizes are between 1-110 micron range, but 2-23 microns is preferred.

Additional Features

Hydrophilic/Hydrophobic Tubes

Figure 57A:
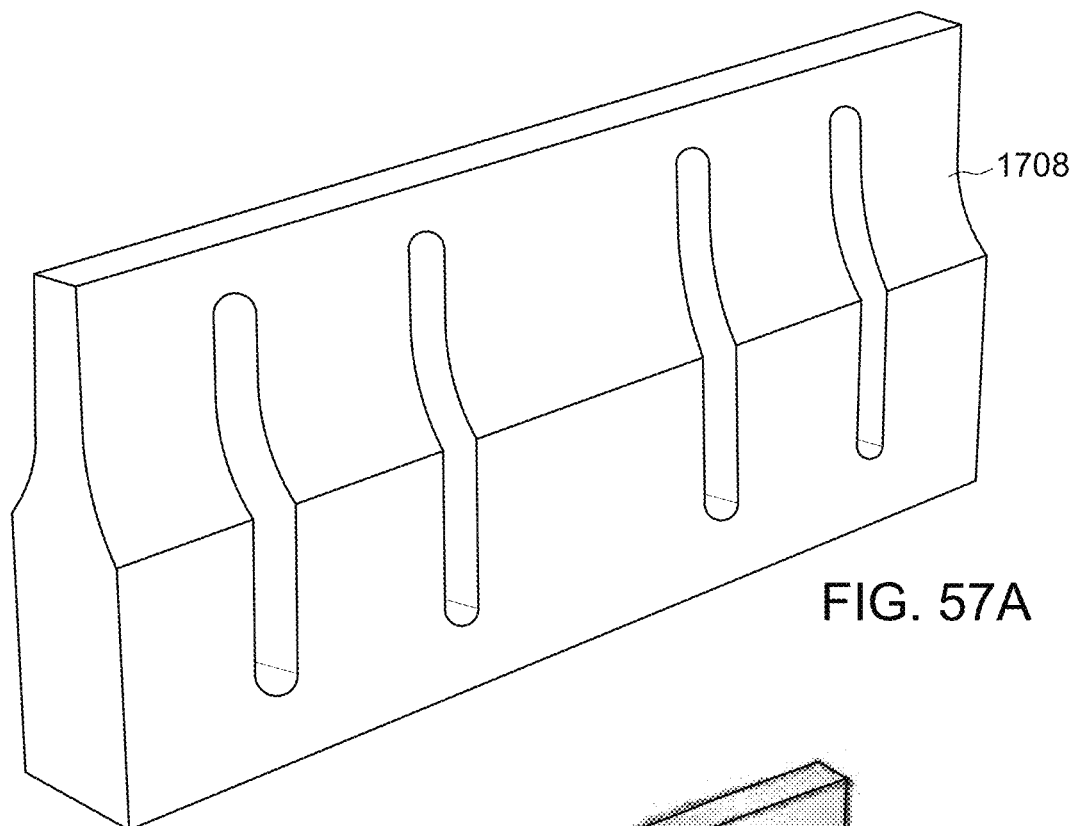
FIGS. 57A and 57B illustrate an unoptimized bar vibrating member and the resulting vibration amplitude map in a droplet delivery device utilizing membrane-driven aerosolization (i.e. "push mode functionality") in accordance with one embodiment of the disclosure.
Figure 57B:
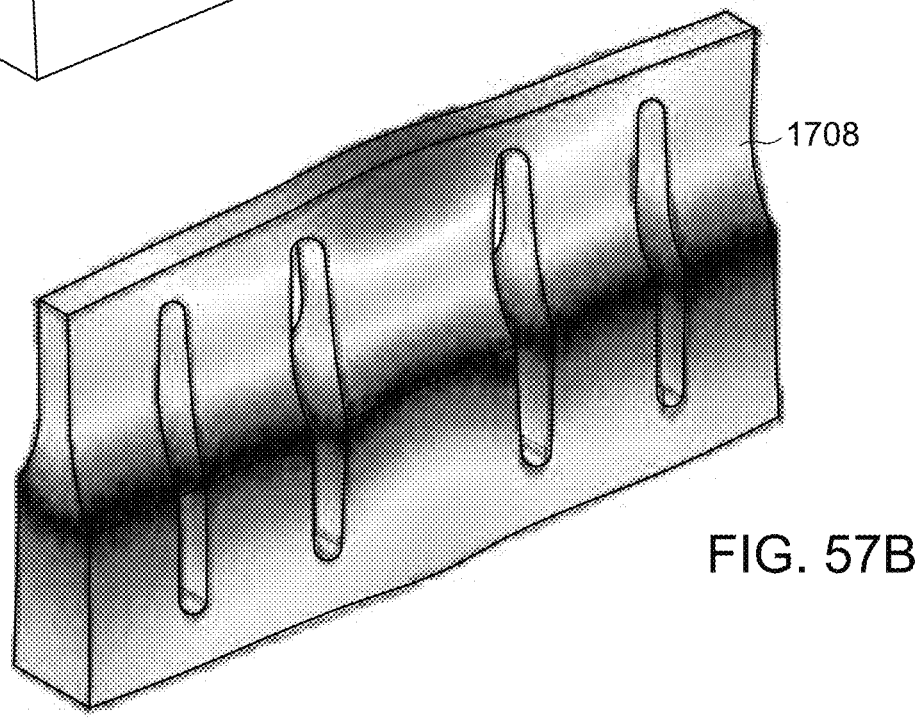
Figure 58A:
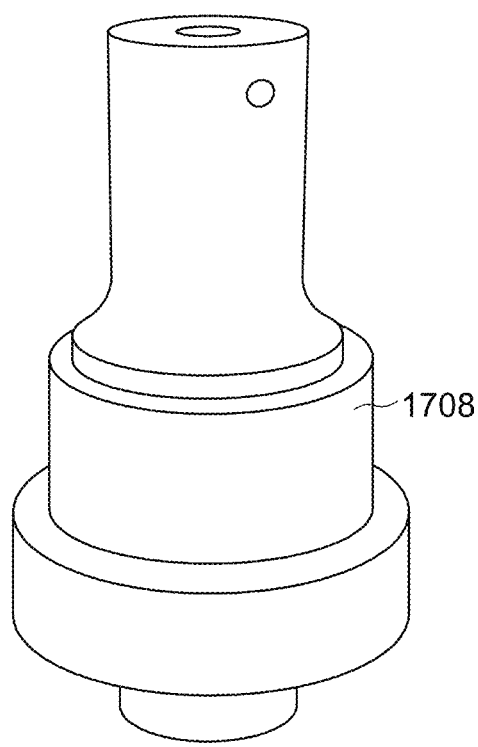
FIGS. 58A and 58B illustrate a perspective view (FIG. 58A) and cross-sectional vibration amplitude view (58B) of a booster vibrating member and the resulting vibration amplitude map in a droplet delivery device utilizing membrane-driven aerosolization (i.e. "push mode functionality") in accordance with one embodiment of the disclosure.
Figure 58B:
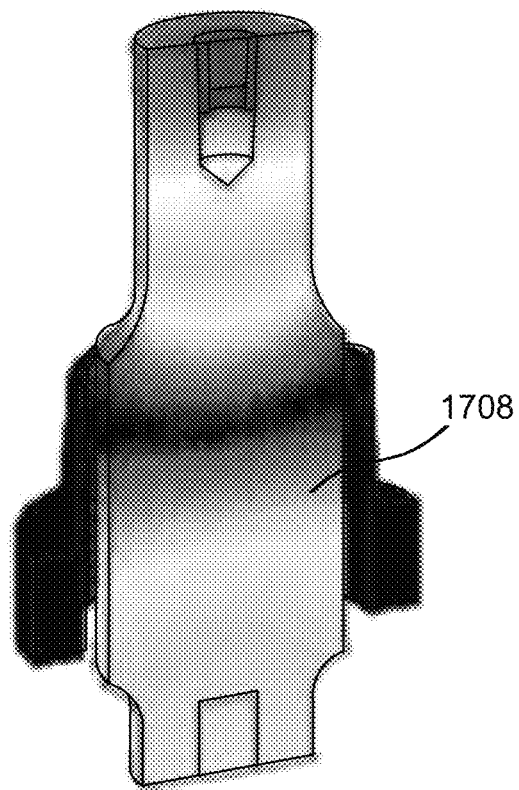
Figure 59A:
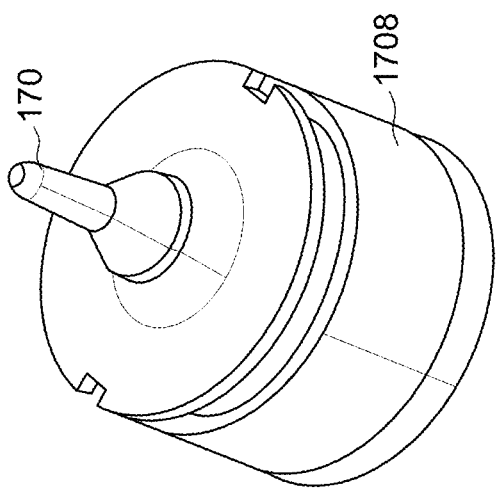
FIGS. 59A-59C illustrate a perspective view (FIG. 59A), top plan view (FIG. 59B) and front plan view (FIG. 59C) of an alternative vibrating member that couples to a transducer of droplet delivery devices in accordance with an embodiment of the disclosure.
Figure 59B:
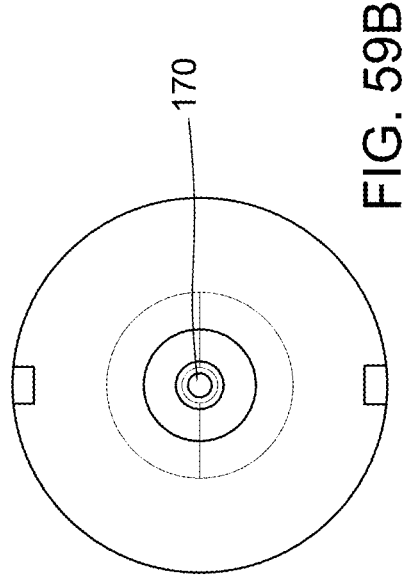
Figure 59C:
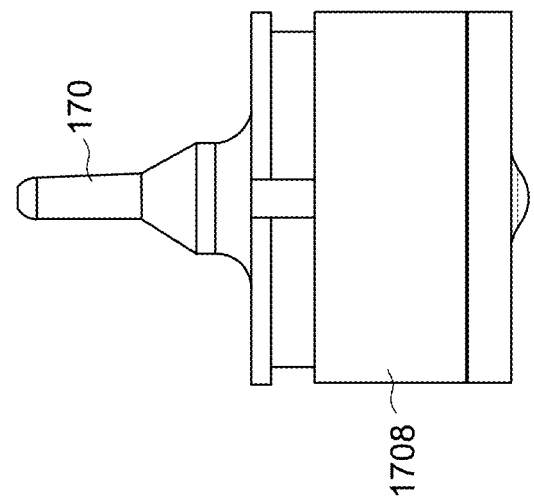
Figure 60A:
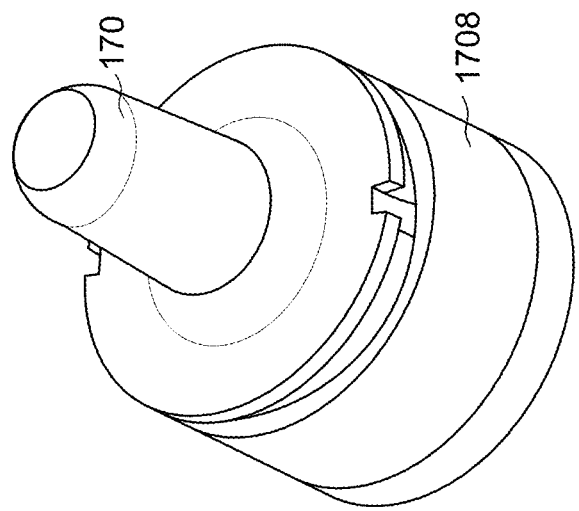
FIGS. 60A-60C illustrate a perspective view (FIG. 60A), top plan view (FIG. 60B) and front plan view (FIG. 60C) of an alternative vibrating member that couples to a transducer of droplet delivery devices in accordance with an embodiment of the disclosure.
Figure 60C:
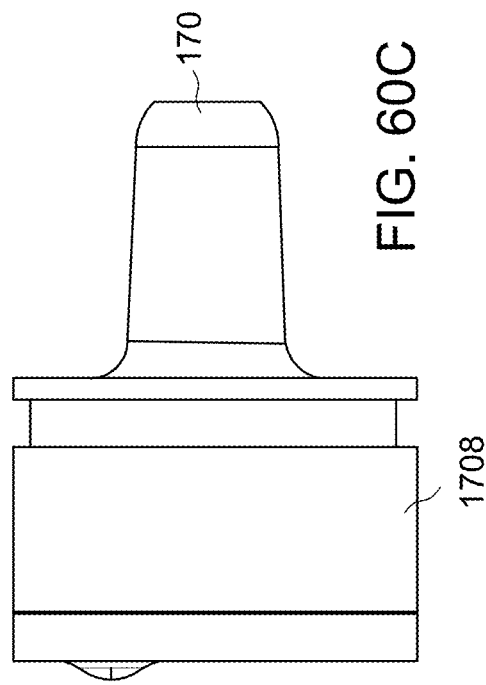
Figure 60B:
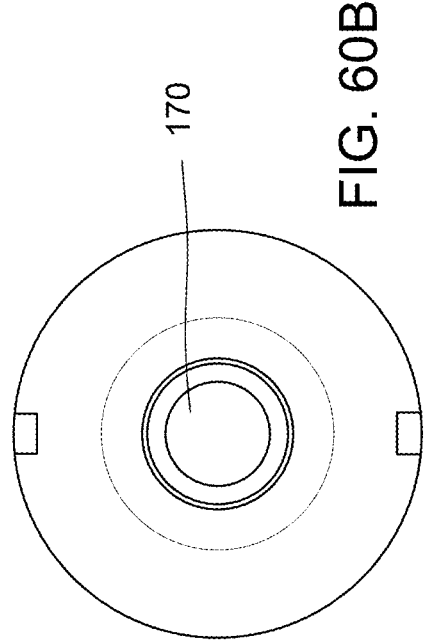
Figure 61A:
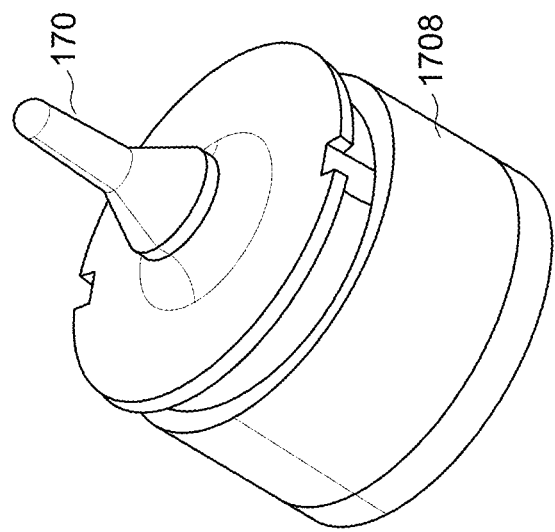
FIGS. 61A-61C illustrate a perspective view (FIG. 61A), top plan view (FIG. 61B) and front plan view (FIG. 61C) of an alternative vibrating member that couples to a transducer of droplet delivery devices in accordance with an embodiment of the disclosure.
Figure 61C:
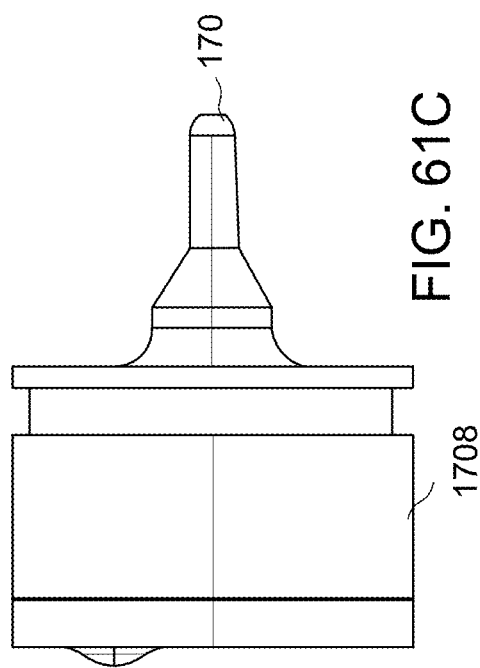
Figure 61B:
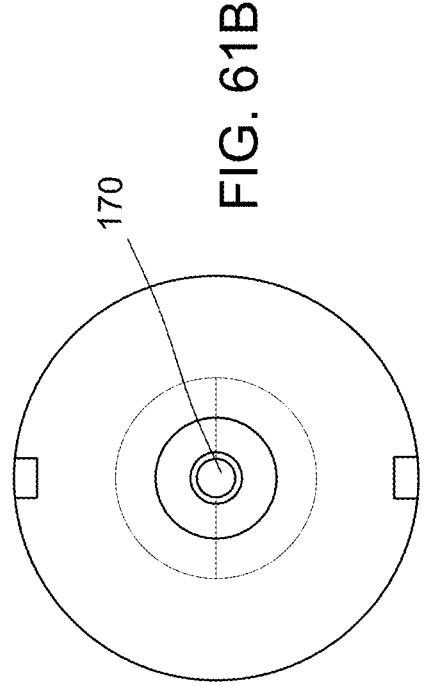
Figure 62A:
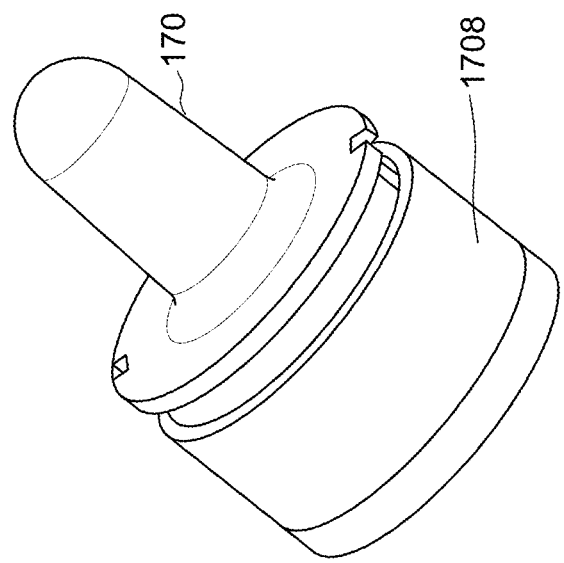
FIGS. 62A-62C illustrate a perspective view (FIG. 62A), top plan view (FIG. 62B) and front plan view (FIG. 62C) of an alternative vibrating member that couples to a transducer of droplet delivery devices in accordance with an embodiment of the disclosure.
Figure 62C:
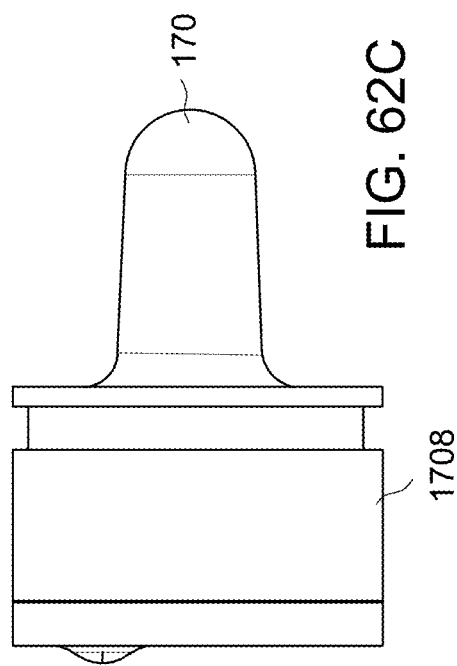
Figure 62B:
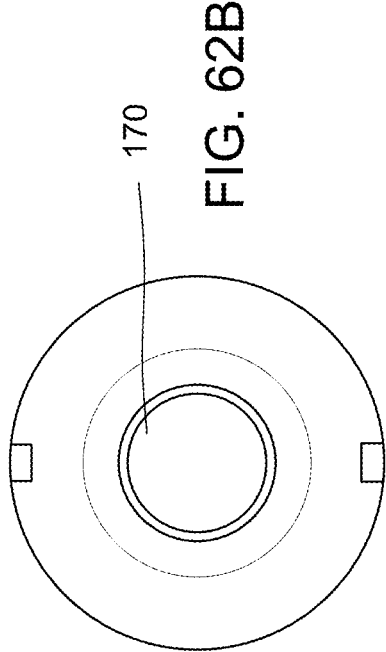
Figure 63A:
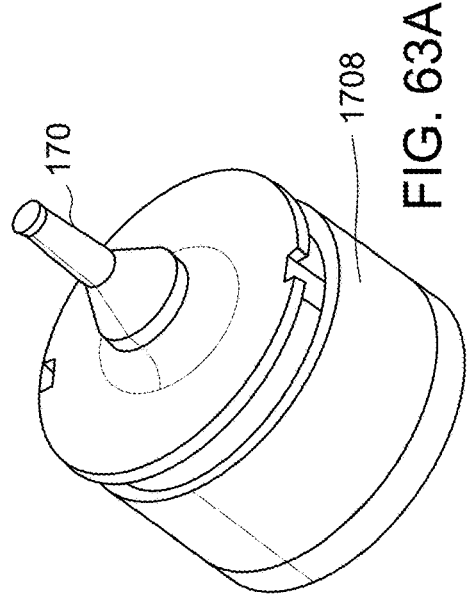
FIGS. 63A-63C illustrate a perspective view (FIG. 63A), top plan view (FIG. 63B) and front plan view (FIG. 63C) of an alternative vibrating member that couples to a transducer of droplet delivery devices in accordance with an embodiment of the disclosure.
Figure 63C:
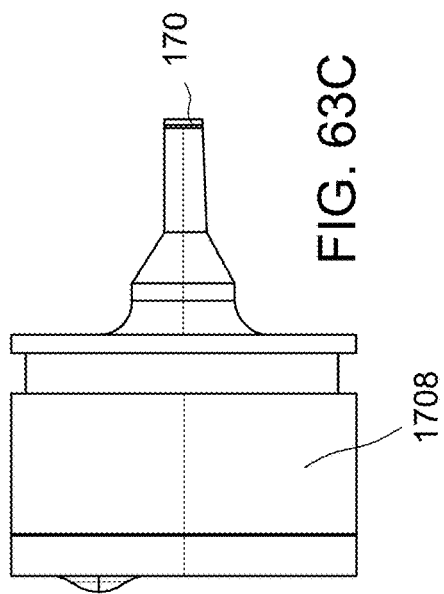
Figure 63B:
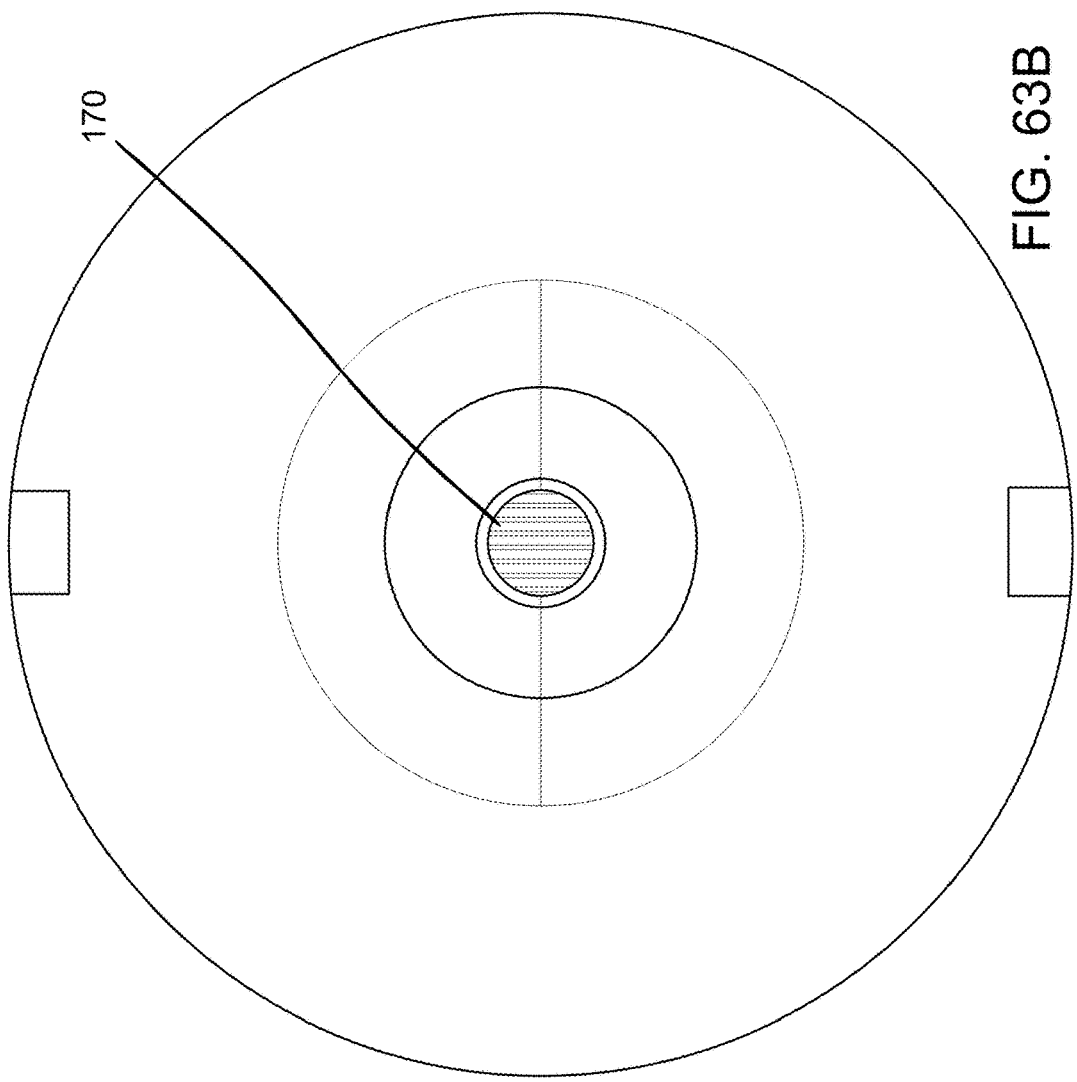
Figure 64A:
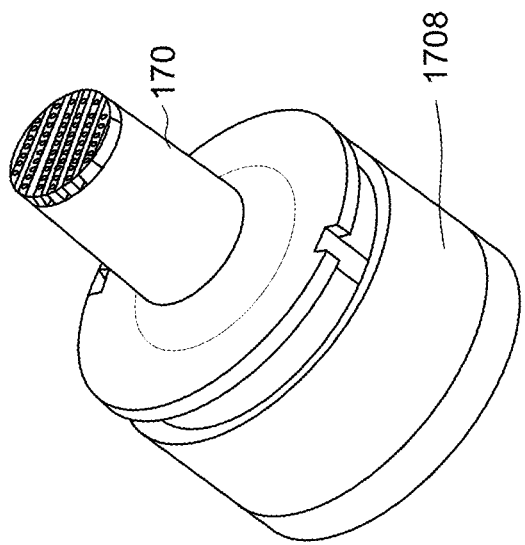
FIGS. 64A-64C illustrate a perspective view (FIG. 64A), top plan view (FIG. 64B) and front plan view (FIG. 64C) of an alternative vibrating member that couples to a transducer of droplet delivery devices in accordance with an embodiment of the disclosure.
Figure 64C:
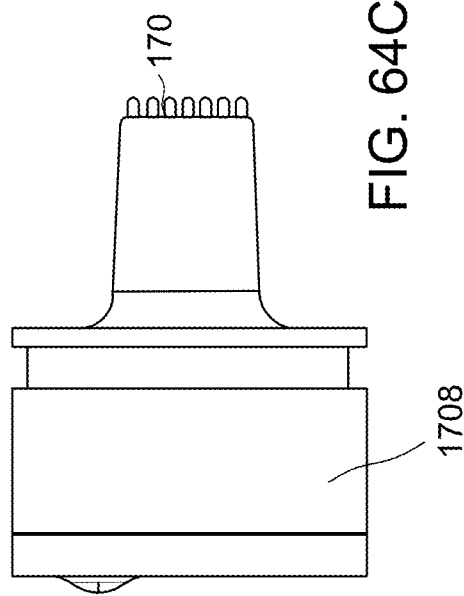
Figure 64B:
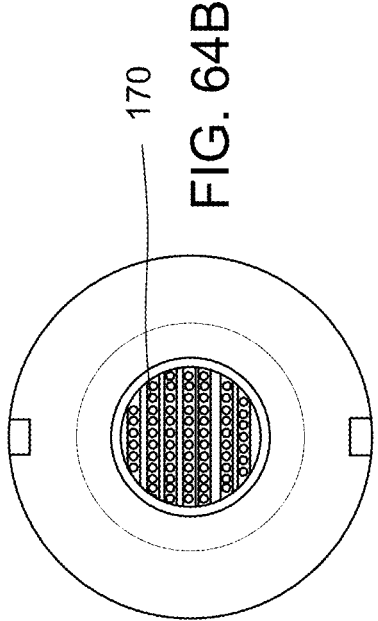
Figure 65A:
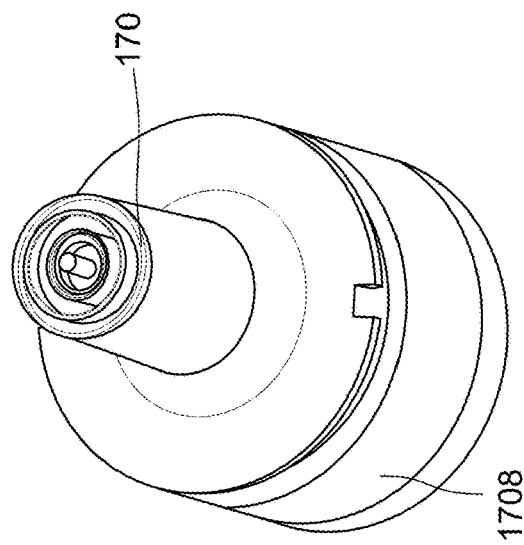
FIGS. 65A-65D illustrate a perspective view (FIG. 65A), top plan view (FIG. 65B), front plan view (FIG. 65C) and cross-sectional view along A-A of FIG. 65B (FIG. 65D) of an alternative vibrating member that couples to a transducer of droplet delivery devices in accordance with an embodiment of the disclosure.
Figure 65D:
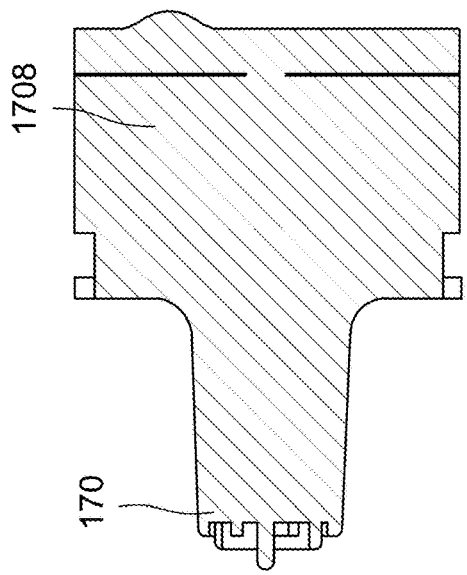
Figure 65B:
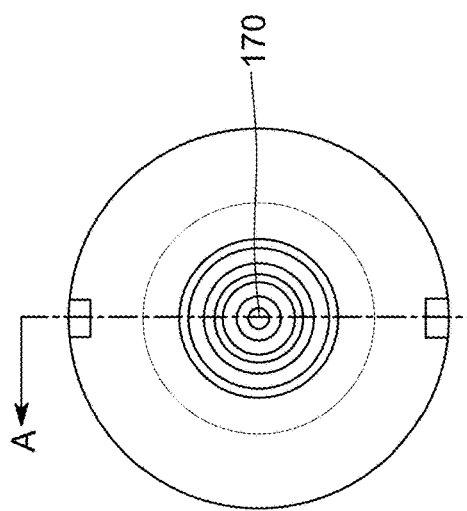
Figure 65C:
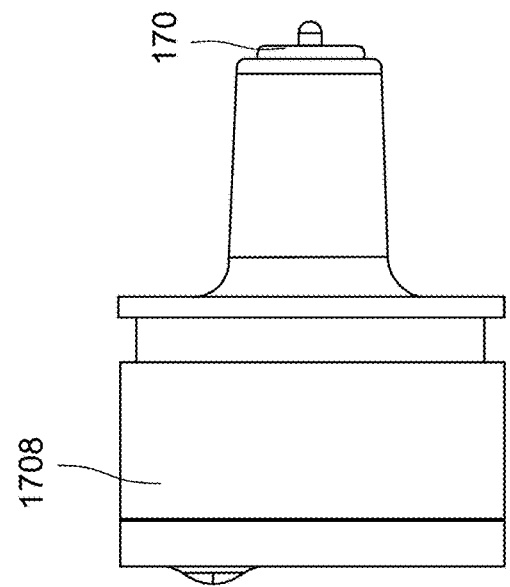
Figure 66A:
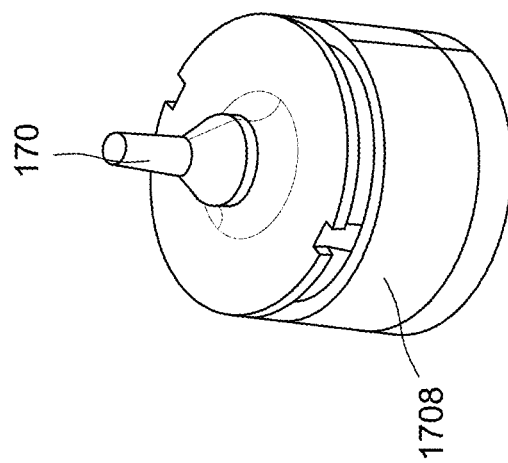
FIGS. 66A-66C illustrate a perspective view (FIG. 66A), top plan view (FIG. 66B) and front plan view (FIG. 66C) of an alternative vibrating member that couples to a transducer of droplet delivery devices in accordance with an embodiment of the disclosure.
Figure 66C:
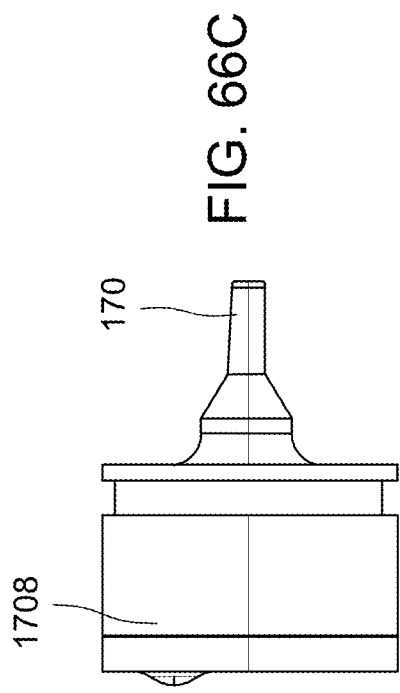
Figure 66B:
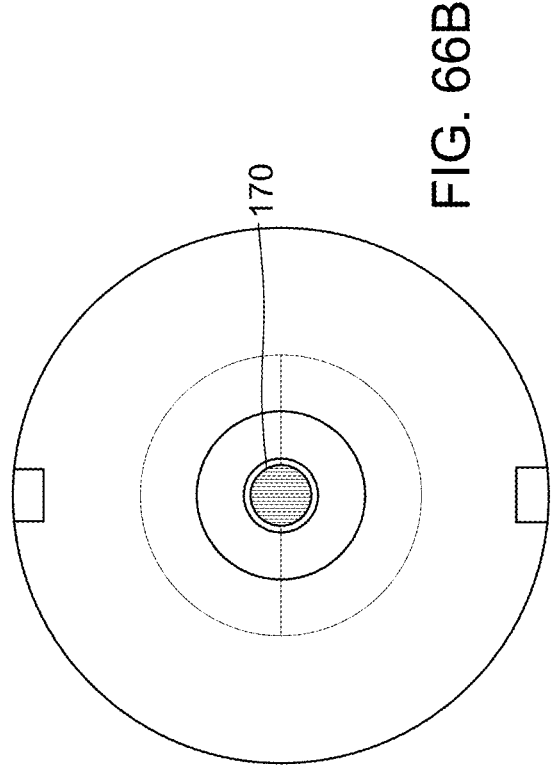
Figure 67A:
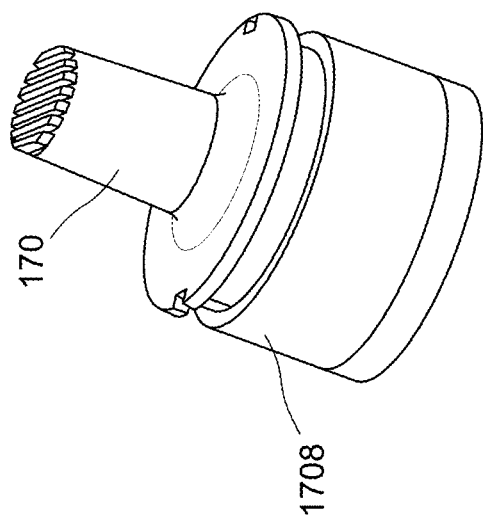
FIGS. 67A-67C illustrate a perspective view (FIG. 67A), top plan view (FIG. 67B) and front plan view (FIG. 67C) of an alternative vibrating member that couples to a transducer of droplet delivery devices in accordance with an embodiment of the disclosure.
Figure 67C:
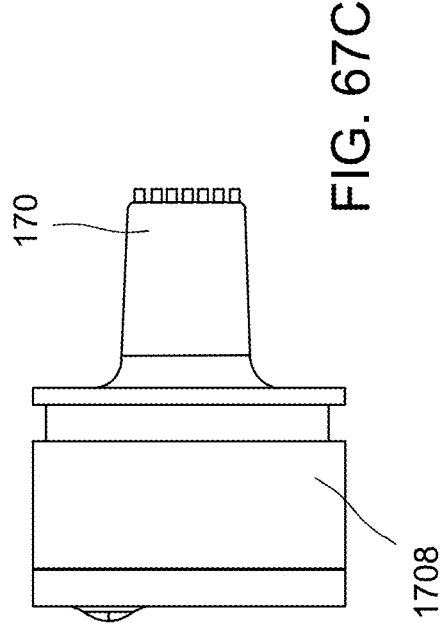
Figure 67B:
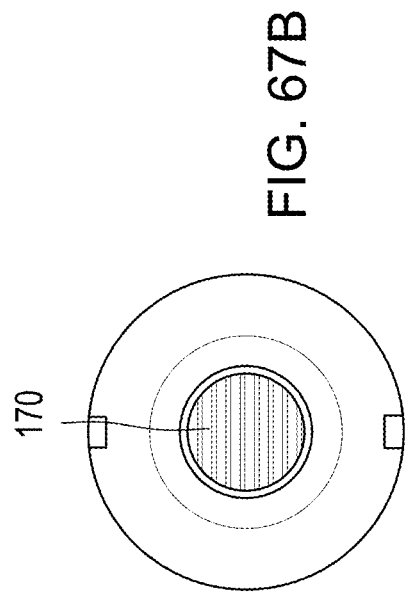
Figure 68A:
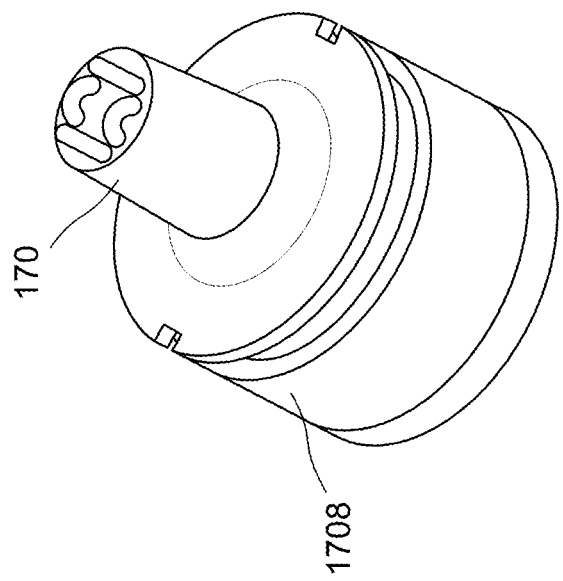
FIGS. 68A-68D illustrate a perspective view (FIG. 68A), top plan view (FIG. 66B), front plan view (FIG. 66C) and side plan view (66D) of an alternative vibrating member that couples to a transducer of droplet delivery devices in accordance with an embodiment of the disclosure.
Figure 68B:
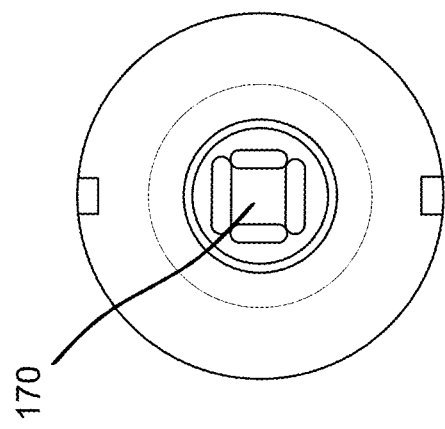
Figure 68C:
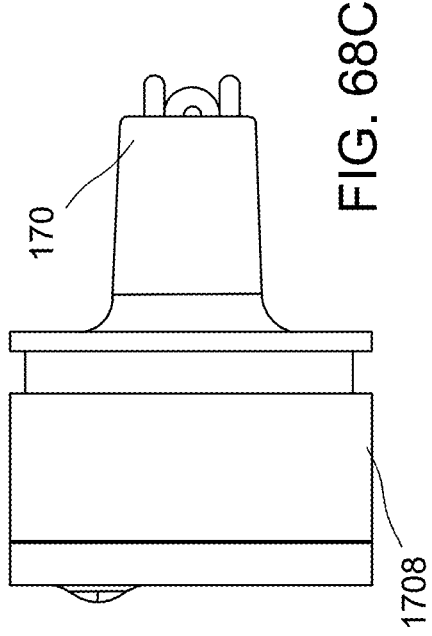
Figure 68D:
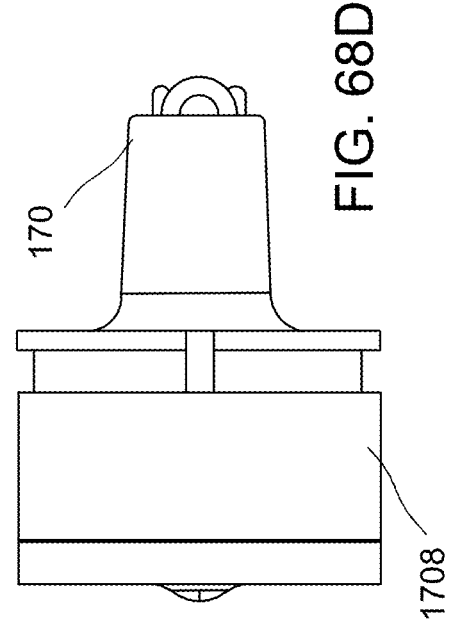
Figure 69B:
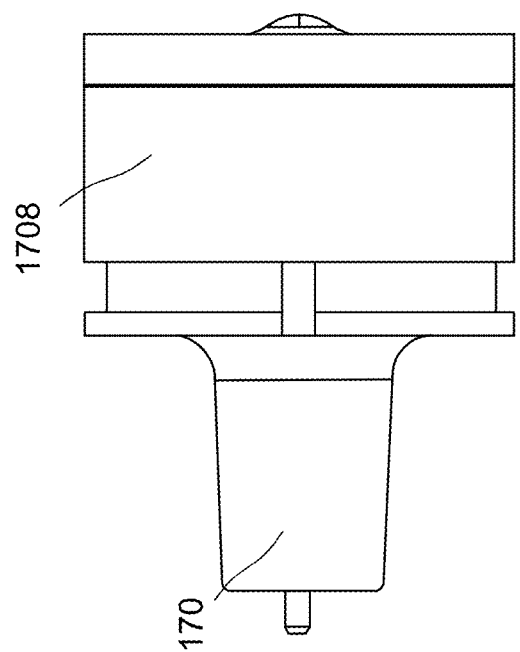
FIGS. 69A and 69B illustrate a perspective view (FIG. 69A) and side plan view (FIG. 69B) of an alternative vibrating member that couples to a transducer of droplet delivery devices in accordance with an embodiment of the disclosure.
Figure 69A:
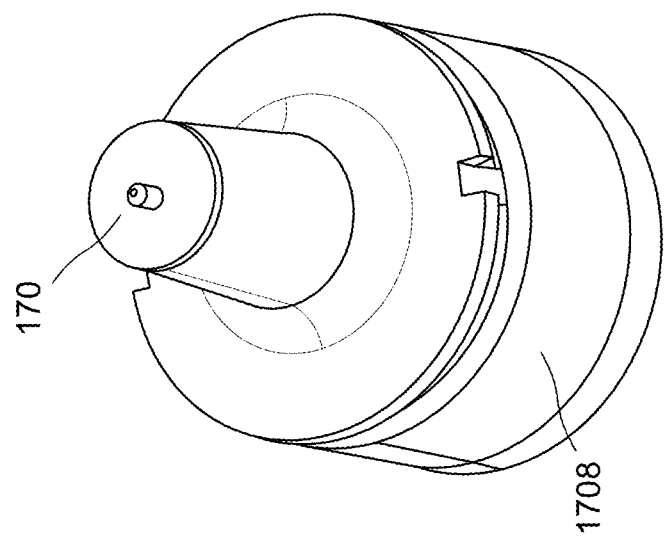
Figure 70B:
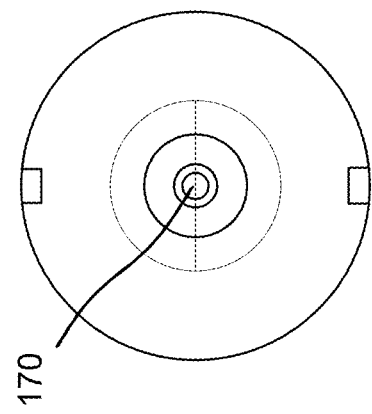
FIGS. 70A-70C illustrate a perspective view (FIG. 70A), top plan view (FIG. 70B) and front plan view (FIG. 70C) of an alternative vibrating member that couples to a transducer of droplet delivery devices in accordance with an embodiment of the disclosure.
Figure 70C:
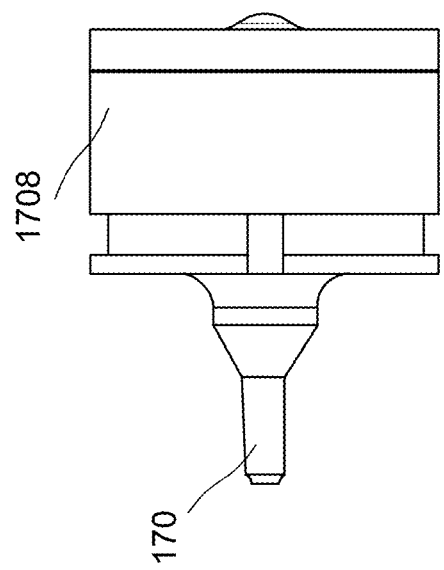
Figure 70A:
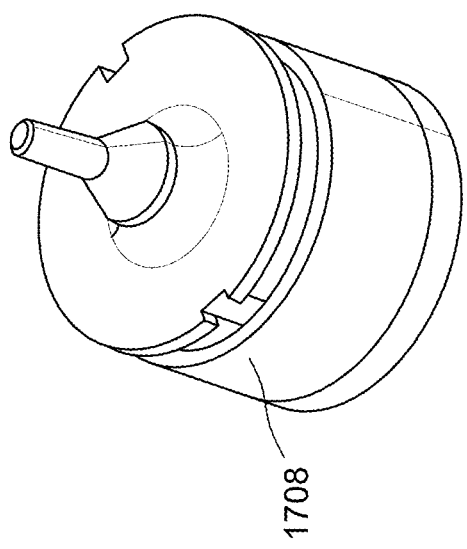
Figure 73A:
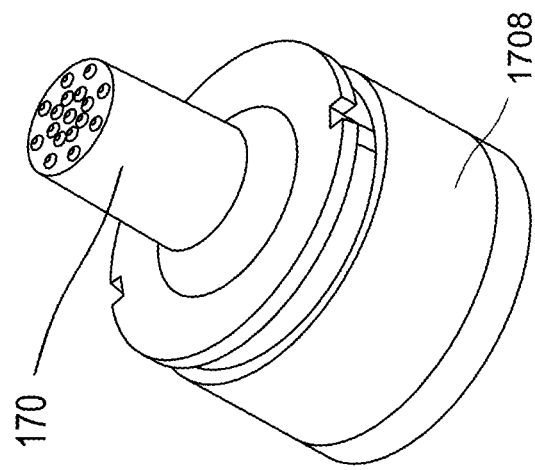
FIGS. 73A-73C illustrate a perspective view (FIG. 73A), top plan view (FIG. 73B) and front plan view (FIG. 73C) of an alternative vibrating member that couples to a transducer of droplet delivery devices in accordance with an embodiment of the disclosure.
Figure 73C:
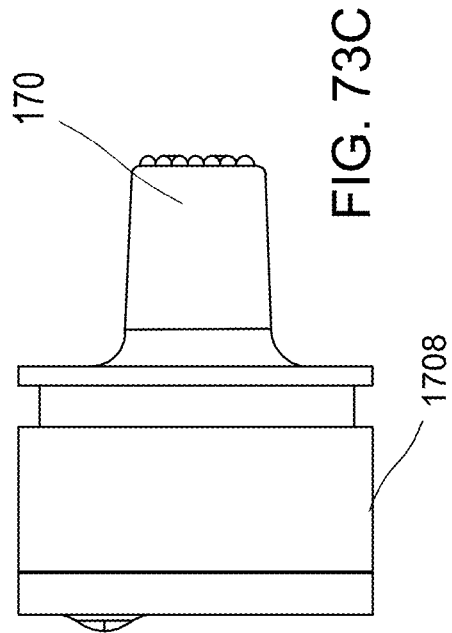
Figure 73B:
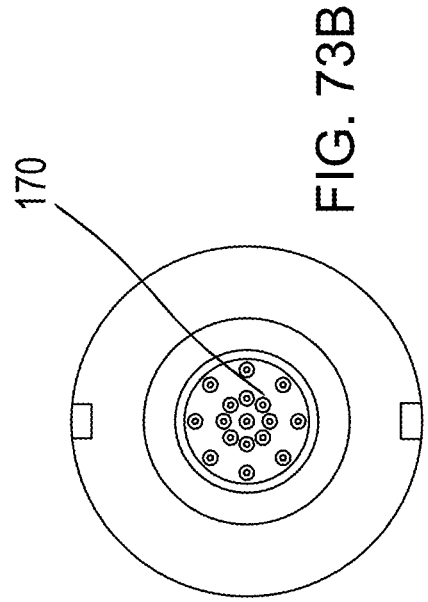
Figure 74A:
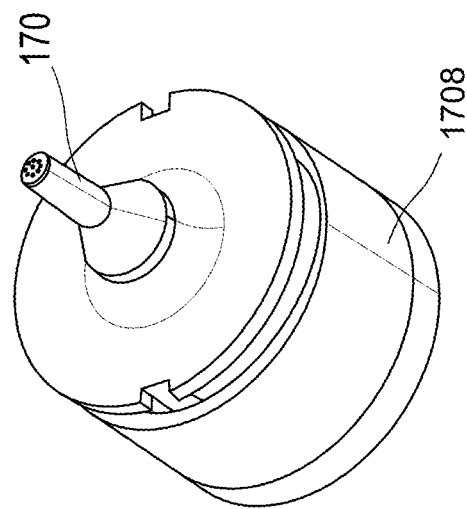
FIGS. 74A-74C illustrate a perspective view (FIG. 74A), top plan view (FIG. 74B) and front plan view (FIG. 74C) of an alternative vibrating member that couples to a transducer of droplet delivery devices in accordance with an embodiment of the disclosure.
Figure 74C:
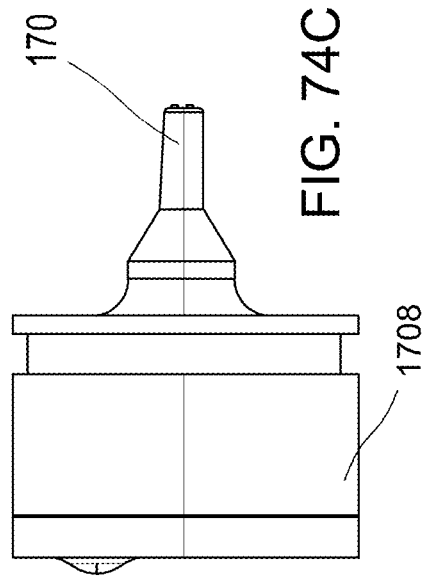
Figure 74B:
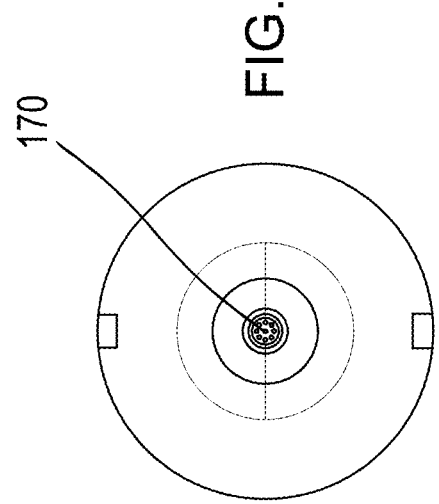
Figure 75A:
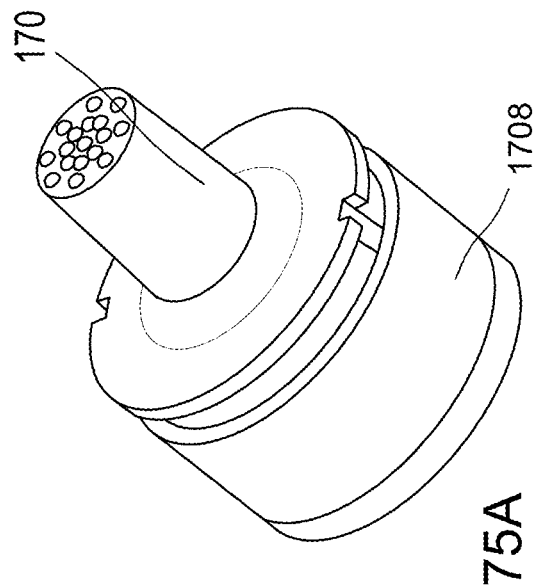
FIGS. 75A-75C illustrate a perspective view (FIG. 75A), top plan view (FIG. 75B) and front plan view (FIG. 75C) of an alternative vibrating member that couples to a transducer of droplet delivery devices in accordance with an embodiment of the disclosure.
Figure 75C:
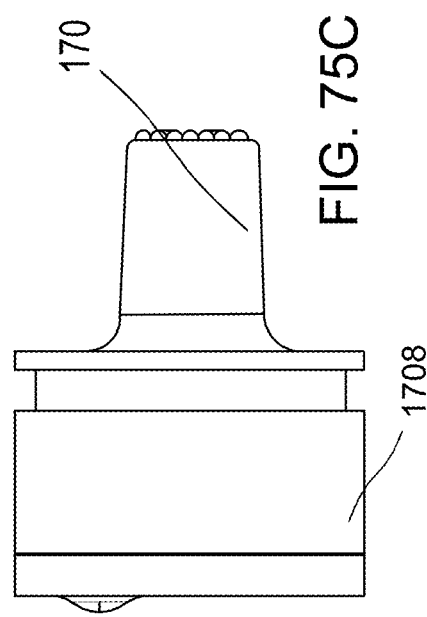
Figure 75B:
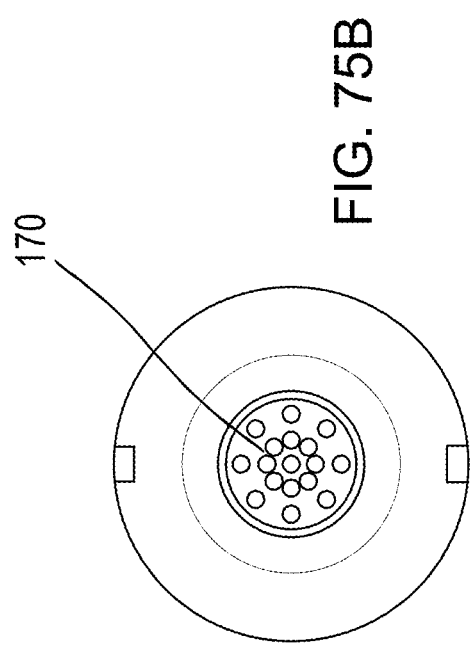
Figure 76A:
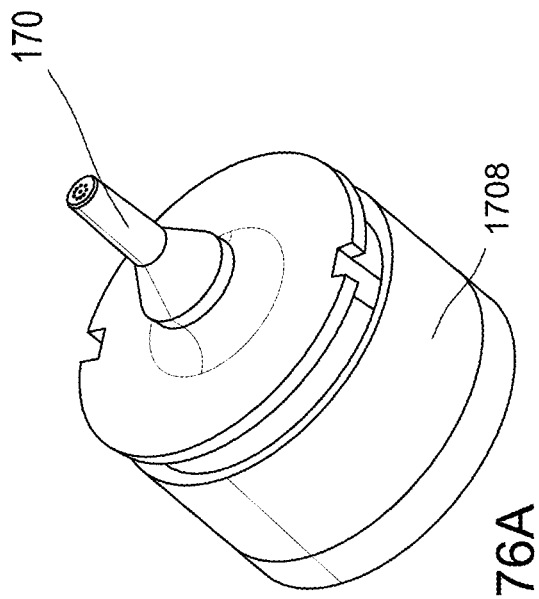
FIGS. 76A-76C illustrate a perspective view (FIG. 76A), top plan view (FIG. 76B) and front plan view (FIG. 76C) of an alternative vibrating member that couples to a transducer of droplet delivery devices in accordance with an embodiment of the disclosure.
Figure 76C:
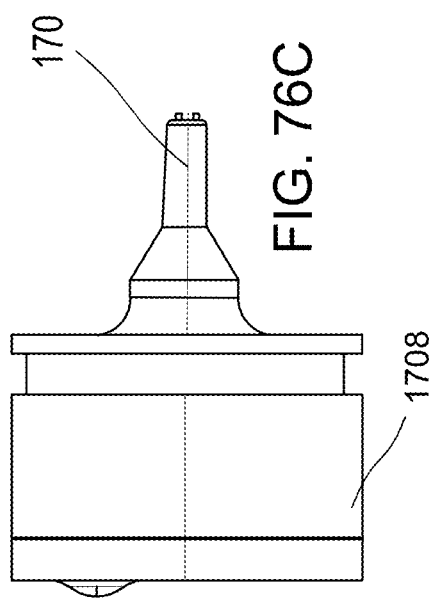
Figure 76B:
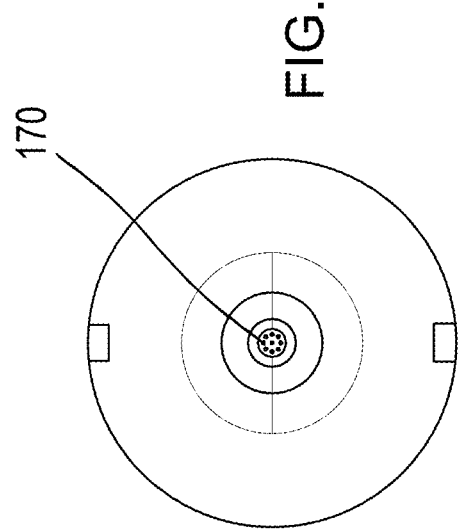
Figure 77A:
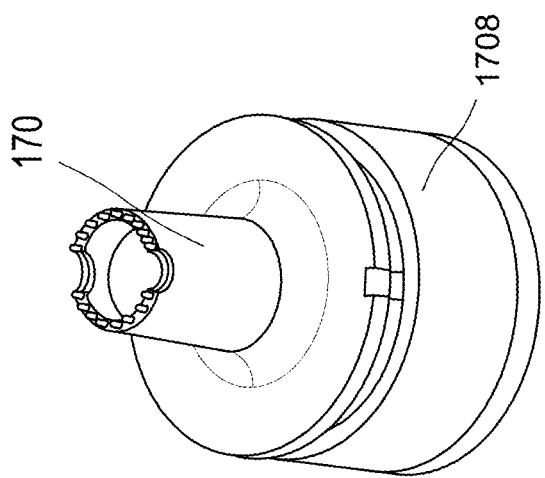
FIGS. 77A-77C illustrate a perspective view (FIG. 77A), top plan view (FIG. 77B), front plan view (FIG. 77C) and side plan view (FIG. 77D) of an alternative vibrating member that couples to a transducer of droplet delivery devices in accordance with an embodiment of the disclosure.
Figure 77D:
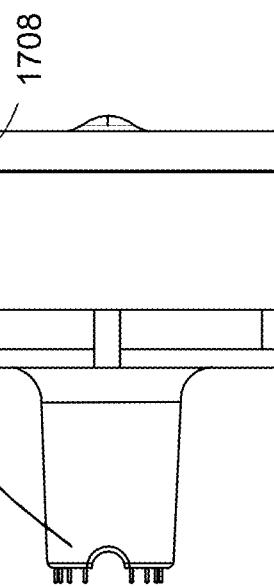
Figure 77C:
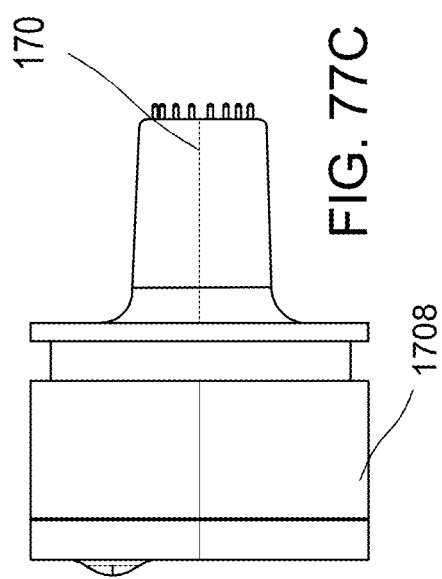
Figure 77B:
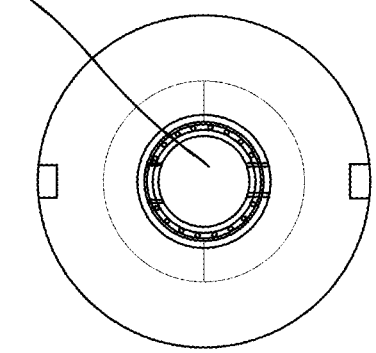
Figure 78A:
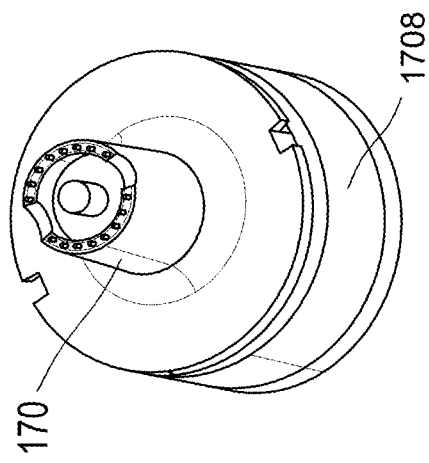
FIGS. 78A-78C illustrate a perspective view (FIG. 78A), top plan view (FIG. 78B) and front plan view (FIG. 78C) of an alternative vibrating member that couples to a transducer of droplet delivery devices in accordance with an embodiment of the disclosure.
Figure 78B:
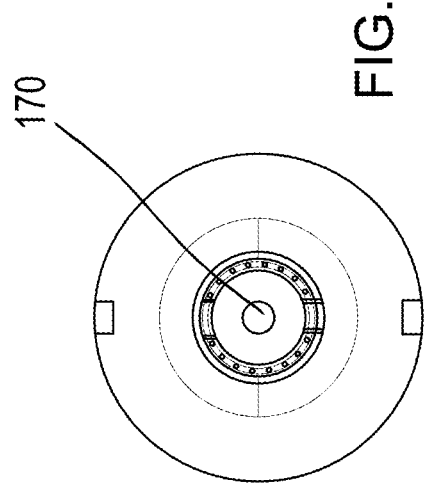
Figure 78C:
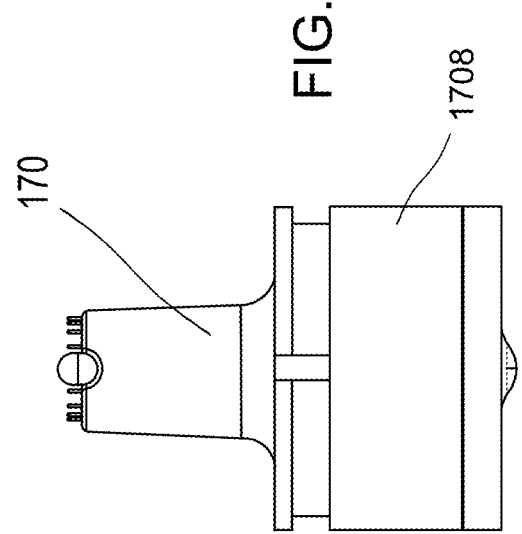
Figure 79A:
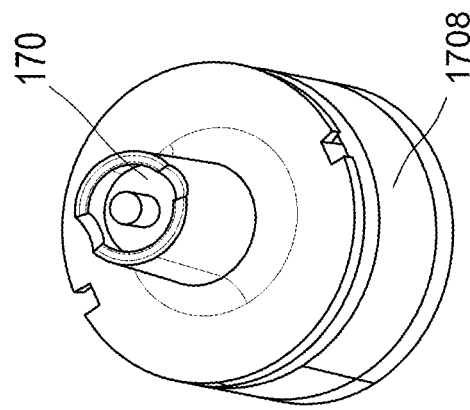
FIGS. 79A-79C illustrate a perspective view (FIG. 79A), top plan view (FIG. 79B) and front plan view (FIG. 79C) of an alternative vibrating member that couples to a transducer of droplet delivery devices in accordance with an embodiment of the disclosure.
Figure 79B:
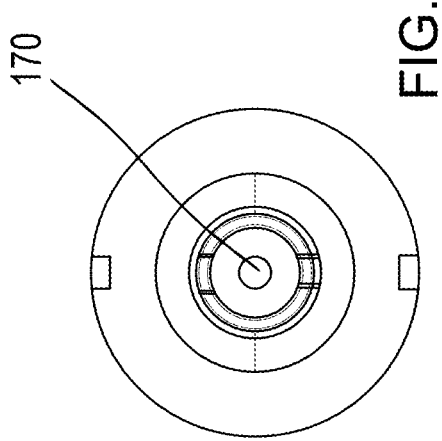
Figure 79C:
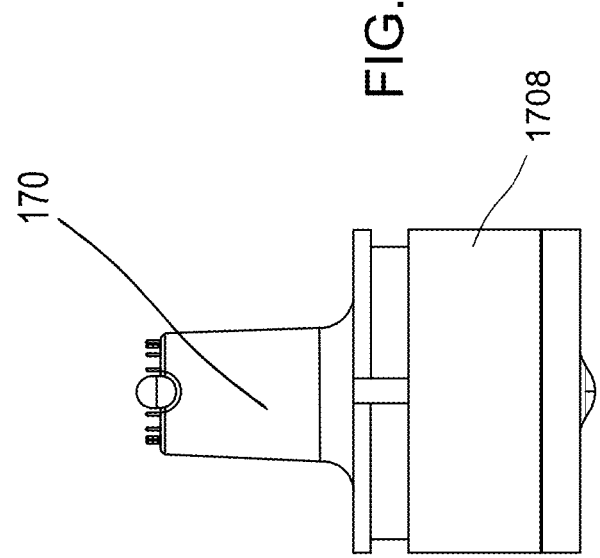
Figure 81A:
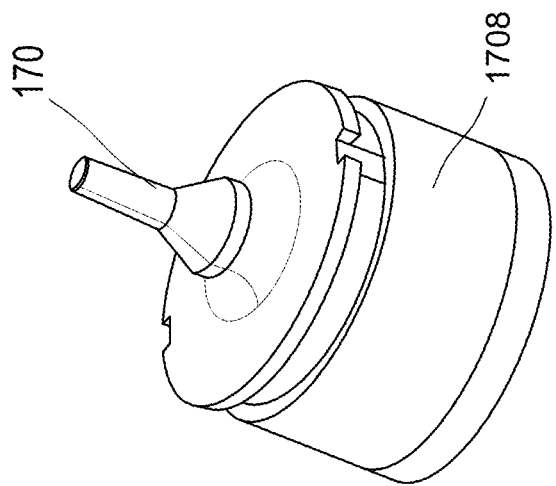
FIGS. 81A-81D illustrate a perspective view (FIG. 81A), top plan view (FIG. 81B), front plan view (FIG. 81C) and side plan view (FIG. 81D) of an alternative vibrating member that couples to a transducer of droplet delivery devices in accordance with an embodiment of the disclosure.
Figure 81D:
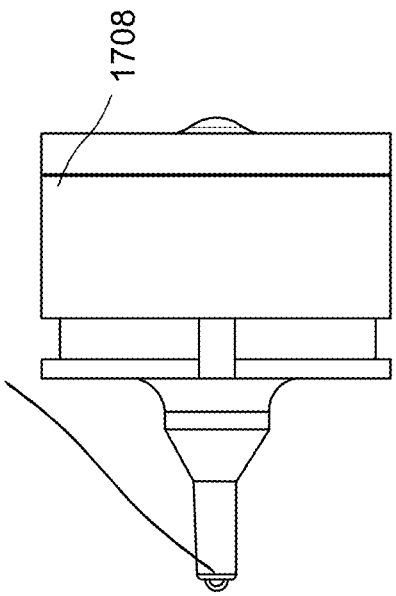
Figure 81C:
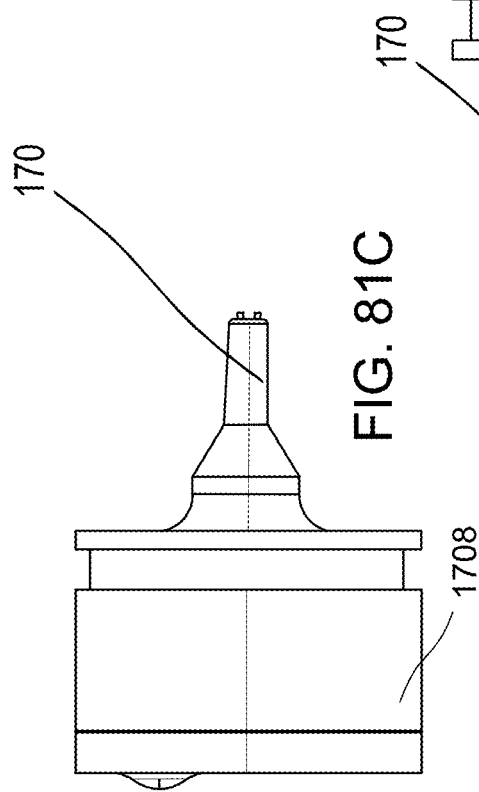
Figure 81B:
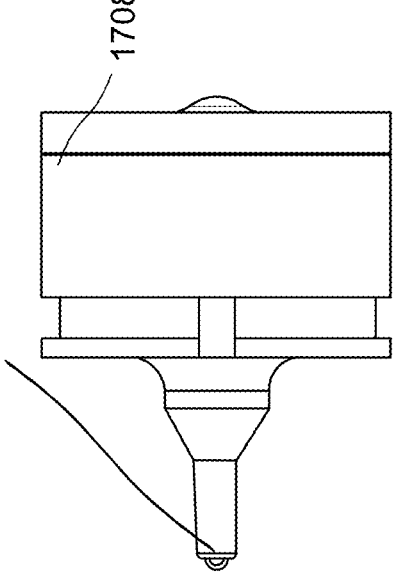
Figure 82A:
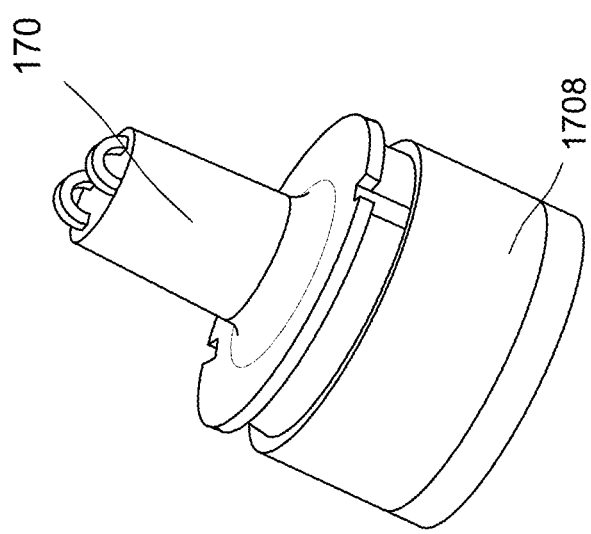
FIGS. 82A-82D illustrate a perspective view (FIG. 82A), top plan view (FIG. 82B), front plan view (FIG. 82C) and side plan view (FIG. 82D) of an alternative vibrating member that couples to a transducer of droplet delivery devices in accordance with an embodiment of the disclosure.
Figure 82D:
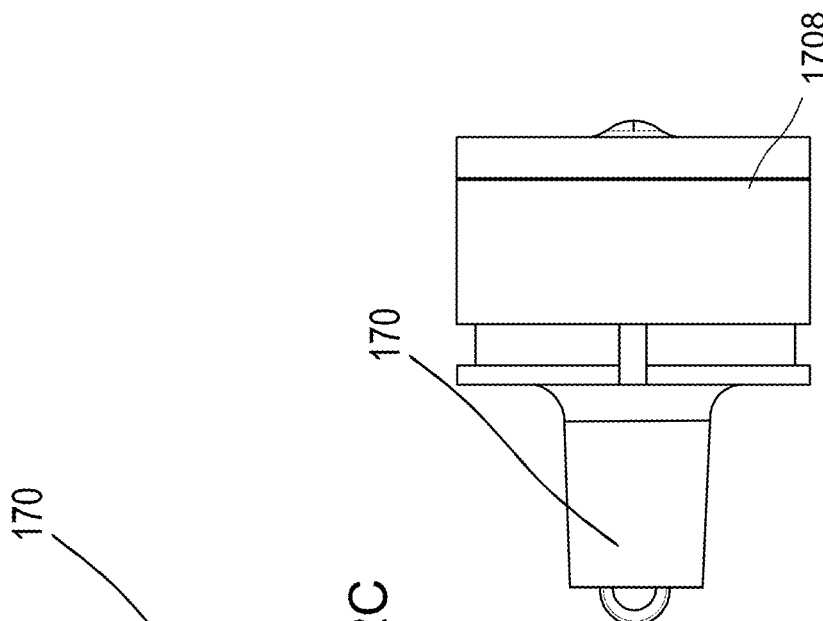
Figure 82C:
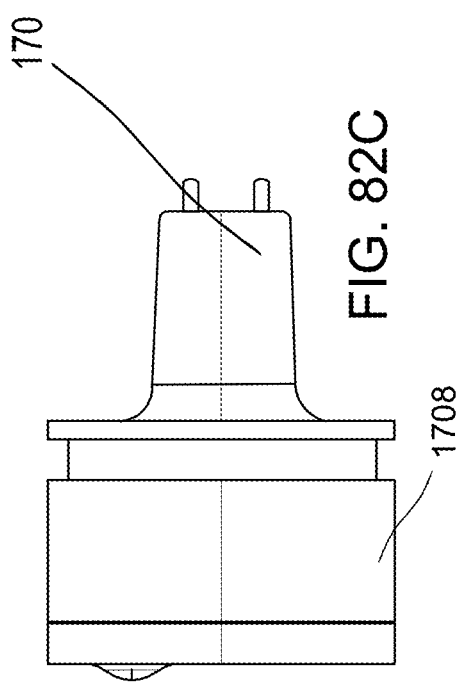
Figure 82B:
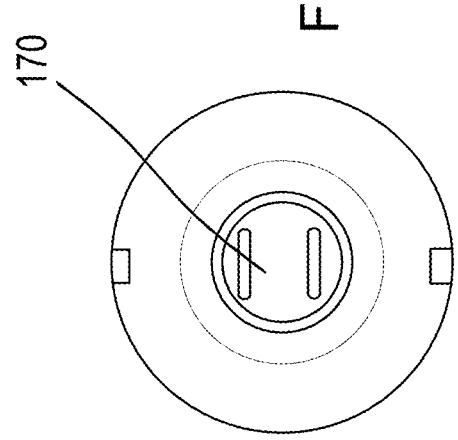
Figure 83A:
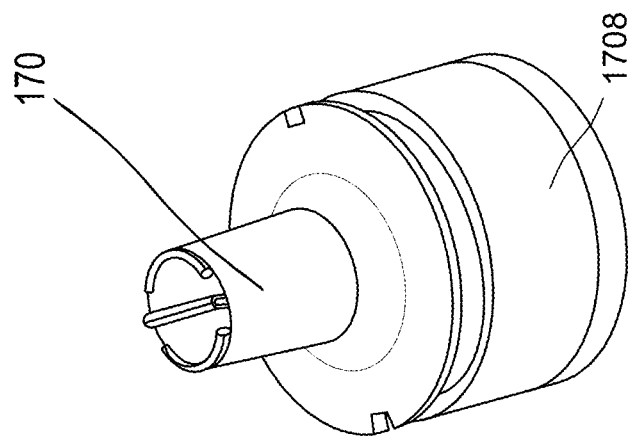
FIGS. 83A-83C illustrate a perspective view (FIG. 83A), top plan view (FIG. 83B) and front plan view (FIG. 83C) of an alternative vibrating member that couples to a transducer of droplet delivery devices in accordance with an embodiment of the disclosure.
Figure 83B:
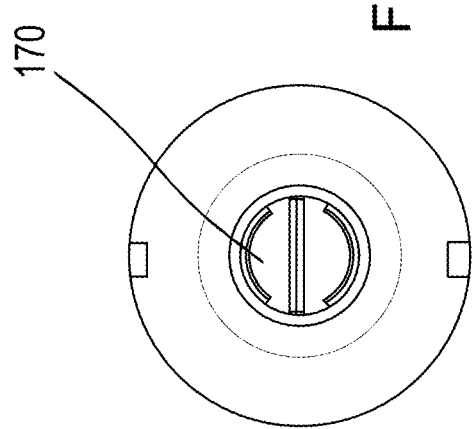
Figure 83C:
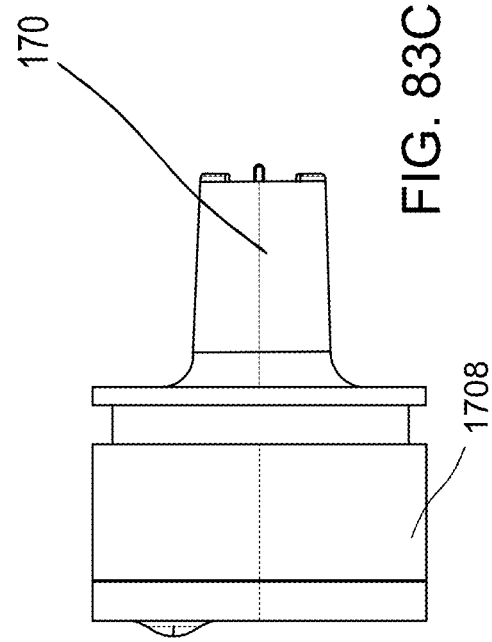

Another embodiment of push mode incorporates a tube with a sensor vibrating member (FIG. 52), spool vibrating member (FIG. 53), slotted cylindrical vibrating member (FIGS. 54 and 55), bar vibrating member (FIGS. 56 and 57), and booster vibrating member (FIG. 58). See also *Industrial resonators* Available at: www.krell-engineering.com/fea/industr/industrial_resonators.htm. (Accessed: 2 Nov. 2021)—incorporated herein by reference.

Figure 50:
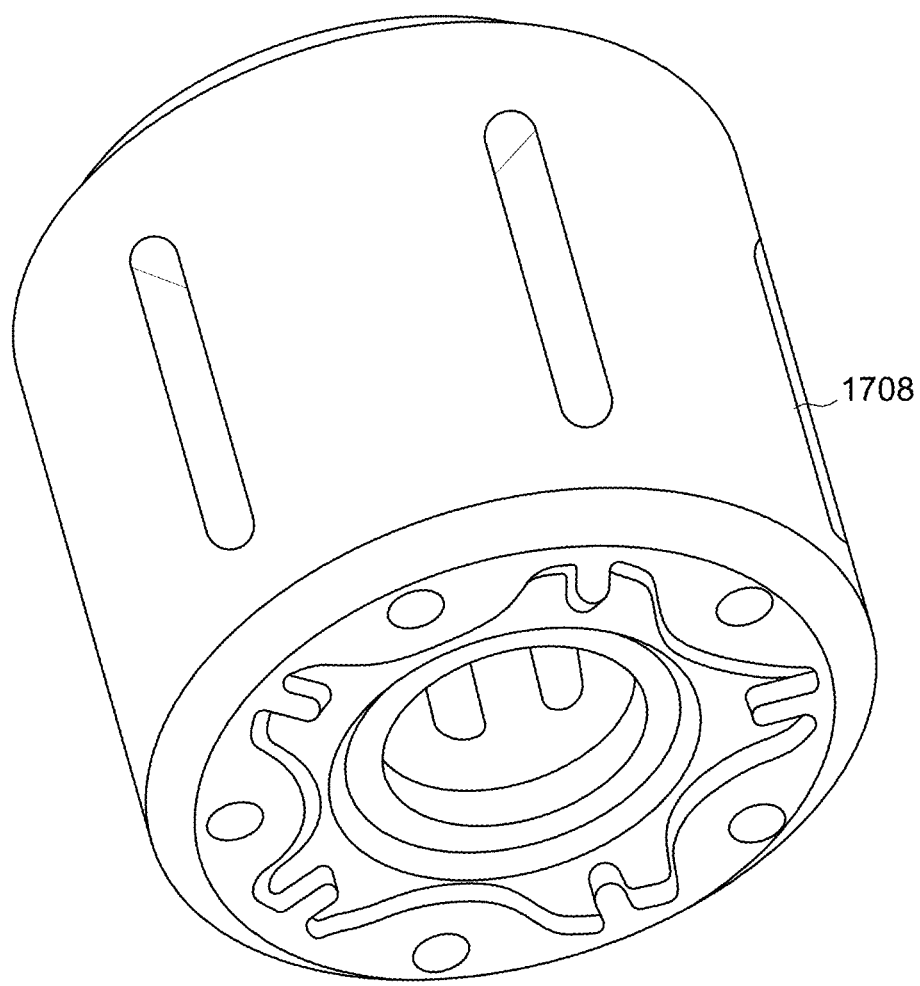
FIG. 50 illustrates a contoured vibrating member in a droplet delivery device utilizing membrane-driven aerosolization (i.e. "push mode functionality") in accordance with one embodiment of the disclosure.

Referring to FIG. 50, vibrating members can be contoured to make intimate contact with the membrane geometry.

Figure 51:
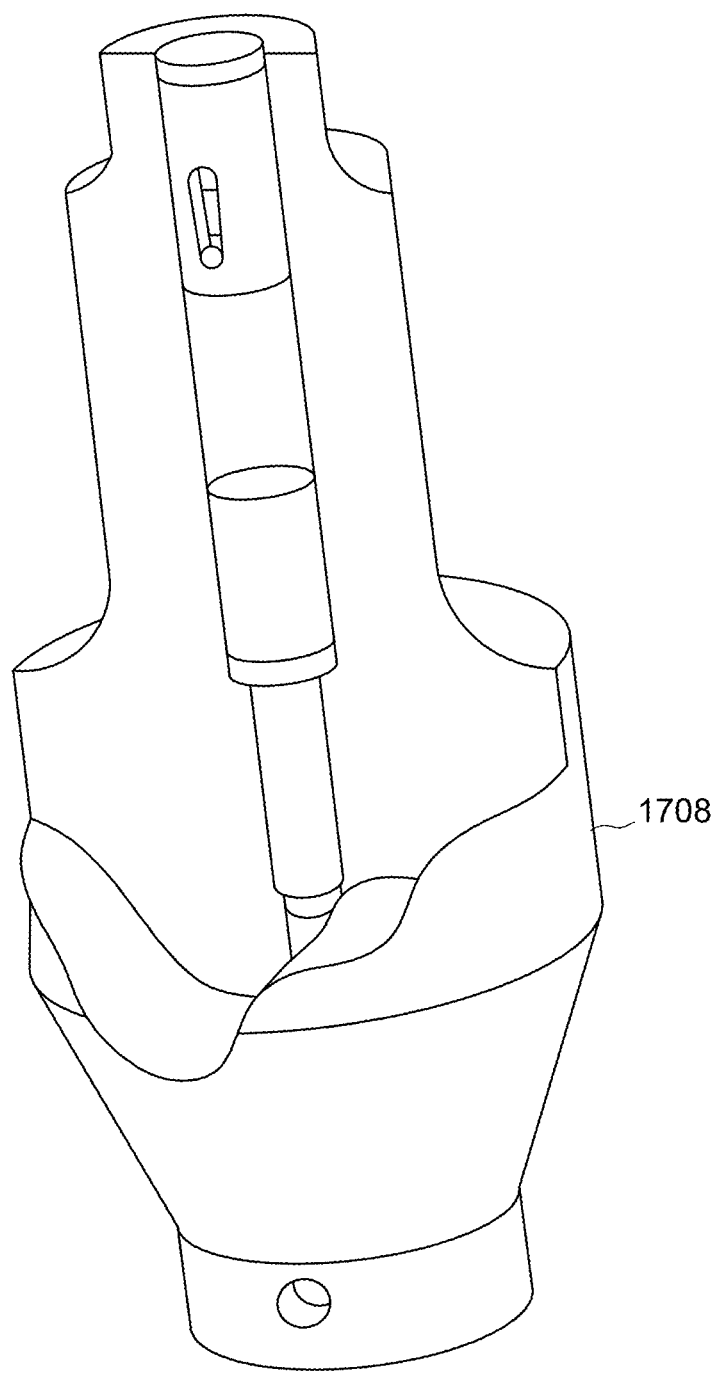
FIG. 51 illustrates a plunger vibrating member in a droplet delivery device utilizing membrane-driven aerosolization (i.e. "push mode functionality") in accordance with one embodiment of the disclosure.

Referring to FIG. 51, plunger members have nodally-mounted plungers that can be used to exert pressure on a given surface of the membrane contacted by the vibrating member.

Figure 52:
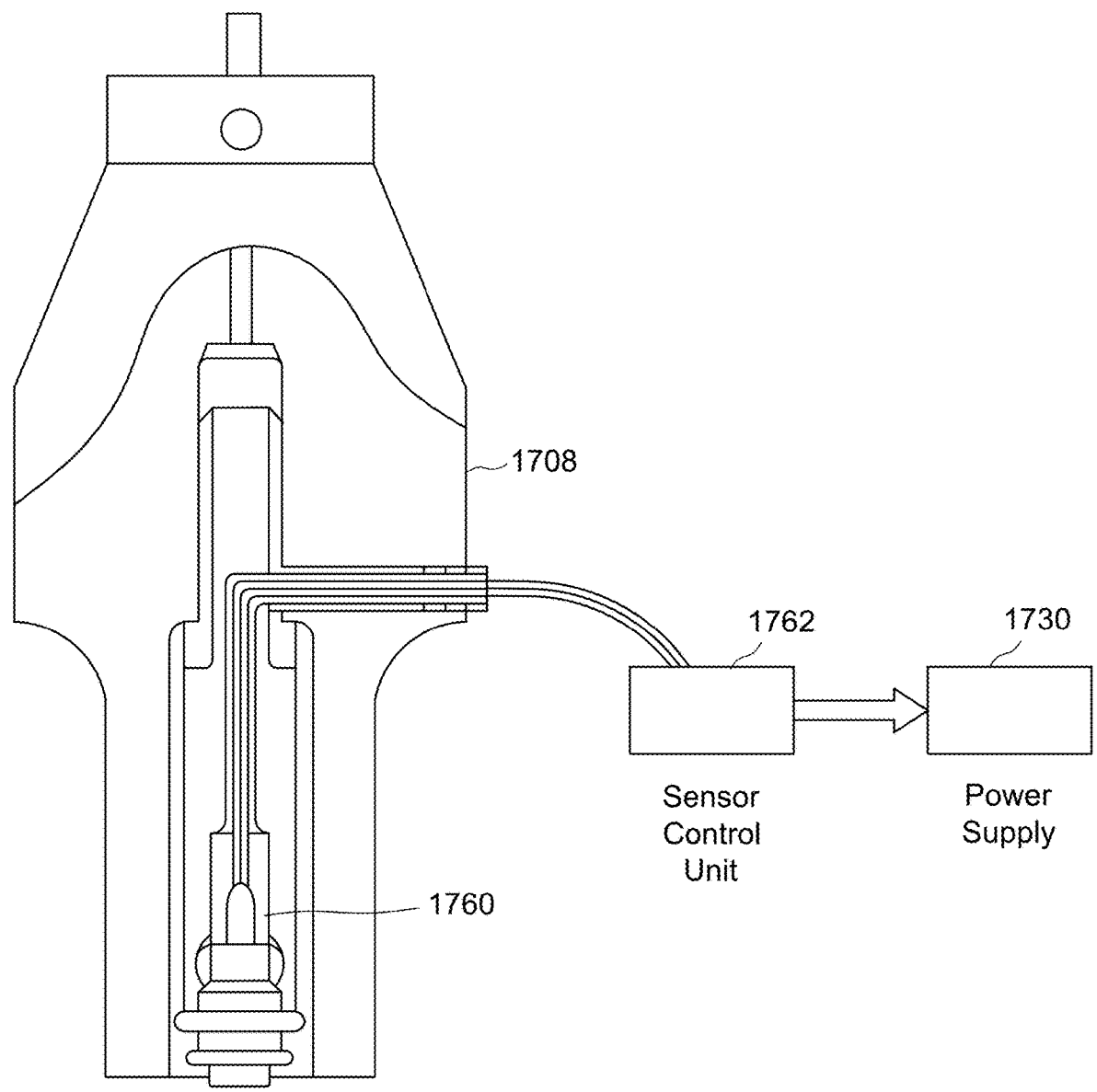
FIG. 52 illustrates a sensor carrier vibrating member in a droplet delivery device utilizing membrane-driven aerosolization (i.e. "push mode functionality") in accordance with one embodiment of the disclosure.

Referring to FIG. 52, sensor carrier vibrating members feature an internal cavity partially or fully encapsulating a nodal-mounted sensing device. The sensing device is coupled with a sensor control unit which outputs a signal to the PCBA. This signal can be used to disable aerosol generation when non-compliant, incorrect, unlicensed, etc. cartridges are attempted to be used.

Figure 53A:
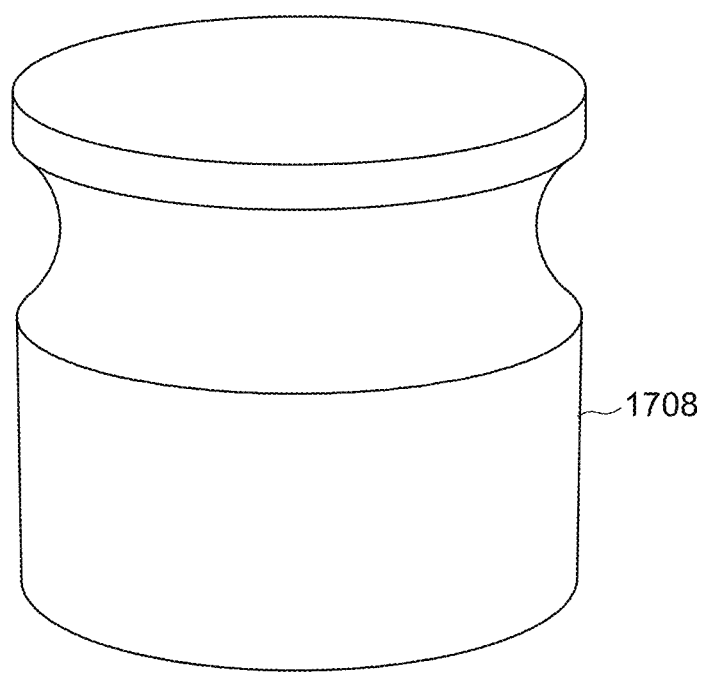
FIGS. 53A and 53B illustrate a spool vibrating member and the resulting vibration amplitude map in a droplet delivery device utilizing membrane-driven aerosolization (i.e. "push mode functionality") in accordance with one embodiment of the disclosure.
Figure 53B:
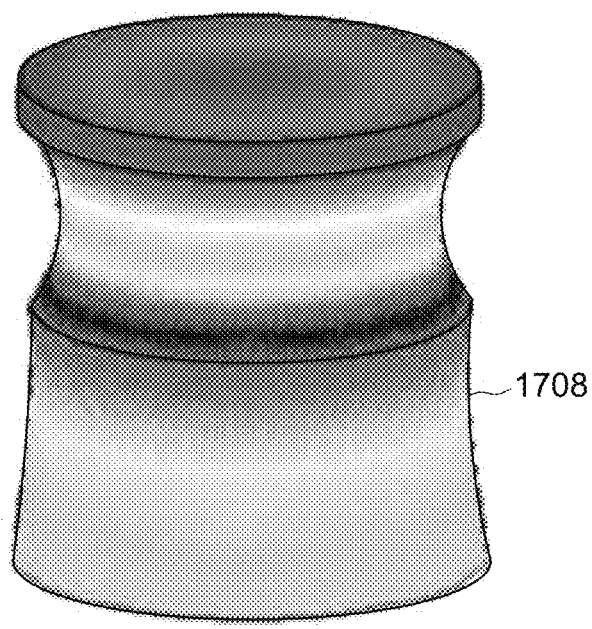

Referring to FIG. 53, spool vibrating members are unslotted cylindrical members featuring undercut sides behind the face to form a spool shape. This spool shape improves the face amplitude uniformity. Because a spool vibrating member does not have slots, its stresses are much lower than comparable slotted cylindrical vibrating members making machining costs much lower. Using cavities, slots, and back extension to optimize axial resonance creates a very uniform amplitude across the members face. The member is one half-wavelength long at axial resonance, as indicated by the single node that is generally transverse to the principal direction of vibration. Spool vibrating members generally have about 1:1 gain, although somewhat higher gain is possible.

Figure 54A:
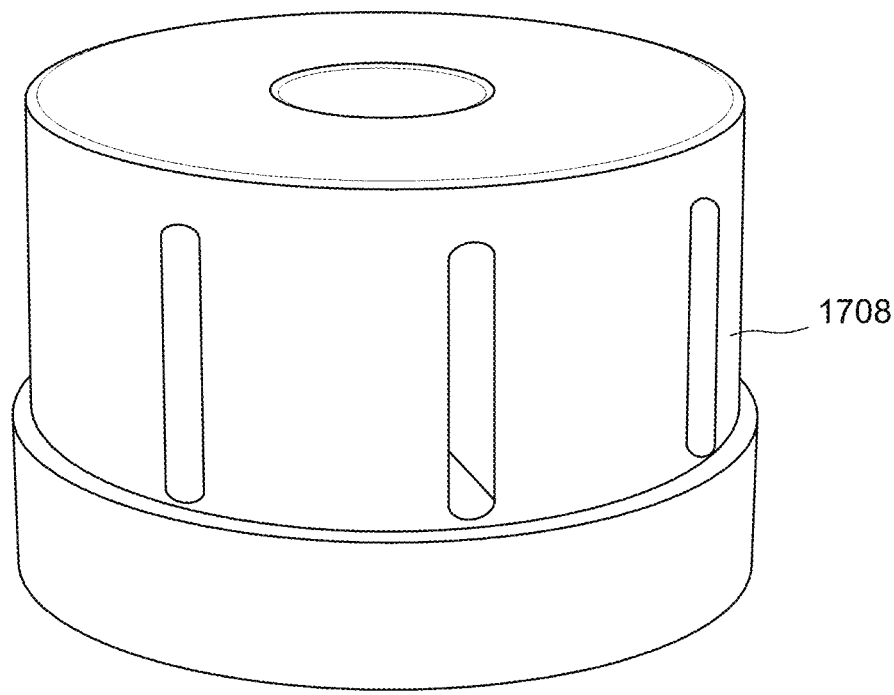
FIGS. 54A and 54B illustrate an optimized cylindrical vibrating member and the resulting vibration amplitude map in a droplet delivery device utilizing membrane-driven aerosolization (i.e. "push mode functionality") in accordance with one embodiment of the disclosure.
Figure 54B:
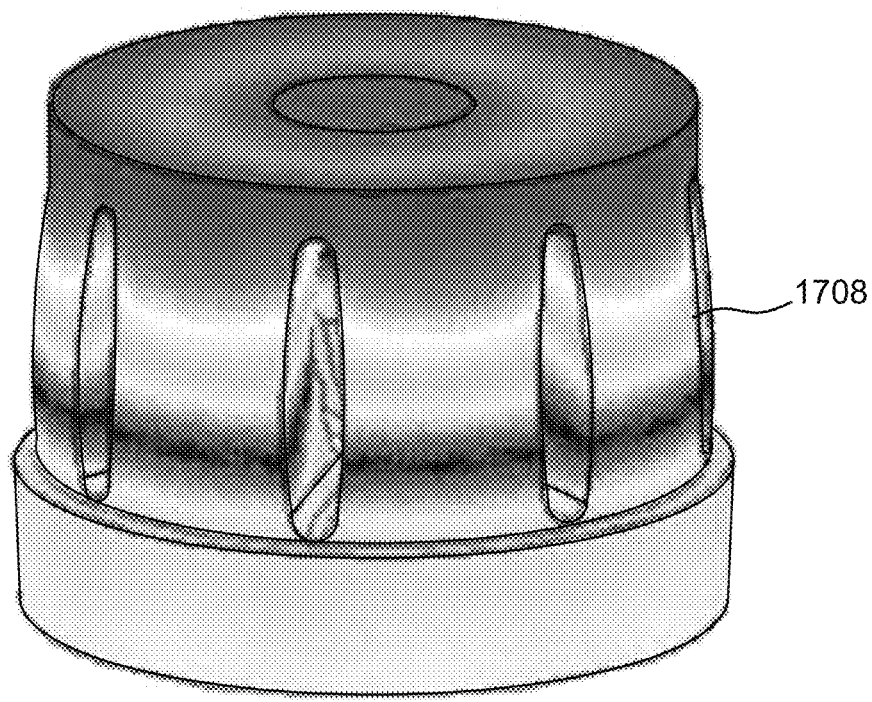
Figure 55A:
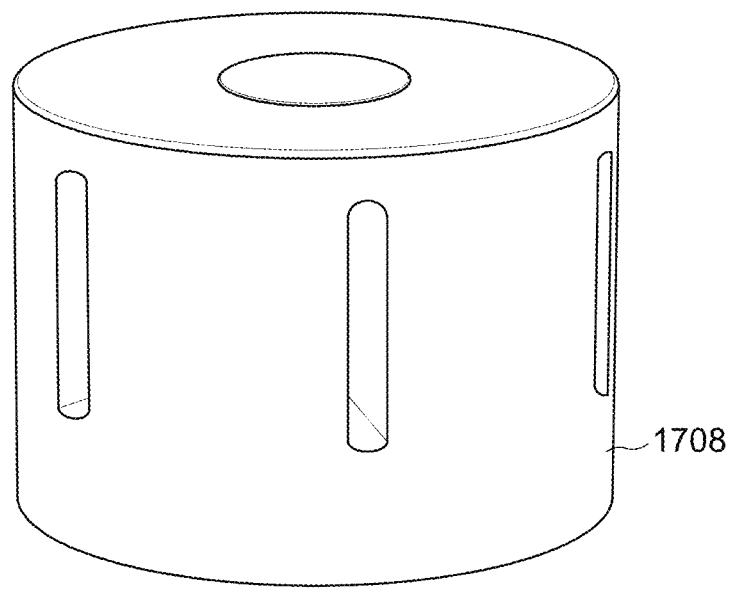
FIGS. 55A and 55B illustrate an unoptimized slotted cylindrical vibrating member and the resulting vibration amplitude map in a droplet delivery device utilizing membrane-driven aerosolization (i.e. "push mode functionality") in accordance with one embodiment of the disclosure.
Figure 55B:
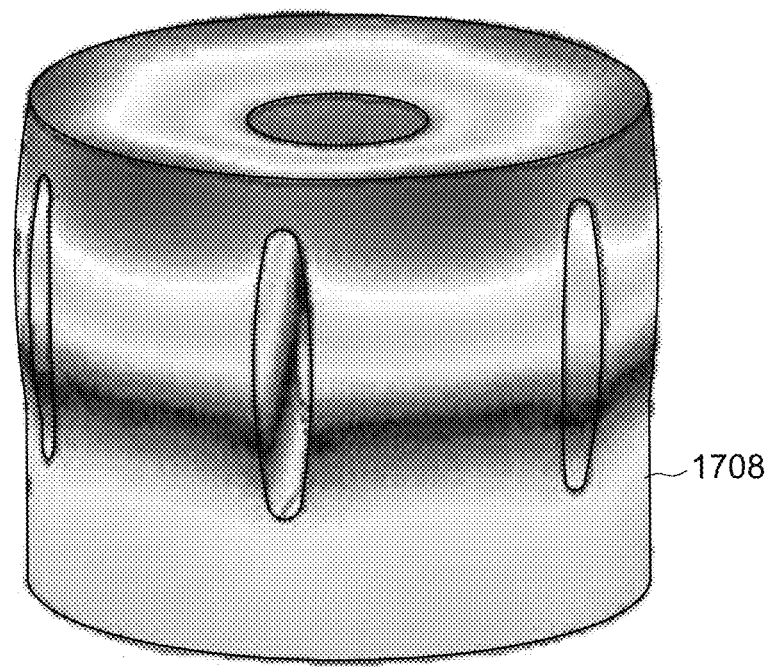

Referring to FIGS. 54 (optimized) and 55 (unoptimized), slotted cylindrical vibrating members feature longitudinal slots used to reduce the transverse coupling due to the Poisson effect. Such slots are usually radial, although other configurations are sometimes useful. Without such slots, the vibrating member will either have very uneven amplitude across the face or may even resonate in a nonaxial manner. They also have a face cavity that extends deep within the member to increase its gain. The vibrating member is one half-wavelength long at axial resonance, as indicated by the single node that is generally transverse to the principal direction of vibration. Slotted cylindrical vibrating members generally have low-to-moderate gain (1:1 to 2:1).

Figure 56A:
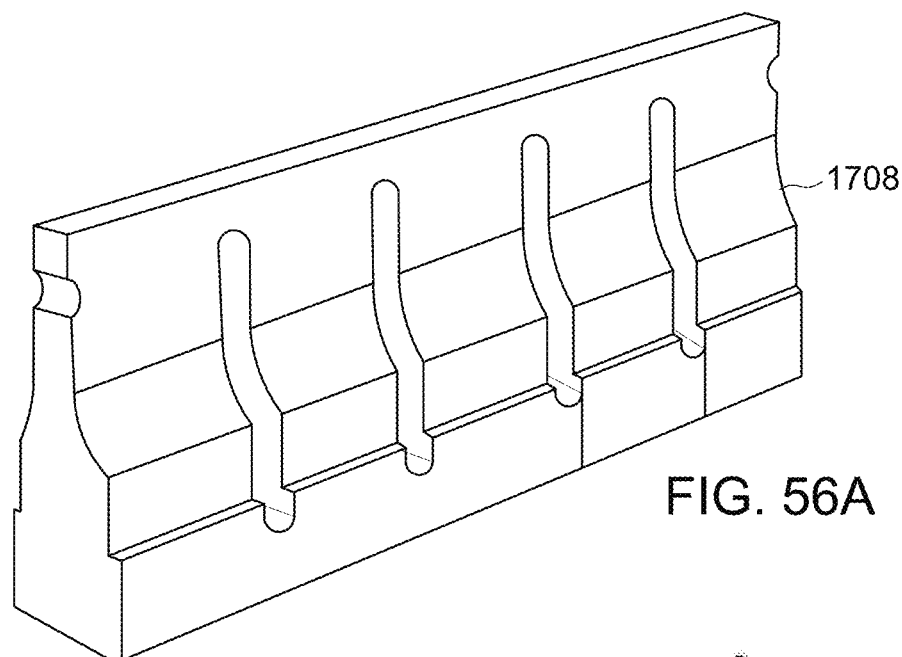
FIGS. 56A and 56B illustrate an optimized bar vibrating member and the resulting vibration amplitude map in a droplet delivery device utilizing membrane-driven aerosolization (i.e. "push mode functionality") in accordance with one embodiment of the disclosure.
Figure 56B:
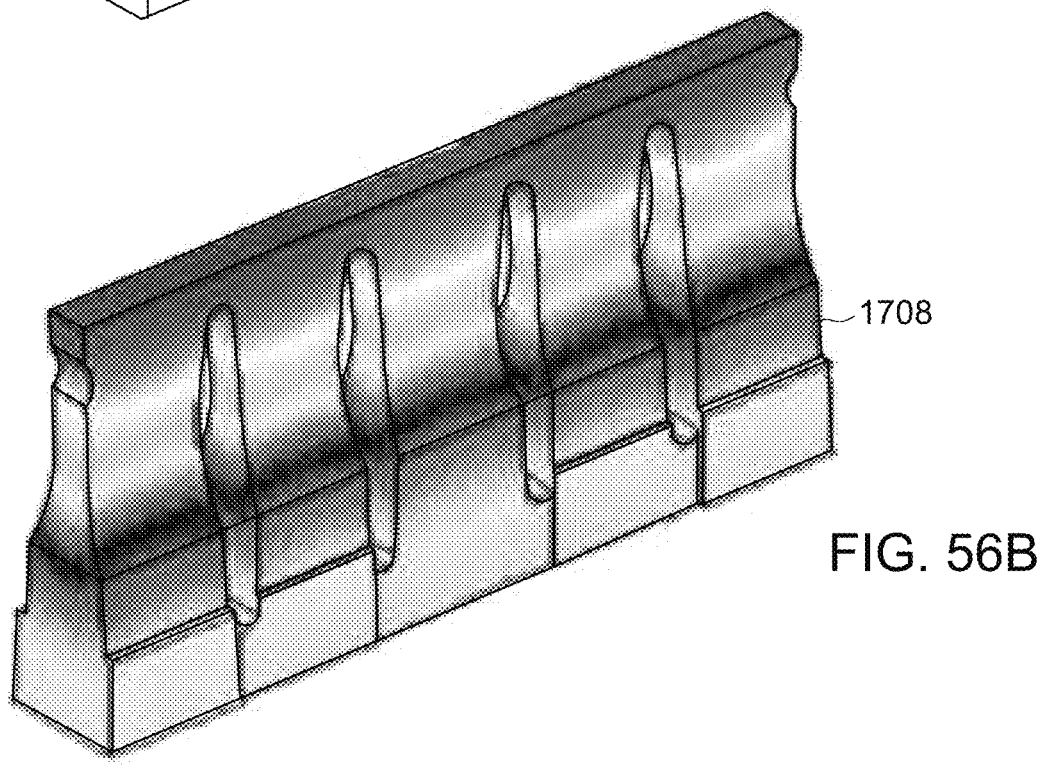

Referring to FIGS. 56 (optimized) and 57 (unoptimized), bar vibrating members are rectangular and either unslotted or slotted only through the thickness. Special design techniques give optimum face amplitude uniformity. The vibrating member's thickness has been reduced in the blade section in order to provide reasonable gain. The vibrating member is one half-wavelength long at the axial resonance, as indicated by the single node that is generally transverse to the principal direction of vibration. Bar vibrating members generally have low-to-moderate gain (1:1 to 4:1).

Referring to FIG. 58, A booster is a coupling resonator that is placed between a transducer and vibrating member in order to change the member's amplitude and or as a means of supporting the resonator stack. The booster body is rigidly supported by a collar that is bonded to the booster's node. Because the rigid booster is constructed only of metal (no compliant elastomers), it has excellent axial and lateral stiffness. For additional stiffness a second collar can be incorporated into a full-wave design. The collar is tuned to isolate the motion of the booster body from the support structure. This is shown is the following image of a displaced booster, where the coolest colors indicate the lowest amplitudes. Each booster has a fixed gain (ratio of output amplitude to input amplitude), generally between 0.5:1 and 3.0:1.

With further reference to FIGS. 59-83, further alternative embodiments of vibrating members 1708 with vibrating member tip 170 that couple to transducers 26 of droplet delivery devices 10 in accordance with various embodiments of the disclosure are shown.

Other Vibrating Member and Membrane Alignments and Designs

Figure 85A:
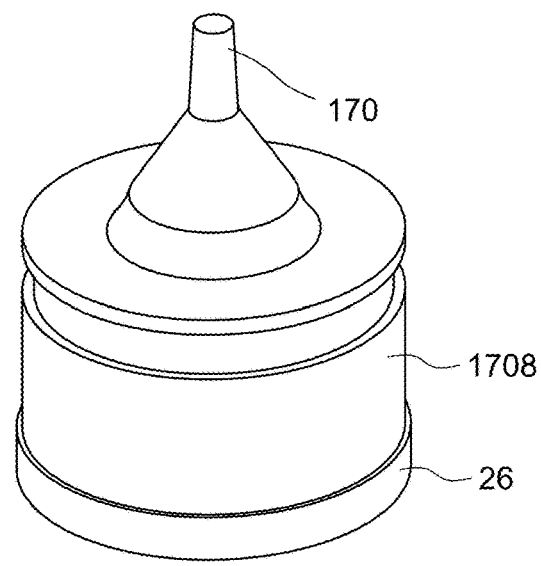
FIG. 85A illustrates an ultrasonic transducer, including a vibrating member tip portion, in a droplet delivery device in accordance with an embodiment of the disclosure.
Figure 85B:
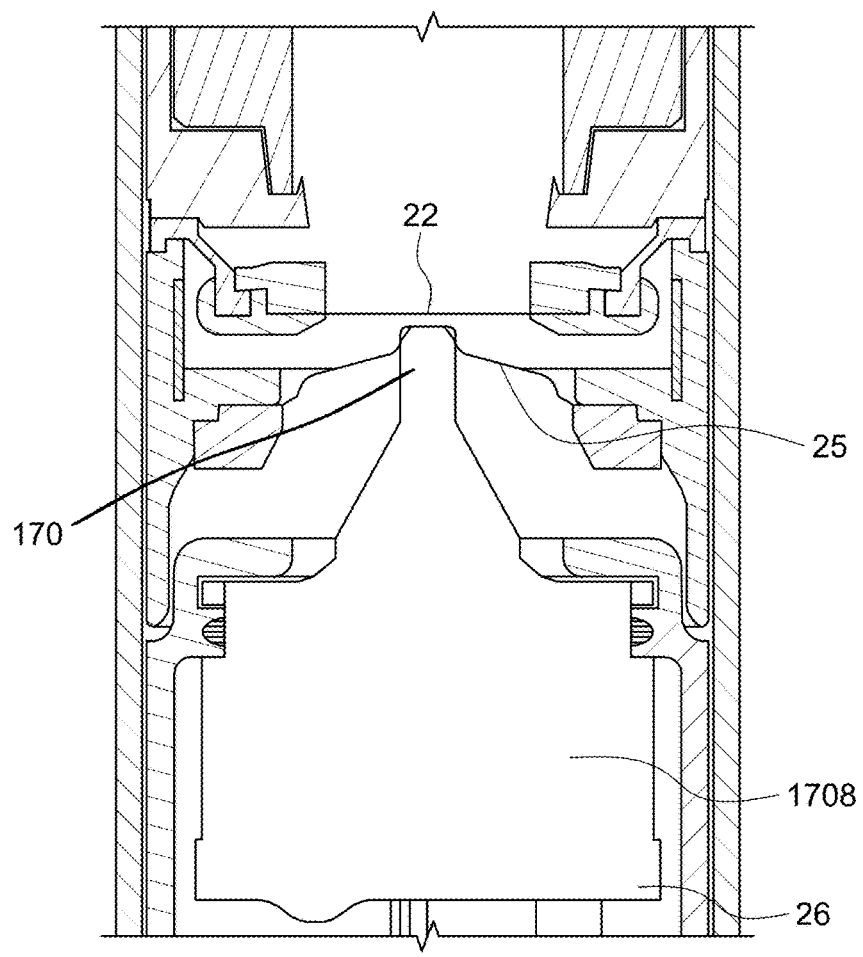
FIG. 85B is a partial cross-sectional top view of the ultrasonic transducer of FIG. 85A coupling to a membrane in a droplet delivery device in accordance with an embodiment of the disclosure.
Figure 85C:
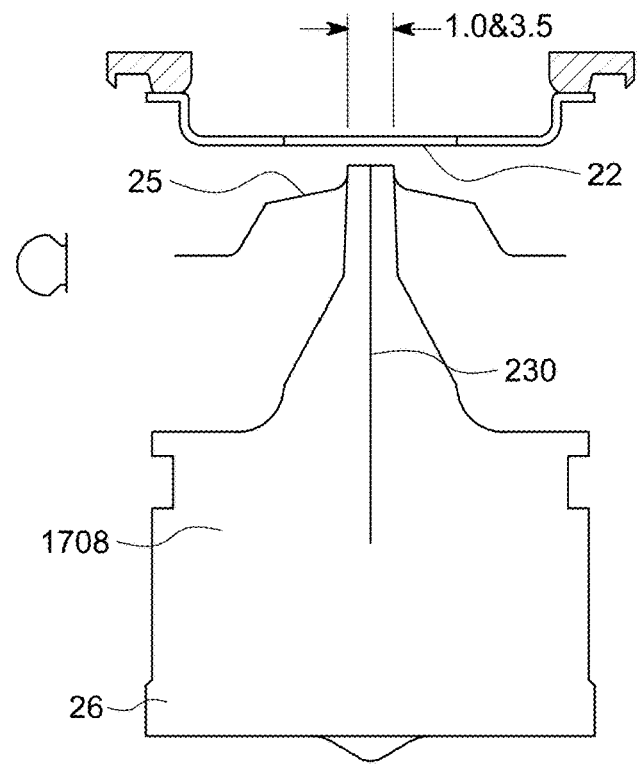
FIGS. 85C and 85D are schematic views of the ultrasonic transducer and membrane of FIG. 85B in droplet delivery devices in accordance with alterative embodiments of the disclosure wherein a mesh includes first securing mechanism in FIG. 85C and second securing mechanism in FIG. 85D.
Figure 85D:
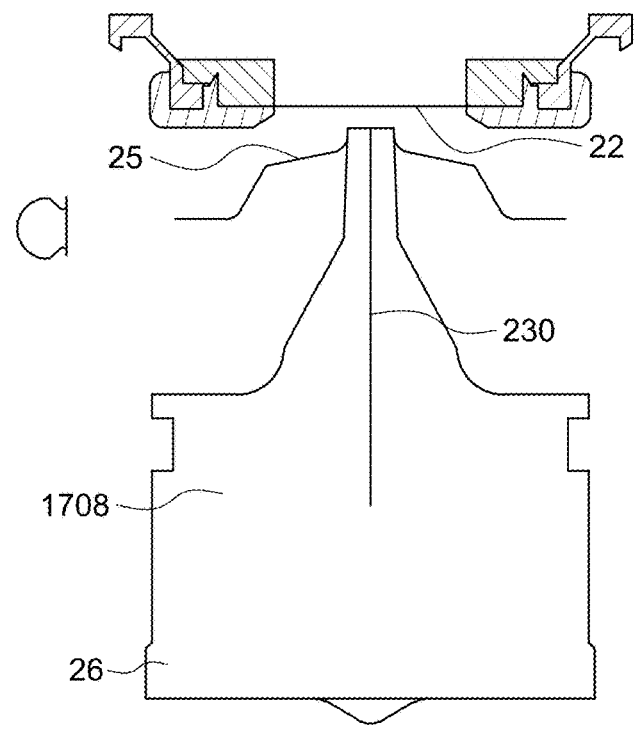

In other embodiments, the vibrating member 1708 may include other shapes and the membrane 25 may also include alternative shapes. For example, FIG. 85A illustrates an ultrasonic transducer coupled to a rod-shaped vibrating member tip portion 170. FIG. 85 shows the vibrating member of FIG. 85A coupled to a centrally peaked or pointed membrane in a droplet delivery device 10. FIGS. 85C and 85D show ultrasonic transducer 26 and membrane 25 of FIG. 85B in alterative embodiments wherein a mesh 22 includes first securing mechanism in FIG. 85C (see FIG. 2 and accompanying description) and second securing mechanism in FIG. 85D (see FIG. 3 and accompanying description).

Figure 86A:
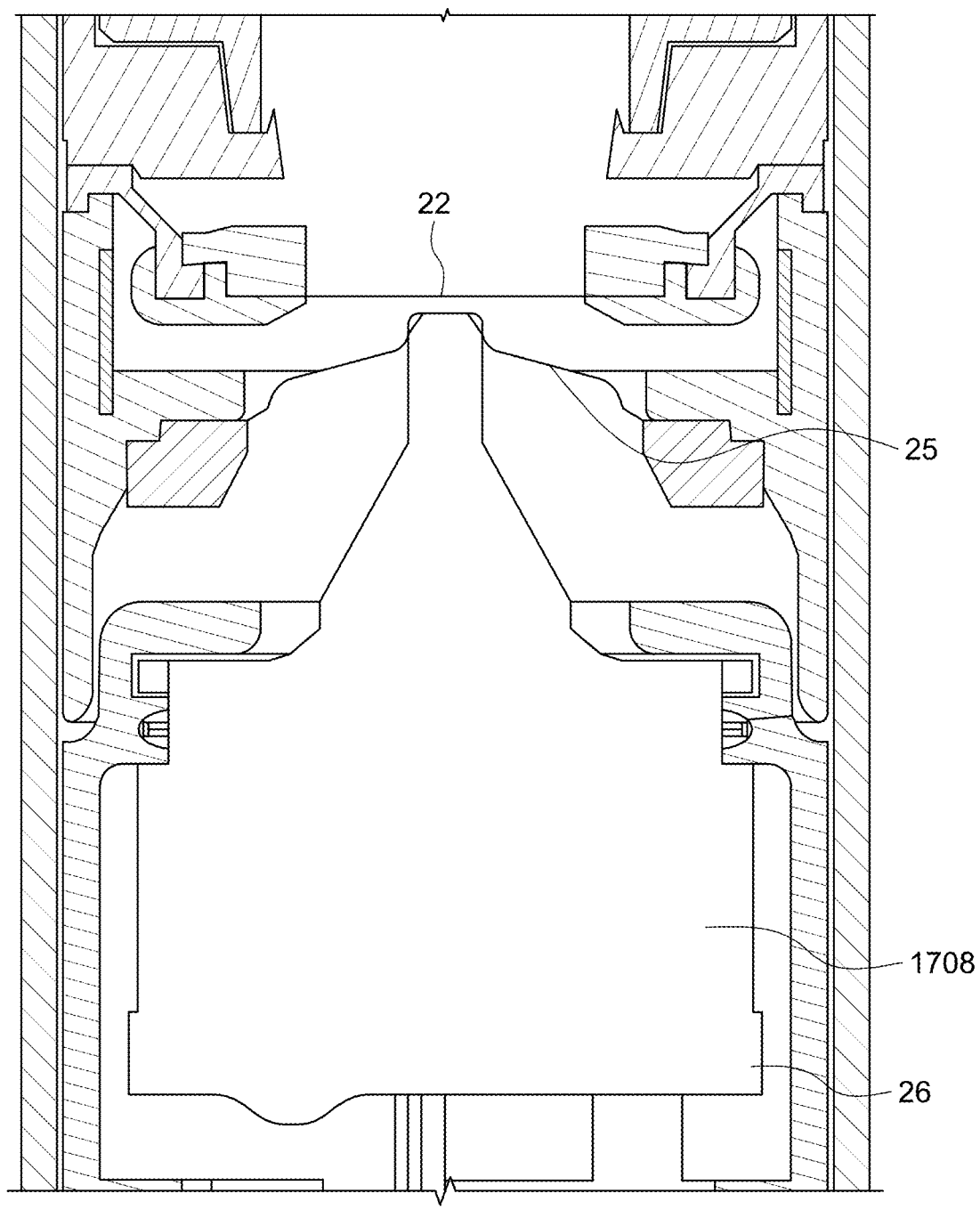
FIG. 86A is a partial cross-sectional top view of an ultrasonic transducer coupled to a membrane in a droplet delivery device in accordance with an embodiment of the disclosure.
Figure 86B:
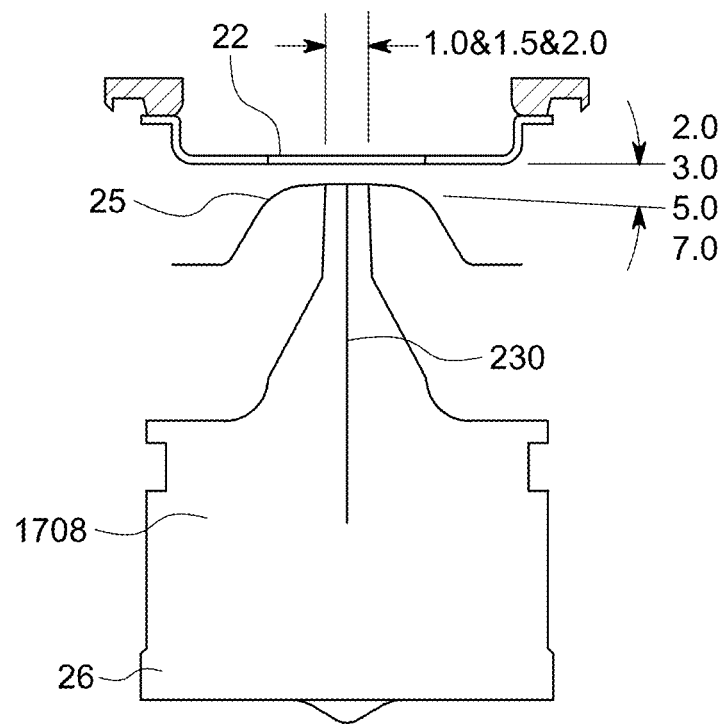
FIGS. 86B and 86C are schematic views of the ultrasonic transducer and membrane of FIG. 86A in droplet delivery devices in accordance with alterative embodiments of the disclosure wherein a mesh includes first securing mechanism in FIG. 86B and second securing mechanism in FIG. 86C.
Figure 86C:
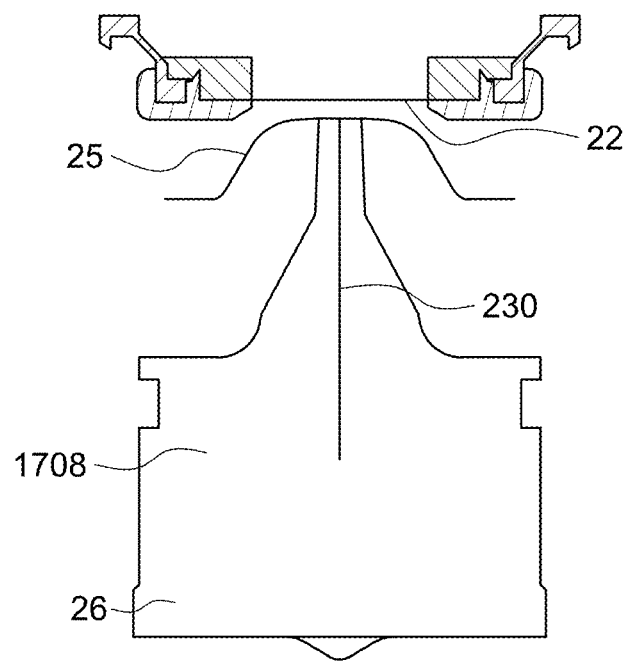

FIG. 86A further illustrates in another embodiment an ultrasonic transducer 26 with a rod-shaped tip portion 170 coupled to a membrane 25 with a wide or dome/rounded exterior surface in a droplet delivery device 10. FIGS. 86B and 86C show ultrasonic transducer 26 and membrane 25 of FIG. 86A in alterative embodiments wherein a mesh 22 includes first securing mechanism in FIG. 86B (see FIG. 2 and accompanying description) and second securing mechanism in FIG. 86C (see FIG. 3 and accompanying description).

Figure 87:
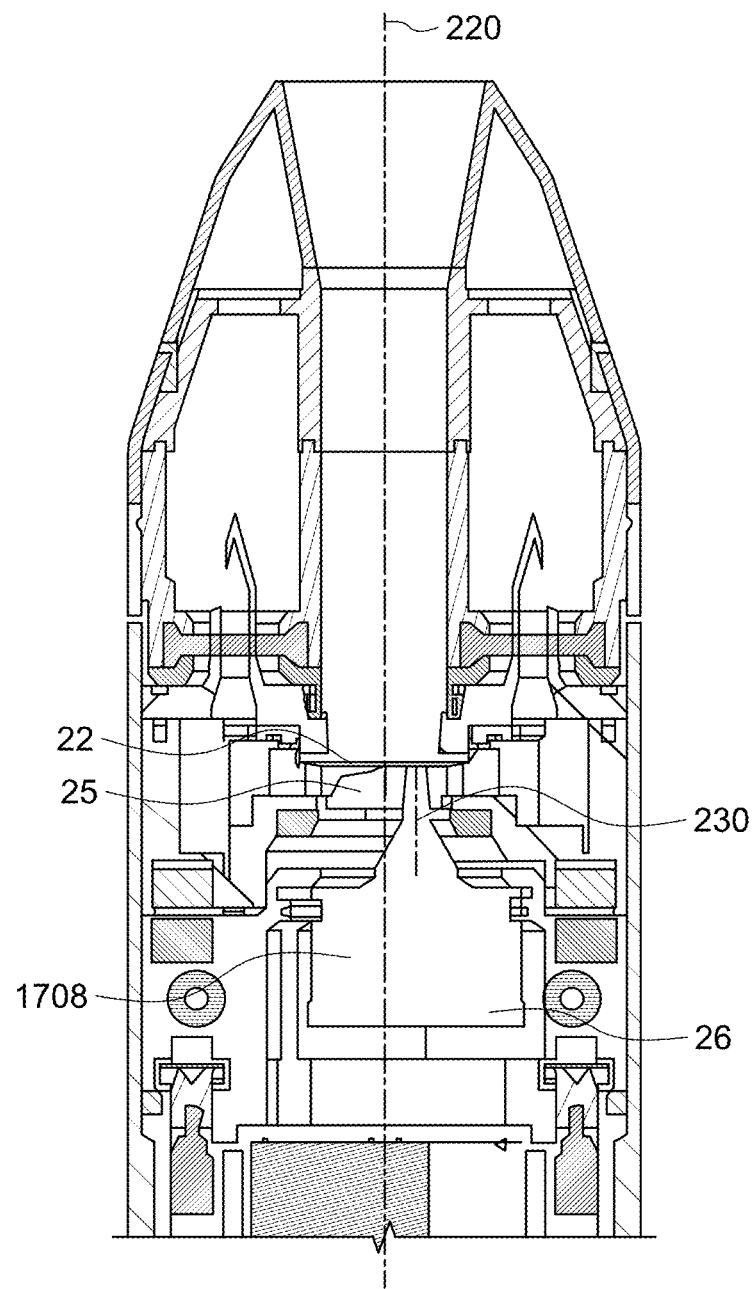
FIG. 87 is partial cross-sectional top view of a droplet delivery device including an ultrasonic transducer with vibrating member tip portion offset from a central axis of the droplet delivery device passing through a slanted membrane and mesh in accordance with an embodiment of the disclosure.

FIG. 87 shows an alternative embodiment of a droplet delivery service including an ultrasonic transducer 26 with rod-shaped vibrating member tip portion 170 offset from a central axis 220 of the droplet delivery device passing through the ejection channel 23, a slanted/sloped membrane 25 and mesh 22 and wherein the central axis of the vibrating member 230 is not aligned with central axis 220 of the device 10.

Figure 88B:
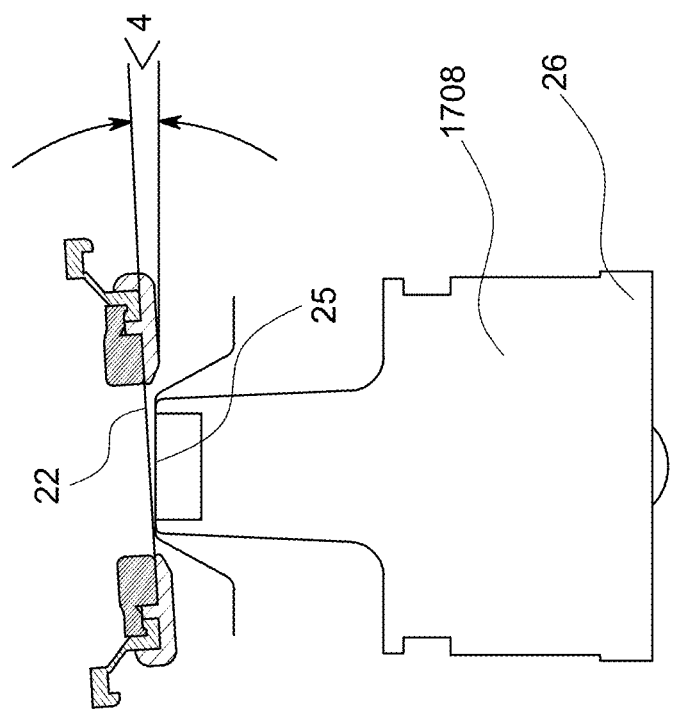
FIG. 88B is a schematic view of the ultrasonic transducer and membrane of FIG. 88A in droplet delivery devices in accordance with an embodiment of the disclosure.
Figure 88A:
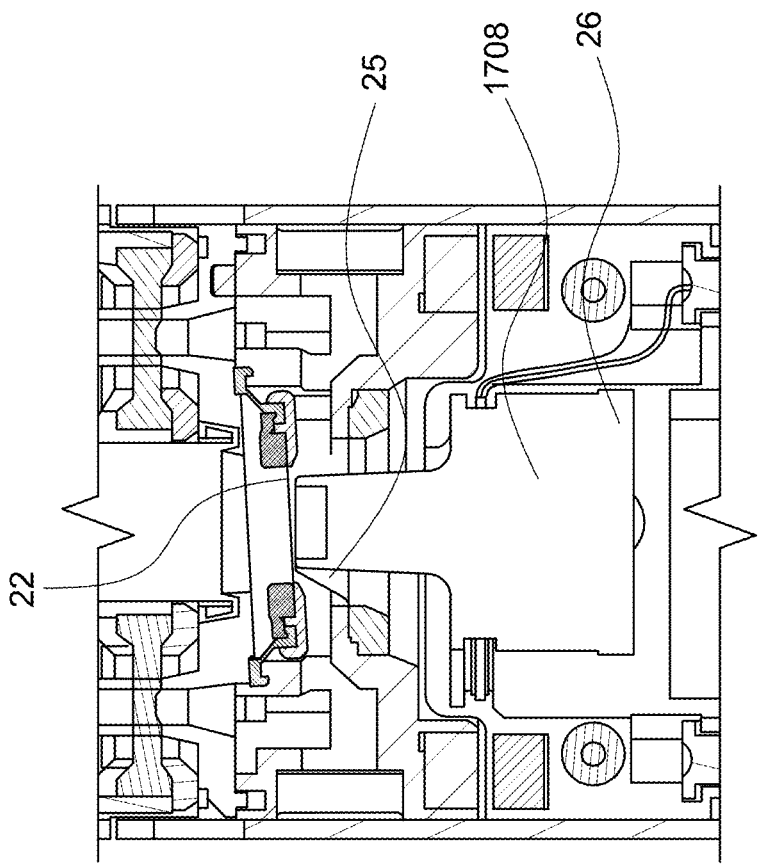
FIG. 88A is a partial cross-sectional top view of an ultrasonic transducer with a non-beveled ring-shaped vibrating member tip portion coupled to a tilted mesh in a droplet delivery device in accordance with an embodiment of the disclosure.

In another embodiment, FIGS. 88A and 88B illustrate an ultrasonic transducer 26 with a non-beveled ring-shaped vibrating member tip portion 170 coupled to a tilted mesh 22 in contact with a membrane 25 having a generally flat exterior top surface (nearest the mesh 22) in a droplet delivery device 10.

Figure 89A:
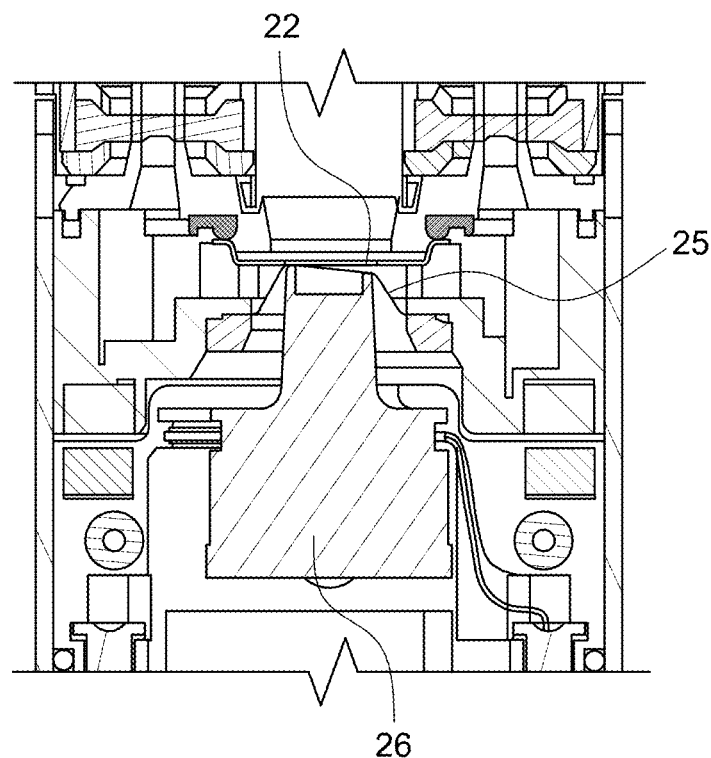
FIG. 89A is a partial cross-sectional top view of an ultrasonic transducer with a beveled ring-shaped vibrating member tip portion coupled to a slanted membrane in a droplet delivery device in accordance with an embodiment of the disclosure.
Figure 89B:
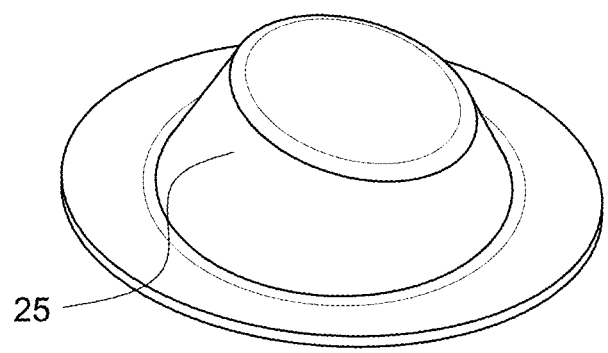
FIG. 89B illustrates a slanted membrane that cooperates with an ultrasonic transducer and mesh illustrated in FIG. 89A.
Figure 89C:
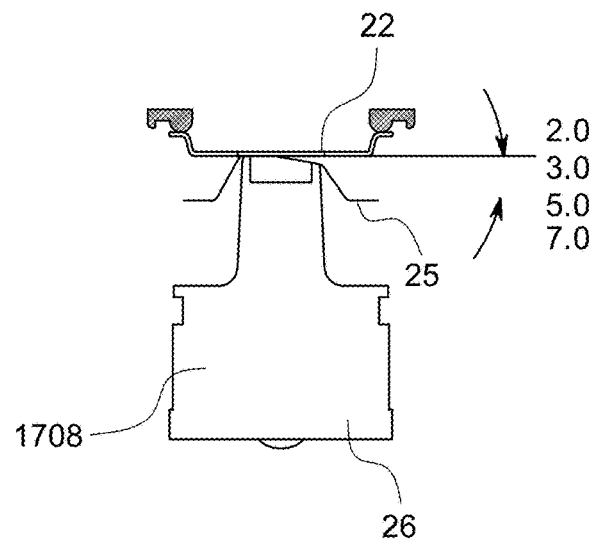
FIGS. 89C and 89D are schematic views of the ultrasonic transducer and membrane of FIG. 89A in droplet delivery devices in accordance with alterative embodiments of the disclosure wherein a mesh includes first securing mechanism in FIG. 89C and second securing mechanism in FIG. 89D.
Figure 89D:
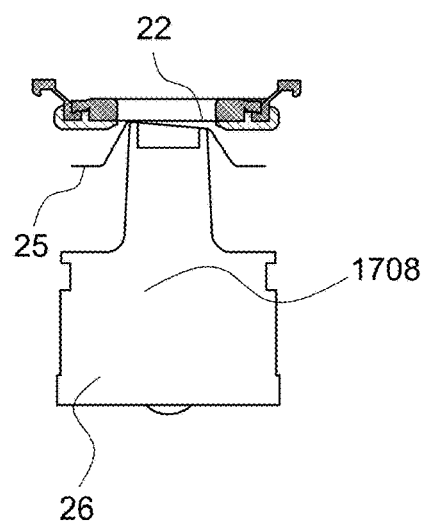
Figure 89E:
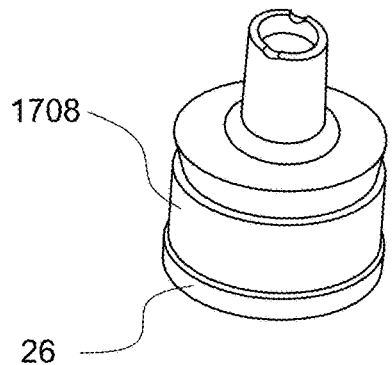
FIG. 89E illustrates an ultrasonic transducer with a beveled ring-shaped vibrating member tip portion of FIG. 89A.

In further embodiment shown in FIG. 89A an ultrasonic transducer 26 with a beveled ring-shaped vibrating member tip portion 170 may be coupled to a slanted/sloped membrane 25 in contact with a membrane 25 in a droplet delivery device 10. FIG. 89B illustrates the slanted membrane 25 of FIG. 89A and FIG. 89E illustrate an ultrasonic transducer with a beveled ring-shaped vibrating member tip portion 170 also shown in FIG. 89A. FIGS. 89C and 89D show the ultrasonic transducer 26 and membrane 25 of FIG. 89A in droplet delivery devices in accordance with alterative embodiments of the disclosure wherein a mesh 22 includes first securing mechanism in FIG. 89C (see FIG. 2 and accompanying description) and second securing mechanism in FIG. 89D (see FIG. 3 and accompanying description).

Figure 90B:
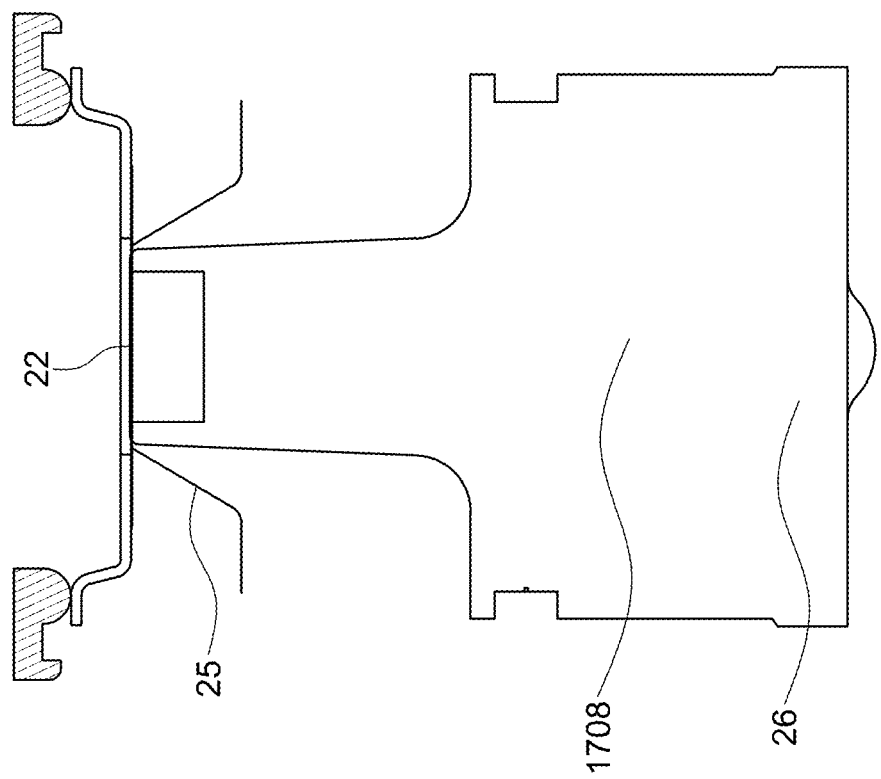
FIG. 90B is a schematic view of the ultrasonic transducer and membrane of FIG. 90A in droplet delivery devices in accordance with an embodiment of the disclosure. This embodiment can be used with a mesh carrier either of push mode I or II.
Figure 90A:
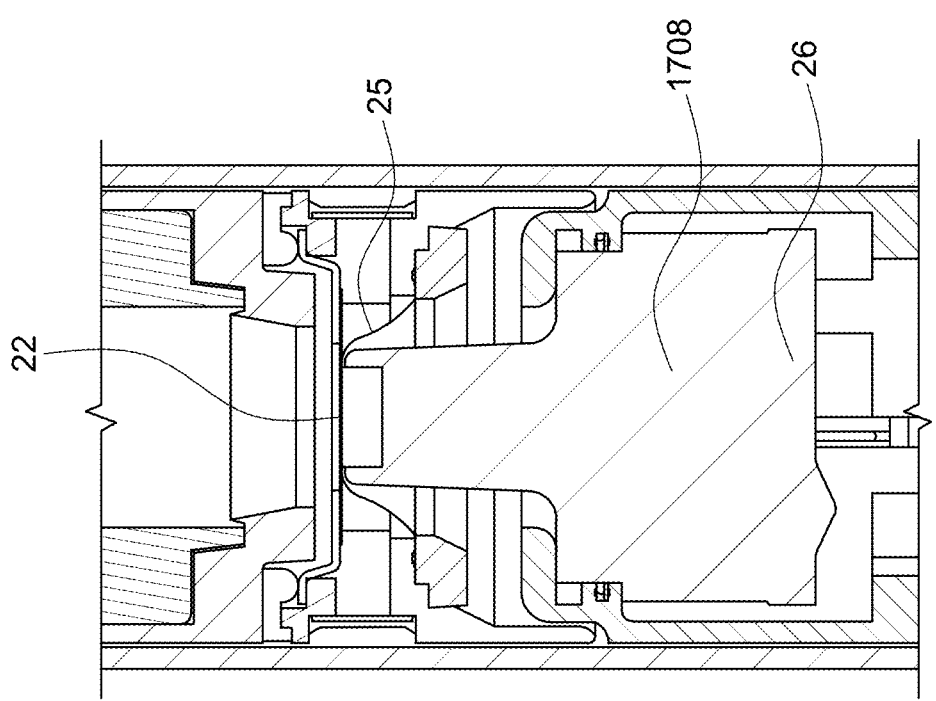
FIG. 90A is a partial cross-sectional top view of an ultrasonic transducer with a non-beveled ring-shaped vibrating member tip portion coupled to a membrane and touching the mesh in a droplet delivery device in accordance with an embodiment of the disclosure.

FIGS. 90A and 90B show an ultrasound transducer 26 with a non-beveled ring-shaped vibrating member tip portion 170 coupled to a membrane with a generally flat exterior surface in contact and in a parallel plane to the plane of the fluid-entry underlying surface of mesh 22.

Figure 91A:
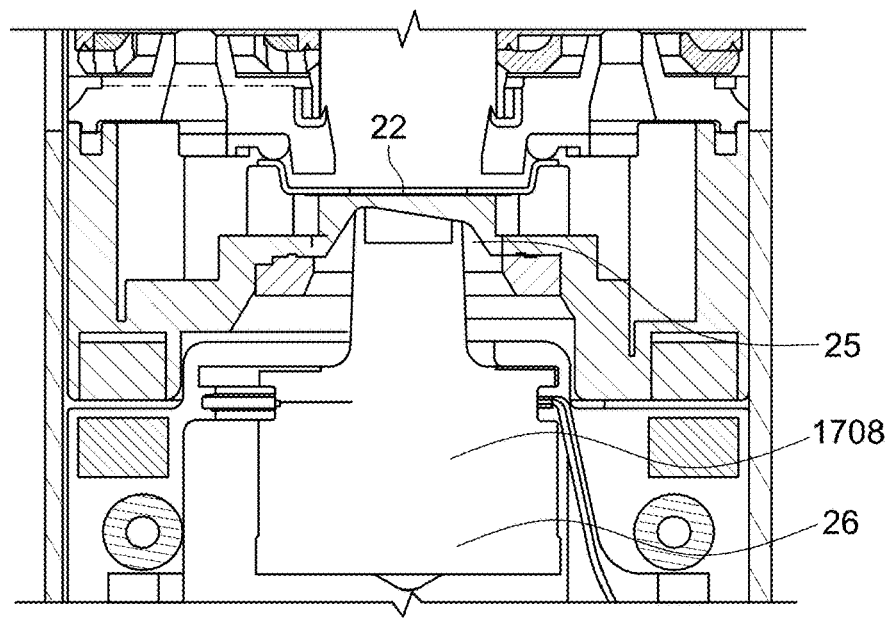
FIG. 91A is a partial cross-sectional top view of an ultrasonic transducer with a beveled ring-shaped vibrating member tip portion coupled to a slanted membrane with a space between the mesh and membrane in a droplet delivery device in accordance with an embodiment of the disclosure.
Figure 91B:
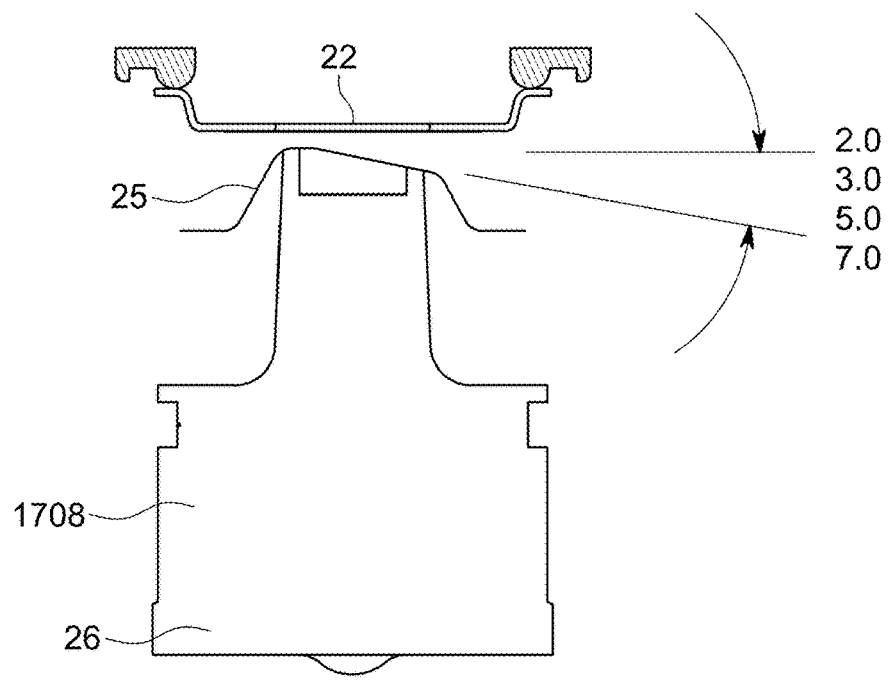
FIG. 91B is a schematic view of the ultrasonic transducer and membrane of FIG. 91A in droplet delivery devices in accordance with an embodiment of the disclosure. This embodiment can be used with a mesh carrier of either push mode I or II.

FIGS. 91A and 91B show ultrasonic transducer 26 with a beveled ring-shaped vibrating member tip portion 170 coupled to a slanted/sloped membrane 25 with a space between the membrane 25 and the mesh 22.

Figure 92:
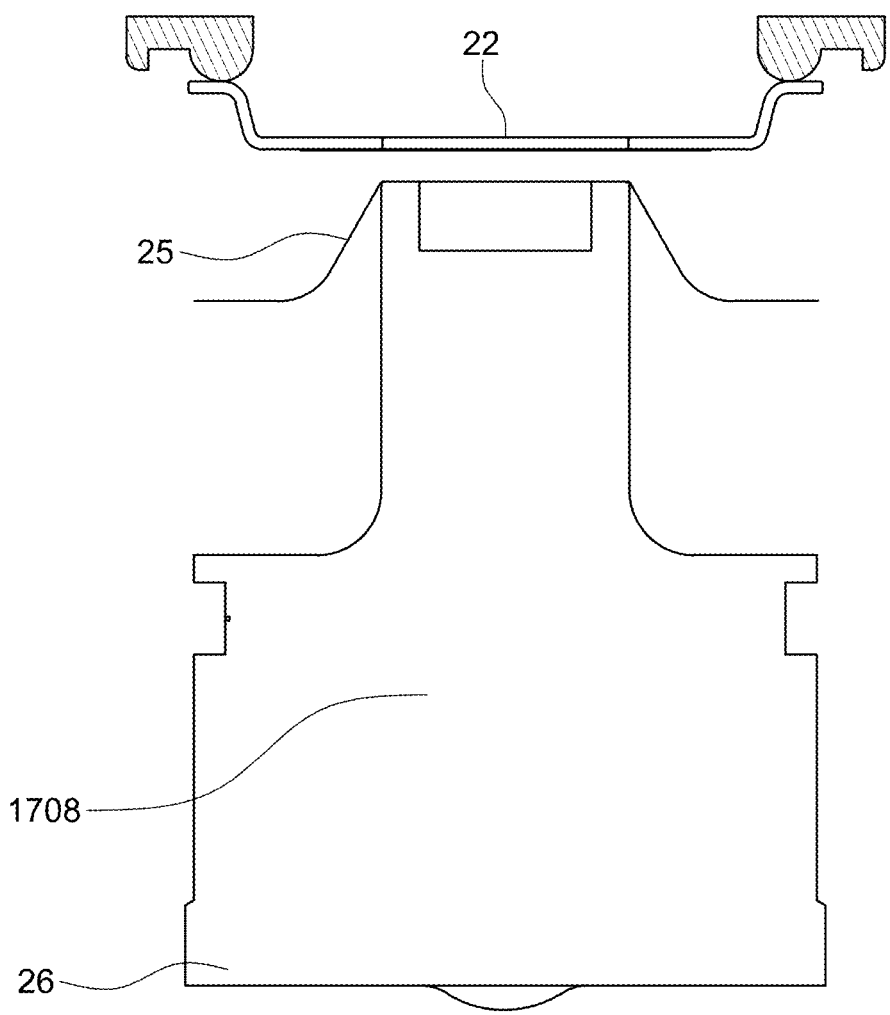
FIG. 92 is schematic view of an ultrasonic transducer with a non-beveled ring-shaped vibrating member tip portion coupled to a membrane with a space between the mesh and membrane in a droplet delivery device in accordance with an embodiment of the disclosure. This embodiment can be used with a mesh carrier of either push mode I or II.
Figure 93A:
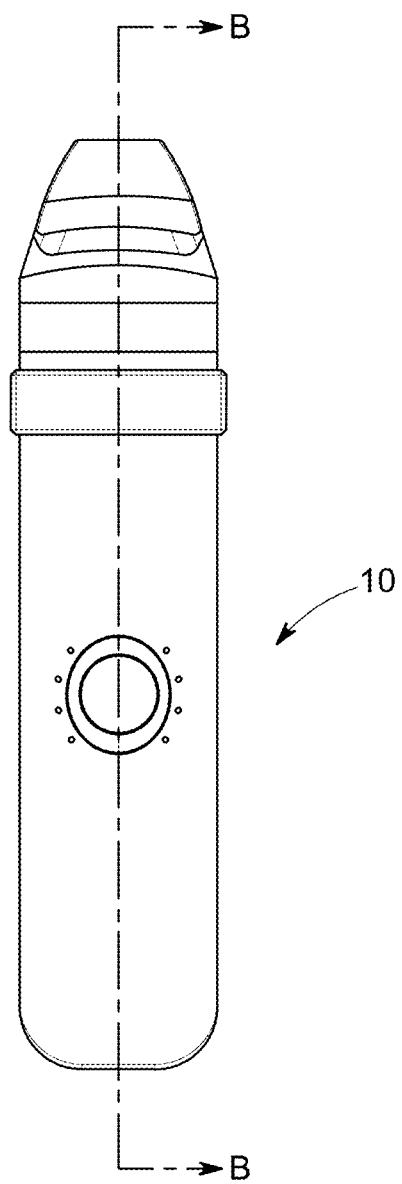
FIGS. 93A-93C are schematic views of an ultrasonic transducer of a droplet delivery device with an isolation view (FIG. 93A) with a cross-sectional view along line B-B of FIG. 93A (FIG. 93B) and a cross-sectional view along line A-A of FIG. 93B (FIG. 93C) of the ultrasonic transducer having a wide and flat vibrating member tip portion together with membrane and mesh in accordance with an embodiment of the disclosure.
Figure 93B:
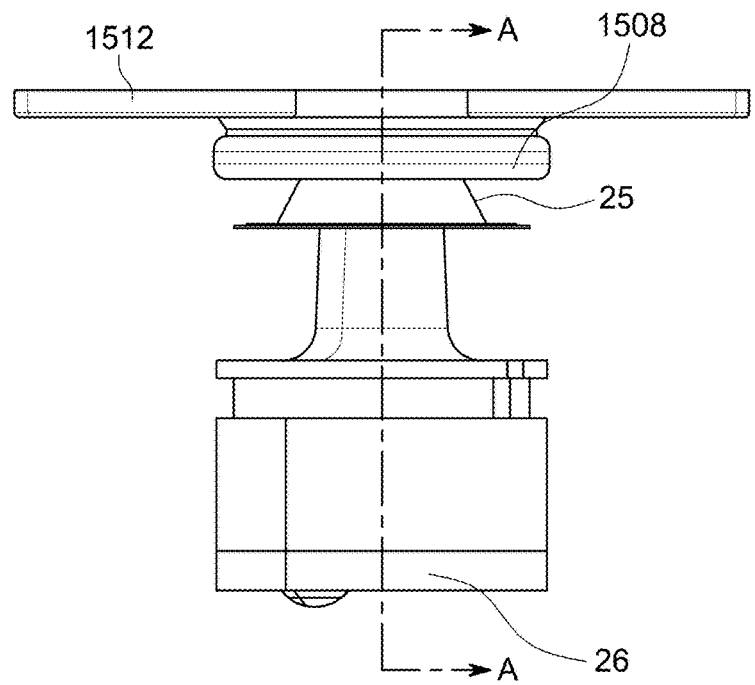
Figure 93C:
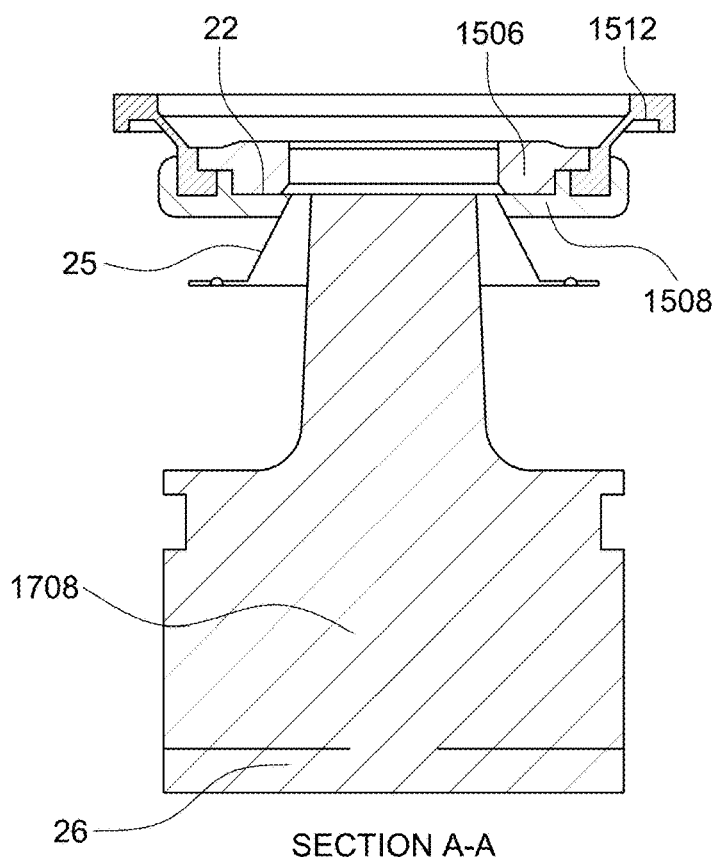
Figure 94A:
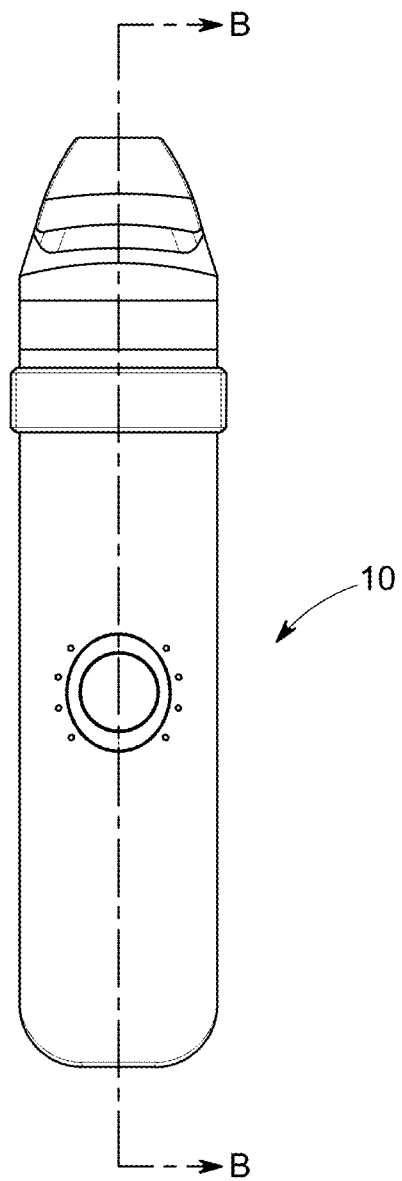
FIGS. 94A-94D are schematic views of a droplet delivery device (FIG. 94A) with a cross-sectional isolation views of the ultrasonic transducer along line B-B of FIG. 94A (FIG. 94B), an isolation view (FIG. 94C) and a cross-section view along line A-A of FIG. 94C (FIG. 94D) of the ultrasonic transducer having a wide and ring-shaped tip portion together with membrane and mesh in accordance with an embodiment of the disclosure.
Figure 94B:
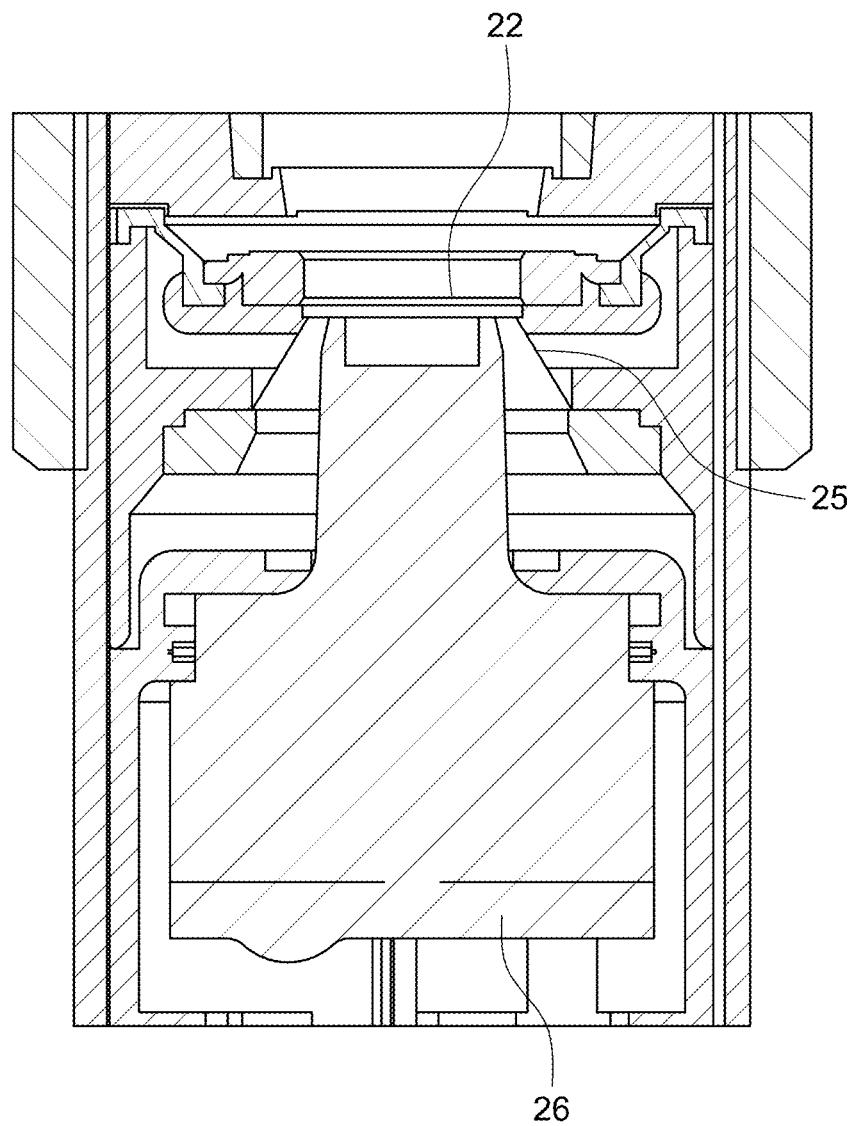
Figure 94C:
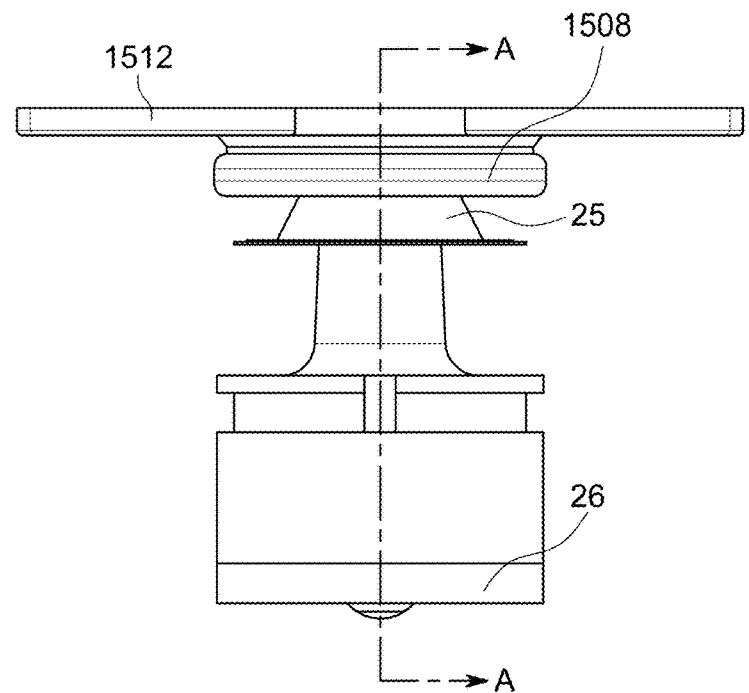
Figure 94D:
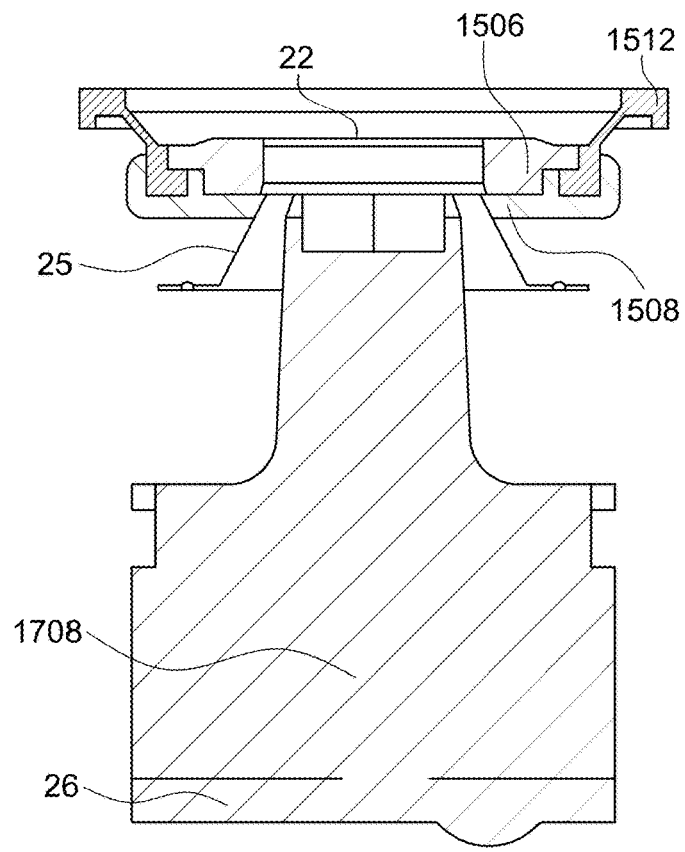

FIGS. 90A and 92B illustrate an ultrasonic transducer 26 with a non-beveled ring-shaped vibrating member tip portion 170 coupled to a membrane 25 having a generally flat and parallel exterior surface relative to and not in contact with the underlying fluid-facing flat surface of the mesh 22 in a further embodiment.

FIGS. 93A-93D show an alternative embodiment of a droplet delivery device with an ultrasonic transducer 26 having a wide and flat vibrating member tip portion 170 together with membrane 25 having a generally flat surface and mesh 22 being generally flat. A preferable suspension system for mesh 22 is further illustrated by FIGS. 30C and 30D.

FIGS. 94A-94D shown another embodiment with an ultrasonic transducer 26 having a wide and ring-shaped tip portion 170 together with membrane 25 having a generally flat surface and mesh 22 being generally flat. A preferable suspension system for mesh 22 is further illustrated by FIGS. 94C and 94D.

Membranes

The membranes 25 of the embodiments are made of materials featuring robust and proper acoustical and mechanical properties such as polyethylene naphthalate, polyethylenimine, poly ether ketone, polyamide, polymethyl methacrylate, polyetherimide, polyvinylidene fluoride, ultra-high molecular weight polyethylene, and the like.

The membranes of the embodiments may have a hydrophobic coating, hydrophobic etching, hydrophilic etching, hydrophilic coating, roughening etch, etc.

In some embodiments, such as shown in FIGS. 96A-96D, membranes may include various shapes and surface textures, including "bumps" in one embodiment.

Meshes

Meshes 22 of the embodiments are to be made of materials featuring robust and proper acoustical and mechanical properties such as poly-methyl methacrylate, poly ether ketone, polyetherimide, polyvinylidene fluoride, ultra-high molecular weight polyethylene, polytetrafluoroethylene (PTFE), Ni, NiCo, Pd, Pt, NiPd, and metal alloys.

In one embodiment, the mesh is made from single crystalline or poly crystalline materials such as silicon, silicon carbide, aluminum nitride, boron nitride, silicon nitride, or aluminum oxide. Different hole shapes can be formed in a single crystalline wafer via high precision photolithography with and without using greyscale masks, and isotropic and/or anisotropic etches. Sputtered films can be deposited on the mesh to modify the wettability of the surface. Thin layers formed or deposited on the surface will have, in certain embodiments, much better adherence than films deposited on metal mesh formed by galvanic deposition or polymer mesh formed by laser ablation. The surfaces on the single crystalline wafers "slices" are atomically smooth and can be etched to produce exact surface roughnesses. Exact surface roughnesses can be used for better adherence of mechanical bonding with glue or other materials. Silicon carbide would be a preferable material because of its high strength and toughness. An important advantage of using semiconductor processes to fabricate hole structures from a single crystalline wafer "slice" in a mesh of embodiment of the push mode invention is that the holes and surface contact angles will be exact without the variation seen in conventional ejector plates using mesh made from galvanic deposition or laser ablation. This mesh, as noted in Table 9 may be fixed as in II, or suspended as in I, and the membrane is coupled with an optimized vibrating member with a thin film sputtering of nonreactive metals such as palladium or gold member tip section to further enhance biocompatibility.

Figure 110:
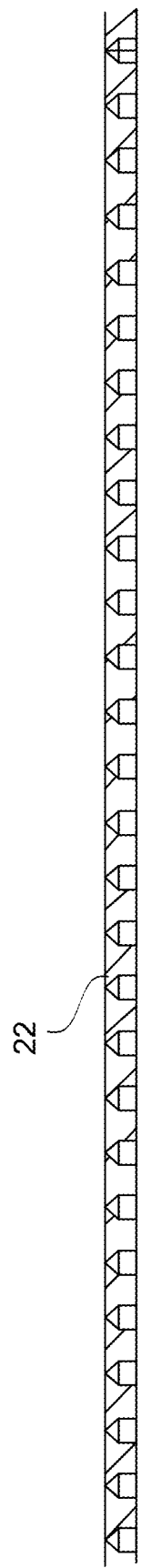
FIG. 110 illustrates a cross-sectional and zoomed view of a crystalline silicon or silicon carbide "wafer"-type mesh with well-type openings that begin larger though the thickness of the mesh and then terminate or are finished with smaller apertures in the openings (and which also may be angled with semiconductor technology processing) in the mesh in a droplet delivery device in accordance with an embodiment of the disclosure.

The hole structures of other embodiments are formed using semiconductor processes such as photo lithography and isotropic and anisotropic etching, laser ablation, femto-second laser ablation, electron beam drilling, EDM (Electrical discharge machining) drilling, diamond slurry grinding, etc. See also FIGS. 109 and 110.

TABLE 9

| Mesh Design | Embodiment | Brief Description |
| --- | --- | --- |
| Single Crystalline Wafer | II | Fixed mesh coupled to optimized vibrating member |
| Single Crystalline Wafer | I | Suspended mesh coupled to optimized vibrating member |

The meshes of the embodiments may have a hydrophobic coating, hydrophobic etching, hydrophilic etching, hydrophilic coating, roughening etch, etc. or a combination thereof.

In other embodiments, FIGS. 97-108 illustrate various implementations of polymer meshes utilized in push mode I and II devices.

Laminar Flow Element

Figure 84A:
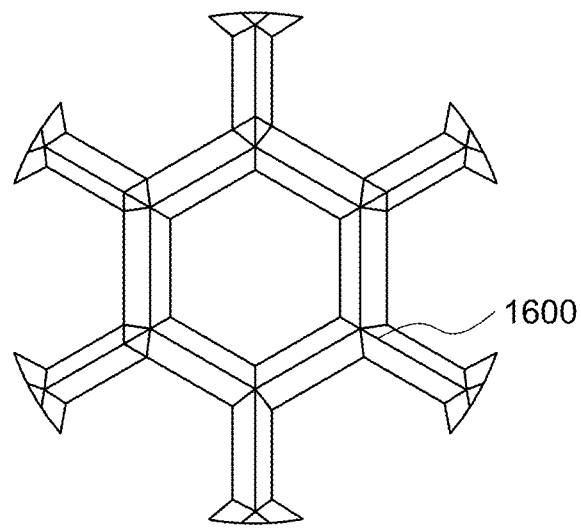
FIGS. 84A-84Q illustrate alternative structures of laminar flow elements of a container assembly of a droplet delivery device in accordance with embodiments of the disclosure.
Figure 84B:
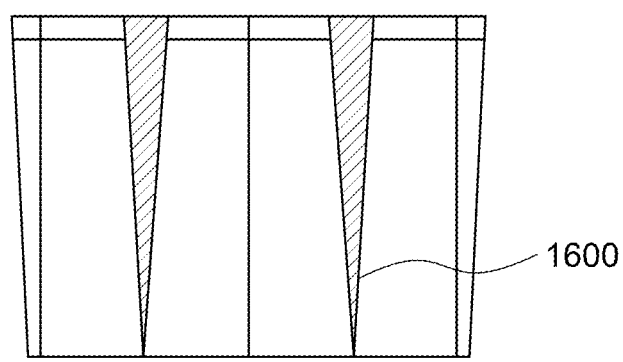
Figure 84C:
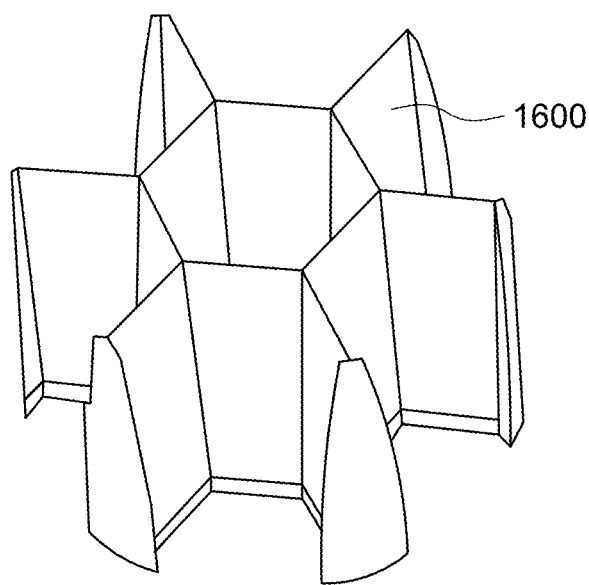
Figure 84D:
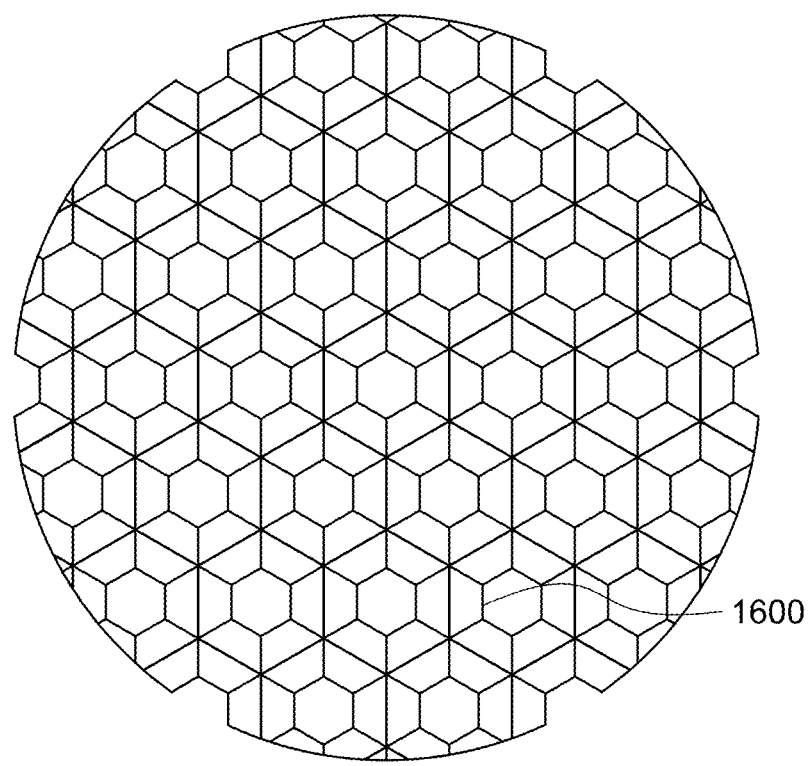
Figure 84E:
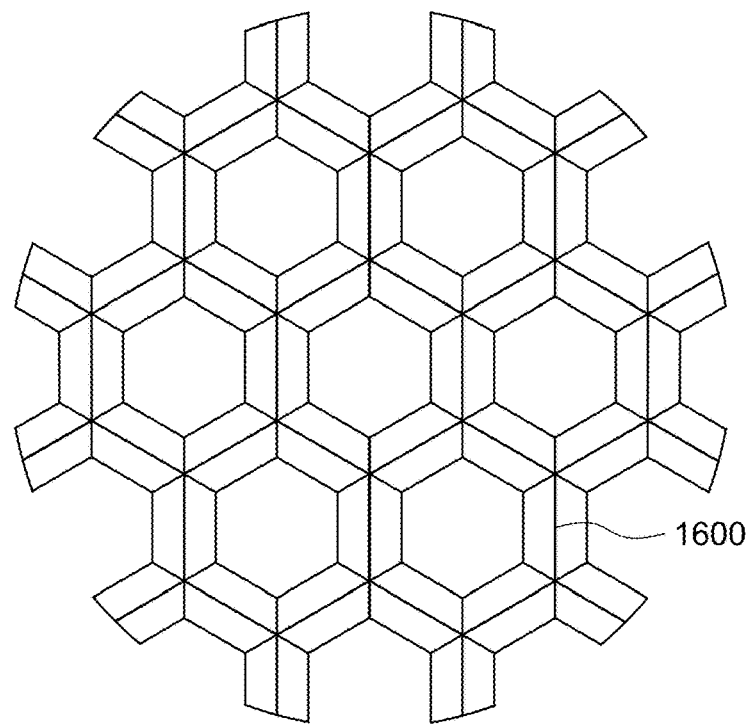
Figure 84F:
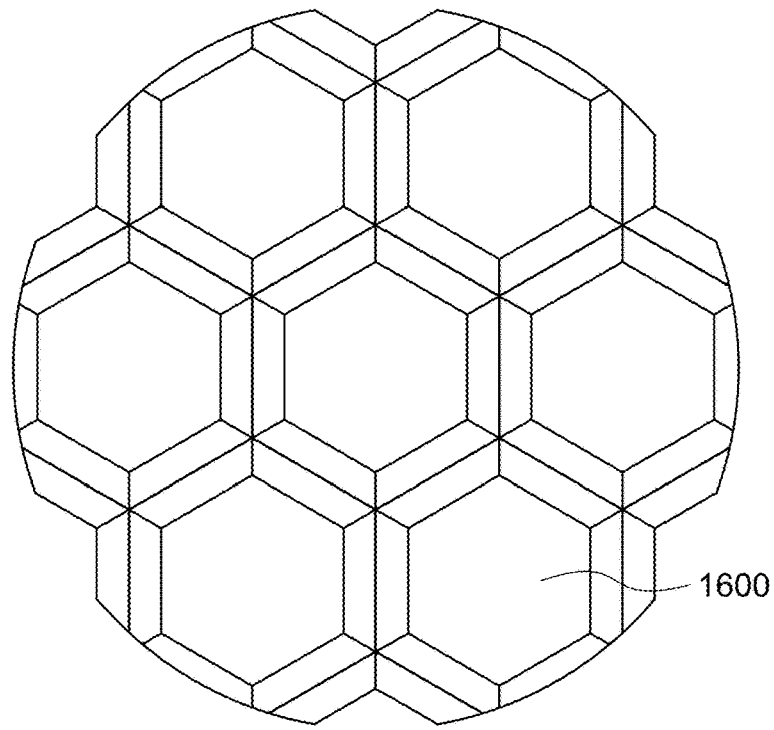
Figure 84G:
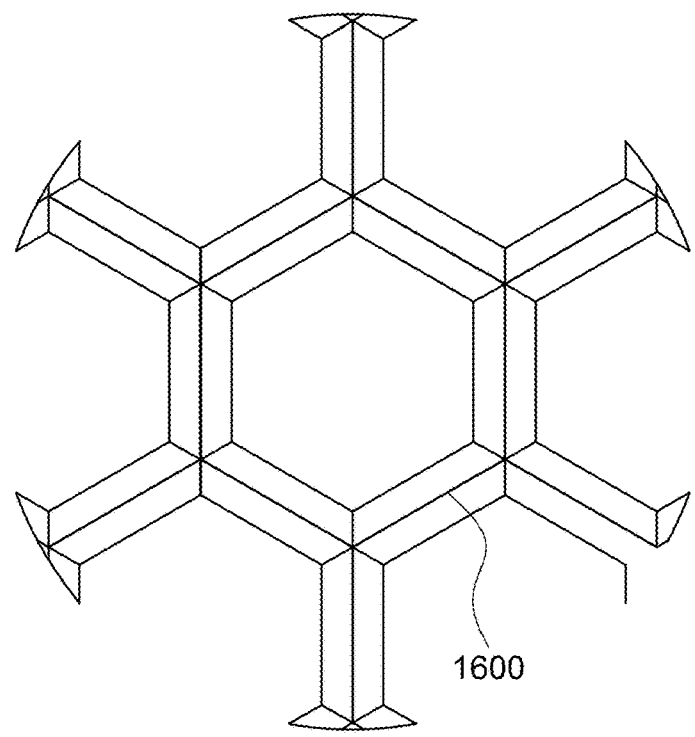
Figure 84H:
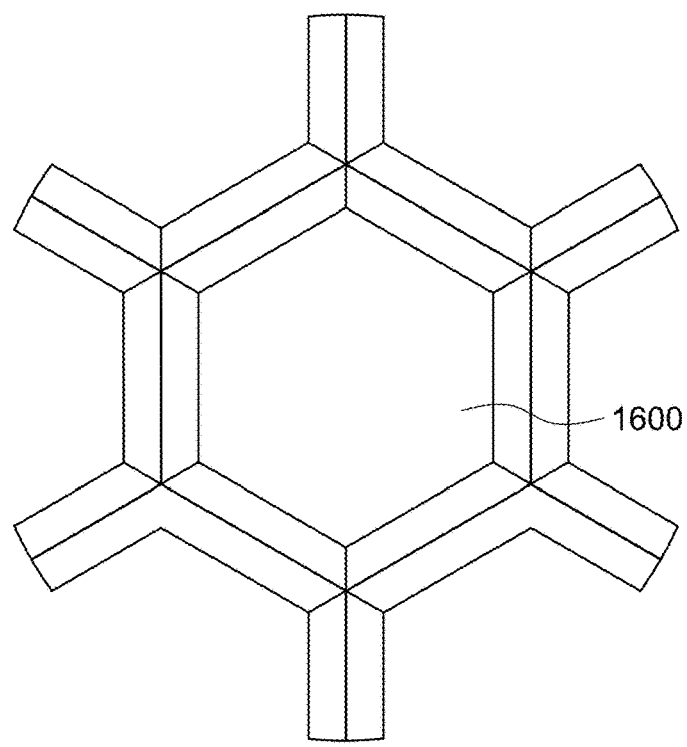
Figure 84I:
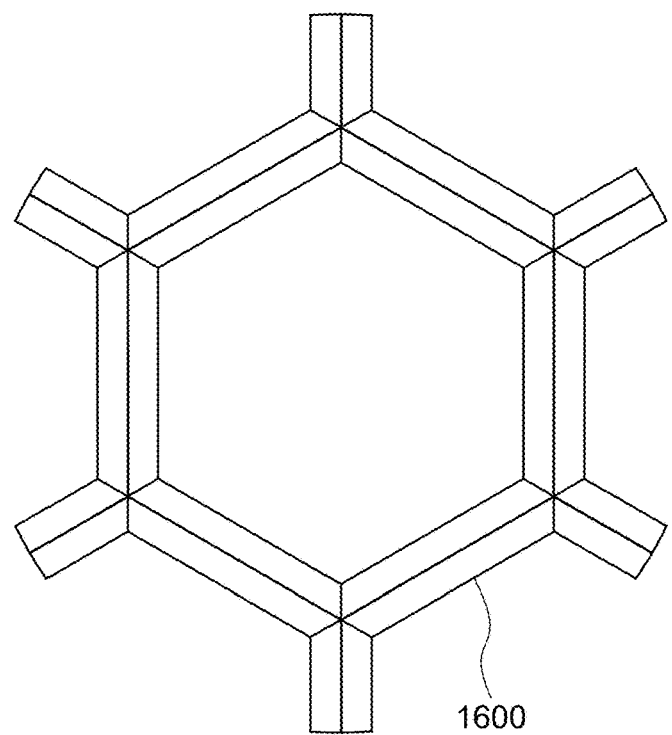
Figure 84J:
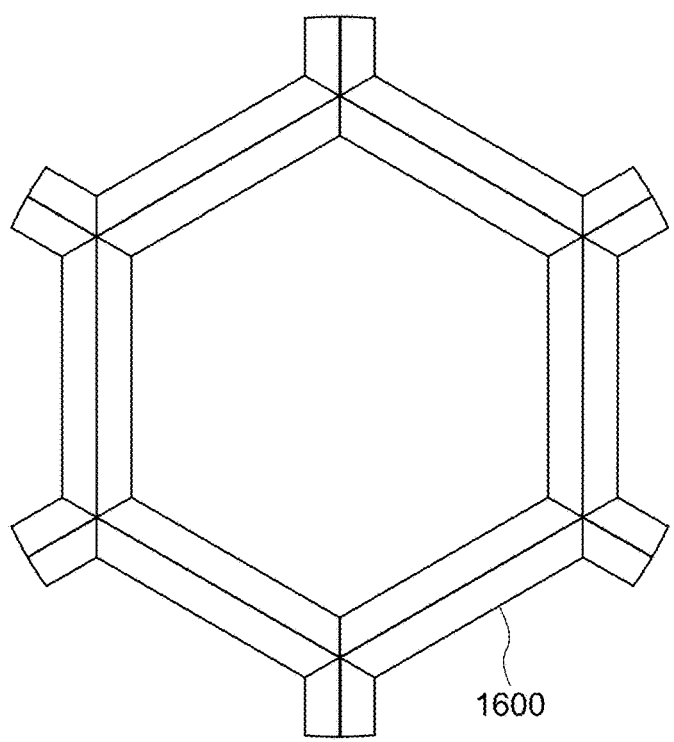
Figure 84K:
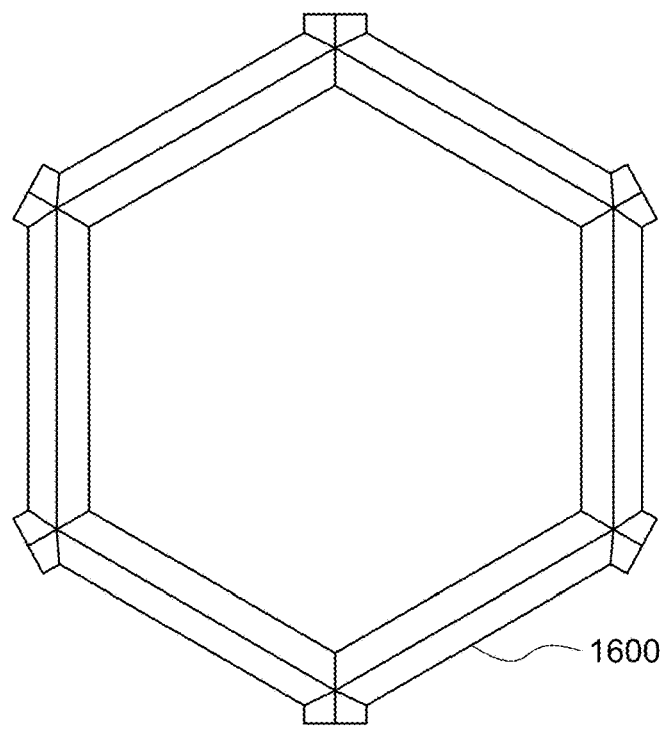
Figure 84L:
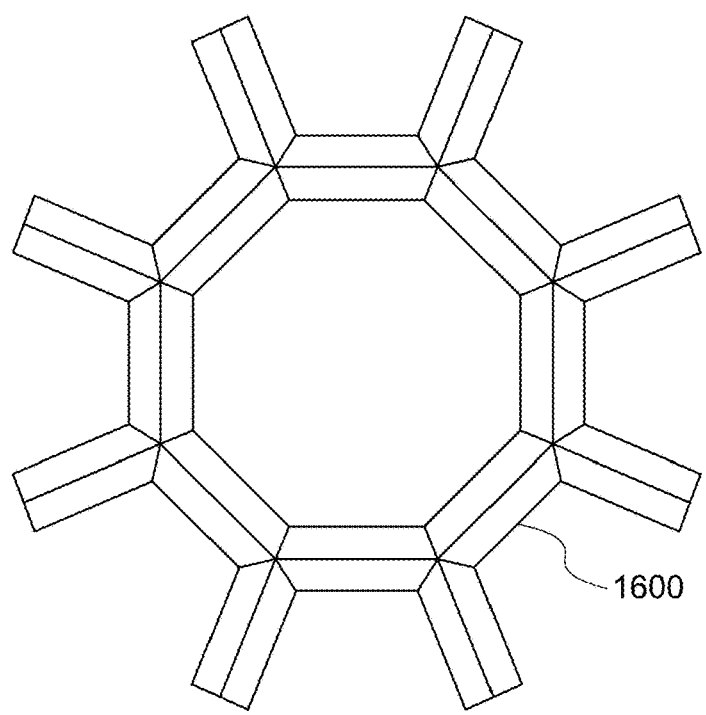
Figure 84M:
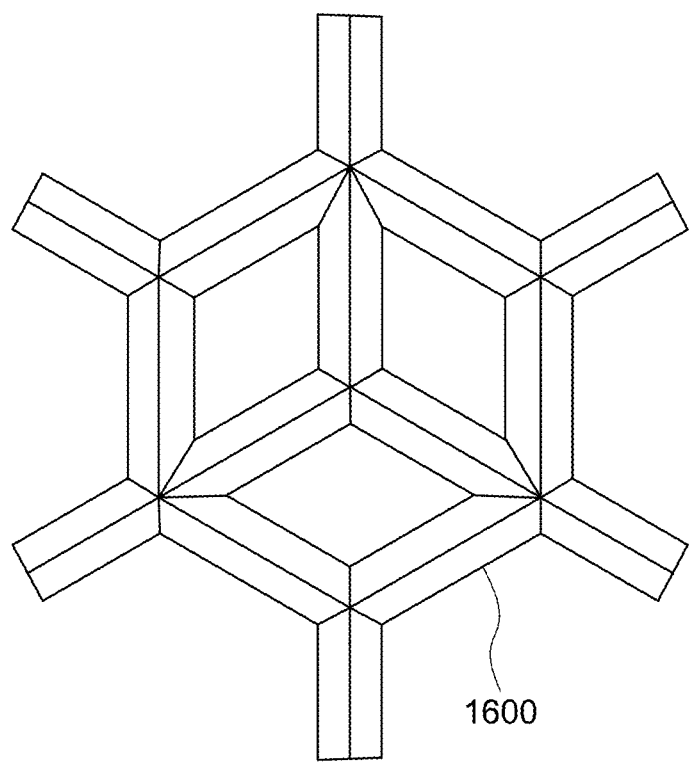
Figure 84N:
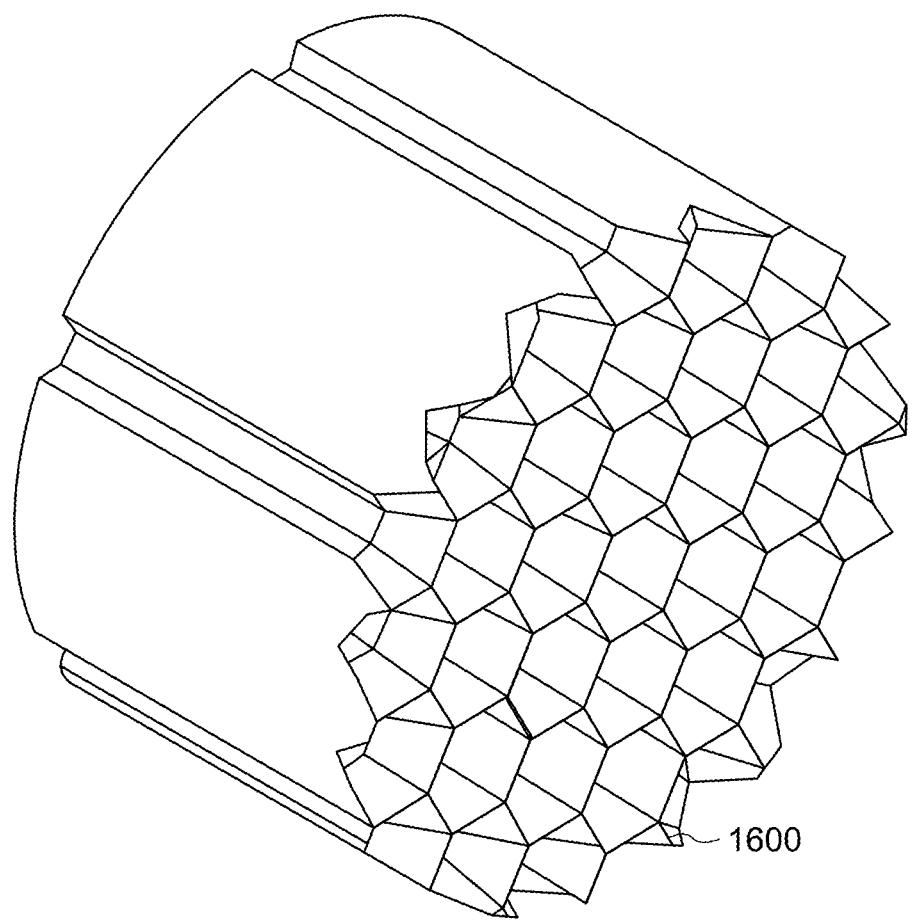
Figure 84O:
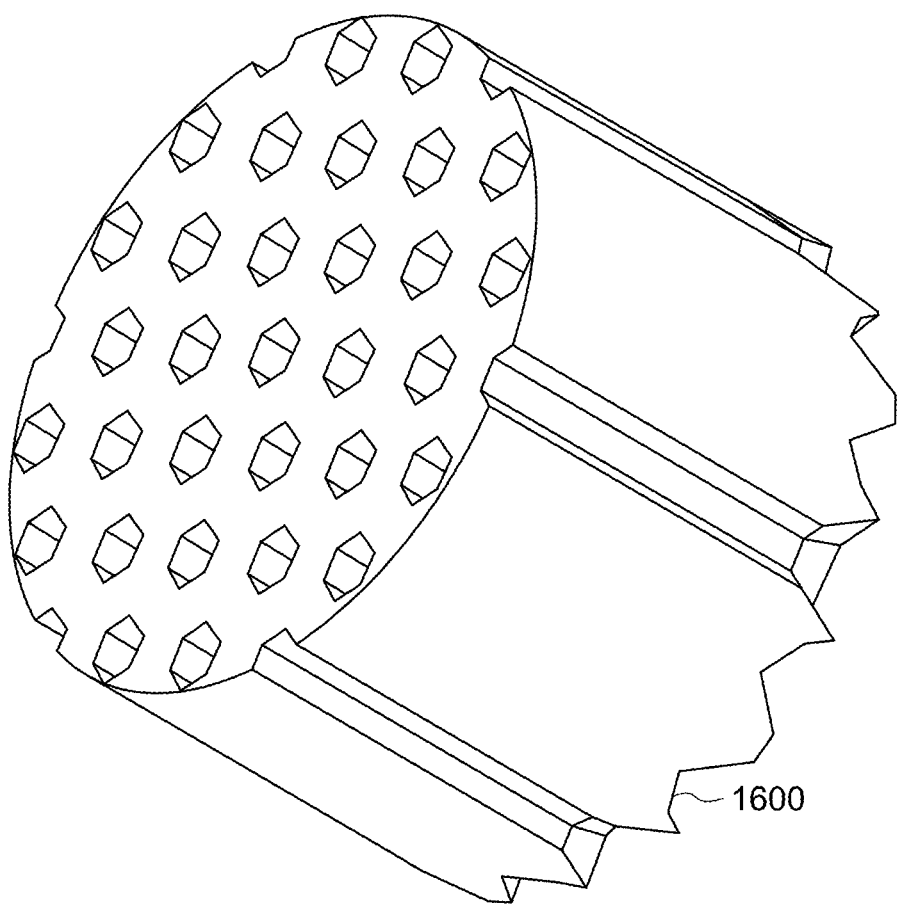
Figure 84P:
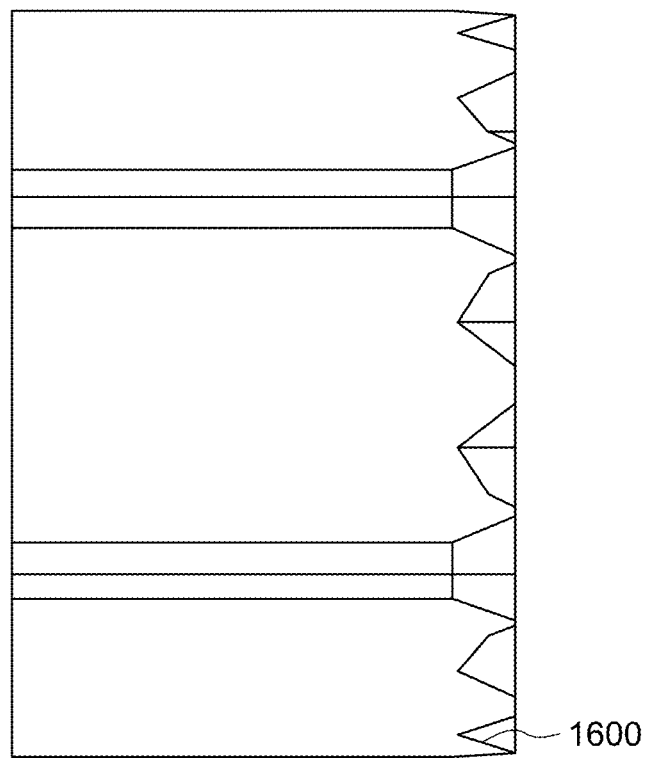
Figure 84Q:
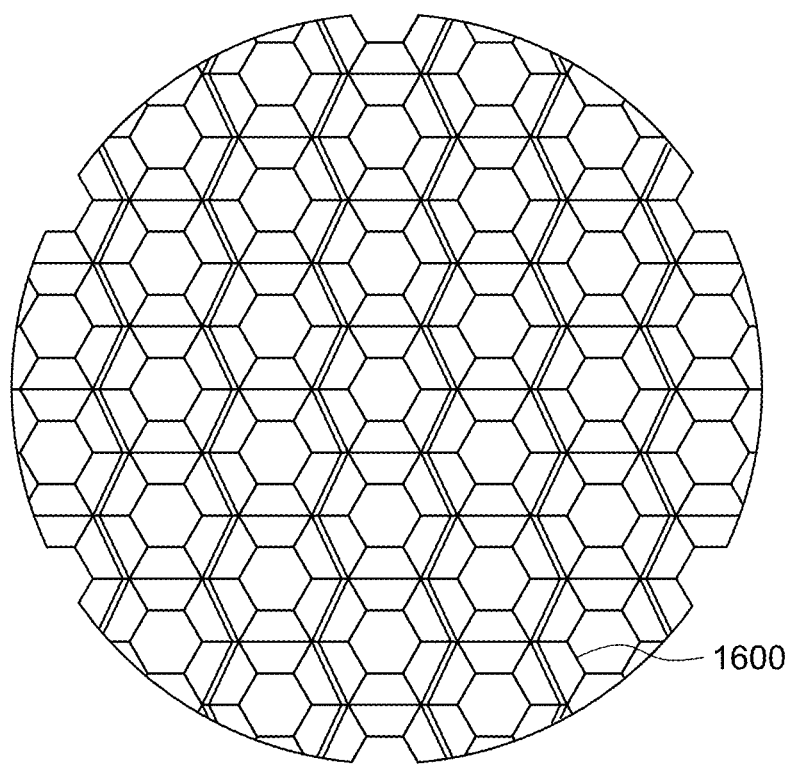

In embodiments of the push mode invention, a laminar flow element 1600, such as shown in FIG. 1B, is preferably secured in the ejection port before the mouthpiece port of a droplet delivery device. In preferable embodiments, laminar flow element includes a plurality of cellular apertures. In some embodiments a laminar flow element includes blade-shaped walls defining the plurality of cellular apertures. In further embodiments, one or more of the plurality of cellular apertures include a triangular prismatic shape, quadrangular prismatic shape, pentagonal prismatic shape, hexagonal prismatic shape, heptagonal prismatic shape or octagonal prismatic shape. FIGS. 84A-84Q show various embodiments of a laminar flow element.

Preventing Oxygen Diffusion

Figure 95:
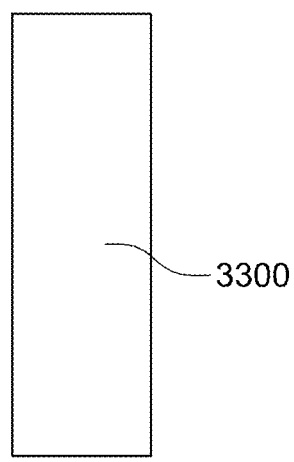
FIG. 95 is a schematic block illustration of an aluminized polymer tab in an embodiment of the disclosure.
Figure 96A:
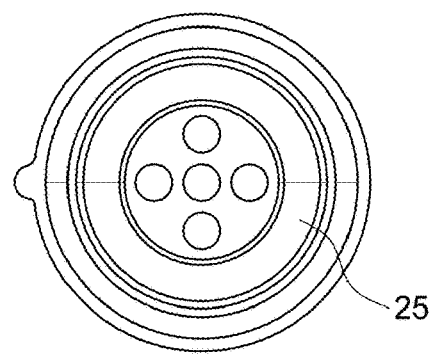
FIGS. 96A-96D are perspective views of a membrane of a droplet delivery device in accordance with an embodiment of the disclosure.
Figure 96B:
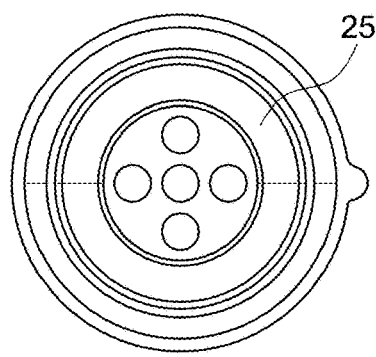
Figure 96C:
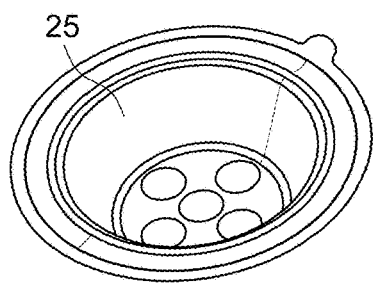
Figure 96D:
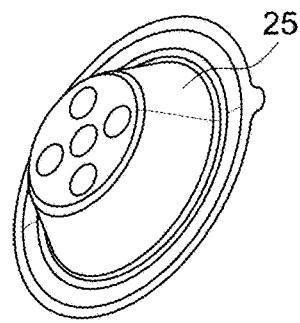
Figures 98A, 98B:
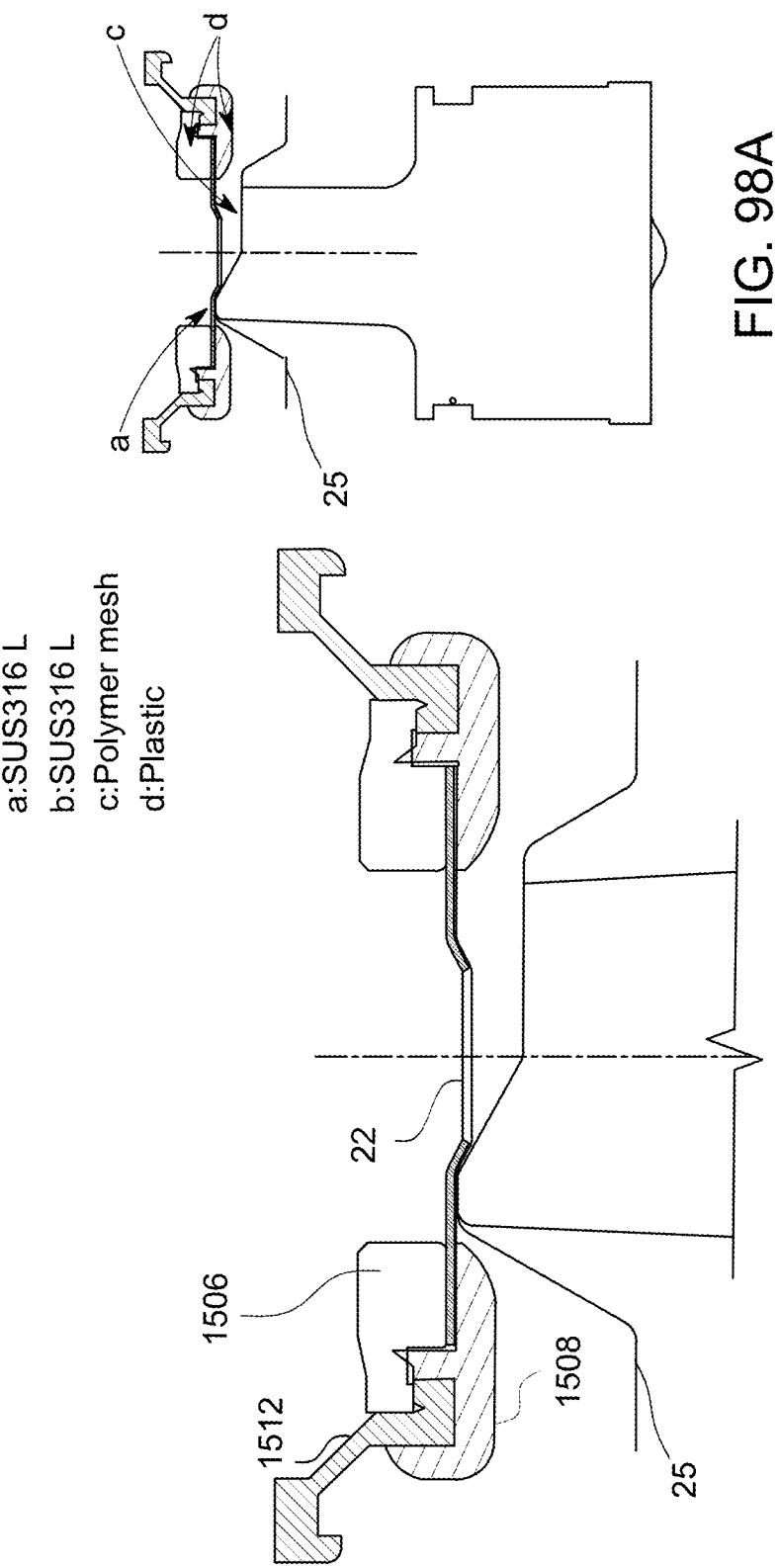
FIGS. 98A and 98B illustrate a cross-sectional view (FIG. 98A) and a zoomed view (FIG. 98B) of a polymer mesh supported in a lowered position by a stainless-steel annulus with respect to a membrane and transducer coupled to a vibrating member having a tip portion in a droplet delivery device in accordance with an embodiment of the disclosure.
Figure 99B:
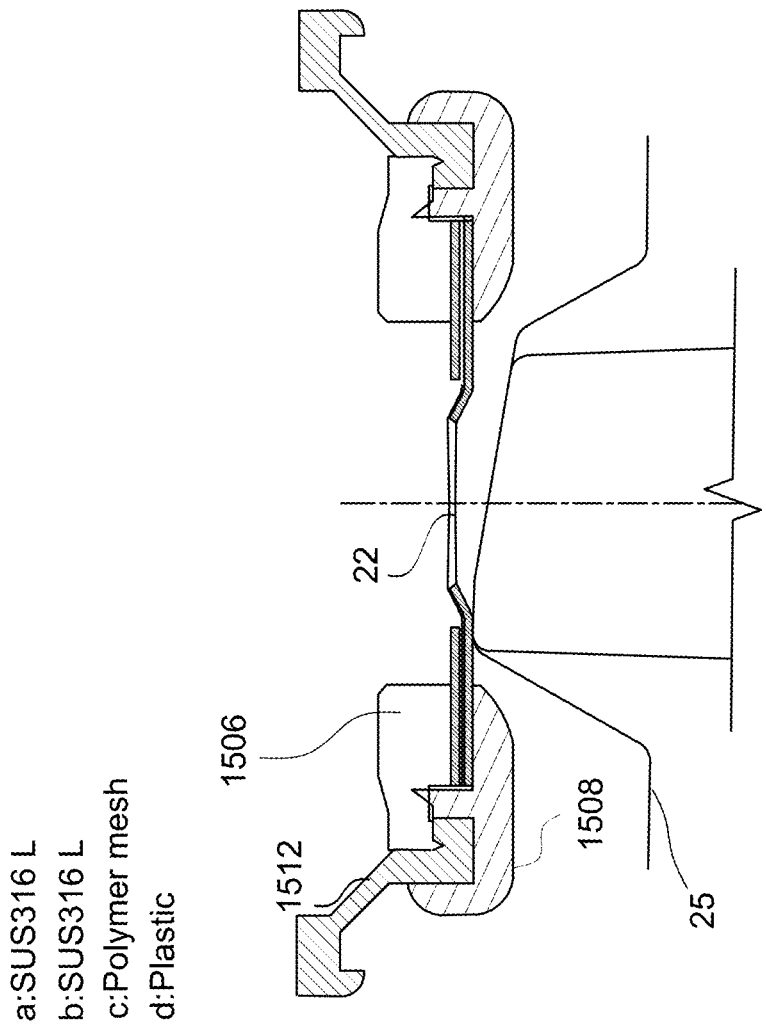
FIGS. 99A and 99B illustrate a cross-sectional view (FIG. 99A) and a zoomed view (FIG. 99B) of a polymer mesh supported in a raised position by a first stainless-steel annulus and having a second stainless steel annulus as a reinforcement coupled, such as by bonding with glue or adhesive, on top of the first annulus with respect to a membrane and transducer coupled to a vibrating member having a tip portion in a droplet delivery device in accordance with an embodiment of the disclosure.
Figure 99A:
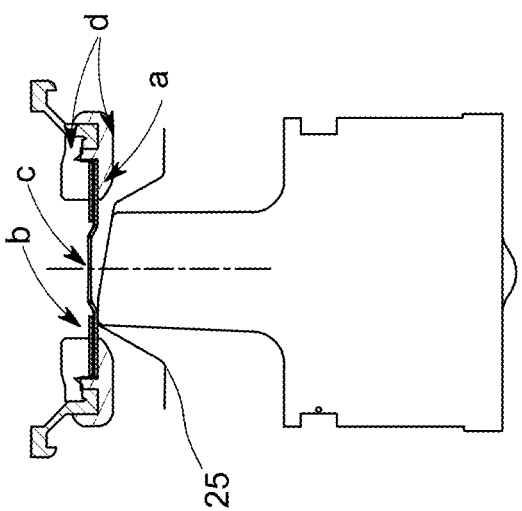
Figure 101C:
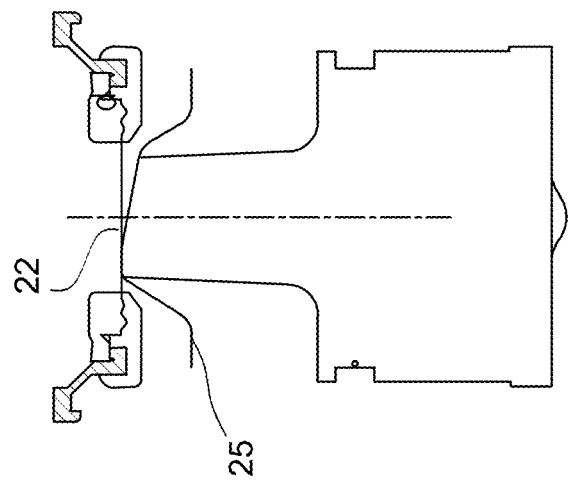
FIGS. 101A-101C illustrate cross-sectional views of a polymer mesh supported in a raised position (FIG. 101A), lowered position (FIG. 101B) and via jagged support (FIG. 101C) with plastic elements of a ring-like support (and without a metal annulus) with respect to membranes and transducer coupled to a vibrating member in droplet delivery devices in accordance with embodiments of the disclosure.
Figure 101B:
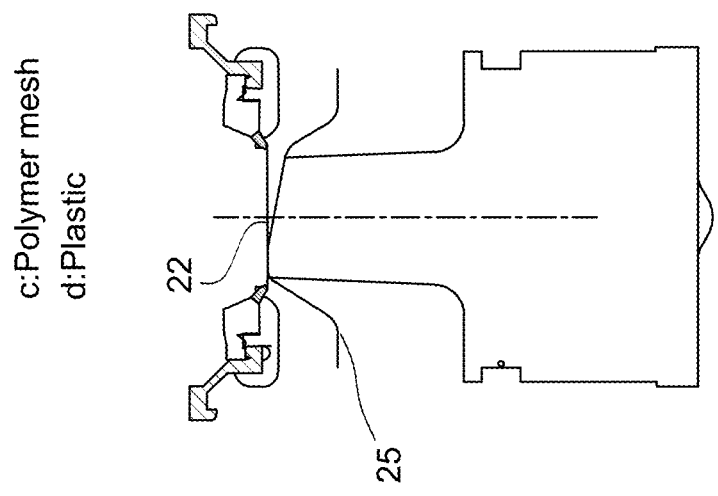
Figure 101A:
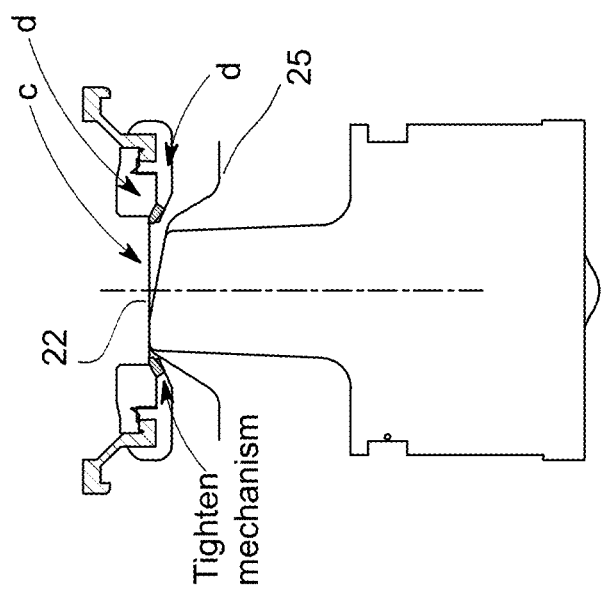
Figure 102C:
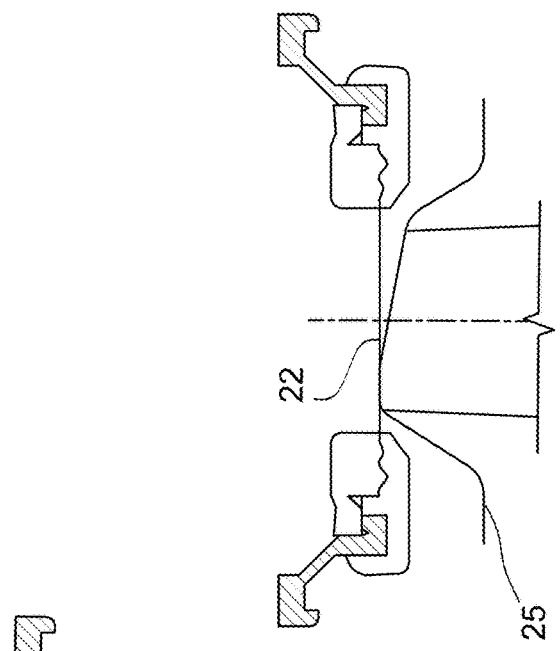
FIGS. 102A-C illustrate zoomed views of FIG. 101A (FIG. 102A), FIG. 101B (FIG. 102B) and FIG. 101C (FIG. 102C).
Figure 102B:
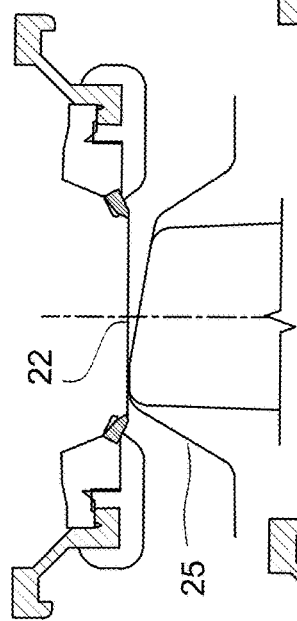
Figure 102A:
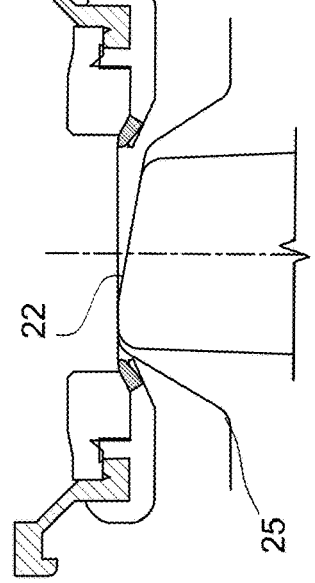
Figure 104:
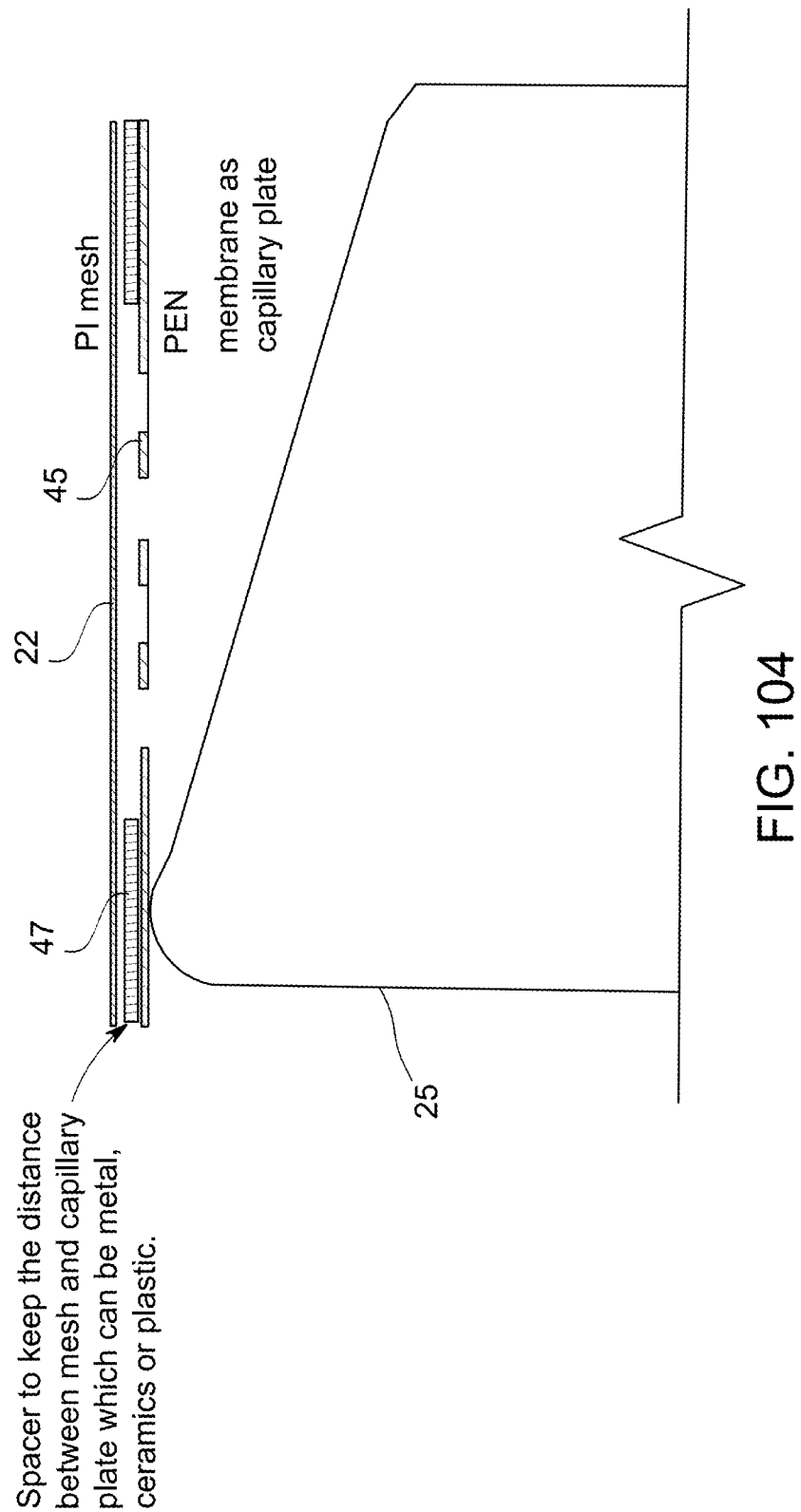
FIG. 104 illustrates a schematic view of a polymer mesh and capillary plate wherein the capillary plate is made of PEN material like the membrane covering the vibrating member (also made of PEN material) and further including a spacer (such as metal, ceramics or plastic) between the capillary plate and the mesh in a droplet delivery device in accordance with an embodiment of the disclosure.
Figure 105B:
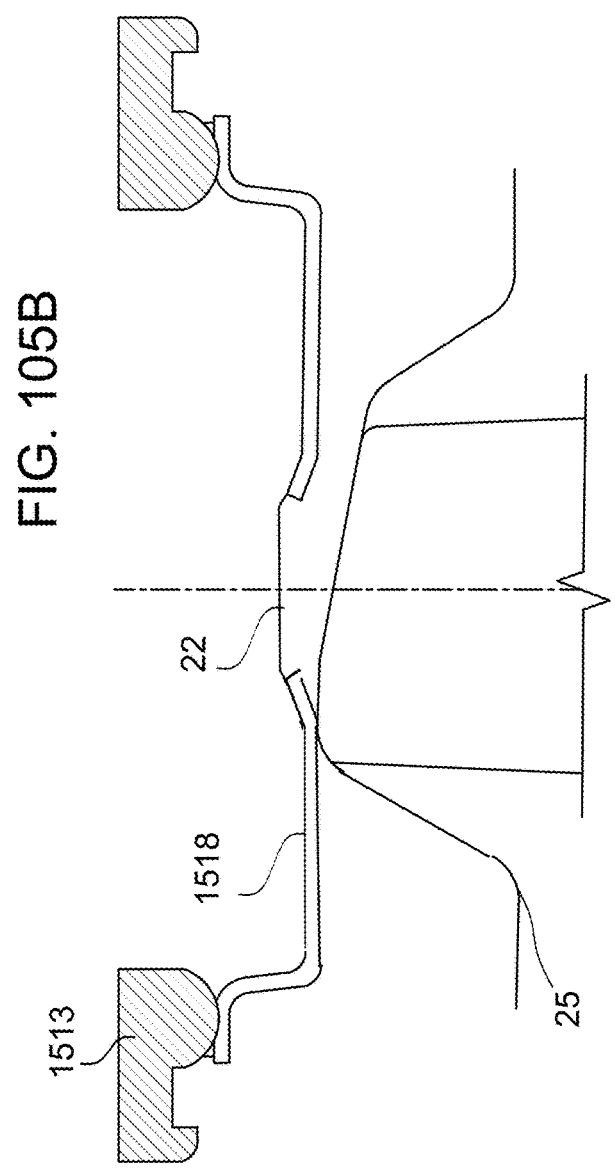
FIGS. 105A and 105B illustrate a cross-sectional view (FIG. 105A) and zoomed view (FIG. 105B) of a polymer mesh with a plastic or silicone ring-shaped type bracket (d) coupled to a stainless steel annulus shaped downward and then up toward a center portion of the annulus that couples to a polymer mesh with respect to a membrane and transducer coupled to a vibrating member having a tip portion in a droplet delivery device in accordance with an embodiment of the disclosure.
Figure 105A:
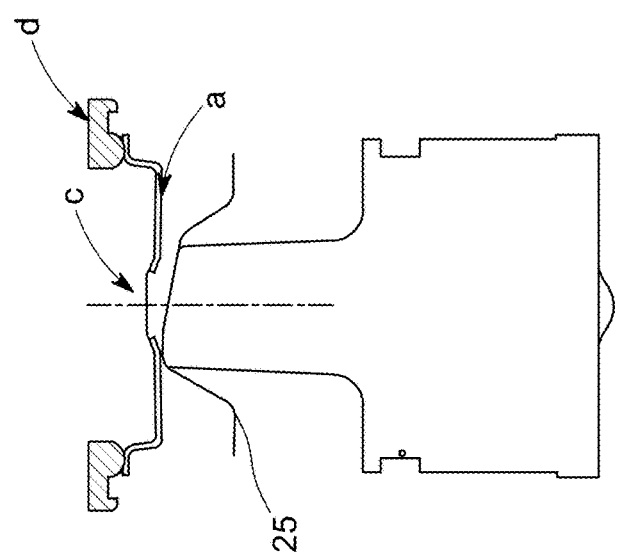
Figure 109B:
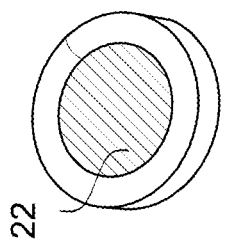
FIGS. 109A-109D illustrate a cross-sectional view (FIG. 109A), a perspective view (FIG. 109B), a top plan view (FIG. 109C) and a cross-sectional zoomed view along line C-C of FIG. 109C (FIG. 109D) of a crystalline silicon or silicon carbide "wafer"-type mesh between ring-structured supports and processed with semiconductor technology to provide exact fabrication of smooth openings, such as pseudospherical, (zoomed cross-sectional view of FIG. 109D intended to show openings fully through mesh), in the mesh in a droplet delivery device in accordance with an embodiment of the disclosure.
Figure 109D:
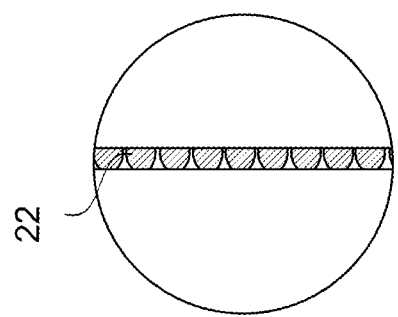
Figure 109A:
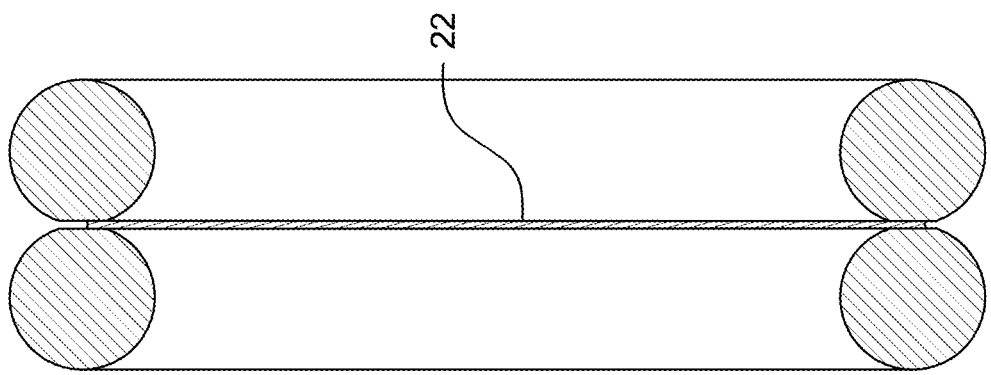
Figure 109C:
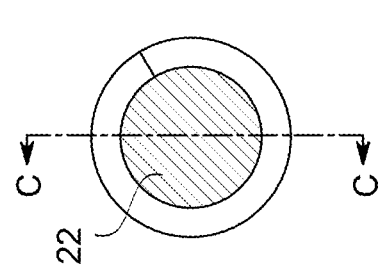

Referring to FIG. 95, a droplet delivery device in an embodiment where an ejector bracket and container assembly are integrated as a single assembly includes a membrane cooperating with a mesh further preferably includes at least one superhydrophobic vent in such single assembly in fluid communication with the reservoir and is covered in storage with a removable aluminized polymer tab 3300 to help prevent oxygen diffusion into the fluid in the reservoir during such storage. In another embodiment of the push mode invention, a droplet delivery device in an embodiment where an ejector bracket and container assembly are integrated as single assembly that includes a membrane cooperating with a mesh further preferably further includes a removable aluminized polymer tab 3300 coupled to an exterior surface of the membrane adjacent the mesh during storage to help prevent oxygen diffusion into the fluid in the reservoir during such storage.

In another embodiment of the push mode invention, a droplet delivery device having a membrane 25 that cooperates with a mesh 22 includes a pre-assembly step of removing a sealed packaging including aluminum and/or aluminum coating that contains the reservoir with a fluid, preferably wherein the reservoir is included in the container assembly that is also packaged for storage in the sealed packaging.

Decreasing Large Droplets in Aerosol

In embodiments of the push mode invention, it is desirable to decrease large droplet formation and encourage smaller droplet sizes to be delivered out of the droplet delivery device and in the aerosol stream.

In one embodiment, a hydrophilic wicking material may be provided to line the mouthpiece of the droplet delivery device. Droplets formed on the outer perimeter of a mesh exit are absorbed by the hydrophilic wicking material and decrease the likelihood of large droplets propelling off the surface of the mesh exit. This wicking material absorption of large droplets increases MMAD repeatability and prevents pooling.

In another embodiment, a one-dimensional hydrophilic lattice (see laminar flow element 1600 but taking such as a cross section), or a series of one dimensional hydrophilic lattices, may be used to absorb large droplets that might "pop" off the mesh due to pooling.

It has been noticed in tests of push mode droplet production that a fog of aerosol may remain within the mouthpiece tube after inhalation. This fog could lead to pulling on the mesh and along the outer perimeter. This pulling happens due to no entrained air pulling the tail end of the aerosol ejection out. Via electronic programming and monitoring through a microcontroller or microchip integrated or coupled in the droplet delivery device, the droplet device can be progammably controlled to start spraying when the air flow rate reaches a threshold and then the droplet delivery device detection controller records your maximum air intake every 2 ms. The droplet delivery device is programmed to stop spraying when the flow rate recedes to a percentage of the maximum flow rate achieved during inhalation. In embodiments, a parameter labeled "pressure cutoff" can be added to a graphical user interface (GUI) for control/programming of the droplet delivery device so that a manufacturer or other device operator and alter the stop condition parameter for the spray.

Referring to FIGS. 111A-111C, in another embodiment a baffle 4000 is inserted into the aerosol path. The baffle 4000 may comprise a plastic piece with fins 4050 to hold it in place in the aerosol tube of the droplet delivery device. The plastic piece has a cylindrical cavity which holds an absorbent plug 4100 (e.g., porous polyester or other wicking materials). The plug 4100 is inserted into the baffle cavity and is long enough to extend beyond the opening of the cavity. The absorbent plug faces the ejector mesh 22. On the side of the baffle opposite the mesh 22, the plastic baffle 4000 has a teardrop shape to direct airflow and prevent eddies from forming. The baffle 4000 is designed to inertially filter the aerosol by capturing large droplets in the absorbent plug 4100 upon ejection. Initial data using 3 ejectors is shown in the table below. As seen in Table 10, the baffle 4000 decreased the MMAD by approximately 0.1-0.2 um for each ejector. This inertial filtering creates a smoother inhalation experience with less irritation. The plastic piece of the baffle 4000 and the absorbent plug 4100 may be various lengths and/or diameters.

TABLE 10

| Baffle Inertial Filtering | | |
|---|---|---|
| Sample | MMAD (um) without baffle | MMAD (um) with baffle |
| 1 | 0.83 | 0.69 |
| 2 | 0.86 | 0.67 |
| 3 | 0.82 | 0.75 |

Figure 112:
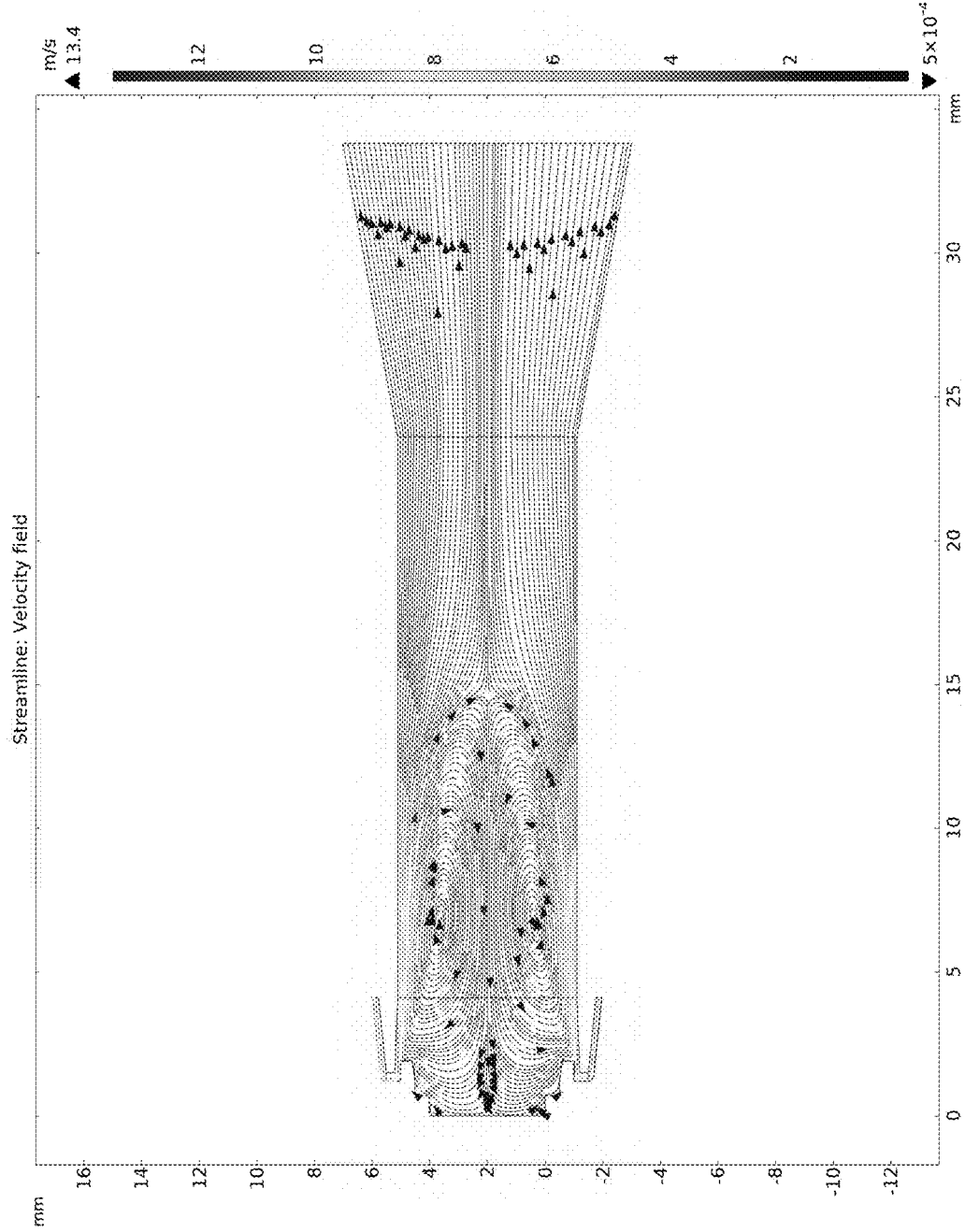
FIG. 112 is a streamline velocity field graphical map of an airflow path of a droplet delivery device including airflow directors without a baffle in accordance with an embodiment of the disclosure.

As described, it is important to get all the small droplets out of the mouthpiece. The small droplets have a very small stopping distance; therefore, the airflow must be close enough to the ejector plate to carry the small droplets. One design was tested wherein airflow directors were used to point the airflow towards the end of the mouthpiece and away from the mesh. As shown in FIG. 112, the airflow path with the airflow directors caused backwards eddies causing the small droplets to stay down by the ejector plate. Taking the airflow directors out helped the airflow catch some of the small droplets; however, the airflow was still leaving behind some of the small droplets. The holder for the ejector plate was sloped to help guide the airflow to the ejector plate. This encourages the air to catch most of the small droplets and send the droplets down the middle of the mouthpiece tube, but the ejector still produces larger unwanted droplets.

Figure 113:
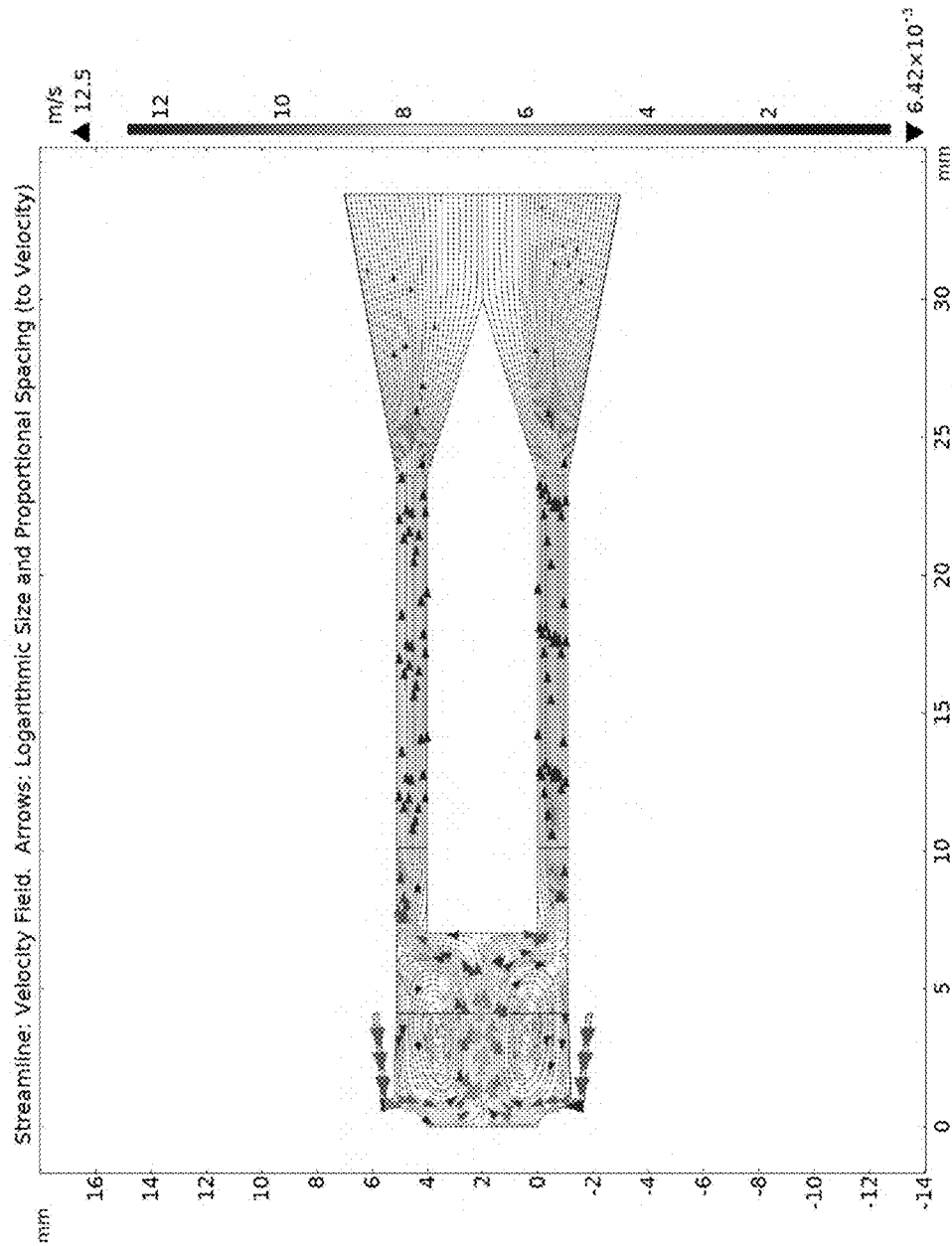
FIG. 113 is a streamline velocity field graphical map of an airflow path of a droplet delivery device including a baffle with wicking material and no airflow directors in accordance with an embodiment of the disclosure.

FIG. 113 illustrates the results when an insertable baffle 4000 was placed in the middle of the mouthpiece tube. This baffle holds a wicking material. As the airflow is pulled down the middle of the mouthpiece tube, the air flows around the baffle. The droplets follow the airflow; however, the larger droplets carry too much momentum and cannot make the turn to flow around the baffle. The larger droplets smash into the wicking material. The wicking material holds the liquid to keep the liquid from falling back onto the ejector plate. The liquid can then evaporate from the wicking material.

Figure 114:
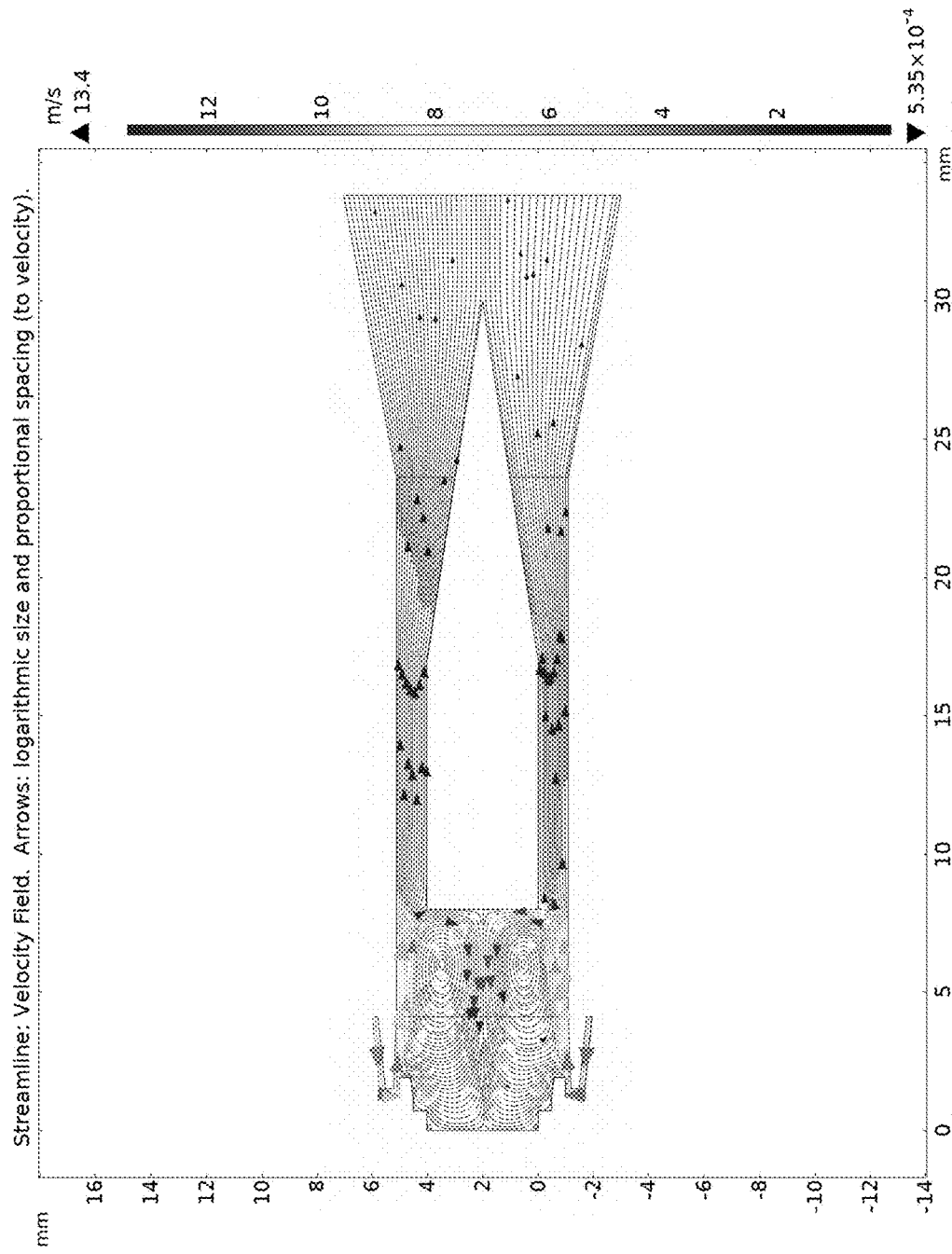
FIG. 114 is a streamline velocity field graphical map of an airflow path of a droplet delivery device including a baffle with wicking material and also including airflow directors in accordance with an embodiment of the disclosure.

FIG. 114 illustrates additional results when an insertable baffle 4000 was also used with airflow directors. This test resulted in airflow coming from the airflow directors and shooting down the sides of the baffle. Eddies were still formed in the middle of the mouthpiece tube and pushed small droplets back onto the ejector plate. These eddies also caused the large droplets to flow around the baffle and resulted in no inertial filtering.

While the push mode invention has been described with reference to exemplary embodiments, it will be understood by those skilled in the art that various changes may be made and equivalents may be substituted for elements thereof without departing from the scope of the push mode invention. In addition, many modifications may be made to adapt a particular situation or material to the teachings without departing from the essential scope thereof. Therefore, it is intended that the push mode invention not be limited to the particular embodiment disclosed as the best mode contemplated for carrying out this invention, but that the push mode invention will include all embodiments falling within the scope of the appended claims.

What is claimed is:

1. A droplet delivery device comprising:
    a container assembly with a mouthpiece port;
    a reservoir disposed within or in fluid communication with the container assembly and configured to supply a volume of fluid;
    an ejector bracket in fluid communication with the reservoir, the ejector bracket including a mesh with a membrane operably coupled to a vibrating member that is coupled to an electronic transducer with the membrane between the vibrating member and the mesh, wherein the reservoir includes a self-sealing mating mechanism configured to couple to a fluid release mating mechanism of the ejector bracket, and wherein the mesh includes a plurality of openings formed through the mesh's thickness, and wherein the transducer is coupled to a power source and is operable to oscillate the vibrating member and the membrane and generate an ejected stream of droplets through the mesh; and an ejection channel within the container assembly configured to direct the ejected stream of droplets from the mesh to an outlet.

2. A droplet delivery device comprising:

a container assembly with a mouthpiece port;

a reservoir disposed within or in fluid communication with the container assembly and configured to supply a volume of fluid;

an ejector bracket in fluid communication with the reservoir, the ejector bracket including a mesh with a membrane operably coupled to a vibrating member that is coupled to an electronic transducer with the membrane between the vibrating member and the mesh, wherein the membrane includes a slanted upper surface configured to contact the fluid supplied from the reservoir, and wherein the mesh includes a plurality of openings formed through the mesh's thickness, and wherein the transducer is coupled to a power source and is operable to oscillate the vibrating member and the membrane and generate an ejected stream of droplets through the mesh; and an ejection channel within the container assembly configured to direct the ejected stream of droplets from the mesh to an outlet.

3. A droplet delivery device comprising:

a container assembly with a mouthpiece port;

a reservoir disposed within or in fluid communication with the container assembly and configured to supply a volume of fluid;

an ejector bracket in fluid communication with the reservoir, the ejector bracket including a mesh with a membrane operably coupled to a vibrating member that is coupled to an electronic transducer with the membrane between the vibrating member and the mesh, wherein the vibrating member includes a ring-shaped beveled tip, and wherein the mesh includes a plurality of openings formed through the mesh's thickness, and wherein the transducer is coupled to a power source and is operable to oscillate the vibrating member and the membrane and generate an ejected stream of droplets through the mesh; and an ejection channel within the container assembly configured to direct the ejected stream of droplets from the mesh to an outlet.

4. A droplet delivery device comprising:

a container assembly with a mouthpiece port;

a reservoir disposed within or in fluid communication with the container assembly and configured to supply a volume of fluid;

an ejector bracket in fluid communication with the reservoir, the ejector bracket including a mesh with a membrane operably coupled to a vibrating member that is coupled to an electronic transducer with the membrane between the vibrating member and the mesh, wherein the vibrating member includes a ring-shaped non-beveled tip, and wherein the mesh includes a plurality of openings formed through the mesh's thickness, and wherein the transducer is coupled to a power source and is operable to oscillate the vibrating member and the membrane and generate an ejected stream of droplets through the mesh; and an ejection channel within the container assembly configured to direct the ejected stream of droplets from the mesh to an outlet.

5. A droplet delivery device comprising:

a container assembly with a mouthpiece port;

a reservoir disposed within or in fluid communication with the container assembly and configured to supply a volume of fluid;

an ejector bracket in fluid communication with the reservoir, the ejector bracket including a mesh with a membrane operably coupled to a vibrating member that is coupled to an electronic transducer with the membrane between the vibrating member and the mesh, wherein the mesh has a bottom surface in a non-parallel configuration with an upper surface of the membrane, and wherein the mesh includes a plurality of openings formed through the mesh's thickness, and wherein the transducer is coupled to a power source and is operable to oscillate the vibrating member and the membrane and generate an ejected stream of droplets through the mesh; and an ejection channel within the container assembly configured to direct the ejected stream of droplets from the mesh to an outlet.

6. A droplet delivery device comprising:

a container assembly with a mouthpiece port;

a reservoir disposed within or in fluid communication with the container assembly and configured to supply a volume of fluid;

an ejector bracket in fluid communication with the reservoir, the ejector bracket including a mesh with a membrane operably coupled to a vibrating member that is coupled to an electronic transducer with the membrane between the vibrating member and the mesh, wherein the mesh has a bottom surface in a non-parallel configuration with an upper surface of the membrane, and wherein the mesh includes a plurality of openings formed through the mesh's thickness, and wherein the transducer is coupled to a power source and is operable to oscillate the vibrating member and the membrane and generate an ejected stream of droplets through the mesh;

an ejection channel within the container assembly configured to direct the ejected stream of droplets from the mesh to an outlet; and a central axis of the droplet delivery device passing through the ejection channel and the membrane, and wherein the vibrating member includes a tip coupling to the membrane at a position offset from the central axis.

7. A droplet delivery device comprising:

a container assembly with a mouthpiece port;

a reservoir disposed within or in fluid communication with the container assembly and configured to supply a volume of fluid;

an ejector bracket in fluid communication with the reservoir, the ejector bracket including a mesh with a membrane operably coupled to a vibrating member that is coupled to an electronic transducer with the membrane between the vibrating member and the mesh, wherein an exterior surface of the membrane, opposite an underlying surface of the membrane contacting the vibrating member, includes a hydrophilic coating, and wherein the mesh includes a plurality of openings formed through the mesh's thickness, and wherein the transducer is coupled to a power source and is operable to oscillate the vibrating member and the membrane and generate an ejected stream of droplets through the mesh; and an ejection channel within the container assembly configured to direct the ejected stream of droplets from the mesh to an outlet.

* * * * *